US012673138B2

(12) United States Patent
Sharfstein et al.

(10) Patent No.: US 12,673,138 B2
(45) Date of Patent: *Jul. 7, 2026

(54) COMPOSITIONS, APPARATUSES AND METHODS FOR MAKING AND USING BIOSCAFFOLDS

(71) Applicant: The Research Foundation for the State University of New York, Albany, NY (US)

(72) Inventors: Susan Sharfstein, Niskayuna, NY (US); Yubing Xie, Cohoes, NY (US); Pujhitha Ramesh, Albany, NY (US); James Castracane, Marshfield, NY (US); Melinda Larsen, Albany, NY (US); Nicholas Moskwa, Bar Harbor, ME (US)

(73) Assignee: The Research Foundation for the State University of New York, Albany, NY (US)

( * ) Notice: Subject to any disclaimer, the term of this patent is extended or adjusted under 35 U.S.C. 154(b) by 270 days.

This patent is subject to a terminal disclaimer.

(21) Appl. No.: 18/108,395

(22) Filed: Feb. 10, 2023

(65) Prior Publication Data

US 2024/0139379 A1 May 2, 2024

Related U.S. Application Data

(63) Continuation-in-part of application No. 17/558,543, filed on Dec. 21, 2021, now Pat. No. 12,503,686.

(60) Provisional application No. 63/128,561, filed on Dec. 21, 2020.

(51) Int. Cl.
| | |
|---|---|
| *A61L 27/52* | (2006.01) |
| *A61L 27/26* | (2006.01) |
| *A61L 27/38* | (2006.01) |
| *A61L 27/54* | (2006.01) |
| *A61L 27/56* | (2006.01) |
| *C08L 5/04* | (2006.01) |
| *C08L 89/06* | (2006.01) |

(52) U.S. Cl.
CPC .............. *A61L 27/52* (2013.01); *A61L 27/26* (2013.01); *A61L 27/3834* (2013.01); *A61L 27/54* (2013.01); *C08L 5/04* (2013.01); *C08L*
*89/06* (2013.01); *A61L 2300/414* (2013.01); *A61L 2430/34* (2013.01)

(58) Field of Classification Search
CPC ...... A61L 27/52; A61L 27/26; A61L 27/3834; A61L 27/54; A61L 2300/414; A61L 2430/34; A61L 27/56; C08L 5/04; C08L 89/06
See application file for complete search history.

(56) References Cited

U.S. PATENT DOCUMENTS

2012/0148500 A1 6/2012 Brizard
2015/0265744 A1 9/2015 Baaijens

FOREIGN PATENT DOCUMENTS

WO WO-2008069760 A1 * 6/2008 ........... D01D 5/0076

OTHER PUBLICATIONS

Horton et al., Extracellular matrix production by mesenchymal stromal cells in hydrogels facilitates cell spreading and is inhibited by FGF-2, Adv. Healthcare Mater. 9, 1901669. Mar. 3, 2020. [Retrieved online] Weblink: < https://doi.org/10.1002/adhm.201901669>.*
Chandy, Thomas, et al., The Development of Porous Alginate/ Elastin / PEG Composite Matrix for Cardiovascular Engineering, Journal of Biomaterials Applications, vol. 17, Apr. 2003, pp. 287-301.

* cited by examiner

Primary Examiner — Sue X Liu
Assistant Examiner — Dongxiu Zhang
(74) Attorney, Agent, or Firm — Peter Fallon

(57) ABSTRACT

The present disclosure relates to compositions, apparatus and methods for generating one or more scaffolds, including: mixing a hydrogel material and/or an extracellular matrix (ECM) protein in an aqueous solvent to generate an aqueous process solution; and cryoelectrospinning the aqueous process solution onto a plurality of conductive probes extending from a conductive surface of a collector plate disposed within a process chamber under conditions sufficient to generate one or more scaffolds configured to mimic a preselected soft tissue decellularized extracellular matrix. Scaffold compositions are also provided having preselected or tuned characteristics. The scaffolds provide a promising stromal cell delivery vehicle for the remediation of fibrosis.

25 Claims, 73 Drawing Sheets
(41 of 73 Drawing Sheet(s) Filed in Color)

<u>100</u>

102

MIXING A HYDROGEL MATERIAL AND/OR AN EXTRACELLULAR MATRIX (ECM) PROTEIN IN AN AQUEOUS SOLVENT TO GENERATE AN AQUEOUS PROCESS SOLUTION

104

CRYOELECTROSPINNING THE AQUEOUS PROCESS SOLUTION ONTO A PLURALITY OF CONDUCTIVE PROBES EXTENDING FROM A CONDUCTIVE SURFACE OF A COLLECTOR PLATE DISPOSED WITHIN A PROCESS CHAMBER UNDER CONDITIONS SUFFICIENT TO GENERATE ONE OR MORE SCAFFOLDS CONFIGURED TO MIMIC A PRESELECTED SOFT TISSUE DECELLULARIZED EXTRACELLULAR MATRIX

FIG. 1

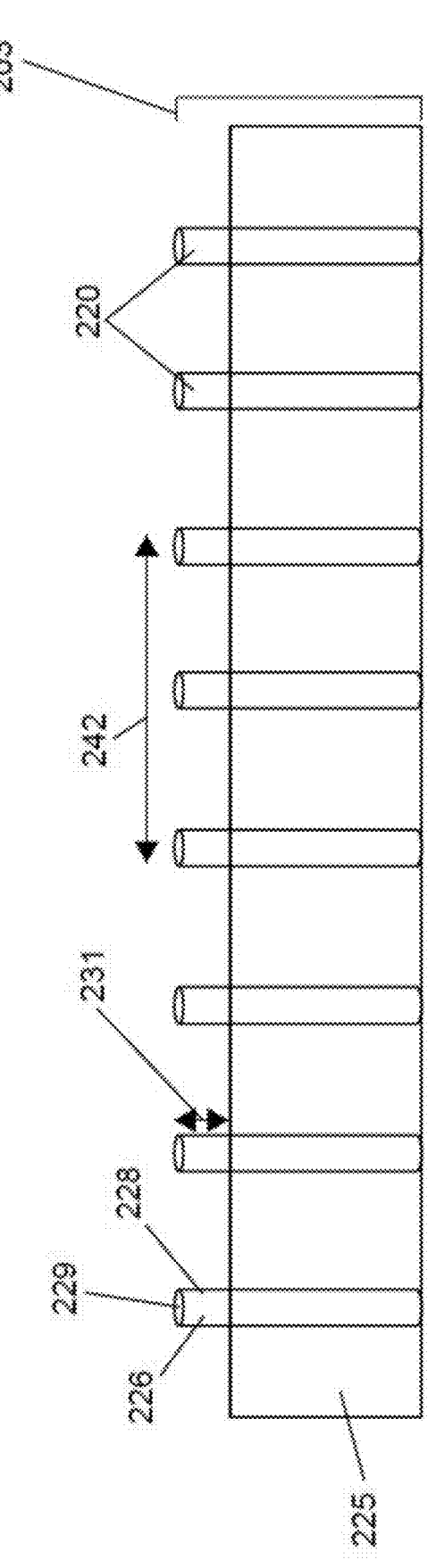
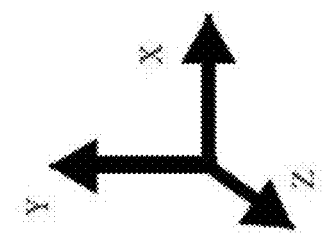
FIG. 3A

Current state-of-the-art of fabricating cryoelectrospun scaffolds (CES) and their properties

| Materials | Solvent | Key Parameters | Scaffold Properties | Purpose | Reference |
|---|---|---|---|---|---|
| PLGA, PEU | Chloroform | CT: -50°C to -70°C RH: >30% | Topography: Loosely packed fibers Stiffness: Breaking lengths of 0.5 km for PLGA, 0.2 km for PEU scaffolds | Generation of porous scaffold | Simonet et al., 2007 |
| PLA | HFIP | CT: -30°C RH: 25-50% | Topography: Loosely packed fibers Stiffness: Tensile strength of ~0.04 MPa | Cell growth in CES | Leong et al., 2009 |
| PLA | HFIP | CT: -30°C RH: 50% | Topography: Loosely packed fibers layered with dense fibrous mat Stiffness: n.d. | Cocultured cell growth in a bi-layered CES | Leong et al., 2010 |
| PLA | HFIP | CT: -35°C RH: 50% | Topography: Loosely packed fibers Stiffness: n.d. | Skin tissue modeling | Leong et al., 2013 |
| *Bombyx mori* SF | HFIP | CT: <0°C RH: Not controlled | Topography: Loosely packed fibers Stiffness: Modulus of ~ 75 MPa | Mucosal tissues modeling | Bulysehva et al, 2014 |
| PLA, PCL, PF | Chloroform | CT: -70°C RH: 4070% | Topography: Loosely packed fibers Stiffness: Tangent moduli of ~200 kPa for PLA, <100 kPa for PCL | Demonstrating control over CES properties | Simonet et al., 2014 |
| PLGA | HFIP, acetone, (THF/DMF) | CT: <0°C RH: "High", not measured | Topography: Loosely packed fibers Stiffness: n.d. | Exploration of effect of varying solvent vapor pressure on CES | Kim et al., 2014 |
| SF, PEO | Water | CT: -90°C RH: Not controlled | Topography: Loosely packed fibers Stiffness: n.d. | Skin tissue modeling | Sheikh et al., 2015 |
| PCL, SF | THF/DMF | CT: -90°C RH: Not controlled | Topography Loosely packed fibers Stiffness: n.d. | Skin tissue modeling | Lee et al., 2016 |
| PCL | Chloroform /Dichlorom ethane with ethanol | CT: -78°C RH: 50% | Topography: Loosely packed fibers Stiffness: 450-5000 Pa (fibers immersed in alginate or alginate sulfate hydrogels) | Cartilage tissue modeling | Formica et al., 2016 |
| PLA | HFIP | CT: -78°C RH: Not controlled | Topography: Loosely packed fibers Stiffness: Young's modulus from 0.57-1.31 MPa. Tensile strength of 0.87 MPa | Kidney tissue modeling | Burton et al., 2018 |
| PCL | GAA | CT: -3.6°C RH: Not controlled | Topography: Loosely packed fibers Stiffness: n.d. | Exploring a hybrid CE technique | Li et al, 2019 |

FIG. 5

Antibodies used for immunocytochemistry analysis

| For SIMS salivary ductal epithelial cells | | | | | |
| --- | --- | --- | --- | --- | --- |
| Primary Antibody | Host Species | Company | Catalog No. | Lot No. | Dilution |
| Anti-Zona Occludin-1 (ZO-1) | Rabbit | ThermoFisher Scientific | 402200 | 1574917A | 1:400 |
| Anti-E-Cadherin | Mouse | BD Biosciences | 610182 | 2307882 | 1:400 |
| Secondary Antibody | Species | Company | Catalog No. | Lot No. | Dilution |
| Cy™3 AffiniPure IgG | Host: Donkey Target: Anti-Rabbit | Jackson ImmunoResearch | 711-165-152 | 130437 | 1:300 |
| Alexa Fluor® 647 AffiniPure F(ab')₂ Fragment IgG | Host: Donkey Target: Anti-Mouse | Jackson ImmunoResearch | 715-606-150 | 121469 | 1:300 |
| For NIH 3T3 fibroblasts | | | | | |
| Primary Antibody | Host Species | Company | Catalog No. | Lot No. | Dilution |
| Anti-Vimentin | Mouse-μ chain specific | ThermoFisher Scientific | V2258 | 044M4772 | 1:400 |
| Anti-α-Smooth Muscle Actin | Mouse | Millipore Sigma | A5228 | 074M4814V | 1:400 |
| Secondary Antibody | Species | Company | Catalog No. | Lot No. | Dilution |
| Alexa Fluor® 488 AffiniPureF(ab')₂ Fragment IgM, μ chain specific | Host: Donkey Target: Anti-Mouse | Jackson ImmunoResearch | 715-546-020 | 116970 | 1:400 |
| Alexa Fluor® 647 AffiniPure F(ab')₂ Fragment IgG | Host: Donkey Target: Anti-Mouse | Jackson ImmunoResearch | 715-606-150 | 121469 | 1:1000 |
| For coculture of SIMS salivary ductal epithelial cells and NIH 3T3 fibroblasts | | | | | |
| Primary Antibody | Host Species | Company | Catalog No. | Lot No. | Dilution |
| Anti-Zona Occludin-1 (ZO-1) | Rabbit | ThermoFisher Scientific | 402200 | 1574917A | 1:300 |
| Anti-E-Cadherin | Mouse | BD Biosciences | 610182 | 2307882 | 1:300 |
| Anti-Vimentin | Mouse-μ chain specific | ThermoFisher Scientific | V2258 | 044M4772 | 1:400 |
| Secondary Antibody | Species | Company | Catalog No. | Lot No. | Dilution |
| Cy™3 AffiniPure IgG | Host: Donkey Target: Anti-Rabbit | Jackson ImmunoResearch | 711-165-152 | 130437 | 1:400 |
| Alexa Fluor® 647 AffiniPure F(ab')₂ Fragment IgG | Host: Donkey Target: Anti-Mouse | Jackson ImmunoResearch | 715-606-150 | 121469 | 1:400 |
| Alexa Fluor® 488 AffiniPure F(ab')₂ Fragment IgM, μ chain specific | Host: Donkey Target: Anti-Mouse-μ chain specific | Jackson ImmunoResearch | 715-546-020 | 116970 | 1:400 |

FIG. 6

| For primary E16 mesenchyme cells | | | | | |
|---|---|---|---|---|---|
| Primary Antibody | Host Species | Company | Catalog No. | Lot No. | Dilution |
| Anti – CD140a | Rat | ThermoFisher Scientific | 14-1401-81 | 2015727 | 1:100 |
| Anti – CD140b | Rabbit | Abcam | ab32570 | GR3241180-2 | 1:200 |
| Anti-Vimentin | Mouse-μ chain specific | ThermoFisher Scientific | V2258 | 044M4772 | 1:2000 |
| Secondary Antibody | Species | Company | Catalog No. | Lot No. | Dilution |
| Alexa Fluor® 488 AffiniPure F(ab')$_2$ Fragment IgG | Host: Donkey Target: Anti-Rabbit | Jackson ImmunoResearch | 711-226-152 | 132511 | 1:250 |
| Cy™3 AffiniPure F(ab')$_2$ Fragment IgG (H+L) | Host: Donkey Target: Anti-Rat | Jackson ImmunoResearch | 712-166-153 | 139421 | 1:250 |
| Alexa Fluor® 647 AffiniPure F(ab')$_2$ Fragment IgM, μ chain specific | Host: Donkey Target: Anti-Mouse-μ chain specific | Jackson ImmunoResearch | 715-606-020 | 135520 | 1:250 |
| For decellularized salivary glands | | | | | |
| Primary Antibody | Host Species | Company | Catalog No. | Lot No. | Dilution |
| Anti-Perlecan | Rat | Santa Cruz Biotechnologies | sc-33707 | F2111 | 1:200 |
| Anti-Collagen I | Rabbit | MilliporeSigma | AB765P | 2328311 | 1:200 |
| Anti-Collagen IV | Goat | MilliporeSigma | AB769 | 2626764 | 1:200 |
| Secondary Antibody | Species | Company | Catalog No. | Lot No. | Dilution |
| Alexa Fluor® 647 AffiniPure F(ab')$_2$ Fragment IgG | Host: Donkey Target: Anti-Rat | Jackson ImmunoResearch | 712-176-150 | 89484 | 1:250 |
| Alexa Fluor® 488 AffiniPure F(ab')$_2$ Fragment IgG | Host: Donkey Target: Anti-Rabbit | Jackson ImmunoResearch | 711-226-152 | 132511 | 1:250 |
| Cy™3 AffiniPure IgG | Host: Donkey Target: Anti-Goat | Jackson ImmunoResearch | 707-166-147 | 88398 | 1:250 |

FIG. 6 Cont.

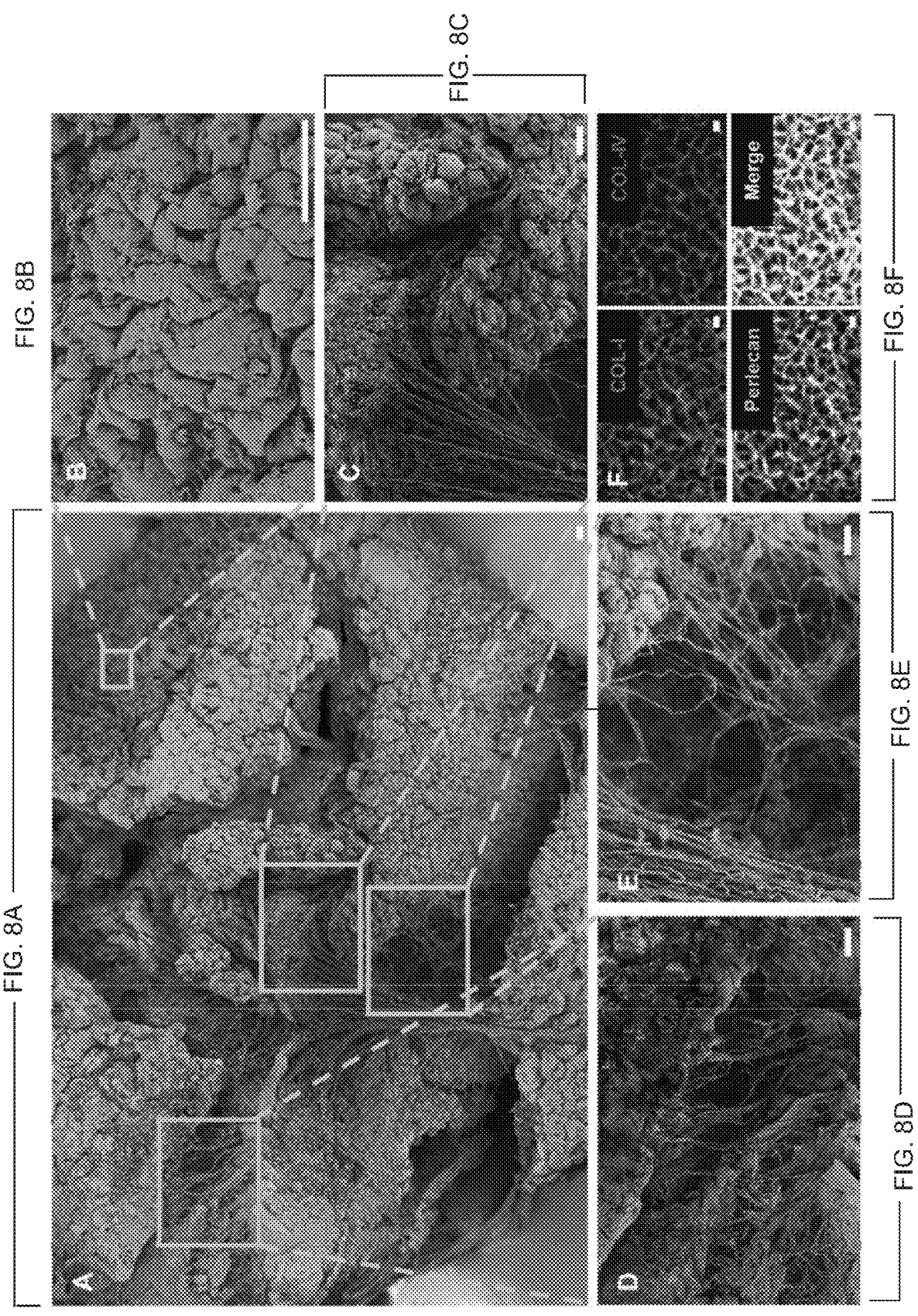

| Topography | Nanofibers | Sponges | Hydrogels | Hydrogel-Nanofiber composites | Decellularized Salivary gland ECM |
|---|---|---|---|---|---|
| | | | Image not available | Image not available | |
| Pore size | ~1 μm | 100-250 μm | ~ 10 nm | < 1 μm | ~30 μm |
| Insoluble backbone | Too much | Too much | Too little | Yes | Yes |
| Soluble gel | Yes | Yes | Yes | Yes | Yes |
| Cell anchorage points | Too many | Too many | Too few | Too few/ Too many | Yes |
| Stiffness | ~ MPa-GPa | ~ 1-30 kPa | ~0.5-30kPa | ~kPa-MPa | ~120 Pa |

FIG. 9

2.5D Nanofibers

2.5D Nanofibers

3D Fibrous Sponges

3D Fibrous Sponges

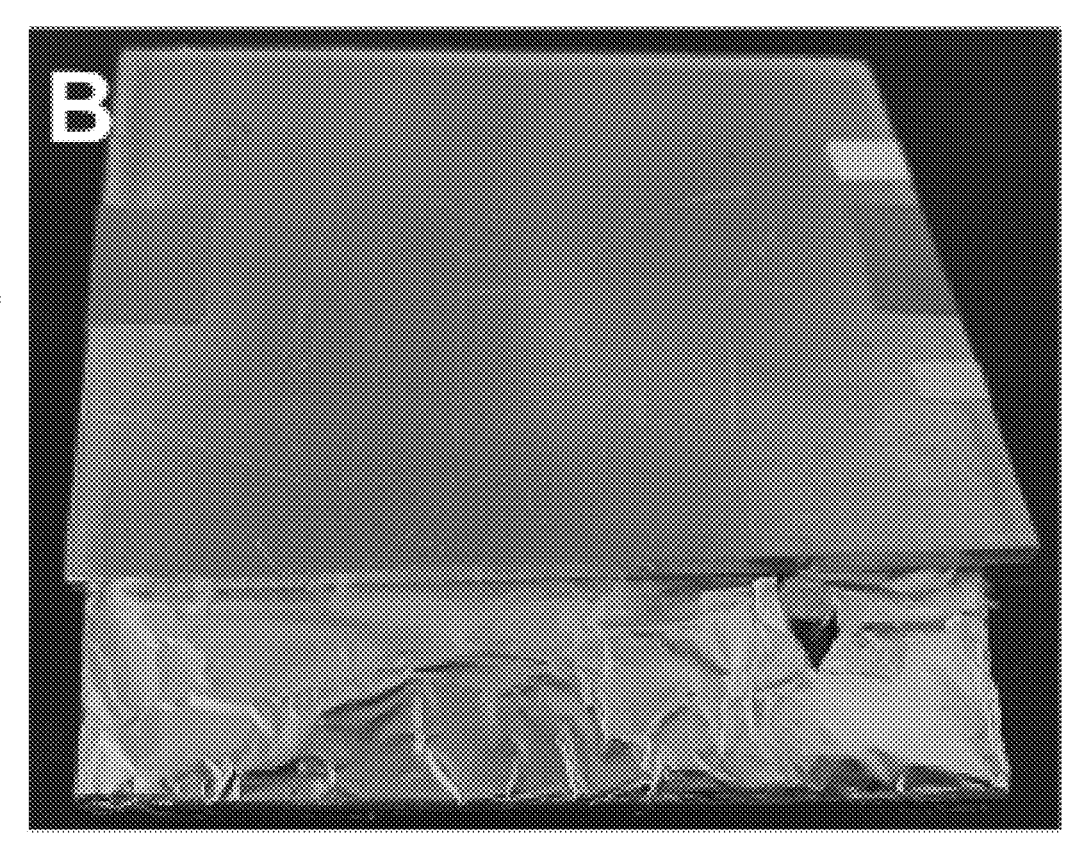
FIG. 14B

E

C

D

A

NF

CES-H

CES-F

FIG. 17A

Side view

NF

CES-H

CES-F

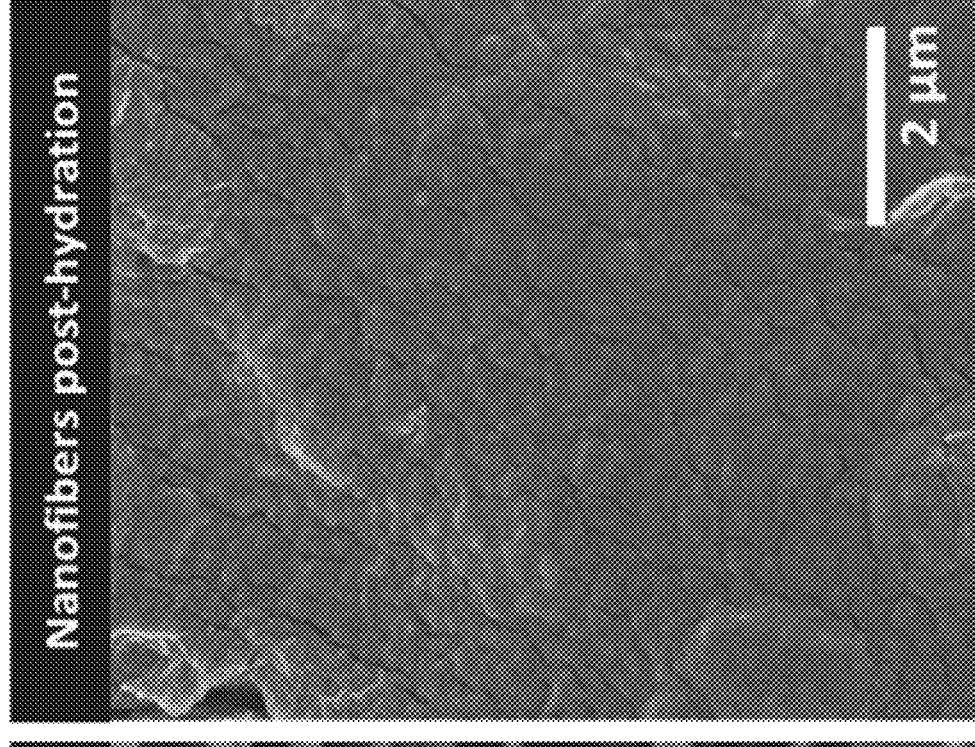
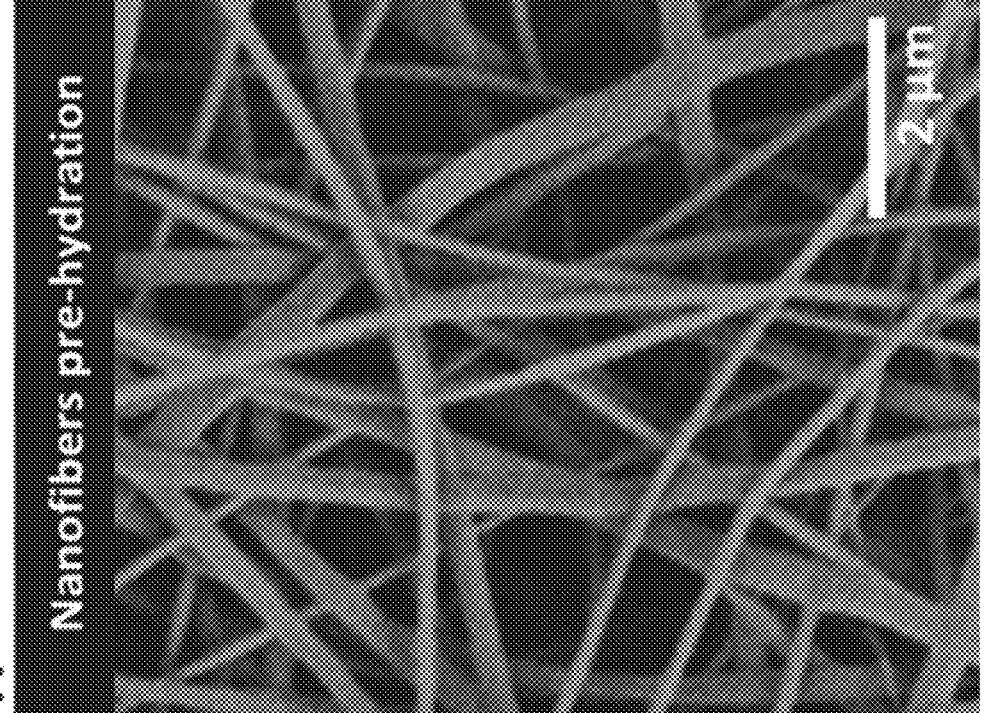
FIG. 18A

B

A
NF
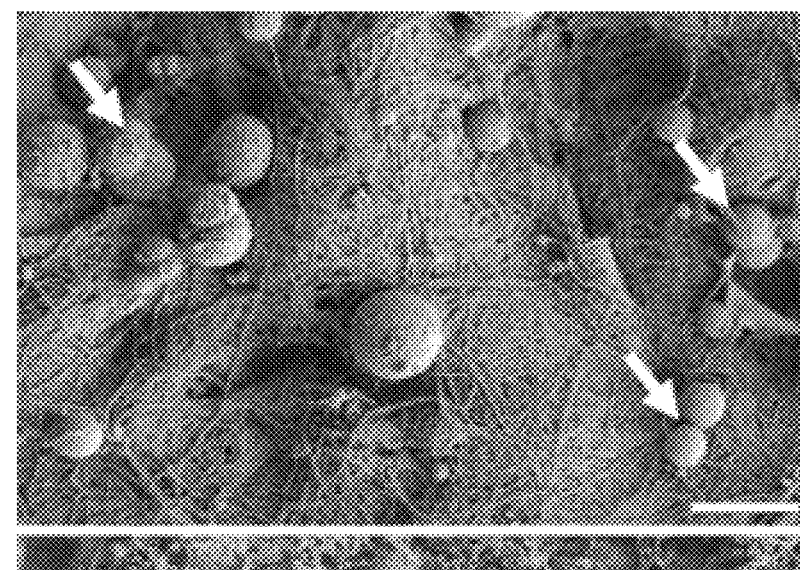
CES-H
CES-F
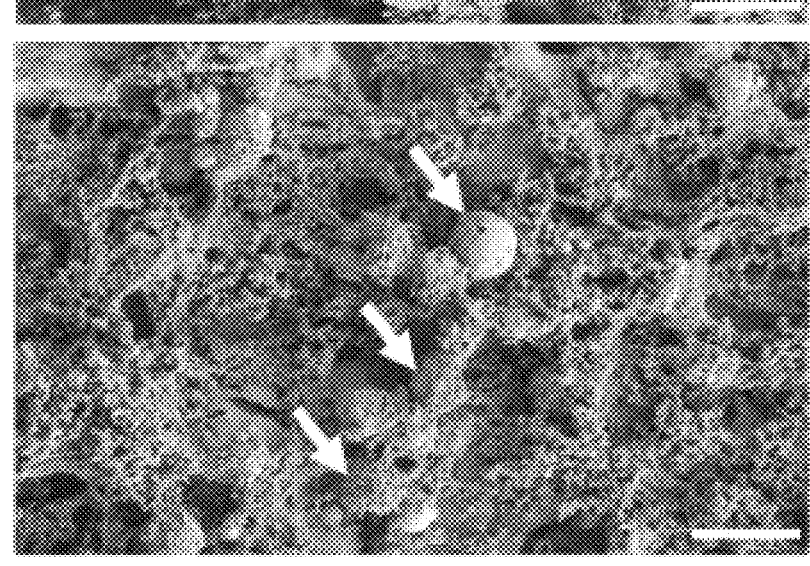
FIG. 20A

FIG. 27

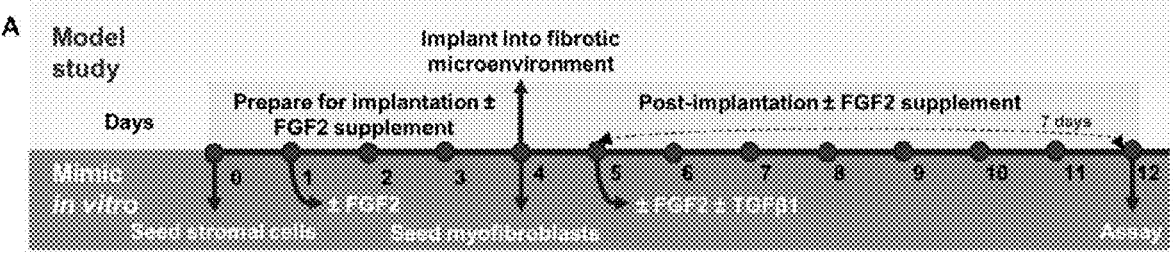
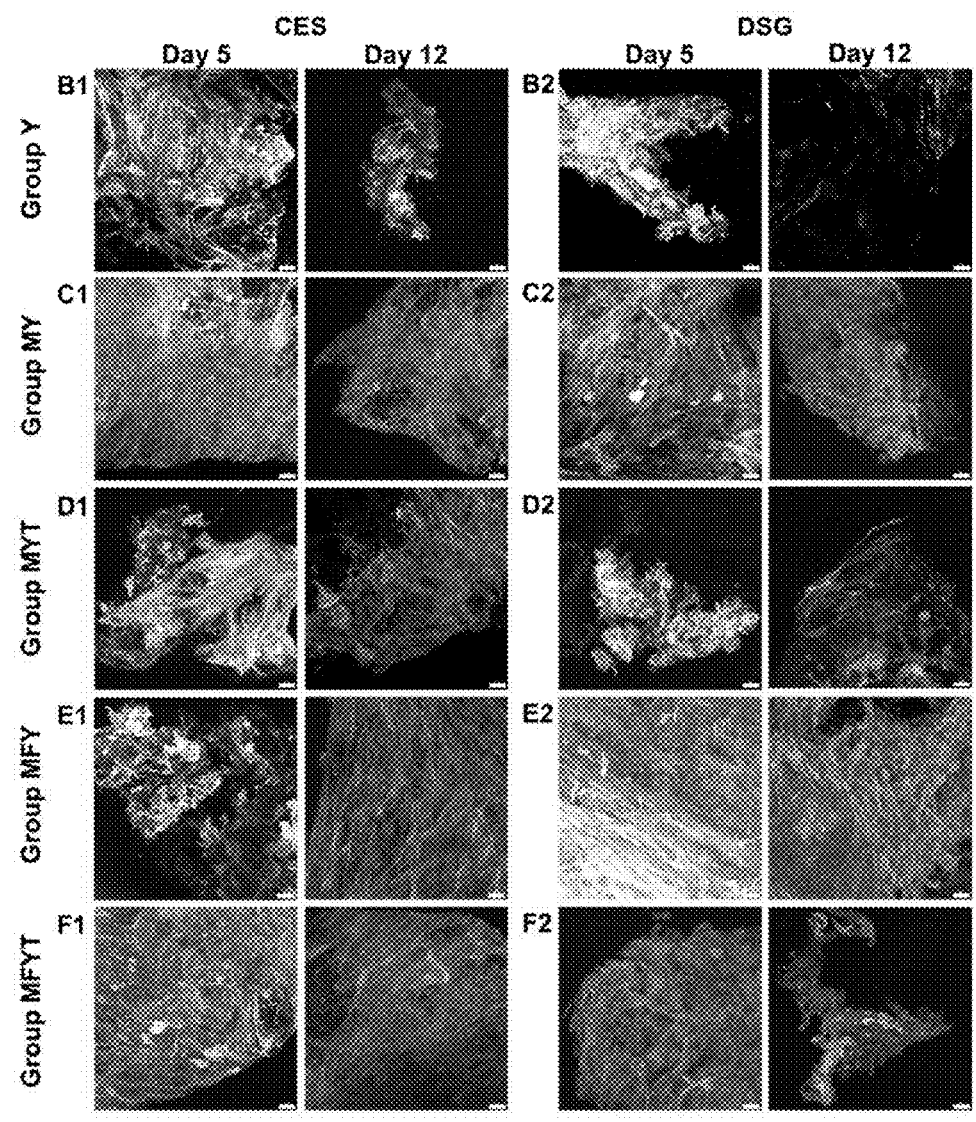
FIG. 28

Overall Trichrome Average between Conditions in Resection Model

*** P < 0.001, P < 0.0001  two-way ANOVA with Bonferroni post-test

COMPOSITIONS, APPARATUSES AND METHODS FOR MAKING AND USING BIOSCAFFOLDS

CROSS-REFERENCE TO RELATED APPLICATIONS

The present application is a continuation-in-part application of U.S. patent application Ser. No. 17/558,543, which was filed on Dec. 21, 2021, and claims the benefit of prior-filed U.S. Provisional Application Ser. No. 63/128,561, that was filed on Dec. 21, 2020, the disclosure of both these applications is hereby incorporated by reference.

GOVERNMENT INTERESTS

This invention was made with government support under grant nos. DE022467 and DE027953 awarded by the National Institutes of Health. The government has certain rights in the invention.

FIELD OF THE INVENTION

The present disclosure generally relates to cryoelectrospinning methods, procedures, apparatuses, and compositions suitable for use in bioengineering one or more three-dimensional porous matrices, and/or compositions suitable for fabricating bioscaffold structures with tuned qualities and/or preselected characteristics. In embodiments, the present disclosure relates to one or more compositions having preselected characteristics such as those that mimic decellularized extracellular matrix.

BACKGROUND

Traditional electrospinning produces scaffolds that vary tremendously, are difficult to reproduce, and have a limited range of physiochemical and mechanical properties. The lack of robust scaffold formation results in deficient scaffold characteristics such as undesirable viscoelasticity, porosity, and three-dimensional shapes, which inhibit or reduce the adhesion, growth, homeostasis, infiltration, and function of various cell types subsequently disposed thereon, as well as the maturation of cell types subsequently seeded thereon into specific tissue lineages. The inventors have found this especially true for scaffolds designed to mimic stromal extracellular matrix (ECM) in soft tissue.

Moreover, the inventors have observed problems relating to scaffold variation are compounded by the need to produce a large number of scaffolds which may be suitable for a specific biological purpose or function. For example, where numerous scaffolds are needed, it is difficult to control the uniformity of a batch of bioscaffolds depending upon process needs.

Prior art of interest includes U.S. Patent Publication No. 2019/0142998 entitled Scaffolds fabricated from electrospun decellularized extracellular matrix to Machluf et al. (herein incorporated entirely by reference). However, the process sequences and solvent selection of this disclosure are different than the present disclosure.

Prior art of interest also includes U.S. Patent Publication No. 20100190254 entitled Three-Dimensional Porous Hybrid Scaffold and Manufacture Thereof to Chian et al. (herein incorporated entirely by reference). However, this reference is deficient in that it does not describe the aqueous process solution of the present disclosure and cryoelectrospinning in accordance with the present disclosure.

Thus, there is a continuing need to develop methods for fabricating one or more electrospun scaffolds that overcomes these limitations, including methods of mass producing substantially similar scaffolds. Further, there is a desire for robust replication of substantially similar scaffolds with preselected viscoelasticity, porosity, and three-dimensional shapes for promoting adhesion, growth, homeostasis, infiltration, and function of various cell types subsequently seeded thereon, as well as the maturation of cell types subsequently seeded thereon into specific tissue lineages.

SUMMARY

In some embodiments, the present disclosure relates to a method of generating one or more scaffolds such as bioscaffolds, as well as scaffold compositions of the present disclosure. For example, in embodiments, a method for generating a scaffold includes mixing a hydrogel material and/or an extracellular matrix (ECM) protein in an aqueous solvent to generate an aqueous process solution; and cryoelectrospinning the aqueous process solution onto a plurality of conductive probes extending from a conductive surface of a collector plate disposed within a process chamber under conditions sufficient to generate one or more scaffolds configured to mimic a preselected soft tissue decellularized extracellular matrix. In some embodiments, the one or more scaffolds configured to mimic a preselected soft tissue decellularized extracellular matrix have a preselected pore structure, and/or a preselected viscoelasticity.

In some embodiments, the present disclosure relates to a method of making a biologically active three-dimensional scaffold capable of supporting growth, maintenance or differentiation of a cell, the method including: cryoelectrospinning an aqueous process solution including a hydrogel material and/or an extracellular matrix protein, and an aqueous solvent onto a plurality of conductive probes extending from a conductive surface of a collector plate disposed within a process chamber under conditions sufficient to generate one or more scaffolds configured to mimic a preselected soft tissue decellularized extracellular matrix; and lyophilizing and/or optionally crosslinking the one or more scaffolds configured to mimic a preselected soft tissue decellularized extracellular matrix such that the one or more scaffolds include a preselected three-dimensional shape, and/or a preselected viscoelasticity.

In some embodiments, the present disclosure relates to a three-dimensional scaffold made by the methods of the present disclosure, including a biologically active three-dimensional scaffold made by the methods of the present disclosure.

In some embodiments, the present disclosure relates to engineered tissue made by contacting a biologically active three-dimensional scaffold of the present disclosure with cells in vivo or in vitro under conditions effective to allow interaction between the biologically active three-dimensional scaffold and the cells.

In some embodiments, the present disclosure relates to a method of using the engineered scaffold of the present disclosure for tissue repair or tissue regeneration, including administering an engineered scaffold of the present disclosure to a mammal in need of tissue repair or tissue regeneration. In embodiments, the engineered scaffold is administered locally in an effective amount or in a therapeutically effective amount. In some embodiments, the present disclosure relates to a method of using the engineered tissue of the present disclosure for tissue repair or tissue regeneration, including administering an engineered tissue of the present disclosure to a mammal in need of tissue repair or tissue regeneration.

In some embodiments, the present disclosure includes a method of making a biologically active three-dimensional scaffold capable of supporting growth, maintenance or differentiation of a cell, the method including: cryoelectrospinning an aqueous process solution including a hydrogel material and/or an extracellular matrix (ECM) protein, and an aqueous solvent onto a plurality of conductive probes extending from a conductive surface of a collector plate disposed within a process chamber under conditions sufficient to generate one or more scaffolds configured to mimic a preselected soft tissue decellularized extracellular matrix. In embodiments, the process sequence further includes lyophilizing and optionally crosslinking the one or more scaffolds configured to mimic a preselected soft tissue decellularized extracellular matrix such that the one or more scaffolds include a preselected three-dimensional topography, and/or a preselected viscoelasticity.

In some embodiments, the present disclosure includes a cryoelectrospun scaffold that contains alginate material that mimics decellularized ECM. In some embodiments, the present disclosure includes a cryoelectrospun scaffold that contains elastin material that mimics decellularized ECM. In some embodiments, the present disclosure includes a scaffold, including: a cryoelectrospun alginate and elastin material that mimics decellularized ECM, wherein the alginate and elastin are cross-linked. In embodiments, the scaffold is characterized as lyophilized scaffold, and wherein the lyophilized scaffold includes 99.9 percent weight to 0.1 percent weight alginate, and 0.1 percent weight to 99.9 percent weight elastin, wherein the percent weight is the percent weight of the total lyophilized scaffold. In embodiments, the lyophilized scaffold includes 100 percent weight alginate and no elastin, wherein the percent weight is the percent weight of the total lyophilized scaffold, and in embodiments, the lyophilized scaffold includes 100 percent weight elastin and no alginate, wherein the percent weight is the percent weight of the total lyophilized scaffold. In embodiments, the lyophilized scaffold includes 60 percent weight to 40 percent weight alginate, and 40 percent weight to 60 percent weight elastin, wherein the percent weight is the percent weight of the total lyophilized scaffold. In embodiments, the lyophilized scaffold includes about 50 percent weight to about 50 percent weight alginate, wherein the percent weight is the percent weight of the total lyophilized scaffold. In embodiments, the lyophilized scaffold is further characterized as rehydrated, and/or includes one or more biodegradable or biocompatible polymers.

Embodiments of the present disclosure include scaffolds containing a plurality of stromal cells. Embodiments of the present disclosure include scaffolds containing a plurality of primary E16 mesenchyme cells. Embodiments of the present disclosure include scaffolds containing one or more growth factors and/or cytokines, such as fibroblast growth factor 2 (FGF2) protein. Embodiments of the present disclosure include scaffolds that provide an anti-fibrotic activity in vitro. Embodiments of the present disclosure include scaffolds that promote healthy stromal and non-fibrotic phenotype of stromal cells in vitro. Embodiments of the present disclosure include scaffolds that promote an anti-fibrotic activity of stromal cells in vitro. Embodiments of the present disclosure include scaffolds that reduce a fibrotic phenotype of myofibroblasts in vitro. Embodiments of the present disclosure include scaffolds that reduce fibrotic phenotype in vitro despite the presence of fibrotic stimulant TGFb1.

Embodiments of the present disclosure include scaffolds that provide an anti-fibrotic activity in vivo. Embodiments of the present disclosure include scaffolds that are viscoelastic and provide an anti-fibrotic activity in vivo.

In some embodiments, the present disclosure includes a method of treating a medical condition which may benefit from cell or scaffold transplantation in a subject in need thereof, including transplanting or administering any scaffold of the present disclosure into the subject such as a subject in need of treatment, thereby treating the medical condition. In embodiments, the scaffold has been pre-seeded with cells. In embodiments, the medical condition is one or more of degenerative disease, neurodegenerative disease, connective tissue degenerative disease, cardiovascular disease, fibrotic disorder, diabetes, COVID-19, pulmonary fibrosis, cardiovascular disease, salivary gland hypofunction, and combinations thereof. In embodiments, the scaffold of the present disclosure is administered in an effective amount, or therapeutically effective amount to a subject in need thereof.

The illustrative aspects of the present disclosure are designed to solve the problems herein described and/or other problems not discussed.

BRIEF DESCRIPTION OF THE DRAWINGS

The patent or application file contains at least one drawing executed in color. Copies of this patent or patent application publication with color drawing(s) will be provided by the Office upon request and payment of the necessary fee. These and other features of this disclosure will be more readily understood from the following detailed description of the various aspects of the disclosure taken in conjunction with the accompanying drawings that depict various embodiments of the disclosure, in which:

FIG. 1 depicts a process flow of an embodiment of the present disclosure.

FIG. 3A is a diagram schematically illustrating a side view of a collector plate 203 of the present disclosure.

FIG. 5 depicts a table with data relating to state-of-the-art fabricating cryoelectrospun scaffolds (CES).

FIG. 6 depicts a table and information relating to antibodies used for immunocytochemistry analysis suitable for use with embodiments of the present disclosure.

FIGS. 8A-8F depict salivary gland ECM topography analyses.

FIG. 9 depicts a comparison of physical and mechanical properties between current state-of-the-art soft-tissue scaffolds and decellularized salivary gland ECM.

FIGS. 14A-14J depict effects of collector plate geometry on scaffold growth in X, Y, Z dimensions.

FIGS. 17A-17D depict effects of scaffold properties on morphology, 3D organization, and marker expression of NIH 3T3 fibroblasts.

FIGS. 18A-18B depict conventionally electrospun nanofiber (NF) mats for cell growth.

FIGS. 20A-20D depict effects of scaffold properties on morphology and 3D organization of SIMS epithelial cells.

FIGS. 27A-27I depicts data related to FGF2 supplementation in various cultures.

Figure 2:
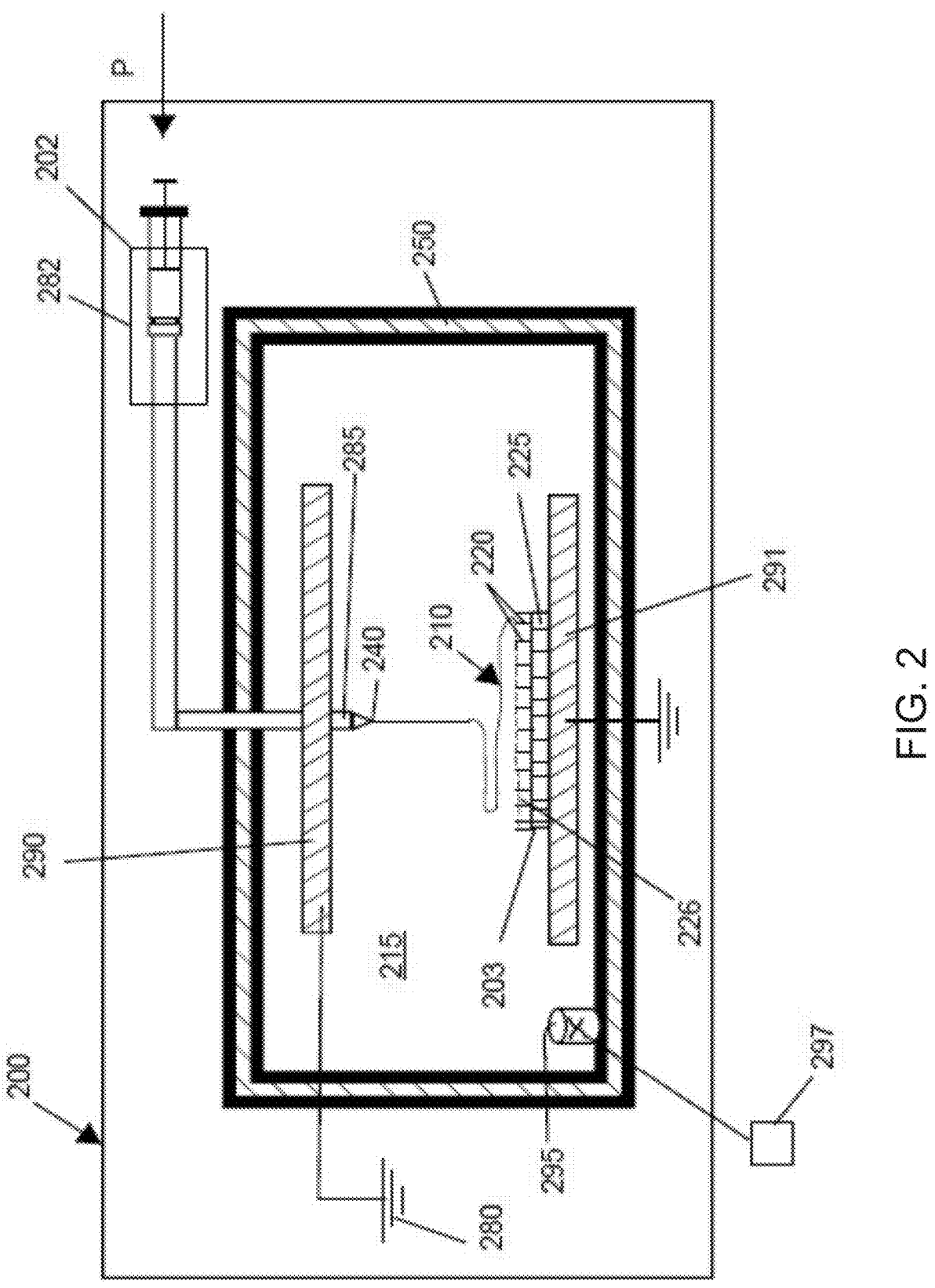
FIG. 2 is a diagram schematically illustrating a side view of a cryoelectrospinning device 200 and collector plate 203 of the present disclosure.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION

The present disclosure relates to methods, apparatuses, and compositions for cryoelectrospinning and/or bioengineering one or more three-dimensional porous matrices suitable for use as bioscaffolds. For example, in embodiments, a method of generating a scaffold, includes: mixing a hydrogel material and/or an extracellular matrix protein in an aqueous solvent to generate an aqueous process solution; and cryoelectrospinning the aqueous process solution onto a plurality of conductive probes extending from a conductive surface of a collector plate disposed within a process chamber under conditions sufficient to generate one or more scaffolds configured to mimic a preselected soft tissue decellularized extracellular matrix. In some embodiments, the present disclosure relates to compositions suitable for fabricating bioscaffold structures with tuned qualities or preselected characteristics. In embodiments, the present disclosure includes bioscaffold compositions, and bioscaffold compositions made by the processes of the present disclosure.

The apparatuses, methods and compositions of the present disclosure advantageously provide one or more bioscaffolds with desirable or preselected viscoelasticity, porosity, and/or three-dimensional shape to promote or enhance adhesion, growth, homeostasis, infiltration, and function of various cell types subsequently disposed or seeded thereon, as well as promote and/or enhance the maturation of cell types subsequently disposed thereon into specific tissue lineages. Further, the apparatuses, methods and compositions of the present disclosure advantageously provide a plurality of substantially similar bioscaffolds with desirable or preselected viscoelasticity, porosity, and/or three-dimensional shape to promote or enhance adhesion, growth, homeostasis, infiltration, and function of various cell types subsequently disposed or seeded thereon.

DEFINITIONS

As used herein, the singular forms "a", "an", and "the" include plural references unless the context clearly dictates otherwise. Thus, for example, references to "a composition" include the use of one or more compositions. "A step" of a method means at least one step, and it could be one, two, three, four, five or even more method steps.

The term "about", as used herein, refers to +/−10% of the stated value or a chemical or obvious equivalent thereof.

As used herein the term "alginate" refers to an alginic acid or a salt of alginic acid such as sodium, calcium, barium, or strontium salt of alginic acid. In some embodiments, the term includes but is not limited to algin, alginic acid, alginate acid, alginic acid sodium salt, sodium alginate, etc.

As used herein the term "alginic acid" or "algin" refers to an insoluble gelatinous carbohydrate in many brown seaweeds. In embodiments, alginic acid includes D-mannuronic acid and L-guluronic acid connected with alpha 1, 4 bonds. In embodiments, alginic acid refers to an insoluble colloidal acid, $(C_6H_8O_6)_n$, found in the cell walls of various kelps.

As used herein the term "cryoelectrospinning" refers to a process in which fibers are formed from a solution or melt by streaming an electrically charged solution or melt through a hole across a potential gradient under conditions where ice crystals are present in the formed fibers. In some embodiments, the term includes but is not limited to cryoelectrospinning, cryo electro-spinning, cryogenic electrospinning, low temperature electrospinning, low-temperature electrospinning, cold electrospinning, ice electrospinning, dry ice electrospinning, etc.

As used herein the term "cryoelectrospun material" is any molecule or substance that forms a structure or group of structures (such as fibers, sponges, webs, or droplets), as a result of the cryoelectrospinning process. This material may be natural, synthetic, or a combination of such and may initially have ice crystals therein.

As used herein the term "elastin" refers to a polypeptide or protein of the extracellular matrix, or a polypeptide that mimics elastin. For example, a highly elastic protein present in connective tissue allowing tissue in the body to resume an initial shape after stretching or contracting. In some embodiments, elastin refers to a protein encoded by the ELN gene.

As used herein, the term "effective amount" refers to that amount of a substance that is necessary or sufficient to bring about a desired biologic effect. An effective amount can but need not be limited to an amount administered in a single administration.

As used herein the term "honeycomb-like" refers to something that resembles the structure or appearance of a honeycomb such as an open-cell grid structure.

As used herein the term "polymer" refers to any natural or synthetic molecule which can form long molecular chains, such as polyolefin, polyamides, polyesters, polyurethanes, polypeptides, polysaccharides, and combinations thereof. In particular, the polymer can include alginate, polyethylene glycol, elastin, chitosan, or any combination of these.

As used herein the term "polyethylene glycol" refers to a polyether compound commonly expressed as H—(O—CH$_2$—CH$_2$)$_n$—OH. In embodiments, polyethylene glycol may refer to polyethylene oxide (PEO) or polyoxyethylene (POE), depending on its molecular weight.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

As used herein, "percent" of a solution refers to the weight/volume % (wt/vol % or w/v %). In embodiments, the percentage concentration is calculated as the fraction of the weight of the solute related to the total volume of the solution.

As used herein the term "pharmaceutically acceptable" substances refers to those substances which are within the scope of sound medical judgment suitable for use in contact with the tissues of subjects without undue toxicity, irritation, allergic response, and the like, and effective for their intended use. In embodiments, cryoelectrospun material of the present disclosure is characterized as pharmaceutically acceptable.

As used herein the term "pharmaceutical composition" refers to the combination of one or more substances such as e.g., one or more cryoelectrospun materials in accordance with the present disclosure and one or more excipients and one or more pharmaceutically acceptable vehicles with which the one or more peptides in accordance with the present disclosure is administered to a subject.

As used herein, stromal cells include, but are not limited to: mesenchymal stromal cells, mesenchymal stem cells (MSCs), primary stromal cells, primary fibroblasts, embryonic stem cell (ESC)-derived stromal cells or fibroblasts, induced pluripotent stem cell (iPSC)-derived stromal cells or fibroblasts, adult stromal cells, adult mesenchymal cells, embryonic stromal cells, embryonic mesenchymal cells, progenitor stromal/fibroblast cells, stromal and fibroblast cell lines.

As used herein, the term "subject" refers to a human or non-human vertebrate. Non-human vertebrates include livestock animals, companion animals, and laboratory animals.

The term "substantially purified," as used herein, refers to a component of interest that may be substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1 (by dry weight) of contaminating components. Thus, a "substantially purified" component of interest may have a purity level of about 70%, about 75%, about 80%, about 85%, about 90%, about 95%, about 96%, about 97%, about 98%, about 99% or greater. In embodiments, cryoelectrospun material of the present disclosure is characterized as substantially purified.

As used herein, the term "treat" as used in reference to a disease or condition shall mean to intervene in such disease or condition so as to prevent or slow the development of, prevent, slow, or halt the progression of, or eliminate the disease or condition.

The term "therapeutically effective amount" as used herein refers to an amount of an agent sufficient to achieve, in a single or multiple doses, the intended purpose of treatment. A "therapeutically effective amount" can vary depending, for example, on the compound, the severity of the disease, the age of the subject to be treated, comorbidities of the subject to be treated, existing health conditions of the subject, and/or the weight of the subject to be treated. A "therapeutically effective amount" is an amount sufficient to alter the subjects' natural state.

The term "treatment" as used herein refers to alleviation of one or more symptoms or features associated with the presence of the particular condition or suspected condition being treated. Treatment does not necessarily mean complete cure or remission, nor does it preclude recurrence or relapses. Treatment can be effected over a short term, over a medium term, or can be a long-term treatment, such as, within the context of a maintenance therapy. Treatment can be continuous or intermittent.

ABBREVIATIONS USED HEREIN INCLUDE

α-SMA, α-smooth muscle actin;
CES, elastin-alginate cryoelectrospun scaffolds;
CES-F, elastin-alginate cryoelectrospun scaffolds with fibrous topography;
CES-H, elastin-alginate cryoelectrospun scaffolds with honeycomb topography;
D-SG, decellularized adult salivary gland matrix;
E16, embryonic day 16;
ECM, extracellular matrix;
FS, elastin-alginate freeze-dried sponges;
GAG, glycosaminoglycan;
HFIP, hexafluoroisopropanol;
MSC, mesenchymal stromal cells;
NF, traditionally electrospun elastin-alginate nanofiber;
PCL, poly(ε-caprolactone); P
EG, poly(ethylene glycol);
PEO, poly(ethylene oxide);
PEU, polyester-urethane;
PF, pyridinium formiate;
PLA, poly(D,L-lactide);
PLGA, poly(lactic acid-co-glycolic acid);
SEM, scanning electron microscopy.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

DETAILED DESCRIPTION OF CERTAIN EMBODIMENTS

In embodiments, the present disclosure relates to methods, apparatuses, and compositions for cryoelectrospinning and/or bioengineering one or more three-dimensional porous matrices suitable for use as bioscaffold material. In embodiments, a method of generating a scaffold of the present disclosure, includes mixing a hydrogel material and/or an extracellular matrix protein in an aqueous solvent; generating an aqueous process solution; and cryoelectrospinning the aqueous process solution onto a substrate. In embodiments, the substrate includes a plurality of probes such as conductive probes extending from a conductive surface of a collector plate disposed within a process chamber. In embodiments, the process chamber includes an inner reaction area maintained under predetermined conditions. For example, in embodiments, the process chamber has an inner reaction area under conditions sufficient to generate one or more scaffolds or the present disclosure. In embodiments, the scaffolds of the present disclosure are formed or configured to mimic a preselected soft tissue such as soft tissue decellularized extracellular matrix. In some embodiments, the present disclosure relates to compositions suitable for fabricating bioscaffold structures with tuned qualities or preselected characteristics. Non-limiting examples of preselected tuned characteristics include a preselected viscoelasticity, a preselected porosity, and/or a preselected three-dimensional shape to promote or enhance adhesion, growth, homeostasis, infiltration, and function of various cell types subsequently disposed or seeded thereon. Moreover, in embodiments, preselected tuned characteristics promote and/or enhance the maturation of cell types subsequently disposed within or upon the bioscaffold structure(s) into specific tissue lineage(s). Further, the apparatuses, methods and compositions of the present disclosure advantageously provide a plurality of substantially similar bioscaffolds with desirable or preselected viscoelasticity, porosity, and/or three-dimensional shape to promote or enhance adhesion, growth, homeostasis, infiltration, and function of various cell types subsequently disposed or seeded thereon.

FIG. 1 depicts a flow diagram illustrating a process 100 for generating one or more scaffolds in accordance with the present disclosure. In embodiments, process 100 includes at process sequence 102 mixing a hydrogel material and/or an extracellular matrix (ECM) protein in an aqueous solvent to generate an aqueous process solution. In embodiments, hydrogel material is provided in an amount sufficient to form one or more scaffolds in accordance with the present disclosure. Non-limiting examples of hydrogel material suitable for use herein includes one or more of alginate, chitosan, and combinations thereof. In embodiments, extracellular matrix (ECM) protein is provided in an amount sufficient to form one or more scaffolds in accordance with the present disclosure. Non-limiting examples of extracellular matrix (ECM) protein includes one or more of elastin, collagen, or combinations thereof. In some embodiments, elastin refers to a polypeptide or protein of the extracellular matrix, or a polypeptide that mimics elastin. Non-limiting examples of one or more polypeptides that mimic elastin are described in Despanie J, Dhandhukia J P, Hamm-Alvarez S F, MacKay J A. *Elastin-like polypeptides: Therapeutic applications for an emerging class of nanomedicines. J Control Release.* 2016; 240:93-108. doi:10.1016/j.jconrel.2015.11.010 (herein entirely incorporated by reference). See e.g., the section entitled "Elastin-like Polypeptides" in this reference. In some embodiments, the aqueous solvent is water, deionized water, or water with ions. In embodiments, the aqueous solvent makes up the balance of the aqueous process solution. For example, the remaining percent weight of the total solution may be water. In embodiments, the aqueous process solution is formulated to include about 89-99% water.

In embodiments, one or more polymers may optionally be provided in an amount sufficient to form one or more scaffolds in accordance with the present disclosure. Non-limiting examples of polymer includes polyethylene oxide, or polyethylene oxide-400 kD (having a molecular weight of 400 kD or about 400 kD). In some embodiments, the aqueous process solution is formulated to include 0.05 to about 3.0 wt/vol % elastin, 0.05 to about 3.0 wt/vol % alginate and 1-5 wt/vol % polyethylene oxide, such as polyethylene oxide-400 kD. In some embodiments, the aqueous process solution includes about 1 wt/vol % elastin, 1.5 wt/vol % alginate, and about 3 wt/vol % polyethylene oxide-400 kD. In some embodiments, the aqueous process solution is formulated to include 0.05 to about 3 wt/vol % collagen, 0.05 to about 3 wt/vol % chitosan and 1-5 wt/vol % polyethylene oxide-400 kD. In some embodiments, the aqueous process solution includes about 0.4 wt/vol % collagen, 0.4 wt/vol % chitosan, and about 3 wt/vol % polyethylene oxide-400 kD. In embodiments, the aqueous process solution includes one or more additional polymers.

Still referring to FIG. 1, process 100 includes a process sequence 104 cryoelectrospinning the aqueous process solution onto a plurality of conductive probes extending from a surface, such as a conductive surface of a collector plate, disposed within a process chamber under conditions sufficient to generate one or more scaffolds configured to mimic a preselected soft tissue such as soft tissue decellularized extracellular matrix. In some embodiments, the one or more scaffolds configured to mimic a preselected soft tissue decellularized extracellular matrix include a preselected pore structure, and/or a preselected viscoelasticity. An apparatus suitable for cryoelectrospinning in accordance with process sequence 104 is shown in FIG. 2.

Referring to FIG. 2, in embodiments, a cryoelectrospinning apparatus 200 may include a high voltage source 280, a pump 282, the pump 282 including a device 202 such as a syringe that contains an aqueous process solution of the present disclosure and configured for transporting aqueous process solution towards the tip 240 of a needle, the needle positioned in a spinneret 285. In embodiments, an electrical field may be formed in a region between a high voltage probe 290 and a lower plate 291. For example, an electric field may be formed from the tip 240 to the lower plate 291 resulting in an extrusion ability of the aqueous process solution at the tip 240 of the needle towards the surface of collection plate 203. The electrical field created, causes the aqueous process solution of the present disclosure to overcome the cohesive forces that hold the aqueous process solution together. As a result of cohesive force compensation by the electrical field, a jet will be drawn from the aqueous process solution droplet, which forms one or more fibers finally collected at the collection plate 203. In some embodiments, a syringe needle including tip 240 is electrically charged by applying a high voltage in the range of 5 kV to 30 kV produced by a power supply. In embodiments, the collector plate 203 is a grounded conductive material. In some embodiments, collected fibers may be randomly oriented on the collector plate 203.

In some embodiments, the cryoelectrospinning apparatus 200 is configured for collecting fiber(s) 210 in a process volume 215 atop or directly atop one or more conductive probes 220 extended from a conductive structure 225, where a network of fiber(s) 210 may appear as a mesh. In some embodiments, uncompressed fiber(s) such as fiber(s) 210 are formed such that the resulting structure is highly porous (e.g., has a pore diameter of about 2 μm or more). In an embodiment, the density of fiber(s) 210 is low enough for cells to disperse into a mesh thereof (e.g., density of about 30-1000 kg/m³), but mechanically stable enough to support tissue culture. In some embodiments, a mesh of fiber(s) 210 can be used as a scaffold or container for materials such as cell culture, cell delivery, and/or drug delivery. In another embodiment, a mesh of fiber(s) 210 can be used as a filter, sponge, or a substrate that can include molecules of interest.

Still referring to FIG. 2, in some embodiments, the cryoelectrospinning apparatus 200 includes a device 202 (e.g., syringe) and a collector plate 203 disposed opposite the device 202 in a process chamber 250. In some embodiments, device 202 is positioned adjacent to (e.g., facing the collection plate 203) the collection plate 203 so that fiber(s) 210 can be drawn out of a tip 240 of the device (e.g., tip of the syringe) or other device across a process volume 215 (e.g., distance of cms to 10 s of cms) between the tip 240 and the collection plate 203 and toward the collection plate 203 based on a potential difference between the tip 240 and the collection plate 203. In an embodiment, two or more devices can feed fiber to the collection structure from different positions to produce a blend of fibers in the mesh. In embodiments, the fiber(s) 210 may include polymers as described herein such as polyethylene oxide, or polyethylene oxide having a molecular weight of 400 kD. In an embodiment, the fiber(s) 210 can be a nanofiber and can have a diameter of about 1 to 10000 nm. In embodiments, an electric field (e.g., about 0.3 kV/cm to 2 kV/cm) is produced between the device 202 and the collection plate 203 using appropriate electronic systems. In embodiments, a potential difference between the tip 240 and the collection plate 203 (e.g., including one or more conductive probes 220) is about 5 kV to 30 kV or about 20 kV, while the distance between the tip 240 and the collection plate is about 5 cm to 30 cm. In embodiments, the potential difference can vary depending on the various distances and dimensions as well as polymers used to make the fiber.

Still referring to FIG. 2, in some embodiments, the cryoelectrospinning apparatus 200 may include a device 202 that feeds one or more fiber(s) 210 towards a collection plate 203. In embodiments, the device 202 includes a tip 240 (e.g., tip of a syringe) that is adjacent the collection plate 203 including a plurality of conductive probes 220 extending from a conductive structure 225 of a collector plate 203 disposed within process volume 215 of process chamber 250. In some embodiments, cryoelectrospinning apparatus 200 is configured to produce one or more scaffolds that mimic a preselected soft tissue decellularized extracellular matrix, wherein the one or more scaffolds are formed directly atop the plurality of conductive probes 220 extending from a conductive structure 225 of a collector plate 203 disposed within process volume 215 of process chamber 250.

In some embodiments, process volume 215 is disposed within and/or formed from a thermally insulated process chamber such as process chamber 250. In embodiments, the walls of the process chamber 250 are formed of thermally insulating material and configured to maintain the process volume 215 at a preselected temperature. For example, in embodiments, the process volume 215 may be maintained or controlled to a low temperature of −10° C. to 10° C. (air temperature) and/or 0° C. to minus 35° C. (collector plate temperature) depending upon process needs. In some embodiments, the collector plate may be maintained or controlled to a low temperature such as 0° C. to minus 35° C., or 0° C. to minus 30° C. in order to tune characteristics of the one or more scaffolds that mimic a preselected soft tissue decellularized extracellular matrix, such as a preselected pore structure, and/or a preselected viscoelasticity. In embodiments, the process volume 215 has a preselected humidity such as relative humidity levels greater than 35% such as between 40% and 99%.

In some embodiments, a reservoir 295 is disposed with the process volume 215. Water or an aqueous solution may be disposed with the reservoir 295 in a manner and amount sufficient to alter the humidity of the process volume 215 depending upon process needs. In embodiments, a controller 297 may be connected to the reservoir 295 in order to alter the humidity of the process volume 215 to a preselected humidity depending upon process needs.

Referring to FIG. 3A, a cross-sectional view of collector plate 203 is shown including a plurality of conductive probes 220, where the distal ends of the plurality of conductive probes 220 extend from the conductive structure 225. In embodiments, each conductive probe 226, of the plurality of conductive probes 220, has a distal end 228 extending out of the conductive structure 225 on the side closest the tip 240 (not shown in FIG. 3A) and ends to a top surface 229 of the conductive probe 226. In embodiments, a portion of each probe 226 extends a distance (as shown by arrow 231) from the surface of the conductive structure 225. In an embodiment, the distal ends of the probes 226 can be considered as two or more sets of distal ends, where each set, in embodiments, can include 1, 10, 100, 1000, 10,000 or more distal ends. In embodiments, a first set of the distal ends are planar (as shown by arrow 242), wherein a plurality of distal ends are equidistant or substantially equidistant from the conductive structure 225 and/or from each other. In embodiments, a plurality of distal ends collectively forms a plane (as shown by arrow 242), wherein the distal ends are positioned at preselected intervals or distances from each other.

Figure 3B:
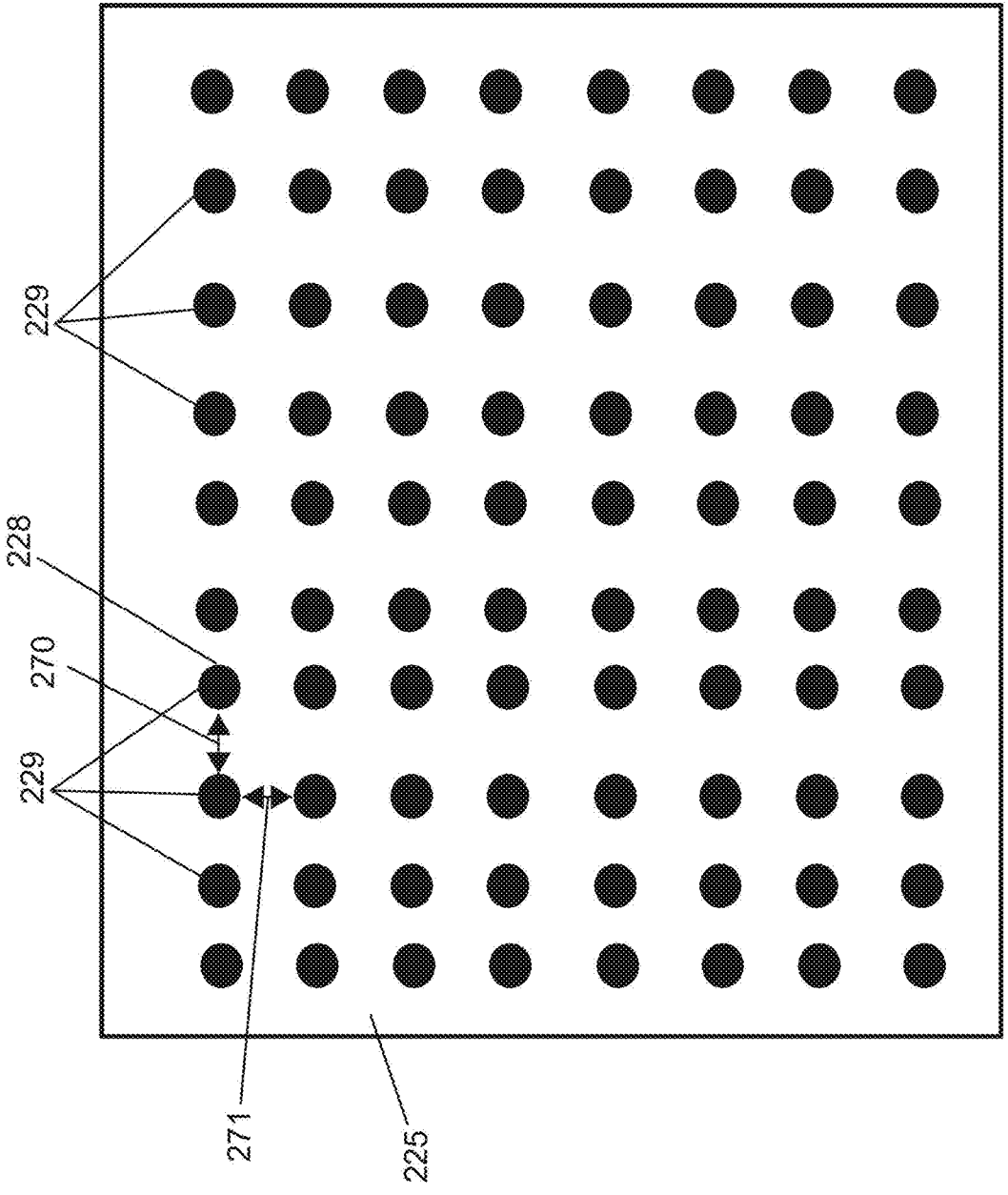
FIG. 3B is a diagram schematically illustrating a top-down view of a collector plate 203 of the present disclosure.

Referring to FIG. 3B a top-down view of collector plate 203 is shown including a plurality of conductive probes. In some embodiments, the top surface 229 of the distal ends of the conductive probes are positioned at a distance (shown by arrows 270 and 271) of at least 5 mm, about 5 mm, or 5 mm from each other. In embodiments, the top surface(s) 229 are configured to form a plurality of uncompressed fibrous mesh of, e.g., one or more scaffolds configured to mimic a preselected soft tissue decellularized extracellular matrix, directly atop top surface(s) 229. In embodiments, including a plurality of conductive probes 220, a plurality of substantially similar scaffolds configured to mimic a preselected soft tissue decellularized extracellular matrix may form directly atop a plurality of top surface(s) 229. In embodiments, a uniform batch of scaffolds is fabricated directly atop a plurality of top surface(s) 229.

In some embodiments, each conductive probe 226 can be set at the same potential relative to one another. In embodiments, the plurality of conductive probes 220 can include about 1.0 to 10, or about 4 to 9 probes per square cm of the conductive structure 225. In some embodiments, the distance between each probe (shown by arrows 270 and 271) or among the probes 226 (FIG. 3A) can be at least about 4.5, 5.0 mm, or 5.5 mm, such as about 5.0 mm, or 5 mm. In some embodiments, the distance (shown by arrow 231) (FIG. 3A) that each probe 226 extends from the surface of the conductive structure 225 can be the same or different, where the distance can be about 1.0 mm to 5 cm, 0.5 cm to 4 cm, or about 0.5 cm, or 0.5 cm, or about 0.4 cm, or 0.4 cm. In some embodiments, the probes 226 can have a diameter of about 100 μm to 0.3 cm or about 500 μm to 1 mm. In embodiments, the probe 226 can be made of or is coated with a conductive material such as steel, stainless steel, nickel, aluminum, precious metals (e.g., gold, silver, platinum, copper, and the like) or a combination thereof. In an embodiment, the probe 226 can be designed so that only a portion of the surface of the distal end of the probe 226 is conductive (e.g., only the tip of the probe), and the remaining surface is covered with a conductive material, although the probe 226 is conductive. In embodiments, the tips of the probes 226 are directed towards or into the process volume 215.

In some embodiments, the configuration of the distal ends top surface(s) 229 of the probes 226 forms an electric field that the fiber passes into, thus the electric field formed as a result of the configuration of the distal ends define at least a portion of or the entire process volume 215 which may direct fiber formation into the space on top of probes 226.

In embodiments, conductive structure 225 can vary depending upon the collection plate 203. In embodiments, the conductive structure 225 can be thin or thick (e.g., encompassing a large portion of the collection plate 203). The structure and the dimensions of the conductive structure 225 can vary upon the application. In embodiments, the conductive structure 225 is disposed atop or directly atop a thermally conductive, and optionally electrically conductive heat sink. In embodiments, the heat sink is configured to maintain the temperature of the collector plate. In some embodiments, the conductive structure 225 can be a thin material that separates the conductive structure 225 from a non-conductive surface underneath the conductive structure 225. In an embodiment, the conductive structure 225 can be a self-supported thin material where an open area (without any material) is behind the conductive structure 225. In embodiments, the conductive structure 225 can be made of a material such as steel, stainless steel, nickel, aluminum, precious metals (e.g., gold, silver, platinum, copper, and the like) and combinations thereof. Referring to FIG. 3A, the height (y-axis) of the conductive structure 225 can be about 0.1 to 1 cm or about 0.2 to 1.0 cm such as 0.3 cm. The length (x-axis) of the conductive structure 225 can be about 5 to 25 cm, about 5 to 15 cm, or about 10 to 15 cm. The width (z-axis) of the conductive structure 225 can be about 5 to 25 cm such as 10 to 15 cm. In embodiments, the thickness of the conductive structure 225 can be about 50 μm to 1.0 centimeters (e.g., about 0.2, about 0.3, about 0.4, or about 0.5 cm), and can be selected based on the design of the device. When the conductive structure 225 is flat, the thickness is about a nanometer to 1.0 centimeters (e.g., about 0.2, about 0.3, about 0.4, or about 0.5 cm) and can vary in the x-, y-, and/or z-direction.

Referring back to FIG. 1, process sequence 104 may include conditions sufficient to generate one or more scaffolds configured to mimic a preselected soft tissue such as soft tissue decellularized extracellular matrix, wherein the one or more scaffolds include a preselected pore structure, and/or a preselected viscoelasticity. In some embodiments, scaffolds with honeycomb topography can be fabricated in a thermally insulated chamber where the conditions of process volume 215 are controlled and/or preselected.

In some embodiments, an exemplary honeycomb-like structure of one or more scaffolds configured to mimic a preselected soft tissue decellularized extracellular matrix may include a body having a longitudinal axis and a length L and include a plurality of intersecting porous walls that form mutually adjoining cells or channels extending axially between opposing end faces. Cell density can be between 100,000 and 200,000 cells per cubic millimeter. As used herein, the term "honeycomb-like" is intended to include a generally honeycomb structure but is not strictly limited to a square, hexagonal, octagonal, triangular, rectangular or any other uniform cell shape. Typical pore sizes contained within the porous walls can be from 0.1 μm to about 100 μm, 1.0 μm to about 75 μm such as about 50-60 μm. In embodiments, pore size is measured as the longest diameter of a particular pore, such as by measuring a straight line passing from side to side of a pore through the center of the pore.

In embodiments, conditions sufficient to generate one or more scaffolds configured to mimic a preselected soft tissue decellularized extracellular matrix may include: relative humidity levels greater than 33% such as between 34% and 99%, or e.g., 35%, air temperature less than 2° C., and collector plate temperature is between 0° C. to minus 35° C., or between minus 10° C. and minus 30° C. In embodiments, relative humidity levels less than 40% or air temperature greater than 2° C. within process volume 215 are not selected or provided.

In some embodiments, the present disclosure relates to a method of generating a scaffold or a plurality of scaffolds, including: mixing a hydrogel material and/or an extracellular matrix (ECM) protein in an aqueous solvent to generate an aqueous process solution; and cryoelectrospinning the aqueous process solution onto a plurality of conductive probes extending from a conductive surface of a collector plate disposed within a process chamber under conditions sufficient to generate one or more scaffolds configured to mimic a preselected soft tissue decellularized extracellular matrix. In embodiments, the present disclosure includes a method of generating a scaffold or a plurality of scaffolds, including: mixing a hydrogel material and/or an extracellular matrix (ECM) protein and/or a polymer in an aqueous solvent to generate an aqueous process solution; and cryoelectrospinning the aqueous process solution onto a plurality of conductive probes extending from a conductive surface of a collector plate disposed within a process chamber under conditions sufficient to generate one or more scaffolds configured to mimic a preselected soft tissue decellularized extracellular matrix. Non-limiting examples of suitable polymers include those described in U.S. Patent Publication No. 20100190254, such as one or more biodegradable and/or biocompatible polymers. Non-limiting examples of suitable polymers for use herein include poly(urethanes), poly(siloxanes), poly(silicones), poly(ethylene), poly(vinyl pyrrolidone), poly(2-hydroxy ethyl methacrylate), poly(N-vinyl pyrrolidone), poly(methyl methacrylate), poly(vinyl alcohol) (PVA), poly(acrylic acid), poly(vinyl acetate), poly-acrylamide, poly(ethylene-co-vinyl acetate), poly(ethylene glycol), poly(methacrylic acid), polylactic acid (PLA), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate), polyvinylhydroxide, poly(ethylene oxide) (PEO) and polyorthoesters, and combinations thereof. In embodiments, the plurality of conductive probes each include a distal end, and the one or more scaffolds configured to mimic a preselected soft tissue decellularized extracellular matrix are generated directly atop at least one distal end or a plurality of distal ends. In some embodiments, the plurality of conductive probes include at least two conductive probes, wherein the at least two conductive probes are separated by a distance of at least about 5 mm.

In some embodiments, the present disclosure relates to a method of generating a scaffold or a plurality of scaffolds, including: mixing a hydrogel material and/or an extracellular matrix (ECM) protein in an aqueous solvent to generate an aqueous process solution; and cryoelectrospinning the aqueous process solution onto a one or more conductive probes extending from a conductive surface of a collector plate. In embodiments, the aqueous process solution includes one or more polymers or polymer adhesives. In embodiments, the polymer, and/or plurality of scaffolds are characterized as biodegradable and/or biocompatible. In embodiments the conductive surface is disposed within a process chamber under conditions sufficient to generate one or more scaffolds configured to mimic a preselected soft tissue such as soft tissue decellularized extracellular matrix. In embodiments, the one or more conductive probes each include a distal end, and the one or more scaffolds configured to mimic a preselected soft tissue decellularized extracellular matrix are generated directly atop at least one distal end or a plurality of distal ends. In some embodiments, the plurality of conductive probes include at least 20-200, or 20-100 conductive probes, wherein the at least two conductive probes are separated by a distance of at least 3-6 mm such as about 5 mm.

In embodiments, the method includes lyophilizing the one or more scaffolds configured to mimic a preselected soft tissue decellularized extracellular matrix, wherein the one or more scaffolds include a preselected pore structure, and/or a preselected viscoelasticity. In embodiments, lyophilizing occurs under conditions and for a duration sufficient to remove ice crystals from the one or more scaffolds configured to mimic a preselected soft tissue decellularized extracellular matrix. In embodiments, lyophilizing occurs at a temperature and pressure to remove ice and/or water from the one or more scaffolds.

In some embodiments, the methods of the present disclosure may further include crosslinking the one or more scaffolds configured to mimic a preselected soft tissue decellularized extracellular matrix to form a crosslinked preselected soft tissue decellularized extracellular matrix. In embodiments, the crosslinking includes contacting the one or more scaffolds configured to mimic a preselected soft tissue decellularized extracellular matrix with a crosslinking agent. Non-limiting examples of crosslinking agents suitable for use herein include N-hydroxysuccinimide (NHS), ethyl dimethylaminopropyl carbodiimide (EDC), and calcium chloride dihydrate.

In some embodiments, the present disclosure relates to a method of generating a scaffold, including: mixing a hydrogel material and/or an extracellular matrix (ECM) protein in an aqueous solvent to generate an aqueous process solution; and cryoelectrospinning the aqueous process solution onto a plurality of conductive probes extending from a conductive surface of a collector plate disposed within a process chamber under conditions sufficient to generate one or more scaffolds configured to mimic a preselected soft tissue decellularized extracellular matrix. In some embodiments, the hydrogel material is alginate, and the ECM protein is elastin. In some embodiments, the process chamber has a relative humidity greater than 40%, and an air temperature less than or equal to 2 degrees Celsius. In some embodiments, the collector plate has a temperature between about zero degrees Celsius to about minus 35 degrees Celsius. In some embodiments, the aqueous solvent is water or deionized water. In some embodiments, the aqueous process solution includes about 1 wt/vol % elastin, about 1.5 wt/vol % alginate and about 3 wt/vol % polyethylene oxide-400 kD, or about 0.4 wt/vol % collagen, about 0.4 wt/vol % chitosan and about 3 wt/vol % polyethylene oxide-400 kD, wherein the wt/vol % refers to wt/vol of the total volume use in the preparation of the aqueous process solution. In some embodiments, the preselected pore structure is characterized as a honeycomb-like shape. In some embodiments, the preselected stiffness is characterized by having an indentation modulus or elastic modulus in the sub kPa to several kPa range, such as e.g., 20 Pa to 100 KPa, or 20 Pa to 50 KPa, or 20 Pa to 20 KPa. In some embodiments, the one or more scaffolds further include a preselected porosity which is about 50% to 99% wherein each pore has an average diameter of about 10-50 micrometers. In some embodiments, the process chamber is thermally insulated. In some embodiments, the one or more scaffolds configured to mimic a preselected soft tissue decellularized extracellular matrix is configured to mimic decellularized extracellular matrix from a preselected tissue including, but not limited to kidney tissue, lung tissue, liver tissue, salivary gland tissue, mammary tissue, pancreatic tissue, or any other suitable preselected tissue. Table I below depicts suitable tissue to mimic in accordance with the present disclosure.

TABLE I

| Organ | Developmental stage | Whole gland stiffness | Reference |
|---|---|---|---|
| Brain | Developmental | 300-500 Pa | Budday, Silvia, Timothy C. Ovaert, Gerhard |
| | Matured | 650-1500 Pa | A. Holzapfel, Paul Steinmann, and Ellen Kuhl. "Fifty shades of brain: a review on the mechanical testing and modeling of brain tissue." Archives of Computational Methods in Engineering 27, no. 4 (2020): 1187-1230. |

TABLE I-continued

| Organ | Developmental stage | Whole gland stiffness | Reference |
|---|---|---|---|
| Heart | Developmental Matured | <200 Pa >20 kPa | Gaetani, Roberto, Eric Adriano Zizzi, Marco Agostino Deriu, Umberto Morbiducci, Maurizio Pesce, and Elisa Messina. "When stiffness matters: mechanosensing in heart development and disease." *Frontiers in Cell and Developmental Biology* 8 (2020): 334. |
| Lacrimal Gland | Matured | 5-10 kPa | Cerit M, Sendur H N. Interobserver Variability and Stiffness Measurements of Normal Lacrimal Gland in Healthy People Using Shear Wave Elastography. Cyprus J Med Sci 2020; 6(1): 93-8. |
| salivary gland stiffness | Developmental Matured | 100-350 Pa 1-4 kPa | Mosier, Aaron P., Sarah B. Peters, Melinda Larsen, and Nathaniel C. Cady. "Microfluidic platform for the elastic characterization of mouse submandibular glands by atomic force microscopy." *Biosensors* 4, no. 1 (2014): 18-27. |
| Thyroid glands | Matured | 65-100 kPa | Weng, Jie, Bi Chen, Mengying Xie, Xinlong Wan, Peng Wang, Xiaoming Zhou, Zhiliang Zhou et al. "Rabbit thyroid extracellular matrix as a 3D bioscaffold for thyroid bioengineering: a preliminary in vitro study." *BioMedical Engineering OnLine* 20, no. 1 (2021): 1-13. |
| Mammary glands | Matured | 0.2-2 kPa | Plodinec, Marija, Marko Loparic, Christophe A. Monnier, Ellen C. Obermann, Rosanna Zanetti-Dallenbach, Philipp Oertle, Janne T. Hyotyla et al. "The nanomechanical signature of breast cancer." *Nature nanotechnology* 7, no. 11 (2012): 757-765. |
| Lungs | Matured | 0.6-35 kPa | Sicard, Delphine, Andrew J. Haak, Kyoung Moo Choi, Alexandria R. Craig, Laura E. Fredenburgh, and Daniel J. Tschumperlin. "Aging and anatomical variations in lung tissue stiffness." *American Journal of Physiology-Lung Cellular and Molecular Physiology* 314, no. 6 (2018): L946-L955. |
| liver | Matured | <6 kPa | Mueller, Sebastian, and Laurent Sandrin. "Liver stiffness: a novel parameter for the diagnosis of liver disease." *Hepatic medicine: evidence and research* 2 (2010): 49. |
| kidney | Matured | <4 kPa | Leong, Sook Sam, Jeannie Hsiu Ding Wong, Mohammad Nazri Md Shah, Anushya Vijayananthan, Maisarah Jalalonmuhali, and Kwan Hoong Ng. "Shear wave elastography in the evaluation of renal parenchymal stiffness in patients with chronic kidney disease." *The British journal of radiology* 91, no. 1089 (2018): 20180235. |
| Pancreas | Matured | ~2.5 kPa | Itoh, Yohei, Yasuo Takehara, Toshihiro Kawase, Kenichi Terashima, Yoshihisa Ohkawa, Yuko Hirose, Ai Koda et al. "Feasibility of magnetic resonance elastography for the pancreas at 3T." *Journal of Magnetic Resonance Imaging* 43, no. 2 (2016): 384-390. |
| Muscle | Matured | 1-300 kPa | Shinohara, Minoru, Karim Sabra, Jean-Luc Gennisson, Mathias Fink, and Mickaél Tanter. "Real-time visualization of muscle stiffness distribution with ultrasound shear wave imaging during muscle contraction." *Muscle & nerve* 42, no. 3 (2010): 438-441. Green, M. A., G. Geng, E. Qin, R. Sinkus, S. C. Gandevia, and L. E. Bilston. "Measuring anisotropic muscle stiffness properties using elastography." NMR in Biomedicine 26, no. 11(2013): 1387-1394. |

Referring now to Table 2, various material properties of certain materials of the present disclosure are shown.

TABLE II

| Scaffold Technique | Material | Tensile Strength (MPa) | Young's Modulus (MPa) | Compressive Modulus (MPa) | Electrical Resistivity (Ωm) | Porosity (%) | Hydrophilicity (contact angle) |
|---|---|---|---|---|---|---|---|
| Nanofibrous | PLA | 1.8 [2]-8.1 ± 1.5 [1] (3-8 [24], 1.89 + 0.12 [25]) | 4.95 ± 0.24 [25]-250 [24] (6.52 ± 0.96 [22], 178 ± 14 [2]) | — | >10$^{15}$ [2] | 83 [2]-89.0 ± 3.97 [22] (85.4 [25]) | 108.5 [2]-119.7 ± 1.5 [1] |
| | PVA Coated PLA | 12.9 [1] | — | — | 6.7 [2] | — | 36.11 ± 1.5 [1] |
| | PLA + CNT | 8.8 ± 0.7 [2] | 461 ± 39 [2] | — | — | 80 [2] | 95.4 ± 1.9 [2] |
| | PLA + Gelatin | 6.2 ± 0.3 [2] | 375 ± 22 [2] | — | — | 73 [2] | 84 ± 2.2 [2] |
| | PCL | 6.87 ± 0.25 [3] | 21.42 ± 0.04 [3] | — | — | 72.9 ± 0.4 [23]-85 [3] | — |
| | PCL/collagen | 8.63 ± 1.44 [3] | 82.08 ± 17.86 [3] | — | — | 90 [3] | — |
| | PLGA | 1.21 ± 0.03 [25] | 1.99 ± 0.09 [25] | — | — | 79 [20]-90.5 [25] | — |
| | PEU | — | — | — | — | 64 [20] | — |
| | Silk | — | 230 [21] | — | — | 88 ± 0.6 [21] | — |
| | SF-gelatin | — | 16.8 ± 1.08-139 ± 4.03 [22] | — | — | 89.0 ± 3.97 [22] | — |
| | PLA/SF-gelatin | — | 10.7 ± 1.23-76.3 ± 3.42 [22] | — | — | 87.1 ± 5.41-87.5 ± 6.29 [22] | — |
| | PCL/PLA | — | — | — | — | 77.2 ± 0.2 [23] | — |
| | PLA/HA | 1-20 [24] | 12-650 [24] | — | — | — | — |
| | PLGA/PLA | 1.33 ± 0.08-1.45 ± 0.03 [25] | 2.75 ± 0.16-3.53 ± 0.07 [25] | — | — | 86.8-88.3 [25] | — |
| | SF/P (LLA-CL) | 0.23 ± 004-2.55 ± 0.21 [36] | | | | | |
| Hydrogels | Collagen | — | 0.960 ± 0.193-5.819 ± 0.552 [4] | 0.030 ± 0.007-0.168 ± 0.040 [5] | — | — | — |
| | Gelatin | — | 3.29E-3 ± 1.02E-3-0.039 ± 6.31E-3 [26] (0.081 [29]) | — | — | — | — |
| | PVA | 1.06 ± 0.35-1.89 ± 0.48 [28] | 0.32 ± 0.07-0.43 ± 0.10 [28] | — | — | — | — |
| | PAA/Gelatin | — | 7.1 ± 0.5 [6] | — | — | — | — |
| | GO/PAA/Gelatin | — | 7.5 ± 0.5-14.9 ± 1 [6] | — | — | — | — |

TABLE II-continued

| Scaffold Technique | Material | Tensile Strength (MPa) | Young's Modulus (MPa) | Compressive Modulus (MPa) | Electrical Resistivity (Ωm) | Porosity (%) | Hydrophilicity (contact angle) |
|---|---|---|---|---|---|---|---|
| | Alginate | 46.72 ± 15.77 [11] | 0.180 ± 0.02- 0.31 ± 0.05 [7] | — | — | 37.2 ± 1.9- 56.7 ± 0.8 [7] | — |
| | Nanocellulose | — | 0.150 ± 0.01- 0.261 ± 0.04 [7] | — | — | 34.2 ± 1.0- 45.6 ± 0.3 [7] | — |
| | Chitosan/GP | — | — | 2E-4 [12] | — | — | — |
| Hydrogel-Nanofiber Composite | Alginate-Collagen | 0.05028 ± 0.01054- 0.06120 ± 0.01368 [11] | 0.14824 ± 0.02637- 0.16510 ± 0.01191 [11] | — | — | — | — |
| | Chitosan/ GP & Silk Fibroin | — | — | 4E-4- 6E-4 [12] | — | — | — |
| | Gelatin/ PCL | 0.03 ± 0.01- 0.32 ± 0.05 [26] | 0.13 ± 0.04- 0.56 ± 0.09 [26] | — | — | — | — |
| | Alginate/ PCL | — | — | 0.202 ± 0.014- 0.298 ± 0.043 [27] | — | — | — |
| | PVA/CNT | 1.30 ± 0.19- 2.06 ± 0.12 [28] | 0.35 ± 0.04- 0.57 ± 0.03 [28] | — | — | — | — |
| Freeze-dried sponge | Collagen | — | 5.7E-4 ± 1.5E-4- 0.7 [31] (0.0076 ± 6E-4 [13]) | 0.025 [14] | — | — | — |
| | Collagen + HA | — | — | 0.030 [14]-1 [30] (0.28 [15]) | — | 85.7 ± 3.9 [30]- 96 ± 0.5 [14] | — |
| | Gelatin | — | — | 0.09- 0.4 [32] | — | 62.69 ± 1.3- 90.09 ± 0.9 [17] | — |
| Porogen-leached sponge | PCL w/ NaCl leaching | — | — | — | — | 74.00 ± 0.51 [16] | — |
| | Gelatin w/ NaCl leaching | — | — | — | — | 72.96 ± 2.3- 88.32 ± 2.6 [17] | — |
| | Starch w/ NaCl leaching | 2.48 ± 0.33- 2.6 ± 0.41 [18] | 20 ± 4.2- 24 ± 5.5 [18] | 7.28 + 2.8- 10.14 ± 2.3 [18] | — | 26-32 [18] | — |
| | Starch + Cellulose w/ NaCl leaching | 3.58 ± 0.74- 4.03 ± 0.48 [18] | 63 ± 2.9- 93 ± 3.6 [18] | 5.23 ± 2.2- 9.71 ± 2.5 [18] | — | 33-52 [18] | — |
| Gas Foaming | PCL | — | — | 7.5 [19] | — | 80 [19] | — |
| | PCL/HA | — | — | 10-20 [19] | — | 75-80 [19] | — |
| | PCL/HNT | — | — | 8-25 [19] | — | 70-80 [19] | — |

TABLE II-continued

| Scaffold Technique | Material | Tensile Strength (MPa) | Young's Modulus (MPa) | Compressive Modulus (MPa) | Electrical Resistivity (Ωm) | Porosity (%) | Hydrophilicity (contact angle) |
|---|---|---|---|---|---|---|---|
| | Gelatin | 0.02 ± 001- 0.23 ± 0.07 [33] | 8.7E-4 ± 1E-4- 0.009 ± 0.001 [33] | — | — | — | — |
| | Calcium Phosphate | — | 100-600 [34] | — | — | — | — |
| 3D Printing/ Bioprinting | PCL | 0.202-0.437 [37] | 0.76-2.03 [37] | 86 ± 14- 207 ± 36 [8] | — | 14 ± 4- 57 ± 2 [8] | — |
| | PCL-HA | — | — | 97 ± 8 -- 220 ± 36 [8] | — | 14 ± 4- 57 ± 2 [8] | — |
| | Gelatin/ Alginate | — | 4.5E-3- 7.6E-3 [10] | 4E-4- 0.06 [9] | — | 35-66 [10] | — |
| | Calcium sulfate | — | 5 ± 4- 30 ± 3 [39] | — | — | — | — |
| | Alginate | — | 0.039 ± 0.006- 0.27 ± 0.006 [40] | — | — | — | — |
| CES | PLGA | — | — | — | — | 75-95 [20] | — |
| | PEU | — | — | — | — | 66-91 [20] | — |
| | Silk | — | 75 [21] | — | — | 93 ± 0.08 [21] | — |
| | PLA | 0.04 ± 0.01 [35] | — | — | — | — | — |
| | PCL composite with alginate hydrogel | 0.0033 ± 6.4E-4- 0.0049 ± 2E-4 [38] | — | — | — | — | — |
| | PCL composite with alginate-sulfate hydrogel | 1.3E-4 ± 3.2E-5- 4.72E-4 ± 3.4E-4 [38] | — | — | — | — | — |

In some embodiments, the plurality of conductive probes extend about 1-5 mm from the conductive surface. In some embodiments, electrospinning further includes flowing the aqueous process solution onto the plurality of probes at an applied voltage of about 5-25 kV and a flow rate of about 5-15 microliters/min, wherein the plurality of probes have an average probe height of 1-10 mm, and average probe interval of about 5 mm. In embodiments, the methods further include lyophilizing the one or more scaffolds to form a lyophilized matrix. In some embodiments, the methods further include contacting the lyophilized matrix with a crosslinker to form a crosslinked biologically active scaffold. In some embodiments, the methods further include seeding the one or more scaffolds with cells in a culture media. In some embodiments, the one or more scaffolds are capable of supporting growth and/or differentiation of one or more cells. In embodiments, scaffold of the present disclosure is capable of supporting growth and/or differentiation of one or more cells to become fibrotic cells, mimicking fibrotic tissues, or to serve as fibrosis model.

In some embodiments, the present disclosure relates to a biologically active three-dimensional scaffold made by the methods of the present disclosure, including, e.g., a method of generating a scaffold, including: mixing a hydrogel material and/or an extracellular matrix (ECM) protein in an aqueous solvent to generate an aqueous process solution; and cryoelectrospinning the aqueous process solution onto a plurality of conductive probes extending from a conductive surface of a collector plate disposed within a process chamber under conditions sufficient to generate one or more scaffolds configured to mimic a preselected soft tissue decellularized extracellular matrix.

In some embodiments, the present disclosure relates to an engineered tissue made by contacting the biologically active three-dimensional scaffold of the present disclosure or made by a process of the present disclosure with cells in vivo or in vitro under conditions effective to allow interaction between the biologically active three-dimensional scaffold and the cells. In some embodiments, the cells are soft tissue cells. Non-limiting examples of soft tissue cells include kidney cells, lung cells, liver cells, salivary gland cells, pancreas cells, mammary cells, fat cells, or combinations thereof. In some embodiments, the cells are epithelial cells. In some embodiments, the cells are at least one of mesenchymal cells, stromal cells, endothelial cells, neural cells, or immune cells. Some embodiments further include an additional substance, wherein the additional substance is a pharmaceutical agent, imaging agent, a biologically active agent and/or a polymer.

In some embodiments, the present disclosure relates to a method of making a biologically active three-dimensional scaffold capable of supporting growth, maintenance and/or differentiation of a cell, the method including: cryoelectrospinning an aqueous process solution including a hydrogel material and/or an extracellular matrix (ECM) protein, and an aqueous solvent onto a plurality of conductive probes extending from a conductive surface of a collector plate disposed within a process chamber under conditions sufficient to generate one or more scaffolds configured to mimic a preselected soft tissue decellularized extracellular matrix; and lyophilizing and optionally crosslinking the one or more scaffolds configured to mimic a preselected soft tissue decellularized extracellular matrix such that the one or more scaffolds include a preselected three-dimensional shape, and/or a preselected viscoelasticity. One of ordinary skill in the art understands the process conditions suitable for lyophilizing the one or more scaffolds formed in accordance with the present disclosure. In some embodiments, the plurality of conductive probes extending from a conductive surface of a collector plate are at a temperature of −10 degrees Celsius to −35 degrees Celsius.

In some embodiments, the present disclosure relates to a method of using the engineered tissue of the present disclosure for tissue repair or tissue regeneration, including administering the engineered tissue of the present disclosure to a mammal in need of tissue repair or tissue regeneration. Non-limiting examples of mammals include a variety of organisms/sources, including, but not limited to human, or non-human mammals. Specific non-limiting examples of suitable mammals include human, murine, porcine and bovine sources. Specific non-limiting examples include beef cattle, dairy cattle, sheep, goats, hogs, poultry, mice, and horses. Specific non-limiting examples also include companion animals, such as dogs, cats and the like.

In embodiments, the scaffolds of the present disclosure are suitable for use in co-cultures one or more different cell types upon or disposed within the scaffold. For example, in embodiments, two or more cell types such as epithelial and stromal cells are cocultured on or within the scaffolds. In embodiments, the present disclosure includes co-culturing epithelial and stromal cells on the scaffolds for a predetermined time such as for extended duration. In embodiments, suitable cell types include, but are not limited to, endothelial cells, neural cells, immune cells, and combinations thereof. In embodiments, suitable cell types are selected from the group consisting of endothelial cells, neural cells, immune cells, and combinations thereof.

In some embodiments, culturing a single cell type upon or within a bioscaffold of the present disclosure may include culturing primary mesenchymal stromal cells (MSCs) such that they are grown on cryoelectrospun scaffolds of the present disclosure to recapitulate stromal phenotype. In embodiments, such scaffolds exhibit anti-fibrotic properties. In embodiments, scaffolds of the present disclosure mimic a healthy stromal tissue, which is an important part of many tissues in other organs.

In some embodiments, the present disclosure includes providing a scaffold of the present disclosure to promote attachment and organization of stromal cells and to mimic stromal tissues.

In some embodiments, the present disclosure includes providing a scaffold of the present disclosure to promote attachment and organization of stromal and epithelial cell populations.

In some embodiments, the present disclosure includes providing a scaffold of the present disclosure to repress fibrotic/diseased cell phenotypes. In embodiments, scaffolds of the present disclosure are provided in a therapeutically effective amount to a subject in need thereof, such as a subject having fibrotic/diseased cell phenotypes. In embodiments, the process sequence may include selecting or identifying a subject in need thereof.

In some embodiments, the present disclosure includes providing a scaffold of the present disclosure as a vehicle to exploit the anti-fibrotic, anti-inflammatory and pro-regenerative properties of mesenchymal stromal cells (MSCs). In embodiments, scaffolds of the present disclosure are provided in a therapeutically effective amount to a subject in need thereof, such as a subject with fibrotic and/or inflammatory disease. In embodiments, the process sequence may include selecting or identifying a subject in need thereof.

In some embodiments, the present disclosure includes providing a scaffold of the present disclosure for cell delivery including stromal cells and stem cells for regenerative therapy. In embodiments, scaffold of the present disclosure including stromal cells and/or stem cells in a therapeutically effective amount to a subject in need thereof. In embodiments, the process sequence may include selecting or identifying a subject in need thereof.

In some embodiments, the present disclosure includes a scaffold, including: a cryoelectrospun alginate and elastin material that mimics decellularized ECM, wherein the alginate and elastin are cross-linked. In embodiments, the scaffold is characterized as lyophilized scaffold, wherein the lyophilized scaffold includes 99.9 percent weight to 0.1 percent weight alginate, and 0.1 percent weight to 99.9 percent weight elastin, wherein the percent weight is the percent weight of the total lyophilized scaffold. In embodiments, the lyophilized scaffold is further characterized as rehydrated. In embodiments the scaffold further includes one or more biodegradable or biocompatible polymers. In embodiments, the scaffold further includes electrospun collagen. In some embodiments, natural polymers suitable for use herein include collagen, gelatin, silk fibroin, hyaluronic acid, chitosan, agarose, and combinations thereof. In embodiments, the scaffold further includes one or more natural or synthetic polymers, such as, those listed above and collagen, or synthetic fibers such as poly(alpha esters) such as poly(lactate acid), poly(glycolic acid), polyorthoesters, polyanhydrides and their copolymers, or combinations thereof. In embodiments, the scaffold further includes one or more ECM proteins such as collagen, elastin, laminin, and the like, and combinations thereof. In embodiments, the decellularized ECM mimics salivary tissue, mammary tissue, heart tissue, pancreatic tissue, fat tissue, or the like. In embodiments, the decellularized ECM mimics one or more soft tissue organs such as salivary tissue, lung tissue, liver tissue, and the like. In embodiments, when hydrated, one or more fibers of the scaffold have a similar organization to native ECM of a preselected organ. In some embodiments, the scaffold is characterized as isolated man-made material. In embodiments, the scaffolds of the present disclosure are characterized as synthetic or man-made. In embodiments, scaffold of the present disclosure is capable of supporting growth and/or differentiation of one or more cells to become fibrotic cells, mimicking fibrotic tissues, or to serve as fibrosis model.

In some embodiments, the present disclosure includes a method of treating a medical condition which may benefit from cell transplantation in a subject in need thereof, including transplanting the scaffold of the present disclosure into the subject, thereby treating the medical condition. In embodiments, the scaffold has been pre-seeded with cells. In embodiments, the medical condition is a cardiac disease or diabetes. In embodiments, the medical condition is one or more of degenerative disease, neurodegenerative disease, connective tissue degenerative disease, cardiovascular disease, fibrotic disorder, diabetes, COVID-19, pulmonary fibrosis, and combinations thereof.

In some embodiments, the present disclosure includes a method of generating a scaffold, including: mixing a hydrogel material and/or an extracellular matrix (ECM) protein in an aqueous solvent to generate an aqueous process solution; and cryoelectrospinning the aqueous process solution onto a plurality of conductive probes extending from a conductive surface of a collector plate disposed within a process chamber under conditions sufficient to generate one or more scaffolds configured to mimic a preselected soft tissue decellularized extracellular matrix. In embodiments, the plurality of conductive probes each comprise a distal end, and wherein the one or more scaffolds configured to mimic a preselected soft tissue decellularized extracellular matrix are generated directly atop at least one distal end. In embodiments, the plurality of conductive probes includes at least two conductive probes, wherein the at least two conductive probes are separated by a distance of at least 5 mm. In embodiments, the methods include lyophilizing the one or more scaffolds configured to mimic a preselected soft tissue decellularized extracellular matrix, wherein the one or more scaffolds comprise a preselected pore structure, and/or a preselected viscoelasticity. In embodiments, the methods include crosslinking the one or more scaffolds configured to mimic a preselected soft tissue decellularized extracellular matrix, wherein the one or more scaffolds comprise a preselected pore structure, and/or a preselected viscoelasticity. In embodiments, the hydrogel material is alginate, and the ECM protein is elastin. In embodiments, elastin and elastin-like peptides are suitable for use herein. In embodiments, the process chamber has a relative humidity greater than 35%, and an air temperature less than or equal to 4 degrees Celsius or less than or equal to 2 degrees Celsius. In embodiments, the collector plate has a temperature between about zero degrees Celsius to about minus 35 degrees Celsius. In embodiments, the aqueous solvent is water or deionized water. In embodiments, the aqueous process solution includes about 1 wt/vol % elastin, about 1.5 wt/vol % alginate and about 3 wt/vol % polyethylene oxide-400 kD, or about 0.4 wt/vol % collagen, about 0.4 wt/vol % chitosan and about 3 wt/vol % polyethylene oxide-400 kD, wherein the wt/vol % refers to wt/vol of a total volume used in a preparation of the aqueous process solution. In embodiments, the one or more scaffolds configured to mimic a preselected soft tissue decellularized extracellular matrix includes a preselected pore structure characterized as a honeycomb-like shape. In embodiments, the one or more scaffolds configured to mimic a preselected soft tissue decellularized extracellular matrix includes a preselected viscoelasticity characterized as a compression modulus below 1000 Pa, 1500 Pa, 2000 Pa, or 3000 Pa. In embodiments, the one or more scaffolds configured to mimic a preselected soft tissue decellularized extracellular matrix further comprise a preselected porosity is about 50% to 99% wherein each pore has an average diameter of about 1-100 micrometer, 2-90 micrometer, 10-250 micrometer, or 10-50 micrometer. In embodiments, the process chamber is thermally insulated. In embodiments, the one or more scaffolds configured to mimic a preselected soft tissue decellularized extracellular matrix is configured to mimic decellularized extracellular matrix from soft tissue organs including but not limiting to kidney tissue, lung tissue, liver tissue, fat tissue, mammary tissue, or salivary gland tissue. In embodiments, the plurality of conductive probes extend about 1-10 mm from the conductive surface. In embodiments, electrospinning further includes flowing the aqueous process solution onto the plurality of probes at an applied voltage of about 5-25 kV and a flow rate of about 5-15 microliters/min, wherein the plurality of probes have an average probe height of 1-10 mm, and average probe interval of about 5 mm. In embodiments, lyophilizing the one or more scaffolds to form a lyophilized matrix. In embodiments, the methods further include contacting the lyophilized matrix with a crosslinker to form a crosslinked biologically active scaffold. In embodiments, the methods further include seeding the one or more scaffolds with cells in a culture media to form a cell-scaffold construct. In embodiments, the methods further include seeding the one or more scaffolds with second cells in a culture media to form a cell-scaffold construct, wherein the second cells are different than the cells. In embodiments, the one or more scaffolds are capable of supporting growth and/or differentiation of one or more cells.

In embodiments, the present disclosure includes a biologically active three-dimensional scaffold made by a method of the present disclosure.

In embodiments, the present disclosure includes an engineered tissue made by contacting the biologically active three-dimensional scaffold of the present disclosure with cells in vivo or in vitro under conditions effective to allow cell-cell interaction and interaction between the biologically active three-dimensional scaffold and the cells. In embodiments, the cells are at least one of mesenchymal cells or stromal cells. In embodiments, the cells are at least one of epithelial cells, endothelial cells, immune cells, or combinations thereof. In embodiments, the engineered tissue further includes an additional substance, wherein the additional substance is a small molecule, macromolecule, pharmaceutical agent, imaging agent, a biologically active agent and/or a polymer.

In embodiments the present disclosure includes a method of making a biologically active three-dimensional scaffold capable of supporting growth, maintenance or differentiation of a cell, the method including: cryoelectrospinning an aqueous process solution including a hydrogel material and/or an extracellular matrix (ECM) protein, and an aqueous solvent onto a plurality of conductive probes extending from a conductive surface of a collector plate disposed within a process chamber under conditions sufficient to generate one or more scaffolds configured to mimic a preselected soft tissue decellularized extracellular matrix; and lyophilizing and optionally crosslinking the one or more scaffolds configured to mimic a preselected soft tissue decellularized extracellular matrix such that the one or more scaffolds comprise a preselected three-dimensional topography, and/or a preselected viscoelasticity. In embodiments the plurality of conductive probes extending from a conductive surface of a collector plate are at a temperature of −10 degrees Celsius to −35 degrees Celsius.

In embodiments, the present disclosure includes a method of using the engineered tissue of the present disclosure for tissue repair or tissue regeneration, including: administering the engineered tissue of the present disclosure to a mammal in need of tissue repair or tissue regeneration.

In embodiments, the present disclosure includes a scaffold, including: a cryoelectrospun alginate and elastin material that mimics decellularized ECM, wherein the alginate and elastin are cross-linked. In embodiments, the scaffold is characterized as lyophilized scaffold, and wherein the lyophilized scaffold includes 99.9 percent weight to 0.1 percent weight alginate, and 0.1 percent weight to 99.9 percent weight elastin, wherein the percent weight is the percent weight of the total lyophilized scaffold. In embodiments, the lyophilized scaffold is further characterized as rehydrated. In embodiments, the scaffold further includes on or more biodegradable or biocompatible polymers. In embodiments, the scaffold further includes electrospun collagen. In embodiments, the scaffold further includes one or more natural polymers such as collagen, gelatin, silk fibroin, hyaluronic acid, chitosan, agarose, or synthetic polymers, such as, poly(alpha esters), such as, poly(lactate acid), poly(glycolic acid), polyorthoesters, polyanhydrides and their copolymers, or combinations thereof. In embodiments, the scaffold further includes one or more ECM proteins such as collagen, elastin, laminin, and the like, and combinations thereof. In embodiments, a cryoelectrospun scaffold mimics the decellularized ECM of one or more soft tissue, salivary tissue, mammary tissue, heart tissue, pancreatic tissue, or the like. In embodiments a scaffold mimics the decellularized ECM of one or more soft tissue organs such as salivary tissue, lung tissue, liver tissue, and the like. In embodiments, the scaffold of the present disclosure, when hydrated, such as with water, has one or more fibers of the scaffold having a similar organization to native ECM of a preselected organ. In embodiments, the scaffold is characterized as isolated man-made material. In embodiments, the scaffold is characterized as substantially pure. In embodiments, the scaffold is capable of supporting growth and/or differentiation of one or more cells to become fibrotic cells, mimicking fibrotic tissues, or to serve as fibrosis model.

In embodiments, the present disclosure includes a method of treating a medical condition which may benefit from cell or scaffold transplantation in a subject in need thereof, including transplanting the scaffold of the present disclosure into the subject, thereby treating the medical condition. In embodiments, the scaffold has been pre-seeded with cells. In embodiments, the scaffold is characterized as cryoelectrospun. In embodiments, the medical condition is a cardiac disease or diabetes. In embodiments, the medical condition is one or more of degenerative disease, neurodegenerative disease, connective tissue degenerative disease, cardiovascular disease, fibrotic disorder, diabetes, COVID-19, pulmonary fibrosis, and combinations thereof.

Summary of Example I

Scaffold-based regenerative strategies that emulate the native extracellular matrix (ECM) of the region of interest can stimulate cell differentiation and function. Existing ECM-mimicking scaffolds, including nanofiber mats, sponges, hydrogels, and nanofiber-hydrogel composites are unable to simultaneously mimic typical composition, topography, pore size, porosity and viscoelastic properties of healthy soft tissue ECM. The present disclosure provides for fabricated scaffold structures with minimal fibrous backbone and pore sizes and structure similar to soft tissue ECM, using cryoelectrospinning. Salivary glands were used as a soft tissue model where the decellularized salivary gland (D-SG) material had a fibrous backbone with 10-30 µm pores, 120 Pa indentation modulus and ~200 s relaxation half time. Elastin and alginate were used as natural, compliant biomaterials and water as the solvent for cryoelectrospinning scaffolds to mimic this structure and viscoelasticity. Process parameters were identified to produce a unique honeycomb topography similar to D-SG, with a high yield >100 scaffolds/run. Using water as solvent was important to generate scaffolds with honeycomb topography; further, it permitted a "greener" fabrication process. The present disclosure demonstrates that cryoelectrospun elastin-alginate scaffolds support stromal and salivary epithelial cell growth for use in salivary gland tissue engineering and regenerative medicine.

Example I

Introduction to Example I: The extracellular matrix (ECM) includes a proteinaceous scaffold within the connective tissue that plays a crucial role in regulating the function of parenchymal tissue in organs. Many pathologies in the human body are promoted by a diseased stroma (See e.g., Ishii K, et al., Role of Stromal Paracrine Signals in Proliferative Diseases of the Aging Human Prostate. *J Clin Med*. Published online 2018; Li et al. Developmental origins and functions of stromal cells in the normal and diseased mammalian kidney. *Dev Dyn*. Published online 2014; and Shi Y, Wang Y, Li Q, et al. Immunoregulatory mechanisms of mesenchymal stem and stromal cells in inflammatory diseases. *Nat Rev Nephroi*. Published online 2018) and are accompanied and/or caused by extracellular matrix (ECM) stiffening, including fibrotic diseases and cancer (See e.g., Lampi M C, Reinhart-King C A. Targeting extracellular matrix stiffness to attenuate disease: From molecular mechanisms to clinical trials. *Sci Transl Med*. Published online 2018; and Iozzo R V., Gubbiotti M A. Extracellular matrix: The driving force of mammalian diseases. *Matrix Biol*. 2018; 71-72:1-9. doi:10.1016/j.matbio.2018.03.023).

In advanced stages of many fibrotic diseases, which contributes to up to 45% of deaths worldwide (See e.g., Wynn T A. Cellular and molecular mechanisms of fibrosis. *J Pathol*. 2008; 214(2):199-210. doi:10.1002/path.2277), a fibrotic stroma ultimately leads to loss of organ function. The conversion of tissue-resident stromal cells into myofibroblasts is thought to drive fibrosis in many organs. (See e.g., El Agha E, Kramann R, Schneider R K, et al. Mesenchymal Stem Cells in Fibrotic Disease. *Cell Stem Cell*. 2017; 21(2):166-177. doi:10.1016/j.stem.2017.07.011). The myofibroblasts produce excess levels of ECM proteins to create a matrix that is stiffer and denser than a homeostatic matrix, which contributes to disease progression. (See e.g., Wynn T A. Cellular and molecular mechanisms of fibrosis. *J Pathol*. 2008; 214(2):199-210. doi:10.1002/path.2277; and Duscher D, Maan Z N, Wong V W, et al. Mechanotransduction and fibrosis. *J Biomech*. 2014; 47(9):1997-2005. doi:10.1016/j.jbiomech.2014.03.031).

Preventing or reversing the conversion of tissue-resident stromal cells into myofibroblasts is one possible strategy for therapeutic remediation of fibrotic diseases. The delivery of mesenchymal stromal cells (MSCs) into diseased organs in mice has shown promise in preventing myofibroblast conversion, remediating disease and improving organ function (See e.g., El Agha E, Kramann R, Schneider R K, et al. Mesenchymal Stem Cells in Fibrotic Disease. *Cell Stem Cell*. 2017; 21(2):166-177. doi:10.1016/j.stem.2017.07.011). MSCs can be delivered through an intravenous injection but show poor engraftment and transient therapeutic effects (See e.g., Pittenger M F, Discher D E, Péault B M, Phinney D G, Hare J M, Caplan A I. Mesenchymal stem cell perspective: cell biology to clinical progress. *npj Regen Med*. Published online 2019. doi: 10.1038/s41536-019-0083-6). Scaffolds that mimic stromal ECM in soft tissue can help in both localizing the MSCs at the organ of interest and preventing their conversion into myofibroblasts by provising key mechanical and biochemical cues. Scaffolds that deliver and extend the therapeutic effect of MSCs may revert tissue-resident myofibroblasts into a normal phenotype, which might, in turn, facilitate normal function of parenchymal cells.

Soft tissue organs have unique ECM compositions that enable tightly regulated biochemical and mechanical properties for specific lineage commitment and differentiation during organ development and maintenance of cellular function in adult organs. Healthy soft-tissue stromal ECM is composed of an insoluble backbone of ECM proteins and soluble hydrogel-forming glycosaminoglycans (GAGs) of varying concentrations, depending on the organ. The mechanical and biochemical cues from ECM (e.g., composition, topography, pore size, porosity, viscoelasticity) modulate cell viability, growth, homeostasis, migration, and differentiation. For examples, in embodiments, pore size is preselected to be 10-250 micrometer, and stiffness is preselected to be 0.01 to 500 kPa. For example, the topography, pore size, and porosity modulate the amount of ECM backbone material interacting with the cell and thereby affect cell viability and growth (See e.g., Yang et al., Biophysical Regulation of Cell Behavior—Cross Talk between Substrate Stiffness and Nanotopography. *Engineering*. 2017; 3(1):36-54; and Wang K, Bruce A, Mezan R, et al. Nanotopographical Modulation of Cell Function through Nuclear Deformation. *ACS Appl Mater Interfaces*. Published online 2016).

The matrix viscoelastic properties and the extent of cell attachment to the matrix regulate the cell-generated traction forces and the substrate resistance the cells experience in response, which impact cell phenotype and differentiation (See e.g., Trappmann et al. Extracellular-matrix tethering regulates stem-cell fate. *Nat Mater*. 2012; 11(7):642-649; Akhmanova et al., Physical, Spatial, and Molecular Aspects of Extracellular Matrix of in Vivo Niches and Artificial Scaffolds Relevant to Stem Cells Research. *Stem Cells Int*. 2015; 2015; Engler et al., Matrix Elasticity Directs Stem Cell Lineage Specification. *Cell*. Published online 2006. doi:10.1016/j.cell.2006.06.044; Reilly G C, Engler A J. Intrinsic extracellular matrix properties regulate stem cell differentiation. *J Biomech*. Published online 2010; and Cameron A R, Frith J E, Cooper-White J J. The influence of substrate creep on mesenchymal stem cell behaviour and phenotype. *Biomaterials*. Published online 2011; and Missirlis et al., Substrate Resistance to Traction Forces Controls Fibroblast Polarization. *Biophys J*. 2020; 119(12):2558-2572). As matrix mechanics drive cell health and disease progression, artificial matrices for in vivo implantation and in vitro culture must closely emulate the native, healthy ECM to maintain cellular function as expected in a healthy organ.

Synthetic scaffolds of various types, including nanofiber mats, sponges, hydrogels, and nanofiber-hydrogel composites, have been engineered to simulate various aspects of ECM. Nanofiber mats have fibrous topography, impenetrable pores, and high stiffness, typically in the MPa range or higher (See e.g., Yao J, Bastiaansen C W M, Peijs T. High Strength and High Modulus Electrospun Nanofibers. *Fibers* 2014; Vol 2, Pages 158-186. 2014; 2(2):158-186; and Jenkins T L, Little D. Synthetic scaffolds for musculoskeletal tissue engineering: cellular responses to fiber parameters. *npj Regen Med* 2019 41. 2019; 4(1):1-14), which make them good candidates for basement membrane mimetics for monolayer epithelial or endothelial growth (See e.g., Kim et al., A collagen gel-coated, aligned nanofiber membrane for enhanced endothelial barrier function. *Sci Reports* 2019 91. 2019; 9(1):1-11; Park et al. Collagen immobilization on ultra-thin nanofiber membrane to promote in vitro endothelial monolayer formation: https://doi.org/101177/2041731419887833.2019; 10. doi:10.1177/2041731419887833; Nishiguchi et al., Basement Membrane Mimics of Biofunctionalized Nanofibers for a Bipolar-Cultured Human Primary Alveolar-Capillary Barrier Model. *Biomacromolecules*. 2017; 18(3):719-727; and Rofaani et al., Fabrication of ultrathin artificial basement membrane for epithelial cell culture. *Microelectron Eng*. 2020; 232: 111407. doi:10.1016/J.MEE.2020.111407). However, they fail to mimic both the 3D topography and the viscoelasticity of soft-tissue stromal ECM. Sponges fabricated by freeze-drying, particulate- or salt-leaching, gas foaming, or phase separation have excessive ECM backbone and excessively large pore sizes when stiffness is in the sub-kPa range; hence, cells attach flush against the backbone, similar to 2D culture (See e.g., Trappmann B, Gautrot J E, Connelly J T, et al. Extracellular-matrix tethering regulates stem-cell fate. *Nat Mater*. 2012; 11(7):642-649). Hydrogels allow tunable viscoelasticity in the kPa range for soft tissue scaffolds. However, bulk hydrogels (e.g., alginate, PEG) lack an insoluble fibrous backbone that mechanically supports cells. Their extremely small pore sizes, in the submicron range, support molecular movement but, without cell attachment sites, impede cellular movement crucial for cell migration and organization. While existing hybrid nanofiber-hydrogel scaffolds reinforce hydrogels with a fibrous backbone, they may have an inadequate number and a non-homogenous distribution of cell anchorage points. Hence, a new fabrication strategy is necessary to produce scaffolds that concurrently mimic these essential properties of soft-tissue stromal ECM, including honeycomb topography, about 10-50 μm pores (See e.g., Aryan et al., Whole-organ tissue engineering: Decellularization and recellularization of three-dimensional matrix liver scaffolds. *J Biomed Mater Res Part A*. 2014; 103(4):1498-1508; Zhang et al. In vivo regeneration of renal vessels post whole decellularized kidneys transplantation. *Oncotarget*. 2015; 6(38); Gupta et al., Modification of decellularized goat-lung scaffold with chitosan/nanohydroxyapatite composite for bone tissue engineering applications. *Biomed Res Int*. 2013; 2013; and Gao et al. Generation of bioartificial salivary gland using whole-organ decellularized bioscaffold. *Cells Tissues Organs*. 2015; 200(4):171-180), insoluble fibrous backbone, soluble hydrogel cushion, and sub-kPa range stiffness.

Figure 4:
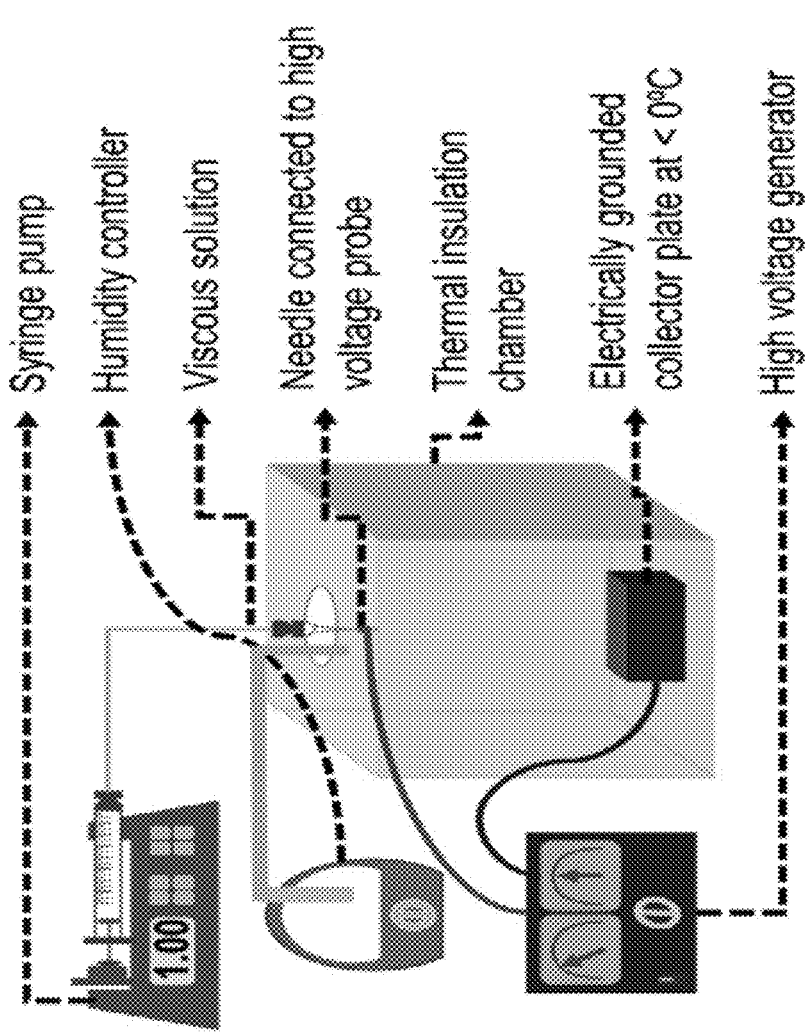
FIG. 4 depicts a diagram schematically illustrating a side view of a cryoelectrospinning device embodiment and collector plate embodiment of the present disclosure.

Cryoelectrospinning, also known as cryogenic electrospinning, low temperature electrospinning, and cold plate electrospinning, is an emerging technique to fabricate 3D nanofibrous scaffolds with high porosity and low bulk viscoelasticity. The cryoelectrospinning process includes a cold collector plate, maintained at a temperature less than 0° C. (See e.g., Leong et al., Cryogenic electrospinning: proposed mechanism, process parameters and its use in engineering of bilayered tissue structures. *Nanomedicine*. 2013; 8(4):555-566. doi:10.2217/nnm.13.39; Bulysheva et al., Low-temperature electrospun silk scaffold for in vitro mucosal modeling. *J Biomed Mater Res—Part A*. 2012; 100 A(3):757-767. doi:10.1002/jbm.a.33288; and Kim et al., Fabrication of three-dimensional poly(lactic-co-glycolic acid) mesh by electrospinning using different solvents with dry ice. *Macromol Res*. 2014; 22(4):377-381. doi:10.1007/s13233-014-2060-7) (See also e.g., FIG. 4) to collect deposited electrospun scaffolds, which are then lyophilized, a major difference from traditional electrospinning techniques. The cryogenically cooled collector plate promotes deposition of atmospheric water vapor as ice crystals on the collector plate and between deposited fibers, which can subsequently be lyophilized to produce air pores. The nucleation of ice crystals allows scalable 3D growth, increased porosity, and consequentially, reduced scaffold density and kPa-range bulk stiffness (See e.g., Formica F A, Öztürk E, Hess S C, et al. A Bioinspired Ultraporous Nanofiber-Hydrogel Mimic of the Cartilage Extracellular Matrix. *Adv Healthc Mater.* 2016; 5(24):3129-3138). The remainder of the cryoelectrospinning process is similar to traditional electrospinning, in which a viscous, long-chain polymer solution becomes electrically charged when passed through a needle tip at high voltage (5-20 kV), and the electrostatic repulsion in the charged fluid exceeds the forces of surface tension, pulling the charged droplet at the needle tip to the nearest electrical ground. The chain-chain interactions of the polymer molecules in the charged droplet prevent the droplet from falling to the electrically grounded collector plate as a drop and instead pull the droplet as a fiber with micro/nanometer diameter to the electrical ground. While the fibers deposit to form a 2.5D nanofiber mat in traditional electrospinning, when cryoelectrospun, they form a 3D fibrous scaffold following lyophilization. As shown in FIG. 5, cryoelectrospinning has primarily been explored with synthetic polymers (e.g., PLA, PLGA, PCL, PEU, PF) (See e.g., Leong et al., Cryogenic electrospinning: proposed mechanism, process parameters and its use in engineering of bilayered tissue structures. *Nanomedicine.* 2013; 8(4):555-566. doi:10.2217/nnm.13.39; Leong et al., In vitro cell infiltration and in vivo cell infiltration and vascularization in a fibrous, highly porous poly(D,L-lactide) scaffold fabricated by cryogenic electrospinning technique. *J Biomed Mater Res—Part A.* 2009; 91(1):231-240. doi:10.1002/jbm.a.32208; Leong et al., Fabrication and in vitro and in vivo cell infiltration study of a bilayered cryogenic electrospun poly(D,L-lactide) scaffold. *J Biomed Mater Res—Part A.* 2010; 94(4):1141-1149. doi:10.1002/jbm.a.32795; Simonet et al., Tailoring the void space and mechanical properties in electrospun scaffolds towards physiological ranges. *J Mater Chem B.* 2014; 2(3):305-313. doi:10.1039/C3TB20995D; Burton T P, Callanan A. A Non-woven Path: Electrospun Poly(lactic acid) Scaffolds for Kidney Tissue Engineering. *Tissue Eng Regen Med.* Published online 2018. doi:10.1007/s13770-017-0107-5; Kim et al., Fabrication of three-dimensional poly(lactic-co-glycolic acid) mesh by electrospinning using different solvents with dry ice. *Macromol Res.* 2014; 22(4):377-381. doi:10.1007/s13233-014-2060-7; Simonet et al., Ultraporous 3D Polymer Meshes by Low-Temperature Electrospinning: Use of Ice Crystals as a Removable Void Template. *Polym Eng Sci.* 2007; 47(12): 2020-2026. doi:10.1002/pen.20914; Formica et al., A Bioinspired Ultraporous Nanofiber-Hydrogel Mimic of the Cartilage Extracellular Matrix. *Adv Healthc Mater.* 2016; 5(24): 3129-3138; Simonet et al., Tailoring the void space and mechanical properties in electrospun scaffolds towards physiological ranges. *J Mater Chem B.* 2014; 2(3):305-313. doi:10.1039/C3TB20995D; Lee et al. Three dimensional poly(ε-caprolactone) and silk fibroin nanocomposite fibrous matrix for artificial dermis. *Mater Sci Eng C.* 2016; 68:758-767. doi:10.1016/j.msec.2016.06.019; Li et al., Facile fabrication of porous polymer fibers via cryogenic electrospinning system. *J Mater Process Technol.* 2019; 266 (June 2018):551-557. doi:10.1016/j.jmatprotec.2018.11.035; Simonet et al., Tailoring the void space and mechanical properties in electrospun scaffolds towards physiological ranges. *J Mater Chem B.* 2014; 2(3):305-313. doi:10.1039/C3TB20995D; Simonet et al., Ultraporous 3D Polymer Meshes by Low-Temperature Electrospinning: Use of Ice Crystals as a Removable Void Template. *Polym Eng Sci.* 2007; 47(12):2020-2026. doi:10.1002/pen.20914) dissolved in toxic organic solvents or glacial acetic acid, but natural polymers, such as silk fibronin (See e.g., Bulysheva et al., Low-temperature electrospun silk scaffold for in vitro mucosal modeling. *J Biomed Mater Res—Part A.* 2012; 100 A(3):757-767. doi:10.1002/jbm.a.33288; Lee et al. Three dimensional poly(ε-caprolactone) and silk fibroin nanocomposite fibrous matrix for artificial dermis. *Mater Sci Eng C.* 2016; 68:758-767. doi:10.1016/j.msec.2016.06.019; and Sheikh et al. 3D electrospun silk fibroin nanofibers for fabrication of artificial skin. *Nanomedicine Nanotechnology, Biol Med.* 2015; 11(3):681-691. doi:10.1016/j.nano.2014.11.007), have also been used. Cryoelectrospun scaffolds have been shown to exhibit stiffness in the kPa or MPa range. While synthetic polymers are easier to manipulate, they do not provide biochemical cues that can be recognized by cells and non-biodegradable polymers require further chemical modification to be biodegradable (See e.g., Gribova et al., A material's point of view on recent developments of polymeric biomaterials: Control of mechanical and biochemical properties. *J Mater Chem.* Published online 2011; and Abbasian et al., Scaffolding polymeric biomaterials: Are naturally occurring biological macromolecules more appropriate for tissue engineering? *Int J Biol Macromol.* Published online 2019. doi:10.1016/j.ijbiomac.2019.04.197). Additionally, organic solvents, even at low residual amounts, can have toxic effects on cells (See e.g., Loh Q L, Choong C. Three-Dimensional Scaffolds for Tissue Engineering Applications: Role of Porosity and Pore Size. *Tissue Eng Part B Rev.* 2013; 19(6):485-502. doi:10.1089/ten.teb.2012.0437) and when used in combination with natural proteins, may alter the conformation of the proteins. It was hypothesized that cryoelectrospinning of natural biomaterials, including ECM proteins and hydrogel materials with water as the solvent could yield biocompatible scaffolds that mimic the topography and viscoelasticity of soft-tissue ECM.

Here, the salivary gland was used as a model for soft tissue organ and comparing the topography and viscoelastic properties of the cryoelectrospun scaffold to a decellularized adult salivary gland. In embodiments, cryoelectrospinning methods described herein fabricate scaffolds that are similar to the natural ECM found in adult submandibular salivary glands. In embodiments, the process of the present disclosure includes fabricating a pliable environment for morphogenesis and, in embodiments, use of a hydrogel material, alginate, and the insoluble ECM protein, elastin, as components of the scaffold to mimic the elastic and gelling ECM composition of soft tissues. To adopt a "greener" approach, the chosen biomaterials were electrospun using water as the solvent rather than organic solvents. The effects of solvent and process parameters were explored on the topography and growth of cryoelectrospun scaffolds, establishing conditions that produce scaffolds with a unique honeycomb topography, replicating not only the salivary gland ECM but also the ECM structure of other soft tissues (Aryan et al. Whole-organ tissue engineering: Decellularization and recellularization of three-dimensional matrix liver scaffolds. *J Biomed Mater Res Part A.* 2014; 103(4):1498-1508. doi:10.1002/jbm.a.35291; Zhang et al. In vivo regeneration of renal vessels post whole decellularized kidneys transplantation. *Oncotarget.* 2015; 6(38). doi:10.18632/oncotarget.6321; and Gupta et al., Modification of decellularized goat-lung scaffold with chitosan/nanohydroxyapatite composite for bone tissue engineering applications. *Biomed Res Int.* 2013; 2013), which has not been previously reported with the cryoelectrospinning technique. The ability of elastin-alginate cryoelectrospun scaffolds (CES) to maintain stromal and parenchymal cell populations was evaluated by analyzing mesenchymal and epithelial cell growth, phenotype, self-organization, and function, focusing on the potential of CES to support the mesenchymal phenotype and prevent the myofibroblast phenotype, and the potential of mesenchyme cultured on honeycomb CES to facilitate epithelial cell function.

Materials and Methods

Scaffolds were fabricated using a soluble form of bovine neck elastin (ES12) from Elastin Products Company (Owensville, MI), alginate, and polyethylene oxide with a molecular weight of 400 kD (PEG-400 kD) from Sigma-Aldrich (St. Louis, MO), 85:15 poly(lactic-co-glycolic acid) (PLGA) (Cat. No. B6006-1) from DURECT Corporation (Cupertino, CA), and hexafluoroisopropanol (HFIP) from Sigma Aldrich. The reagents for crosslinking the scaffold were N-hydroxysuccinimide (NHS) from Thermo Fisher Scientific (Waltham, MA), ethyl dimethylaminopropyl carbodiimide (EDC), and calcium chloride dihydrate from Sigma-Aldrich. The reagents for cell culture were DMEM (high glucose), fetal bovine serum (heat-inactivated), Penicillin-Streptomycin (10,000 units/mL of penicillin and 10,000 µg/mL of streptomycin) from Thermo Fisher Scientific, or Antibiotic-Antimycotic Solution (10,000 units/mL penicillin, 10,000 µg/mL streptomycin and 25 µg/mL amphotericin B) from R&D Systems. Primary embryonic day 16 (E16) mesenchyme cells were isolated using collagenase/hyaluronidase (Cat. No. 7912) from StemCell Technologies, dispase II (Cat. No. 17105041), phosphate buffered saline (PBS), DMEM/F12 (Cat. No. 11039047), fetal bovine serum (FBS) (Cat. No. 10082147), and penicillin-streptomycin from Thermo Fisher Scientific, 70 µm cell strainers (Cat. No. 087712) from Corning (Corning, NY) and 40 µm cell strainers (Cat. No. 22363547) from Thermo Fisher Scientific. Well-plates were coated with ultra-low adhesion polymer Lipidure from Amsbio (Cambridge, MA). Cell viability assays were performed with calcein-AM and ethidium homodimer from Sigma-Aldrich. Cell proliferation assays were performed using Cell Titer Glo-3D reagent from Promega (Madison, WI). Primary antibodies used for immunocytochemistry are detailed in FIG. 6, including vimentin (clone LN-6) from Sigma-Aldrich, Zona Occludin-1 (ZO-1) from Thermo Fisher Scientific, and E-cadherin from BD Biosciences (San Jose, CA) for cell culture samples.

Antibodies against collagen I and collagen IV from MilliporeSigma (Burlington, MA), and perlecan from Santa Cruz Biotechnology (Dallas, TX) were used for immunohistochemistry of decellularized salivary gland. Secondary antibodies used were Cyanine Cy3 AffiniPure IgG, Alexa Fluor-488 AffiniPure F(ab')$_2$ Fragment IgM, and Alexa Fluor-647 AffiniPure F(ab')$_2$ fragment from Jackson ImmunoResearch Laboratories (West Grove, PA). Other reagents used for immunocytochemistry include paraformaldehyde, Tween 20, bovine serum albumin, and phalloidin-rhodamine from Thermo Fisher Scientific, glutaraldehyde, Triton X-100, sodium chloride, and 4',6-diamidino-2-phenylindole (DAPI) from Sigma-Aldrich, normal donkey serum (Cat. No. 017-000-121) from Jackson ImmunoResearch Laboratories, and Fluoro-Gel mounting medium from Electron Microscopy Sciences (Hatfield, PA). Triton X-100 from Sigma-Aldrich, NH$_4$OH from Thermo Fisher Scientific, and DNase I from StemCell Technologies (Vancouver, CA) were used in preparation of decellularized salivary glands for immunohistochemistry. Confocal imaging of decellularized salivary glands were performed using 50 mm glass bottom dishes (Cat. No. P50G-1.5-14F) from MatTek (Ashland, MA). Reagents used for the preparation of cell culture samples and decellularized salivary glands for scanning electron microscope (SEM) imaging include glutaraldehyde, sucrose, phosphate buffer, and hexamethyldisilazane (HMDS) from Sigma-Aldrich, and ethanol from Decon Labs (King of Prussia, PA).

Animals

Mice used to source salivary glands were either CD-1 strain from Charles River Laboratories (Wilmington, MA) or C57B6 strain from Jackson Laboratories (Bar Harbor, ME). The care and handling of mice and tissue collection conformed to the requirements of and was approved by the Institutional Animal Care Use Committee (IACUC) of University at Albany, State University of New York.

Decellularization of Salivary Glands

Whole organs were resected from adult female CD-1 or C57Bl/6 mice. A pair of salivary glands were rotated via inversion at 4° C. in 40 mL sterile distilled water for 2 days in a 50 mL conical tube with water removal and replacement after one day. After water-induced lysis was complete, the water was replaced with 40 mL clearing solution (0.5% Triton X-100, 0.05% NH$_4$OH) and tumbled for one additional day at 4° C. Decellularized samples were washed three times in 1× phosphate buffered saline, pH 7.4 (PBS). DNA was removed from these samples using 0.5 mg/mL DNase I in PBS for 30 minutes. These decellularized salivary glands were stored at 4° C. in preservation medium composed of DMEM/F12, 10% fetal bovine serum, and 1% penicillin-streptomycin (10,000 U/mL).

Immunofluorescent Staining and Imaging of Decellularized Glands

Whole decellularized salivary glands were immunostained for collagen I, collagen IV, and perlecan using 500 µL of diluted antibody solution/gland (FIG. 6). All primary antibodies were incubated overnight at 4° C., followed by three washes using PBS. Secondary antibody incubations were at least 4 hours at room temperature. DAPI was used for nuclei staining. Immunostained glands were imaged in 50 mm glass bottom dishes. Imaging was performed using an EVOS® FL Cell Imaging System (Thermo Fisher Scientific) with the same exposures and/or laser configurations for all samples within an experiment.

Scanning Electron Microscopy (SEM)

Decellularized salivary glands and scaffolds seeded with cells were fixed with 4% paraformaldehyde-0.25% glutaraldehyde in 5% (w/v) sucrose and 0.6×PBS for 4 hours and 20 minutes, respectively, followed by 3% glutaraldehyde in 0.1 M sucrose-0.1M phosphate buffer (pH 7.4) for 2 hours. Samples were then washed in 0.1 M sucrose-0.1M phosphate buffer three times for 10 minutes each. Samples were dehydrated in graded ethanol series incubation of 25, 50, 70, 80, 95, 100, 100% for 15 minutes at each ethanol concentration. Samples were subsequently chemically dried at 3:1, 1:1, and 1:3 ethanol: HMDS for 15 min each and then in 100% HMDS thrice for 15 minutes each time. Samples were allowed to air dry overnight. Chemically dried biological samples and lyophilized scaffolds were sputter-coated with iridium-palladium for imaging. SEM imaging was performed using a Zeiss Leo 1550 field emission scanning electron microscope (Zeiss Leo Electron Microscopy Ltd., Cambridge, UK).

Scaffold Fabrication and Modification

Cryoelectrospinning was performed using protein-polymer solutions of 1% elastin, 1.5% alginate, and 3% PEG-400 kD in deionized water or 4% elastin and 4% PLGA in HFIP. The protein-polymer solution of choice was loaded into a 3-mL syringe. The syringe was connected to non-conductive perfluoroalkoxy tubing, which was, in turn, connected to a 25 G needle. The collector plate was placed in a Styrofoam box and surrounded by adequate amounts of dry ice and ice to reach specific collector plate temperatures. The Styrofoam box was placed inside a repurposed cell culture incubator at 25° C. with a water pan to maintain humidity levels inside the chamber. The 25 G needle was connected to a high voltage power source (Gamma High Voltage Research, Ormond Beach, FL) and the collector plate to the electrical ground. The fabrication was conducted at 17 kV needle voltage, 10 μL/min syringe flow rate, and 15 cm needle tip-to-collector spacing for 1 hour. After 1 hour, the collector plate with the scaffold was immediately transferred to a lyophilizer (FreeZone freeze drier, Labconco, Kansas City, MI) and lyophilized for 2-3 hours.

The lyophilized elastin-alginate-PEG scaffolds were individually crosslinked in a 96-well plate with EDC and NHS crosslinking solution to crosslink the elastin and alginate chains, respectively. PEG-400 kD does not have pendant groups that can be crosslinked and dissolves away in water. The crosslinking solution was prepared by dissolving 1.48 mg EDC and 1.78 mg NHS per 100 μL of 95% ethanol per scaffold. Scaffolds were rocked in crosslinking solution at 45 rpm for 2 hours, followed by a series of graded ethanol washes with 95, 70, 50, and 0% ethanol with 1.5% $CaCl_2$ for 15 min each to wash away residual EDC and NHS, and simultaneously ionically crosslink the alginate chains. The scaffolds were then frozen at −80° C. and lyophilized for 4 hours.

Elastin-alginate nanofiber (NF) mats were fabricated by traditional electrospinning using 1% elastin, 1.5% alginate, and 3% PEG-400 kD in deionized water in a process similar to the cryoelectrospinning process described above, except that the collector plate was maintained at room temperature, and the relative humidity levels were maintained below 35% using dehumidified air input.

All scaffolds were UV sterilized, soaked in 70% ethanol for 30 min, washed with 0.9% NaCl for 10 min and then hydrated in cell culture medium with 10% fetal bovine serum (FBS) and 5% Antibiotic-Antimycotic Solution (penicillin-streptomycin-amphotericin B) overnight before cell culture.

Cell Culture

Mouse embryonic NIH 3T3 fibroblasts (See e.g., Jainchill J L, Aaronson S A, Todaro G J. Murine Sarcoma and Leukemia Viruses: Assay Using Clonal Lines of Contact-Inhibited Mouse Cells. *J Virol*. Published online 1969. doi:10.1128/jvi.4.5.549-553.1969) of passage 12-17 were maintained in DMEM (High Glucose) medium containing 10% FBS and 1% penicillin-streptomycin. The NIH 3T3 fibroblasts were subcultured on day 3 or 4 when they were 70-80% confluent. Salivary gland ductal epithelial SIMS cells (Laoide et al., Immortalised mouse submandibular epithelial cell lines retain polarised structural and functional properties. *J Cell Sci*. Published online 1996) were maintained in DMEM (high glucose) medium containing 10% FBS and 1% penicillin-streptomycin. SIMS cells were subcultured every 2 or 3 days when they were 80-95% confluent. Cells were incubated in a 37° C., 5% $CO_2$ humidified incubator.

Primary mesenchyme were isolated from embryonic day 16 (E16) submandibular salivary glands dissected from timed-pregnant CD-1 female *Mus musculus* ordered from Charles River Laboratories, as described previously. Hosseini et al., FGF2-dependent mesenchyme and laminin-111 are niche factors in salivary gland organoids. *J Cell Sci*. Published online 2018. doi:10.1242/jcs.208728; Hosseini et al., Generating Embryonic Salivary Gland Organoids. *Curr Protoc cell Biol*. 2019; 83(1):e76. doi:10.1002/CPCB.76. The primary E16 mesenchyme was separated away from the primary epithelium using enzymatic digestion in 1× collagenase/hyaluronidase and 1.6 U/ml of dispase II diluted in 1×PBS at 37° C. for 30 minutes. After digestion, the mesenchyme and epithelium were separated using gravity sedimentation. The epithelium was further strained away from the mesenchymal fraction using centrifugation at 10 g for 1 minute then filtered through 70 μm and 40 μm cell strainers. The enriched E16 mesenchyme was pelleted at 300 g for 8 minutes and the buffer was replaced using DMEM/F12 containing 10% FBS, 1% penicillin-streptomycin. The isolated primary E16 mesenchyme cells were cultured in DMEM/F12 medium supplemented with 10% FBS and 1% penicillin-streptomycin and incubated in a 37° C., 5% $CO_2$ humidified incubator for 3-4 days until 90-95% confluent. The primary E16 mesenchyme cells were subcultured for 1 or 2 passages.

Cell Culture on Scaffolds

Mouse embryonic NIH 3T3 fibroblasts (See e.g., Jainchill J L, Aaronson S A, Todaro G J. Murine Sarcoma and Leukemia Viruses: Assay Using Clonal Lines of Contact-Inhibited Mouse Cells. *J Virol*. Published online 1969. doi:10.1128/jvi.4.5.549-553.1969) and salivary gland ductal epithelial SIMS cells (See e.g., Laoide et al., Immortalised mouse submandibular epithelial cell lines retain polarised structural and functional properties. *J Cell Sci*. Published online 1996) were seeded at 75,000 cells/scaffold in 25 μL DMEM (high glucose) medium containing 10% FBS, 1% penicillin-streptomycin, and 25 mM $CaCl_2$ in ultra-low adhesion, polymer-coated, round-bottom, 96-well plates and incubated on a rotary shaker at 30 rpm for 2 hours to facilitate cell attachment to the scaffolds. Primary E16 mesenchyme cells were seeded in a similar fashion in DMEM/F12 medium supplemented with 10% FBS, 1% penicillin-streptomycin, and 25 mM $CaCl_2$. Cell culture media were supplemented with 25 mM $CaCl_2$, a concentration at which cell culture was not negatively impacted, to prevent rapid disintegration of the scaffold. After two hours, each well was supplemented with 175 μL of fresh medium, and the well plate was incubated with rotary shaking for another 22 hours to increase the cell attachment efficiency. Well plates were transferred onto a static surface 24 hours after cell seeding. Cells were cultured on scaffolds for up to 7 days.

For coculture of SIMS and NIH 3T3 fibroblasts on scaffolds, 50,000 NIH 3T3 cells were first seeded on the scaffold in a similar fashion as described above and grown for 2 days to provide stromal support and then 50,000 SIMS cells were seeded in a similar fashion as described above.

Immunocytochemistry and Confocal Imaging of Cell Culture Samples

Samples were fixed in 4% paraformaldehyde-0.25% glutaraldehyde in 5% (w/v) sucrose, 0.6×PBS for 15 minutes, permeabilized with 0.1% Triton X-100 in 1×PBS for 15 min, blocked with 20% donkey serum-3% bovine serum albumin in wash buffer (0.9% NaCl-50 mM $CaCl_2$ in deionized water) for 2 hours at room temperature, incubated with primary antibodies at 4° C. overnight, followed by incubation with DAPI and secondary antibodies at room temperature for 2 hours. NIH 3T3 cells were immunostained for vimentin and α-SMA and SIMS cells were stained for E-cadherin and ZO-1. All cells were co-stained with DAPI to reveal the nuclei within the total cell population. Rhodamine-phalloidin was used to reveal cytoskeletal F-actin. Antibody combinations and concentrations used are detailed in FIG. 6. Samples were then mounted with Fluoro-Gel mounting medium for imaging. Confocal imaging was performed using a Leica SP5 confocal laser scanning microscope (Leica Microsystems, Mannheim, Germany).

Indentation Testing

Mechanical properties including indentation modulus and sample viscoelastic relaxation time were determined using a micro-indentation tester (CellScale Biomaterials Testing, Ontario, Canada) as described previously (Kulwatno J, Gearhart J, Gong X, et al. Growth of tumor emboli within a vessel model reveals dependence on the magnitude of mechanical constraint. *Integr Biol.* 2021; 13(1): 1-16. doi: 10.1093/INTBIO/ZYAA024). Briefly, samples were glued to a glass slide, immersed in a PBS bath, and then indented/loaded using a 3-mm spherical bead attached to a cantilever. Samples were deformed at a constant displacement rate of 4 μm/s. Upon reaching an indentation depth of 10% of the initial sample height, samples were held in their deformed state for up to 350 s (hold phase) and then allowed to relax by removal of the indentation force. Force (F) and displacement (δ) of the cantilever tip were measured as a function of time. The indentation modulus was determined as the elastic modulus ($E_i$) from the Hertz model by fitting the data from the loading region of the force-displacement curve measured by indentation to the Hertz contact equation for a spherical indenter $$\left( F = \frac{4}{3} \frac{E_i R^{\frac{1}{2}}}{1 - \nu^2} \delta^{\frac{3}{2}} \right).$$

Here, R is the radius of the spherical indenter (1.5 mm) and ν is the Poisson ratio of the sample (set at 0.49 to represent elastic, almost incompressible hydrogel materials (See e.g., Castilho M, Hochleitner G, Wilson W, et al. Mechanical behavior of a soft hydrogel reinforced with three-dimensional printed microfibre scaffolds. *Sci Rep.* Published online 2018. doi:10.1038/s41598-018-19502-y)). The matrix relaxation half time is a measure of the viscoelastic nature of a sample and is evaluated by its stress relaxation response. The stress relaxation response is observed during the hold phase of the force-time curve where the sample relaxes towards an equilibrium state, and the loading force required to maintain a constant strain reduces and reaches a steady-state value. The relaxation half time was computed from the stress relaxation response of the samples as the amount of time required for the stress/loading force to reach half of its peak value while maintaining a constant strain equal to 10% of the initial sample height.

LIVE/DEAD Assay

Cell-scaffold constructs were incubated with 0.2 M calcein-AM and 0.4 M ethidium homodimer for 25 min at 37° C. and imaged using Leica SP5 confocal laser scanning microscope (Leica Microsystems, Mannheim, Germany) to reveal live cells in green and dead cells in red fluorescence. Quantitative analysis of live and dead cells was performed using ImageJ (See e.g., J S, I A-C, E F, et al. Fiji: an open-source platform for biological-image analysis. *Nat Methods.* 2012; 9(7):676-682. doi:10.1038/NMETH.2019).

The images were opened in ImageJ, and two separate images were obtained for live and dead cells by using the 'Split Channels' feature in Image>Color menu. The threshold of each image was adjusted. The numbers of live and dead cells were quantified by using the 'analyze particles' feature under the Analyze menu, setting the particle size range to 10-3000 μm², circularity to '0-1', and excluding particles on edges.

Cell Proliferation Assay

Cell-Titer Glo® 3D Viability Assay was performed to evaluate cell proliferation at 1, 4, and 7 days after cell seeding onto scaffolds per manufacturer's instruction. Briefly, cell-scaffold constructs in the 96-well plate and Cell-Titer Glo® 3D Viability Assay reagent were equilibrated to room temperature for 30 min. After samples were gently washed with 1×PBS, 75 μL of cell culture media and 75 μL of CellTiter-Glo 3D reagent was added. The contents of the well were vigorously pipetted up and down to disintegrate the scaffold and release the cells. The well plate was then shaken on a rotary shaker at 120 rpm, at 37° C. for 15 min, and then incubated at room temperature for 30 min to stabilize the reaction. 50 μL of the reaction mixture from each well was transferred into a 96-well white luminescence plate, diluted with 50 μL of cell culture media, and mixed well. Luminescence was determined using a Tecan Infinite 200 plate reader (Tecan US, Morrisville, NC).

Scaffold Pore Size Analysis Using ImageJ

SEM images of cryoelectrospun scaffolds and fluorescence microscopy images of decellularized salivary glands were analyzed for pore size using ImageJ's 'analyze particles' feature. The threshold for each image was adjusted (Image>Adjust>Threshold) to identify the pores from the scaffold background. Under the 'Analyze', 'Set Measurements' menu, the 'fit ellipse' feature was selected to identify the major and minor axis diameter of the pores. Pore size was analyzed by using the 'analyze particles' feature by setting the particle size range to 10-3000 μm², circularity to '0-1', and excluding particles on edges.

Statistical Analysis

Data are presented as mean±standard deviation. All in vitro cell culture and material characterization experiments were performed in triplicate, unless otherwise indicated. One-way ANOVA followed by Tukey's post hoc test was performed using GraphPad Prism 9.2.0. p<0.05 was considered significant.

Results

Figure 7A:
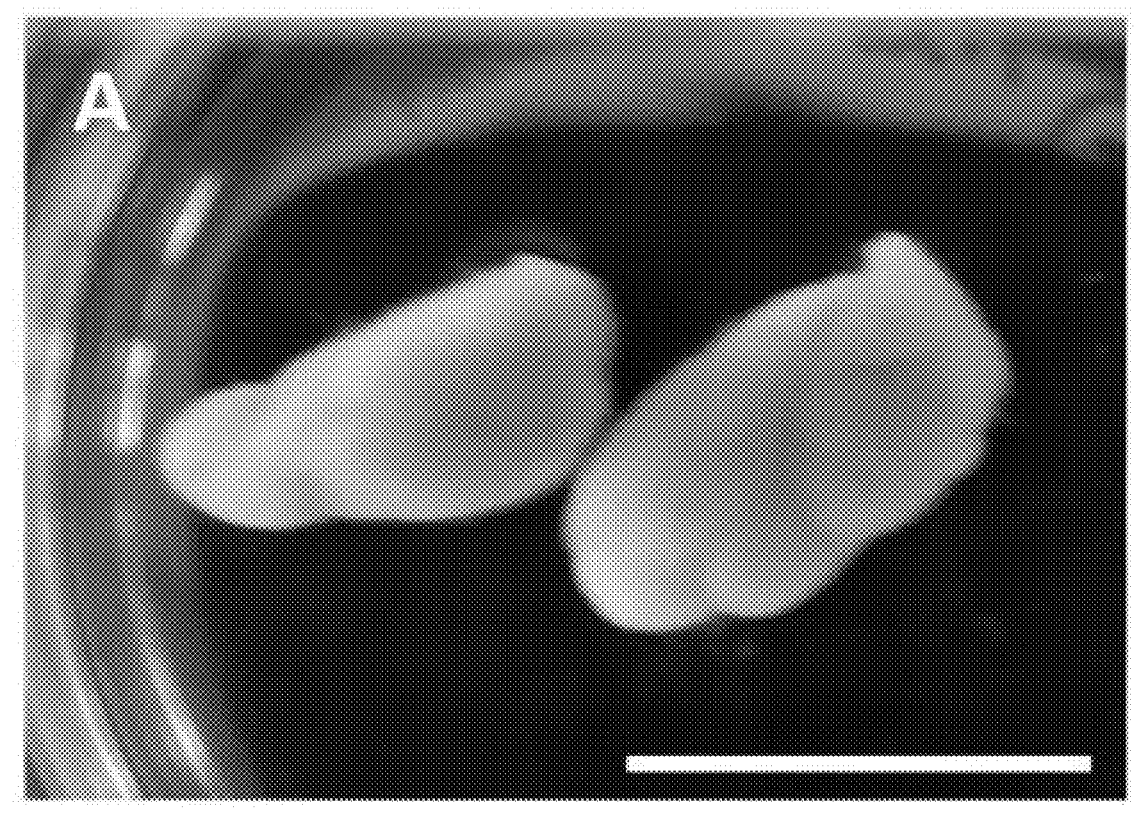
FIGS. 7A-7D depict images of mouse adult salivary glands before and after decellularization.
Figure 7B:
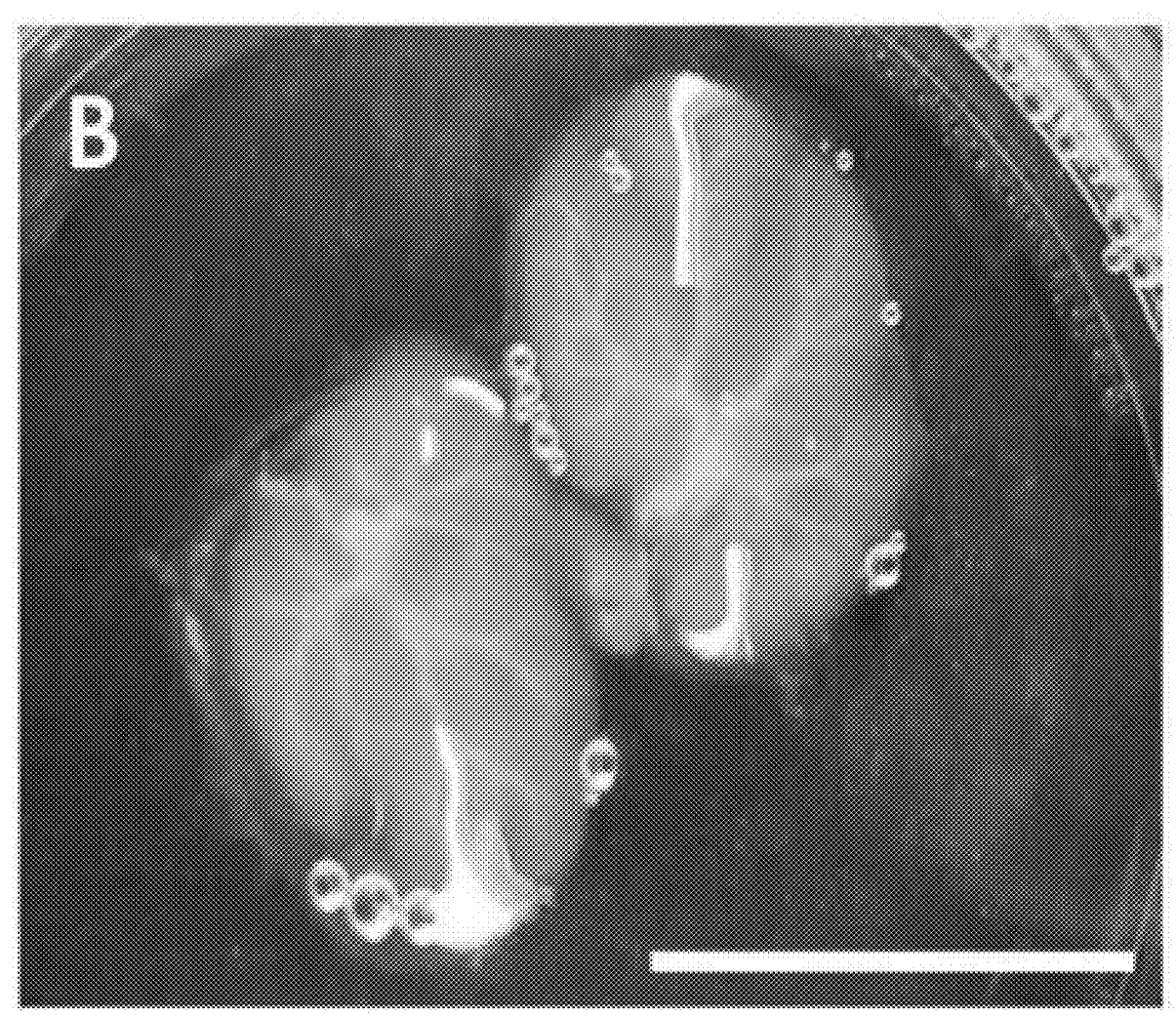
Figure 7C:
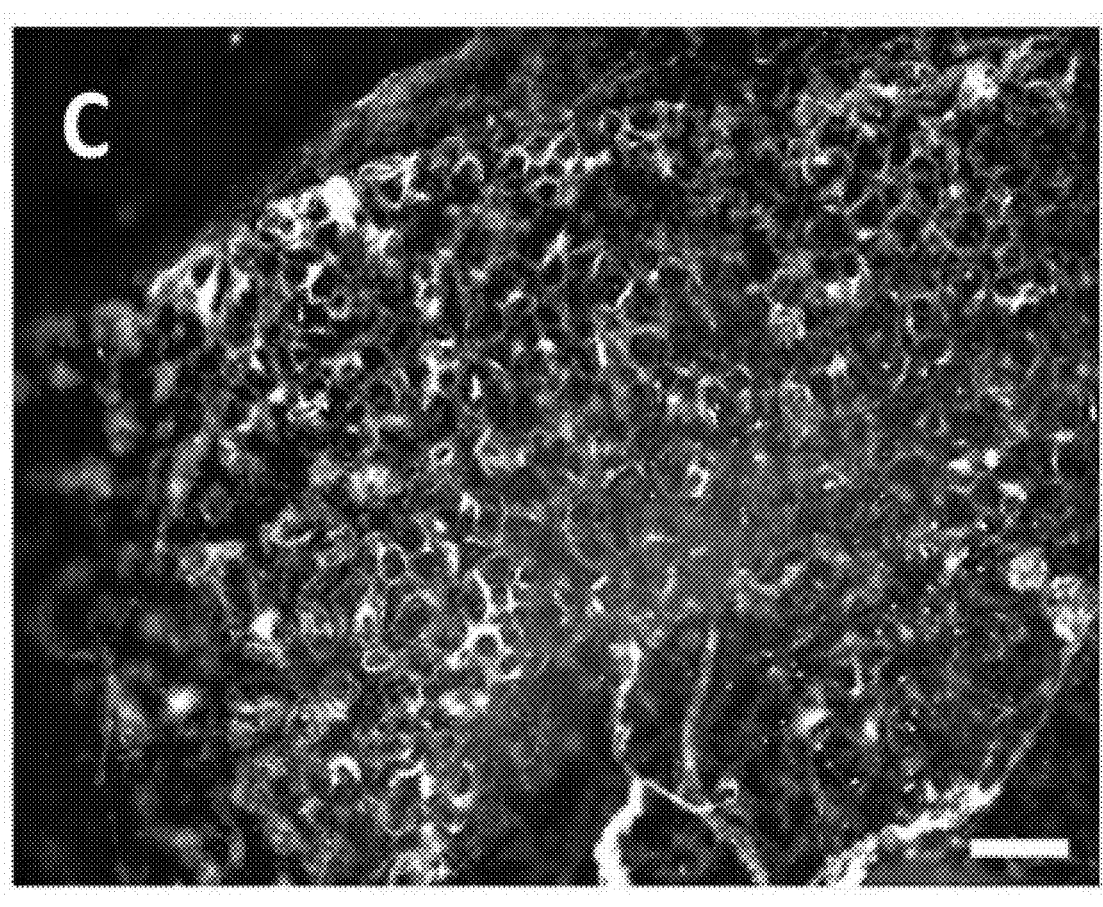

Decellularized Salivary Gland ECM Exhibits Honeycomb-Like Topography with Minimal Backbone To fabricate matrices with physiologically relevant ECM topography, the native ECM topography was first examined in decellularized female adult mouse submandibular salivary glands using both immunofluorescent imaging and SEM. Decellularized adult mouse submandibular salivary glands were formed following a modified decellularization protocol developed for the lung, a similarly structured organ (See e.g., Grey J F E, Campbell-Ritchie A, Everitt N M, Fezovich A J, Wheatley S P. The use of decellularised animal tissue to study disseminating cancer cells. *J Cell Sci.* Published online 2019. doi:10.1242/jcs.219907). An additional DNase treatment was necessary to remove lingering DNA adhering to the ECM. (See e.g., FIGS. 7A-7D). FIGS. 7A-7D depict images of mouse adult salivary glands before and after decellularization. Bench top images of salivary glands (See FIG. 7A) pre-decellularization and (FIG. 7B) post-decellularization. FIG. 7C depicts decellularized sali-

Figure 7D:
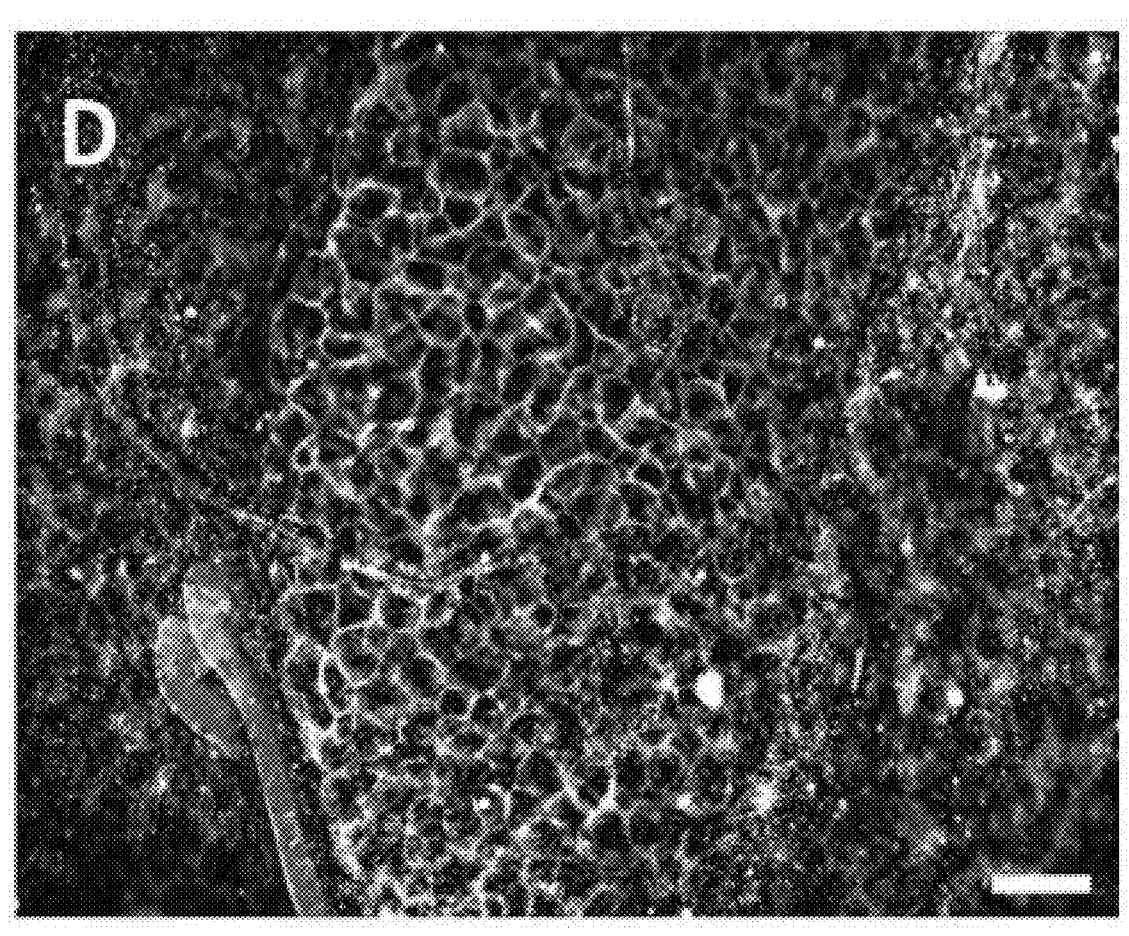

41 vary glands and FIG. 7D depicts decellularized salivary glands treated with DNase and both stained with DAPI (blue) revealing that (FIG. 7C) residual DNA sticks to the matrix and (FIG. 7D) DNase treatment effectively removes any residual DNA from the matrix. (FIGS. 7A, B) Scale bar=10 mm. (FIGS. 7C, D) Scale bar=100 µm.

SEM imaging of the decellularized salivary glands (FIG. 8A) showed a fibrous basement membrane folded as lobes to support acinar epithelium (FIG. 8B), fibers or fiber bundles supporting ductal epithelium (FIG. 8C) and tethering adjacent acinar epithelium (FIG. 8D). Stromal ECM is expected to surround epithelial basement membrane; however, it was not abundantly visible, possibly due to removal of GAGs, the predominant soluble ECM components, during the decellularization process (FIG. 8E).

Further, stromal content is higher during morphogenesis but is significantly reduced in adult tissue (See e.g., Cintron C, Covington H, Kublin C L. Morphogenesis of rabbit corneal stroma. *Investig Ophthalmol Vis Sci.* Published online 1983). To further reveal ECM structure, the decellularized salivary glands were immunostained for predominant ECM proteins collagen I, collagen IV, and heparan sulfate proteoglycan (perlecan) and viewed their arrangement by fluorescence microscopy. The ECM proteins were generally arranged in a honeycomb pattern, forming 10-30 µm pores with delicate winding fibers (FIG. 8F). To evaluate existing scaffolds as suitable scaffolds to support mesenchymal or stromal cells, the topography of the decellularized salivary gland ECM was compared with current ECM mimics including nanofiber mats, sponges, hydrogels, or hydrogel-nanofiber composites, as shown in FIG. 9 (showing a comparison of physical and mechanical properties between current state of the art soft tissue scaffolds and decellularized salivary gland ECM (See also Annabel B, Michelle O. Fracture behaviour of nanofibrous hydrogel composites. *Front Bioeng Biotechnol.* 2016; 4. doi:10.3389/CONF.FBIOE.2016.01.00045/2893/10TH_WORLD_BIO-MATERIALS_CONGRESS/ALL_EVENTS/EVENT_AB-STRACT). None of these currently available ECM-mimetic scaffolds truly recapitulate the topography and viscoelasticity of the native ECM of adult mouse salivary glands.

More specifically, FIGS. 8A-8E depict salivary gland ECM topography analyses. Scanning electron microscopy images of a cross-section of decellularized adult mouse salivary glan. Scale bar=20 micrometers. FIG. 8A depicts a zoomed out image of overall overall cross-section depicting the acinar and ductal regions. FIG. 8B depicts basement membrane of acinar epithelium. FIG. 8C depicts acinar clusters. FIG. 8D depicts interstitial region between lobes. FIG. 8E depicts stromal region. FIG. 8F depicts immunocytochemistry of ECM protein expression in decellularized adult mouse salivary gland matrices showing honeycomb arrangement of ECM. Decellularized ECM immunostained with collagen I (COL-I, green), Collagen IV (COL-IV, red), and perlecan (grey) and merged (yellow). Scale bar=20 µm. Cryoelectrospinning of Elastin-Alginate with Water as Solvent Produces 3D Fibrous Porous Scaffolds The choice of ECM proteins for scaffold fabrication is crucial since there are ~300 ECM core proteins (See e.g., Hynes R O, Naba A. Overview of the matrisome—An inventory of extracellular matrix constituents and functions. *Cold Spring Harb Perspect Biol.* 2012; 4(1):1-16. doi: 10.1101/cshperspect.a004903), each providing unique biochemical and/or mechanical triggers to cells in the matrix. Of the 300 ECM proteins, collagen, elastin, and fibronectin have well-characterized functions in soft tissue ECM (See e.g., Frantz C, Stewart K M, Weaver V M. The extracellular matrix at a glance. *J Cell Sci.* 2010; 123(24):4195-4200. doi:10.1242/jcs.023820). Since morphogenetic environments require a pliable matrix for constant remodeling, and excess collagen increases the stiffness of the matrix, triggering a fibrotic phenotype in cells (See e.g., Marinković A, Liu F, Tschumperlin D J. Matrices of physiologic stiffness potently inactivate idiopathic pulmonary fibrosis fibroblasts. *Am J Respir Cell Mol Biol.* 2013; 48(4):422-430. doi: 10.1165/rcmb.2012-0335OC), only elastin was used, a compliant protein, and alginate, a viscous hydrogel as the biomaterials for fabrication, to emulate the viscoelastic nature of soft tissue ECM. Serum in the cell culture medium was relied on for our fibronectin source. To eliminate the use of toxic solvents for fabrication, water was used as the solvent, as both alginate and elastin can be dissolved in water. To delineate the effects of aqueous solvent on cryoelectrospinning, cryoelectrospun scaffolds fabricated using an aqueous or an organic solvent were compared. Prior studies showed that traditional electrospinning of 4% elastin-4% PLGA in the organic solvent HFIP produced 2.5D mats with nanofibrous topography and improved elasticity over PLGA alone (See e.g., Foraida Z I, Kamaldinov T, Nelson D A, Larsen M, Castracane J. Elastin-PLGA hybrid electrospun nanofiber scaffolds for salivary epithelial cell self-organization and polarization. *Acta Biomater.* 2017; 62:116-127. doi:10.1016/j.actbio.2017.08.009; Soscia D A, Sequeira S J, Schramm R A, et al. Salivary gland cell differentiation and organization on micropatterned PLGA nanofiber craters. *Biomaterials.* Published online 2013. doi: 10.1016/j.biomaterials.2013.05.061; and Jean-Gilles R, Soscia D, Sequeira S, et al. Novel modeling approach to generate a polymeric nanofiber scaffold for salivary gland cells. *J Nanotechnol Eng Med.* Published online 2010. doi:10.1115/1.4001744). Solutions for electrospinning require long-chain polymers to facilitate chain entanglement, which permits the deposition of fibers instead of microdroplets (See e.g., Pillay V, Dott C, Choonara Y E, et al. A review of the effect of processing variables on the fabrication of electrospun nanofibers for drug delivery applications. *J Nanomater.* Published online 2013. doi:10.1155/2013/789289; Mirjalili M, Zohoori S. Review for application of electrospinning and electrospun nanofibers technology in textile industry. *J Nanostructure Chem.* Published online 2016. doi:10.1007/s40097-016-0189-y; and Motamedi A S, Mirzadeh H, Hajiesmaeilbaigi F, Bagheri-Khoulenjani S, Shokrgozar M. Effect of electrospinning parameters on morphological properties of PVDF nanofibrous scaffolds. *Prog Biomater.* Published online 2017. doi:10.1007/s40204-017-0071-0). While PLGA was used for this purpose in previous work, PLGA also increases the stiffness of the scaffolds into the MPa range. Hence, PEG-400 kD was included to the 1% elastin-1.5% alginate solution at a concentration of 3% wt/v in water, to both facilitate chain entanglement and maintain the stiffness of the scaffolds low in the sub-kPa range. Cryoelectrospun scaffolds fabricated using 4% elastin-4% PLGA in the organic solvent HFIP were compared with ones fabricated using 1% elastin-1.5% alginate-3% PEG in water, to analyze the effects of an aqueous solvent. The results showed that the elastin-PLGA cryoelectrospun scaffolds were very dense (FIG. 10A, 10B), and did not emulate the honeycomb-like, porous topography of salivary gland ECM (see FIG. 8F). In contrast, it was observed that cryoelectrospinning of elastin-alginate-PEG in water produced a taller, more porous, 3D scaffold when compared with elastin-PLGA electrospun in HFIP for the same fabrication duration (FIG. 10C vs. 10A). Further, it was observed that at specific process conditions (described herein), the aqueous solvent facilitated the fabrication of scaffolds with honeycomb topography and a minimal fibrous backbone (FIGS. 10D, 10E top left panel). The backbone of the cryoelectrospun scaffolds with honeycomb topography had some inherent surface roughness (See e.g., FIG. 11 depicting a SEM image showing surface roughness of the backbone of elastin-alginate honeycomb cryoelectrospun scaffolds (CES-H). Scale bar=2 μm) that could facilitate cell attachment. Functionalized PEG-400 kD was attempted with carboxyl groups for crosslinking since PEG is a widely used hydrogel material; however, the length of the PEG polymer was a deterrent and prevented functionalization (data not shown). Therefore, PEG-400 kD was used solely for the purpose of increasing the electrospinnability of elastin-alginate solution. The PEG-400D dissolved away in water post EDC/NHS crosslinking due to the lack of cross-linkable pendant groups, yielding an elastin-alginate scaffold.

Figure 10A:
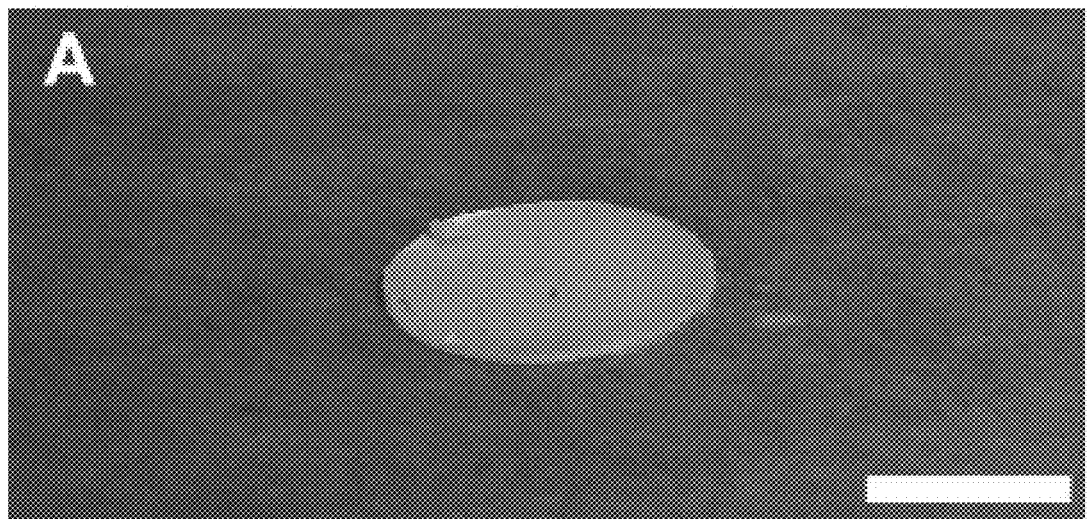
FIGS. 10A-10E are images depicting the effects of solvent on topography and 3D growth of cryoelectrospun scaffolds.
Figure 10B:
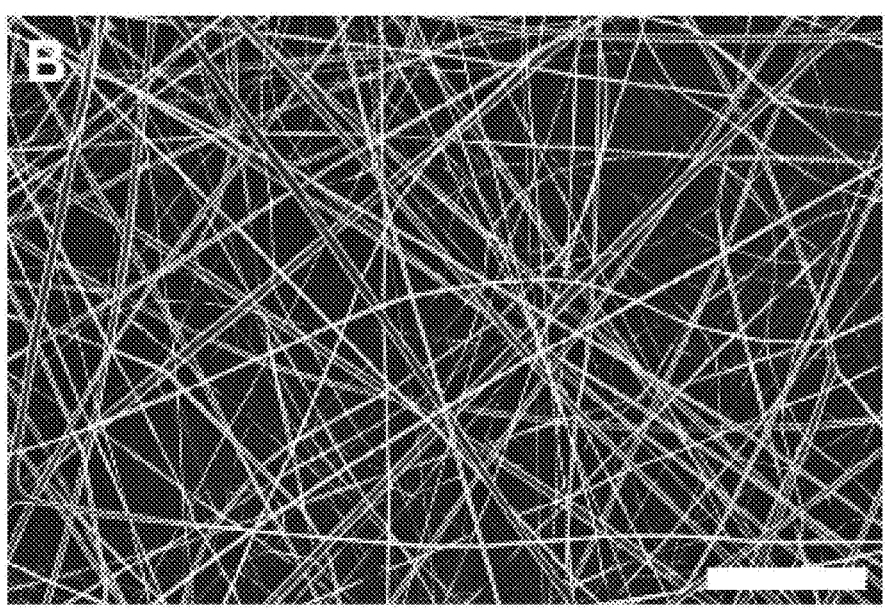
Figure 10C:
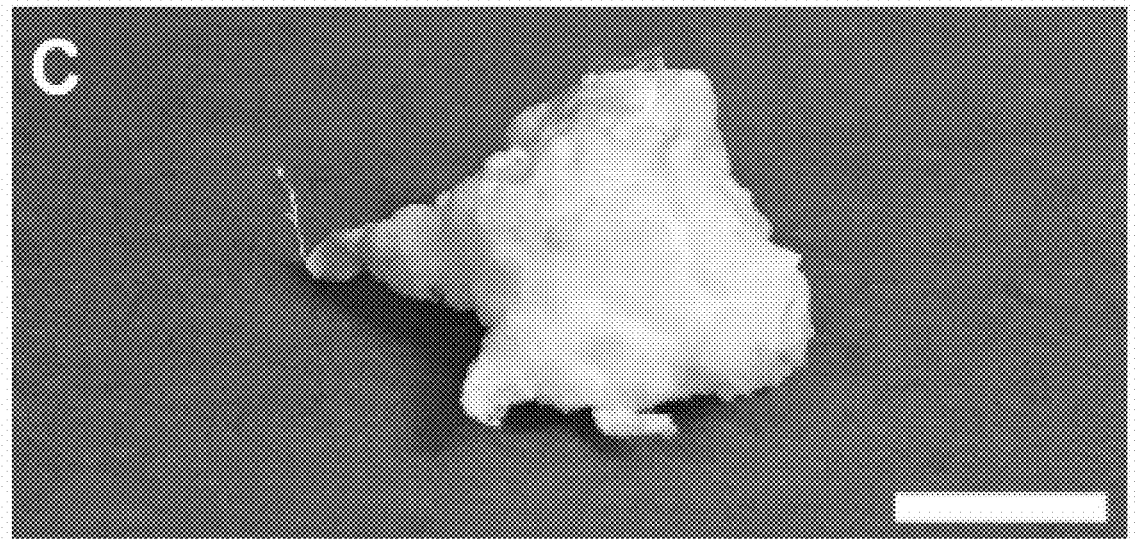
Figure 10D:
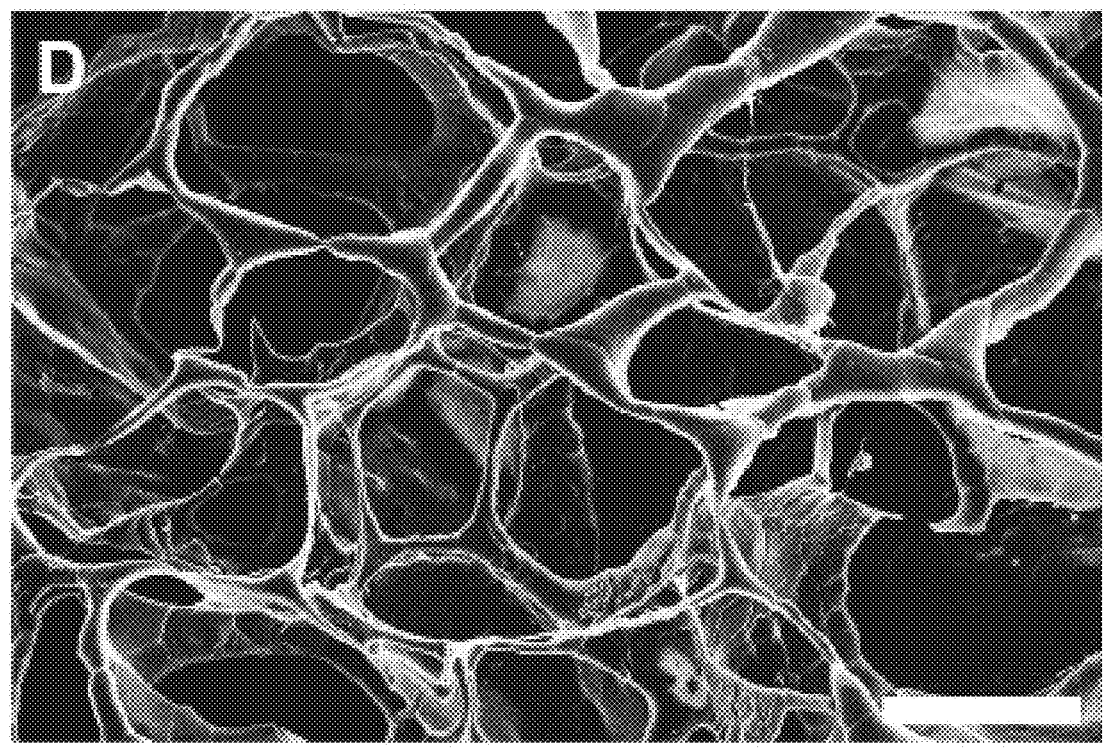

More specifically, FIGS. 10A-10E depict effects of solvent on topography and 3D growth of cryoelectrospun scaffolds. FIGS. 10A and 10B depict 2.5D Elastin-PLGA nanofibers fabricated with organic solvent HFIP. FIGS. 10C and 10D depict 3D Elastin-Alginate-PEG cryoelectrospun sponges fabricated with water as solvent. Water as solvent allowing 3D growth of cryogenically electrospun scaffolds with honeycomb topography, higher porosity, and microscale interconnected pores. FIGS. 10A and 10C depict bench top photos. Scale bar=5 mm. FIGS. 10B and 10D) SEM images. Scale bar=10 μm. E) Effect of process parameters on scaffold topography. Scale bar=10 μm. Humidity >35% and air temperature <2° C. promoting honeycomb topography (top left panel). Other combinations promoting fibrous topography. Collector plate temperatures between −35 and −10° C. promoting homogenous growth in X, Y, and Z dimensions.

Figure 10E:
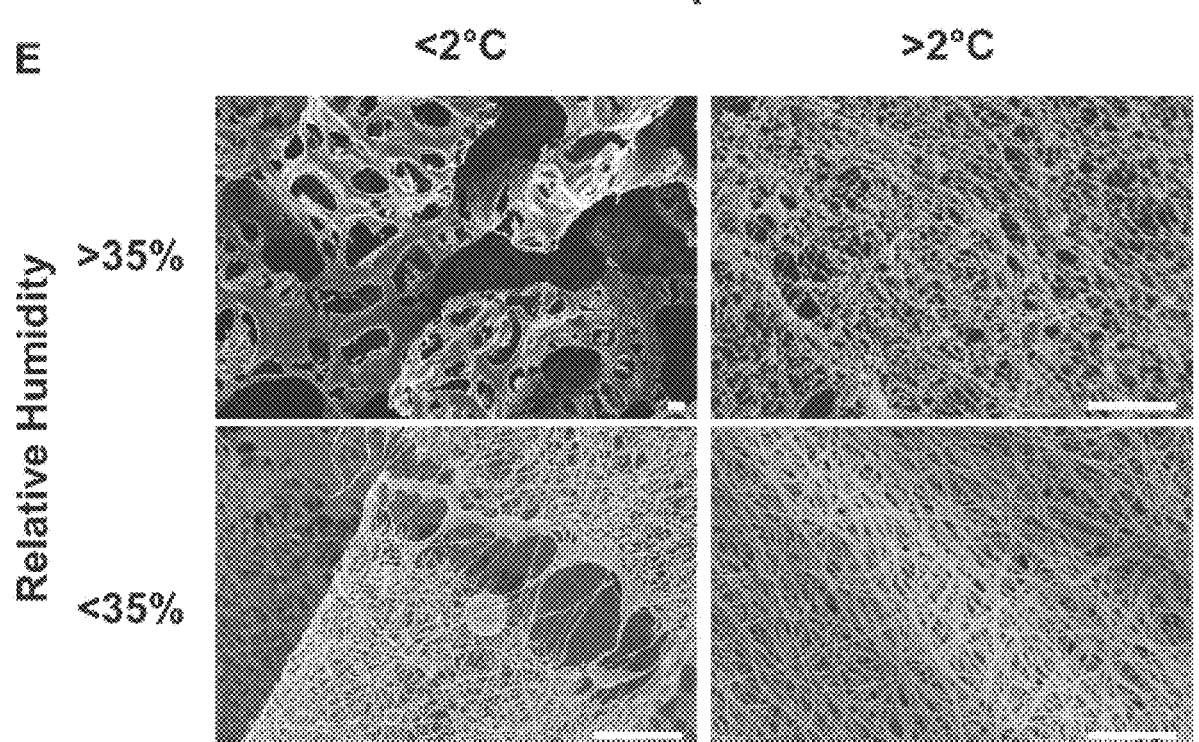
Figure 11:
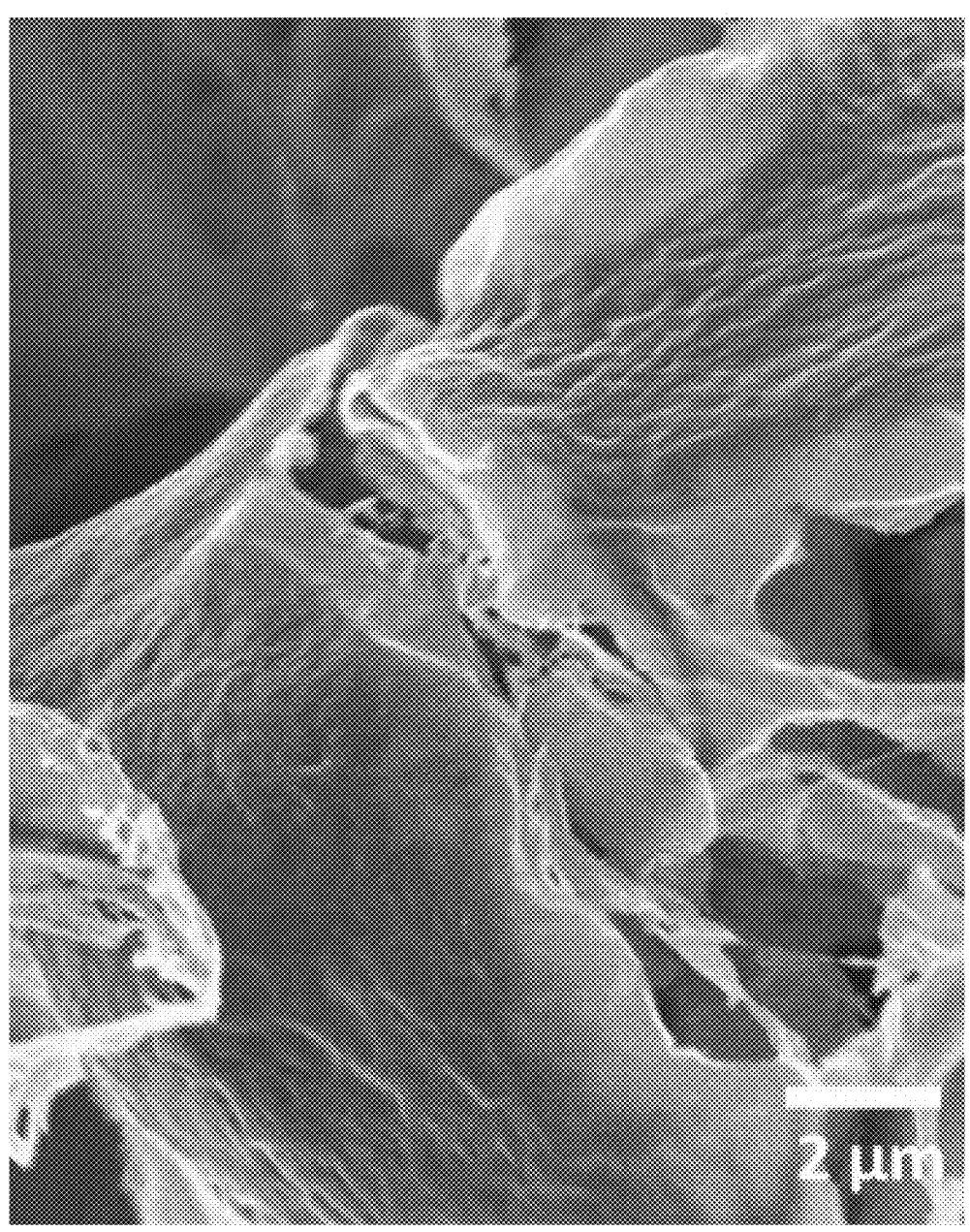
FIG. 11 depicts a SEM image showing surface roughness of the backbone of elastin-alginate honeycomb cryoelectrospun scaffolds (CES-H). Scale bar=2 μm.

High Humidity and Low Air Temperatures Promote Honeycomb Topography in Cryoelectrospun Scaffolds To delineate the effects of collector plate temperature, chamber relative humidity, and air temperature on CES topography, two parameters were maintained as a constant, while modulating the third parameter. Atmospheric conditions had a substantial impact on the topography of the scaffolds by altering ice nucleation based on relative humidity levels in the electrospinning chamber. Collector plate temperature could also potentially impact scaffold growth and topography by affecting the rate of ice nucleation. The air temperature and humidity levels at collector plate temperatures above −35° C. were independently modulated. It was observed that collector plate temperatures between −35 and −10° C. permitted homogenous scaffold growth (See e.g. FIG. 10E), whereas air temperature and humidity affected the topography of these scaffolds. At collector plate temperatures ranging between −35 and −10° C., when the air temperature was >2° C., irrespective of the relative humidity levels, the resulting scaffolds had fibrous topography (fibrous CES) (FIG. 10E, right panels), whereas when the air temperature was between −10 and 2° C. and relative humidity levels >35%, the scaffolds had honeycomb topography (honeycomb CES) (FIG. 10E, top left panel). Temperatures lower than −35° C. resulted in increased ice nucleation in the Z dimension instead of homogenous growth in the X, Y, and Z dimensions, frequently causing the scaffold to collapse onto itself (FIG. 12A) and showing heterogeneous scaffold growth (FIG. 12B). Therefore, optimal conditions were defined as higher collector plate temperatures (between −35 and −10° C.), air temperatures between −10 and 2° C., and a relative humidity >35%.

Figure 12A:
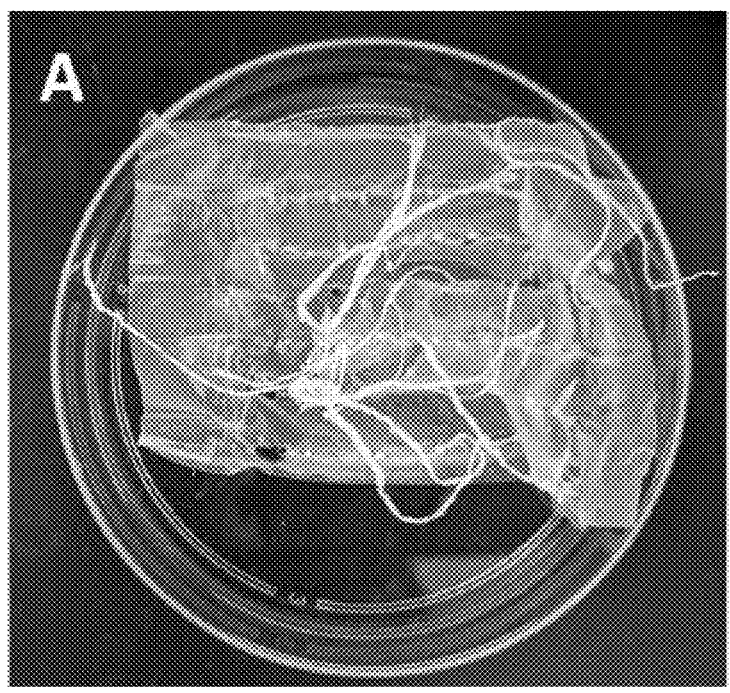
FIGS. 12A and 12B depict scaffolds cryoelectrospun at collector plate temperature <−35° C.
Figure 12B:
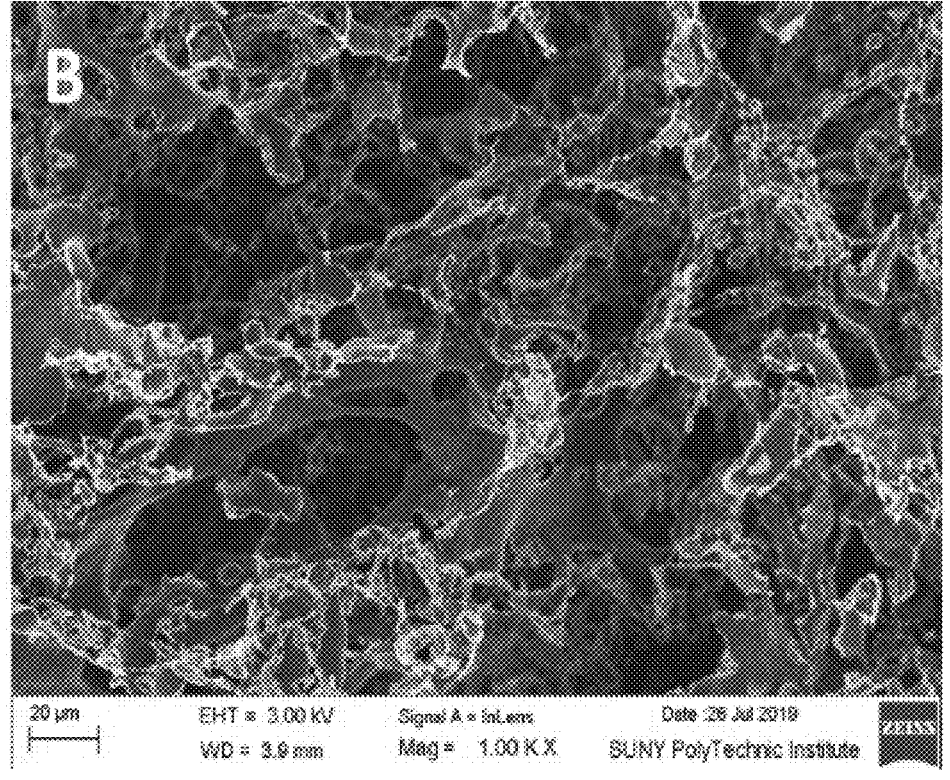

More specifically, FIGS. 12A and 12B depict scaffolds cryoelectrospun at collector plate temperature <−35° C. The scaffolds having heterogeneous growth in X, Y, Z dimensions, often growing only in Z dimension, and collapsing upon lyophilization. FIG. 12A depicts a bench top image of collapsed scaffold. FIG. 12B depicts a SEM image of scaffold with heterogeneous growth. Scale bar=20 μm.

Figure 13A:
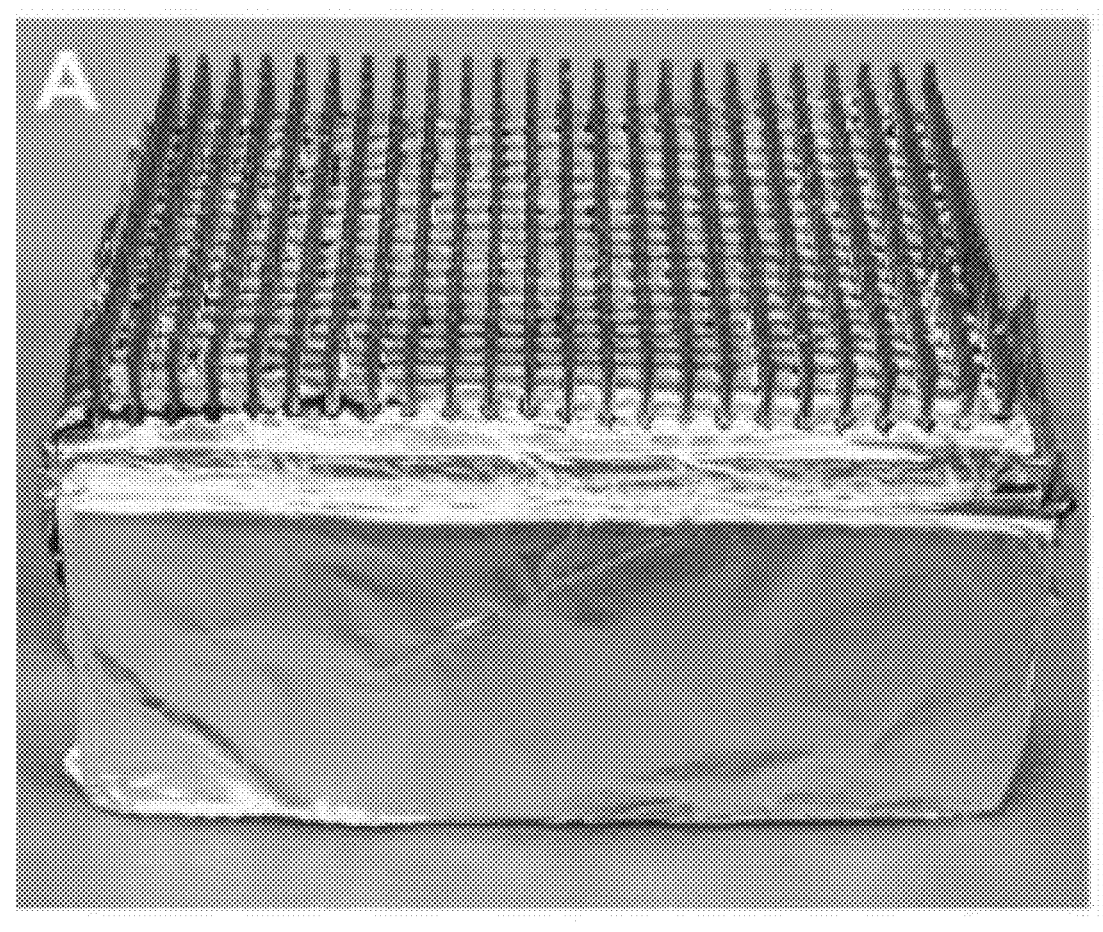
FIGS. 13A-13D depict cryoelectrospinning onto the 3 mm probe-array collector.
Figure 13B:
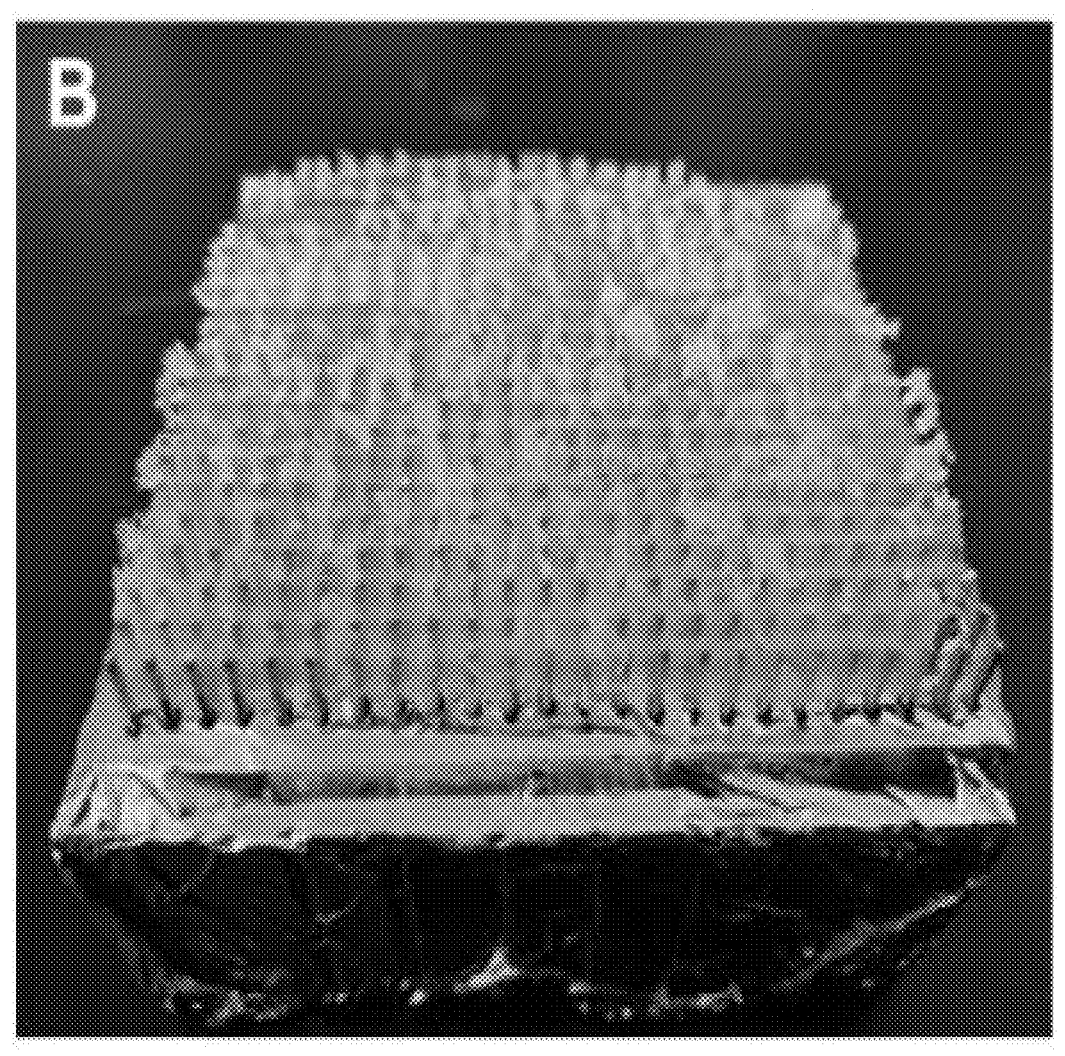
Figure 13C:
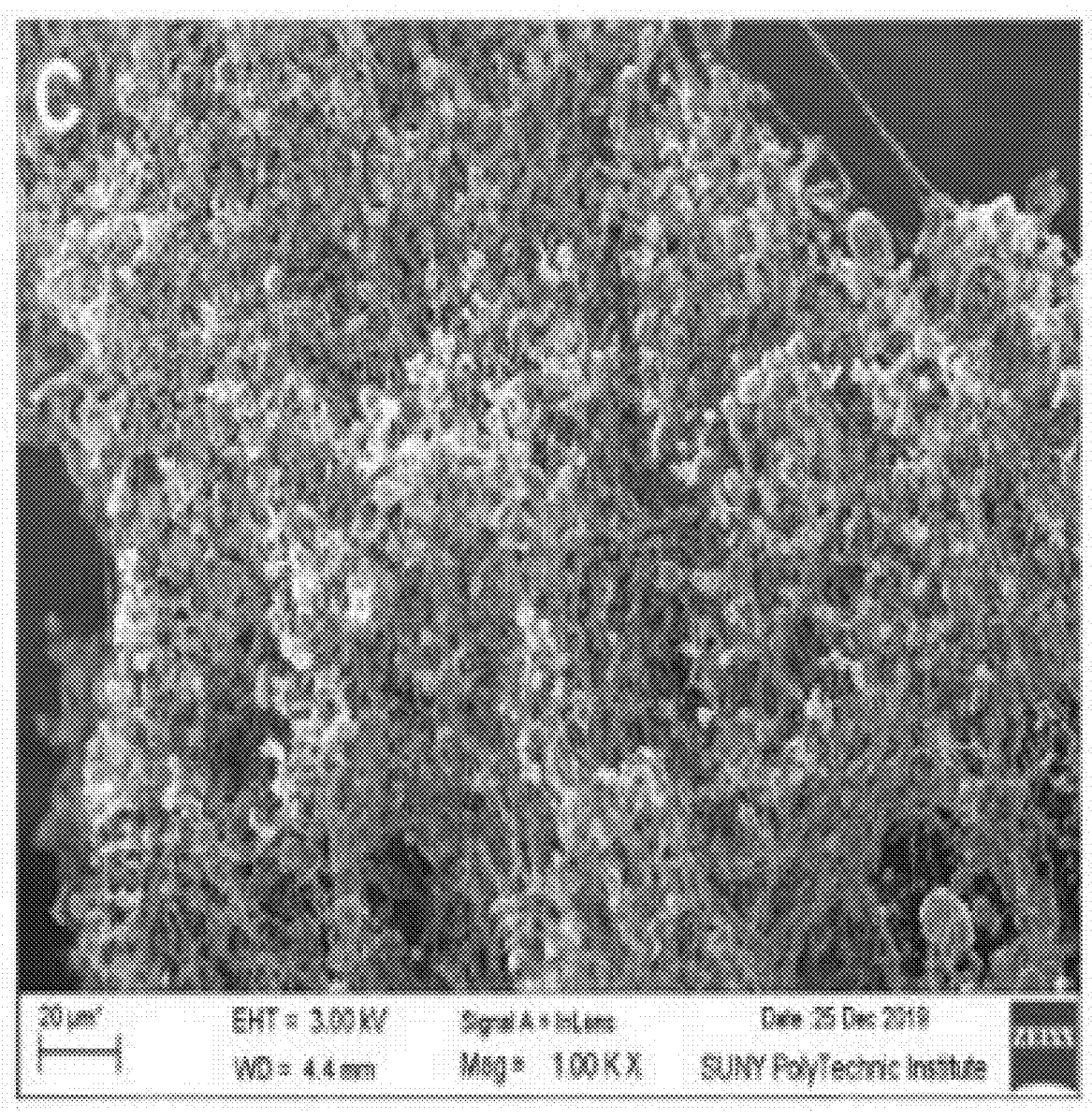
Figure 13D:
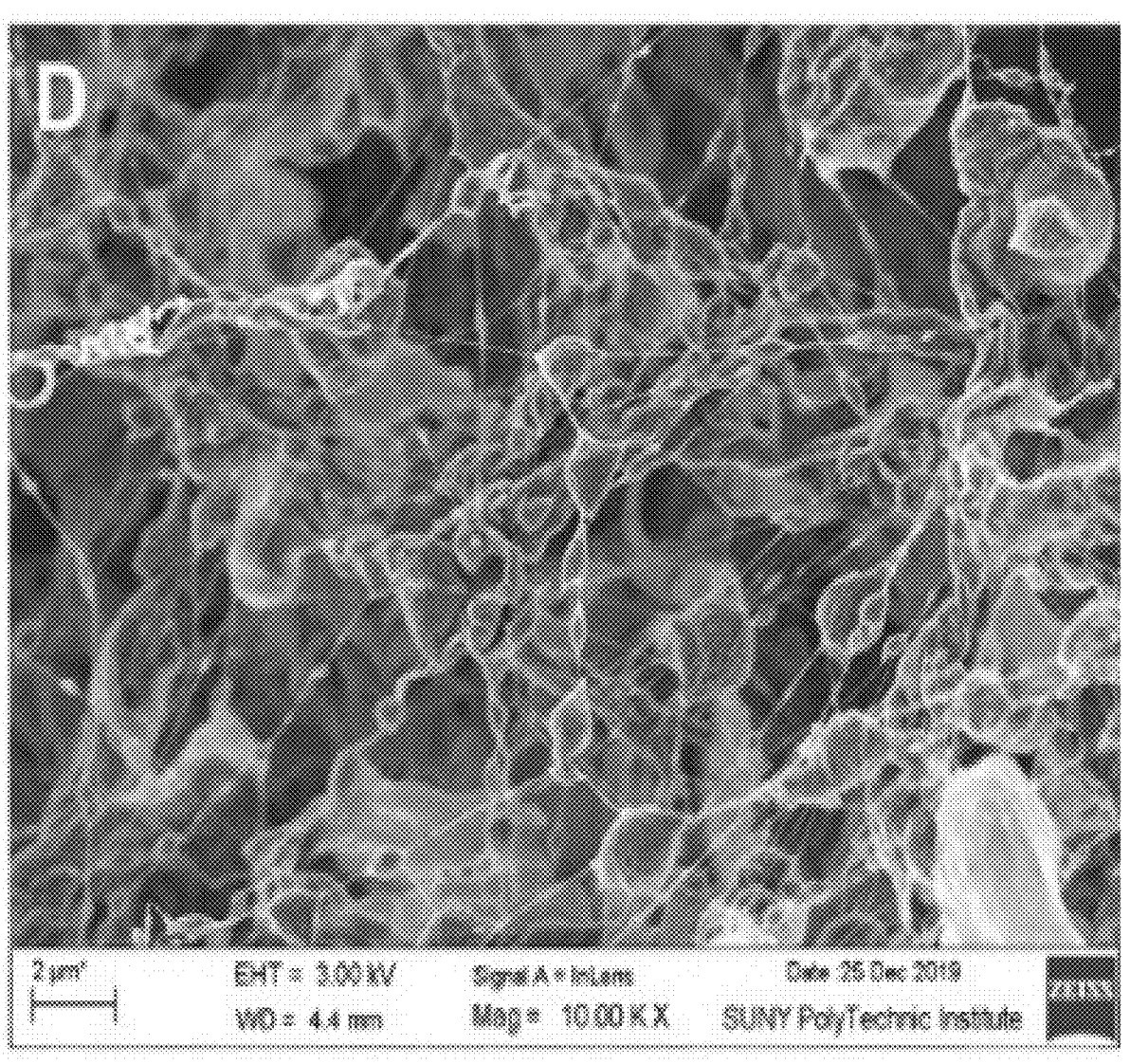
Figure 14A:
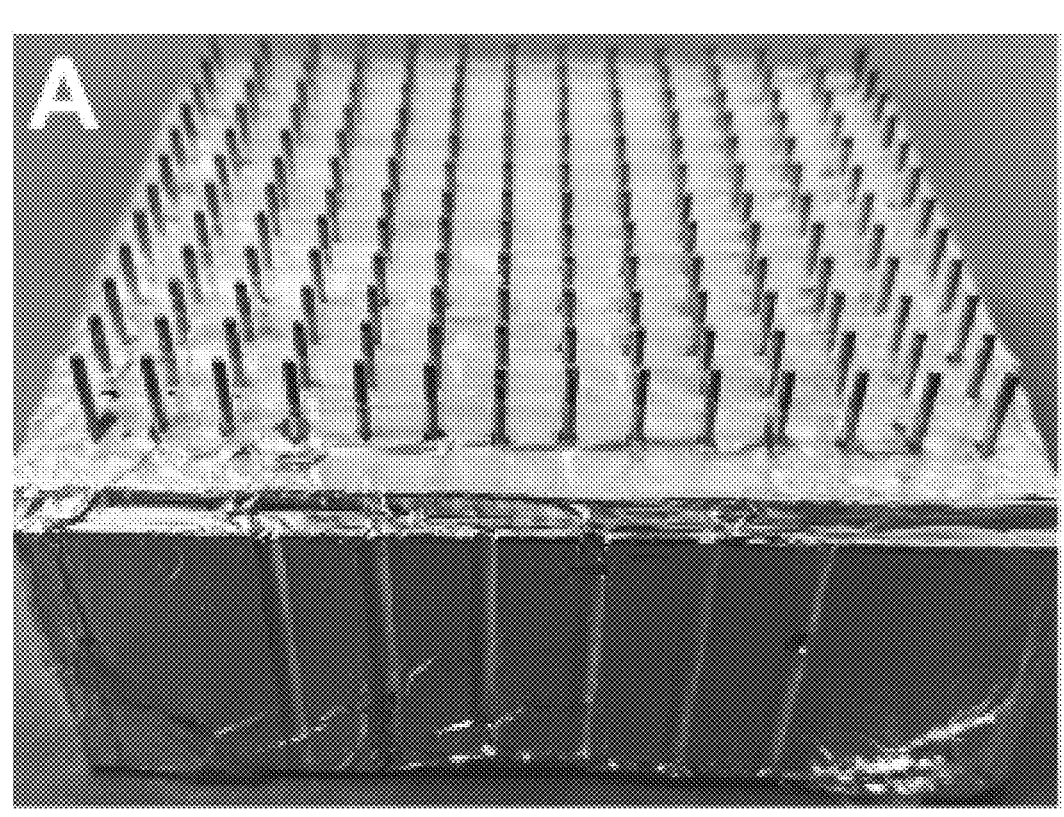

Probe-Array Collector Plate Geometry Promotes Homogenous and Distributed Growth of Cryoelectrospun Scaffolds Reproducibility and yield of a fabrication process are important factors affecting the scalability of scaffold production in future applications. To obtain homogenous, distributed scaffold growth, different collector plate geometries were explored. It was hypothesized that homogenous distribution of the electric field over the collector plate could increase the yield of cryoelectrospun scaffolds. Hence, a metallic probe-array collector plate was designed, which increases the surface area in contact with the electrical ground, and compared scaffold growth on metallic probe-arrays with 3-mm (FIGS. 13A-13D) and 5-mm probe distancing (FIG. 14A) with that on a flat metal plate (FIG. 14B). Using COMSOL Multiphysics software, the electric field potential was simulated on the surface of the two types of collector plates used and observed the electric field potential to be focused on the probes (FIG. 14C) and to be approximately uniform over all the probes with a value of ~800 V (FIG. 14E), whereas the electric field potential was distributed over the flat plate (FIG. 14D) and varied across the working surface area from ~300 to ~800 V (FIG. 14F). This uniform potential over the probe-array collector plate allowed similar sized scaffolds with the same topography to grow over most of the probes and hence, an overall homogenous scaffold growth over the probes (FIG. 14G) compared to that over the surface of the flat collector (FIG. 14H). Furthermore, the 5-mm probe array permitted a consistent yield of ~100 scaffolds/run. The surface topography of these scaffolds remained relatively unaffected between the flat plate and 5-mm probe-array collector upon cryoelectrospinning at similar process parameters (FIG. 14I, 14J), demonstrating the capacity of the probe-array collector plate to homogenously generate 3D elastin-alginate scaffolds with a high yield. While the 3-mm probe-array collector allowed relatively homogenous growth of scaffolds in comparison with the flat collector, these scaffolds were too small to handle and difficult to remove from the collector. Furthermore, scaffolds fabricated on the 3-mm probe-array collector had mostly fibrous topography instead of honeycomb topography under similar process parameters (FIGS. 13C and 13D). Hence, to homogenously fabricate honeycomb cryoelectrospun scaffolds, a 5-mm probe-array collector was selected. More specifically, FIGS. 13A-13D depict cryoelectrospinning on the 3 mm probe-array collector. FIG. 13A depicts a 3 mm probe-array collector. FIG. 13B depicts a cryoelectrospun scaffolds deposited on the 3 mm probe-array collector. FIGS. 13C and 13D depict SEM images of scaffolds growing on 3 mm probe-array collector. FIG. 13C depict Scale bar=20 μm. FIG. 13D depicts scale bar=2 μm.

Figure 14C:
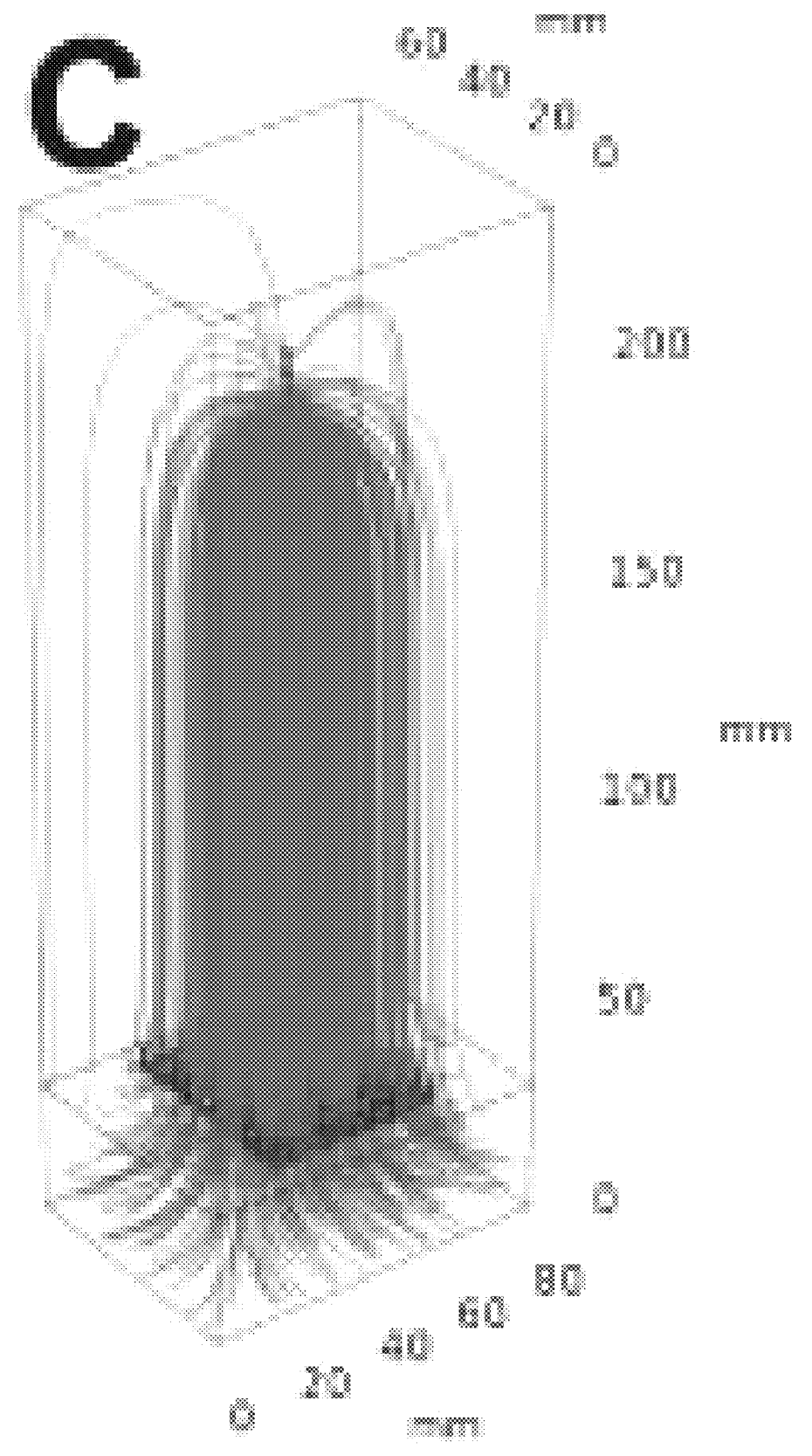
Figure 14D:
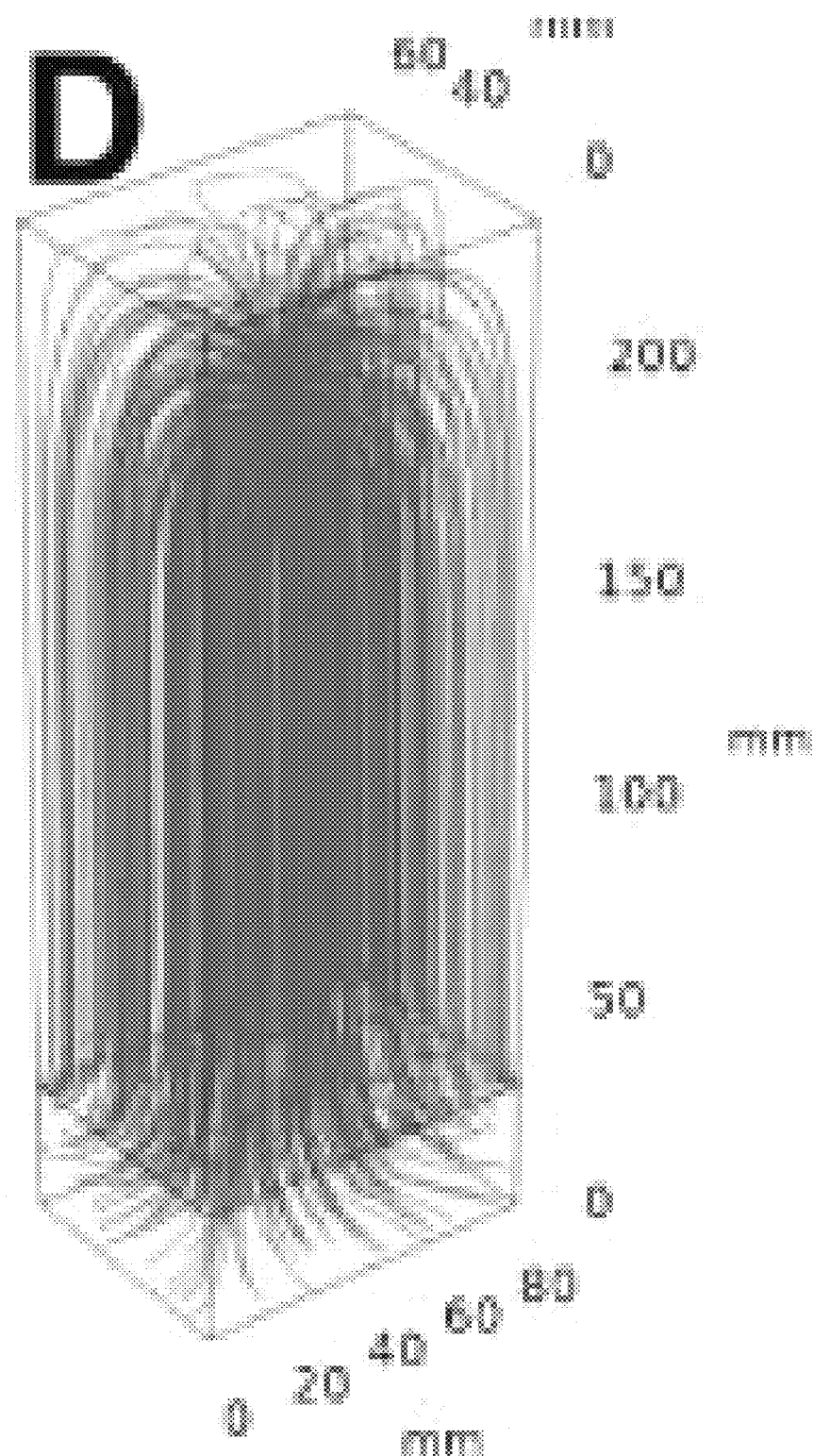
Figure 14E:
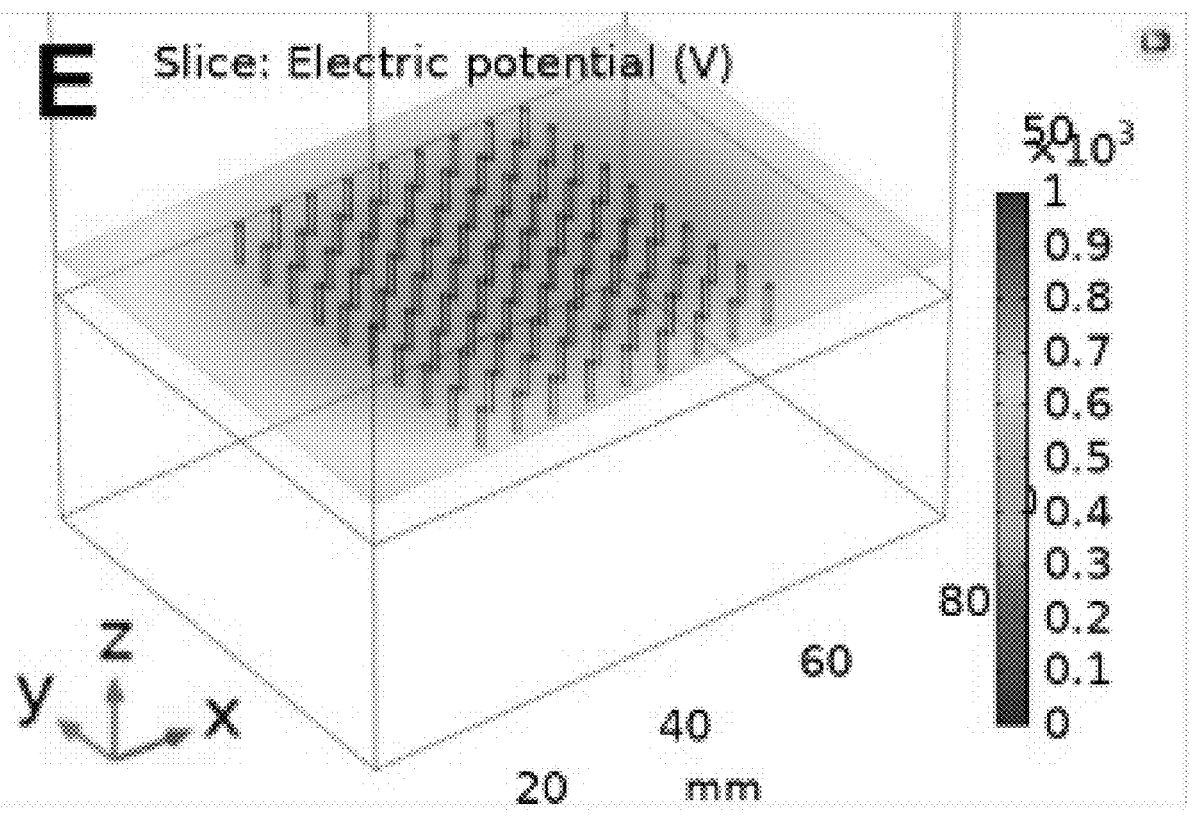
Figure 14F:
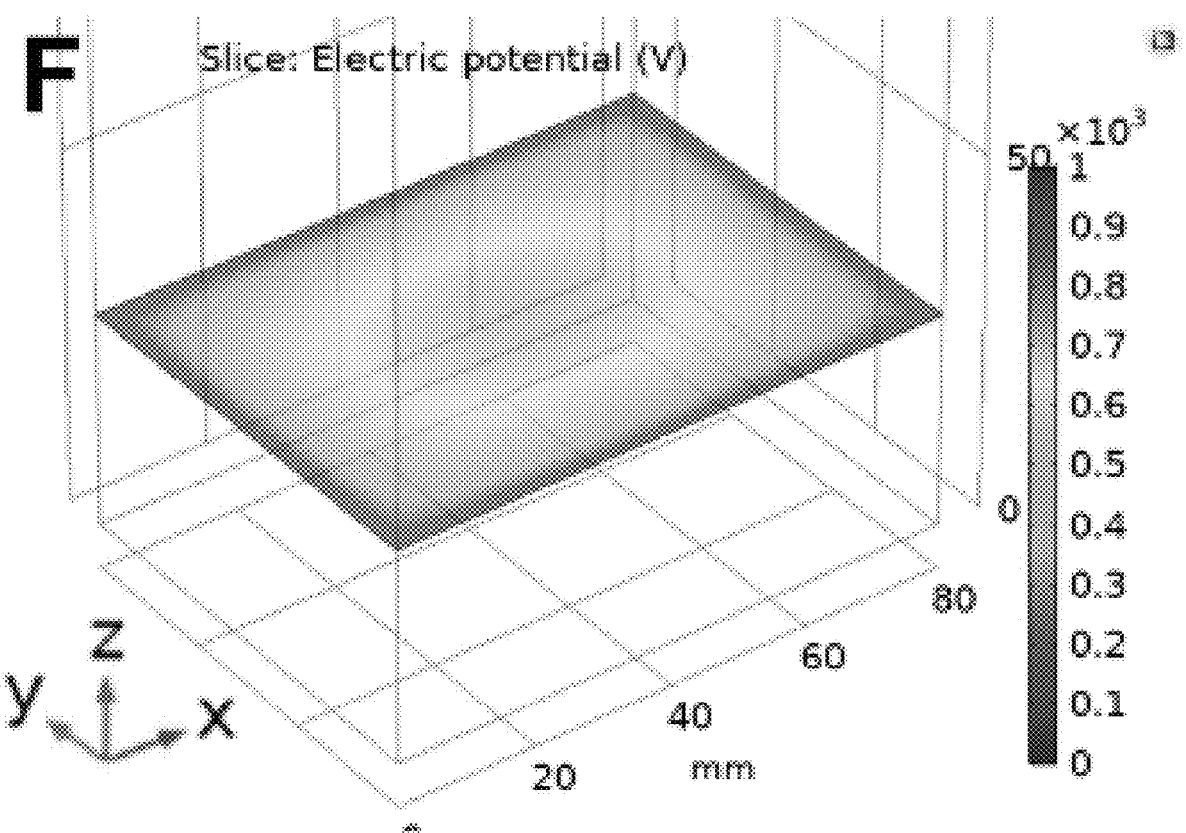
Figure 14G:
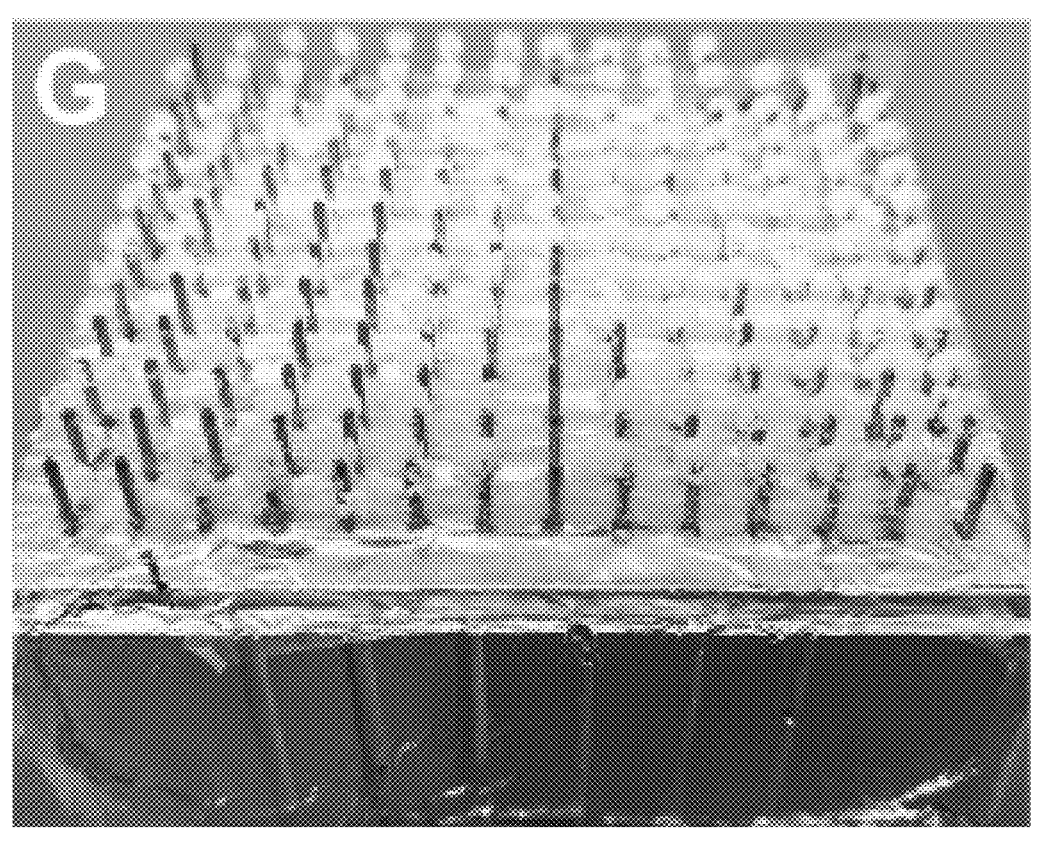
Figure 14H:
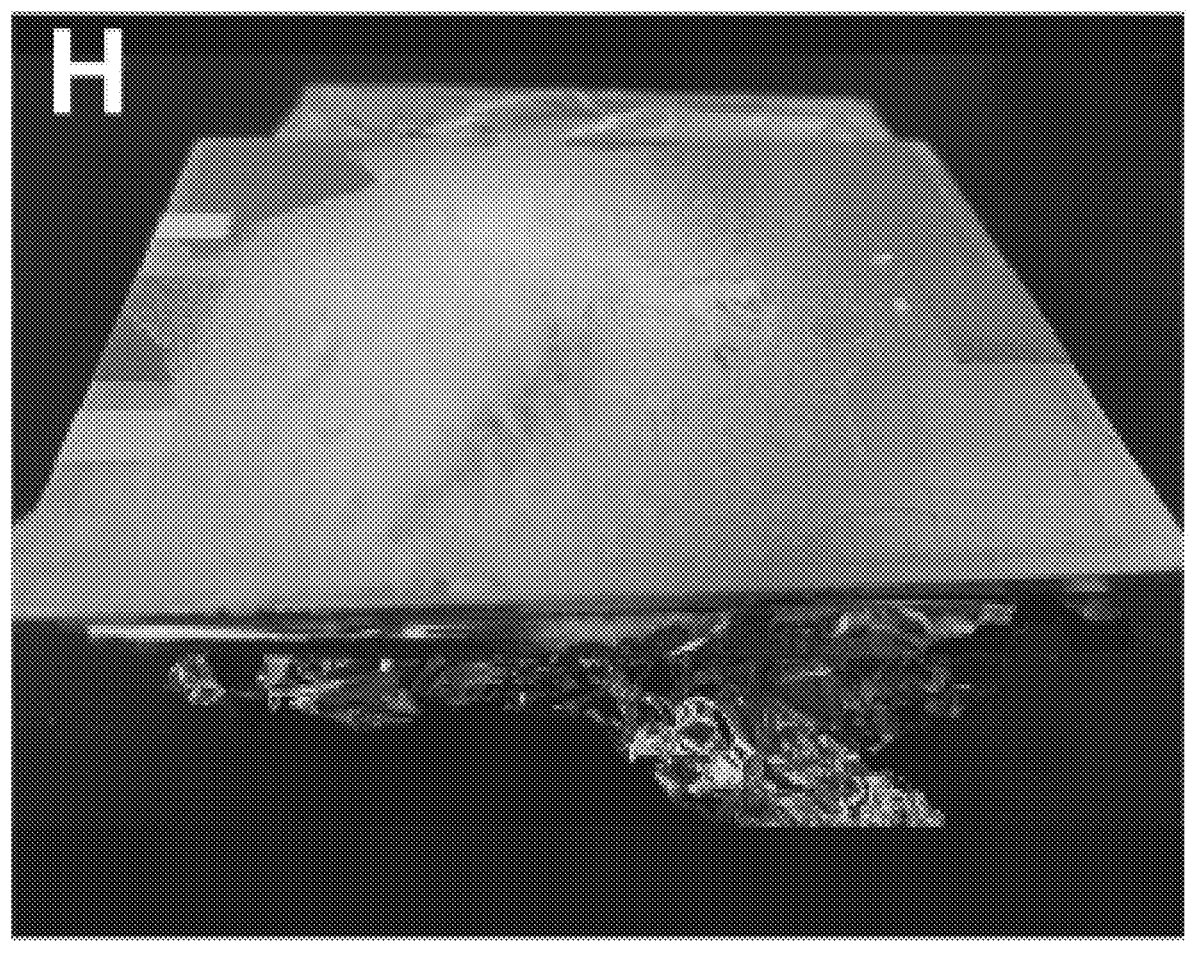
Figure 14I:
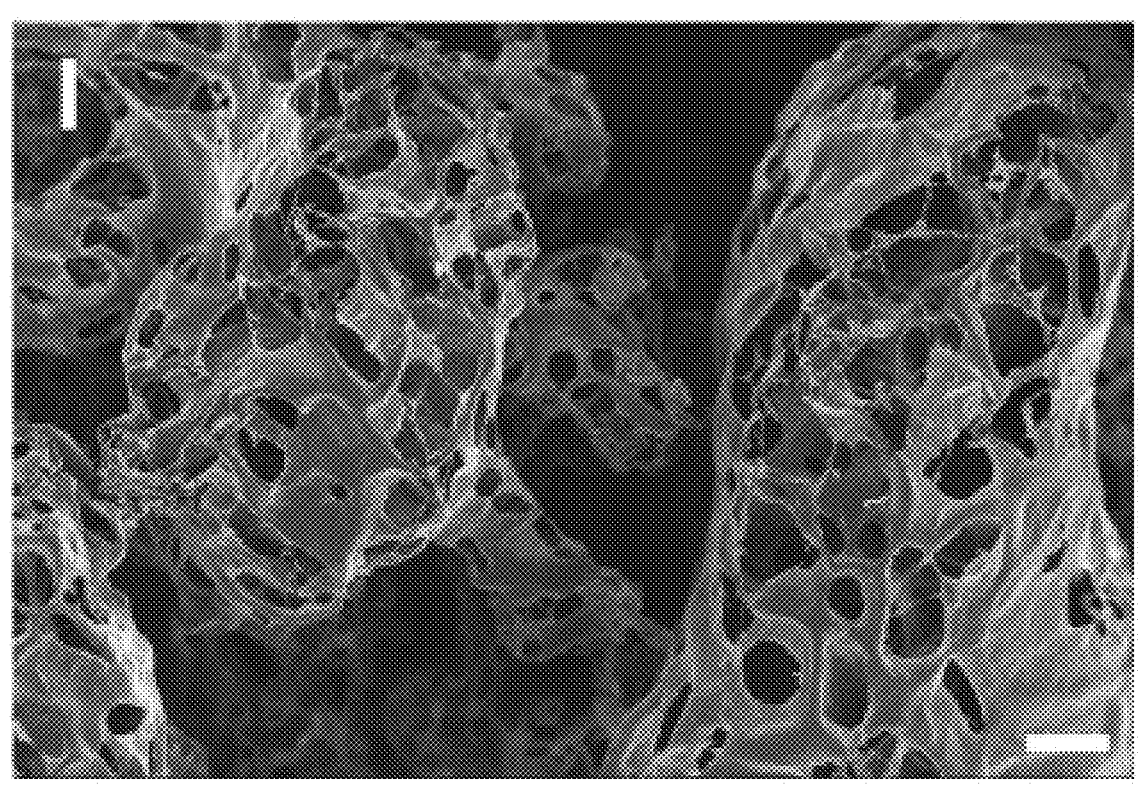
Figure 14J:
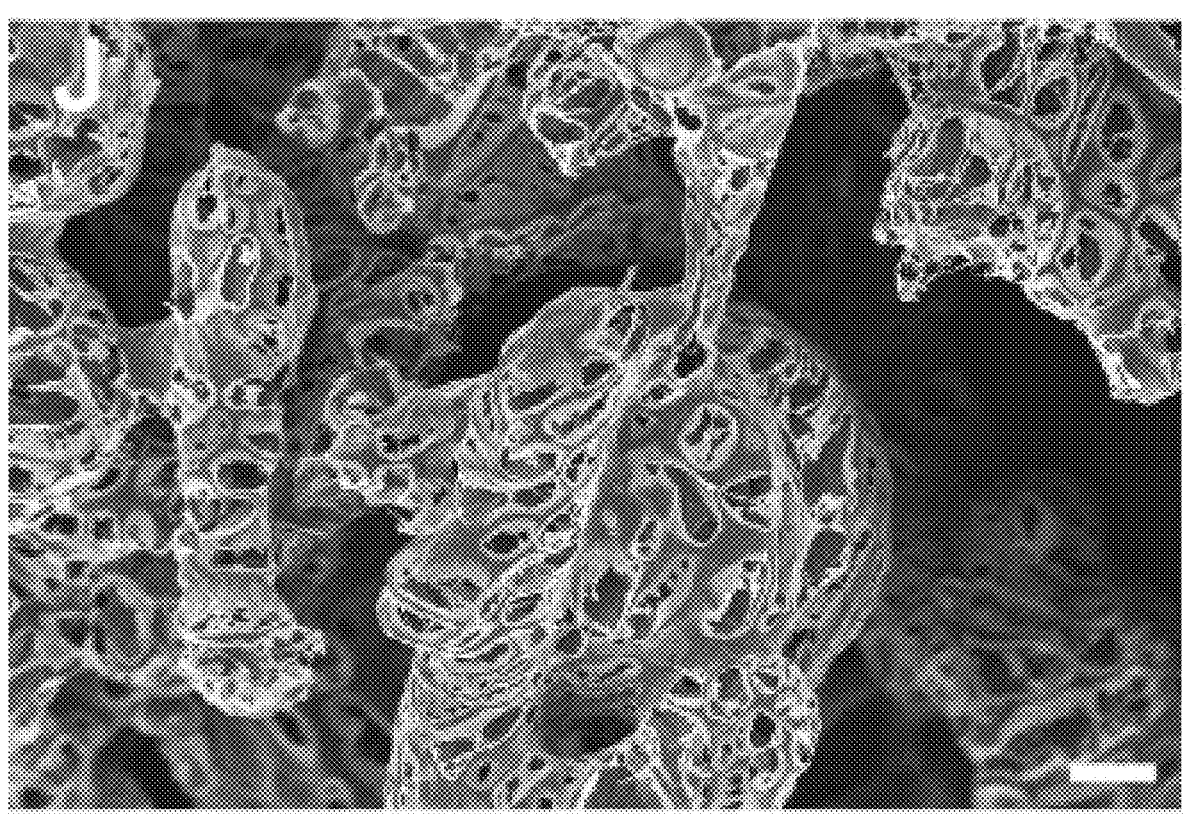

More specifically, FIGS. 14A-14J depict the effect of collector plate geometry on scaffold growth in X, Y, Z dimensions. FIGS. 14A and 14B depict bench top photos of the collector plate. FIGS. 14C and 14D depict COMSOL simulation demonstrating the electric field lines distribution over the collector plate. FIGS. 14E and 14F depict COMSOL simulation demonstrating the electric potential distribution over the collector plate. FIGS. 14G and 14H depict bench top photos and FIGS. 14E and 14F depict SEM images of scaffolds grown on a metallic probe-array collector having 5 mm probe spacing and flat collector, respectively. Scale bar=20 μm. Metallic probe-array promoting distributed individual scaffold growth and increased growth in the Z dimension due to reduced electrical surface area in the X and Y dimensions. (FIGS. 14A,C,E,G,I) Metallic probe-array collector plate. (FIGS. 14B,D,F,H,J) Flat collector plate.

Elastin-Alginate Cryoelectrospun Scaffolds with Honeycomb Topography Resemble the Topography and Viscoelasticity of Decellularized Salivary Gland ECM To evaluate the ability of elastin-alginate honeycomb CES topography to emulate salivary gland ECM, their topography and viscoelastic properties were compared with that of decellularized adult salivary gland matrix (D-SG) by SEM and indentation testing, respectively. The honeycomb CES and the D-SG exhibited honeycomb topography and pores of ~20-30 μm size (See e.g., FIGS. 15A, 15B). It was further determined the indentation modulus and relaxation half time of honeycomb CES and D-SG by micro-indentation testing. Honeycomb CES and D-SG had very low indentation moduli of ~120 Pa, whereas elastin-alginate freeze-dried sponges (FS) fabricated with the same material composition and crosslinked with the same materials as honeycomb CES exhibited a significantly higher indentation modulus of ~850 Pa. Further, it was observed that both FS and honeycomb CES demonstrated similar relaxation dynamics as D-SG (FIGS. 15C, 15D) despite the differences in observed viscoelasticity/indentation modulus.

Honeycomb CES Promote 3D Stromal Growth and Survival

Figure 16A:
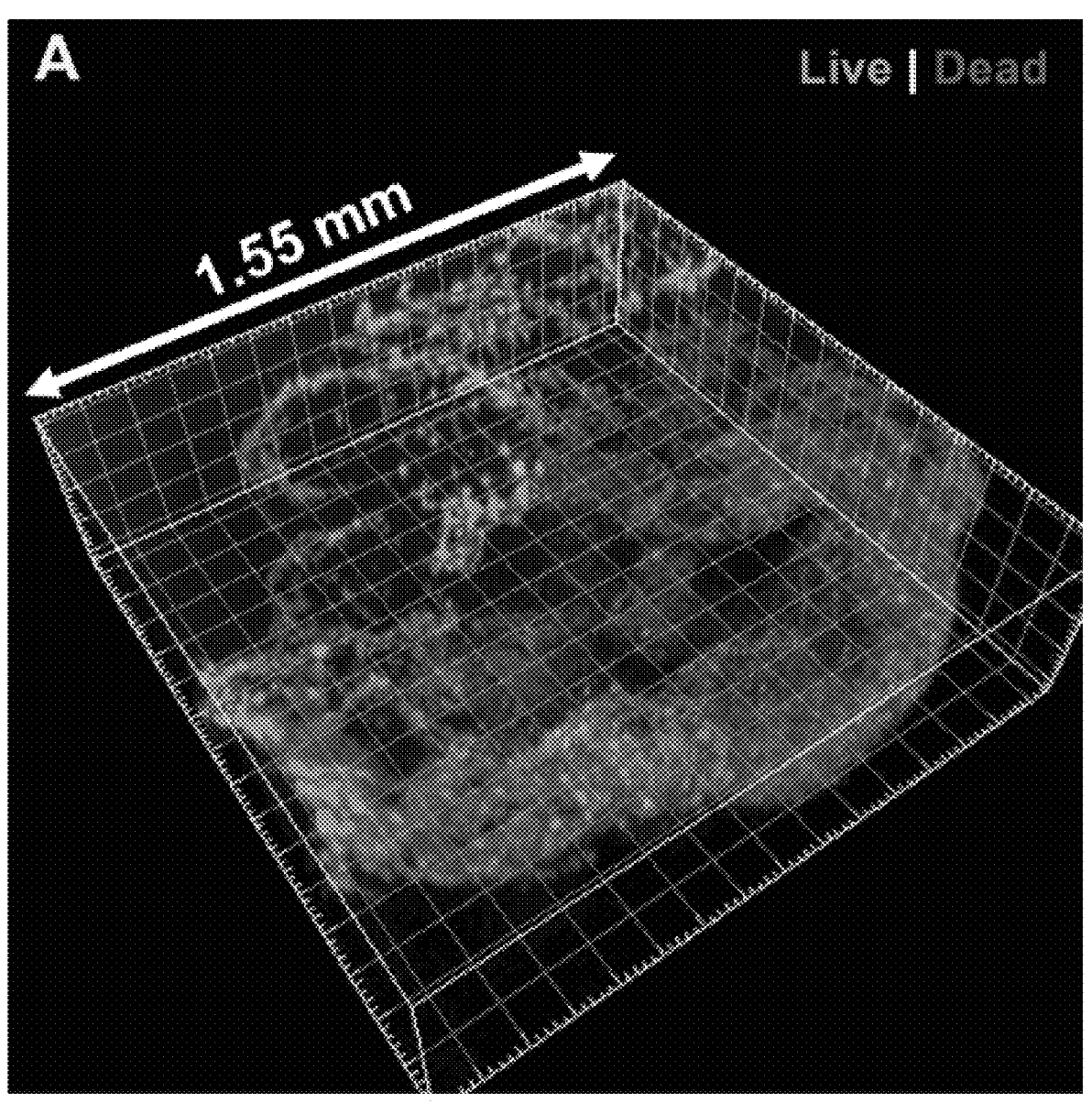
FIGS. 16A-16D depict elastin-alginate cryoelectrospun scaffolds with honeycomb topography (CES-H) promoting viable 3D cell penetration and growth.
Figure 16B:
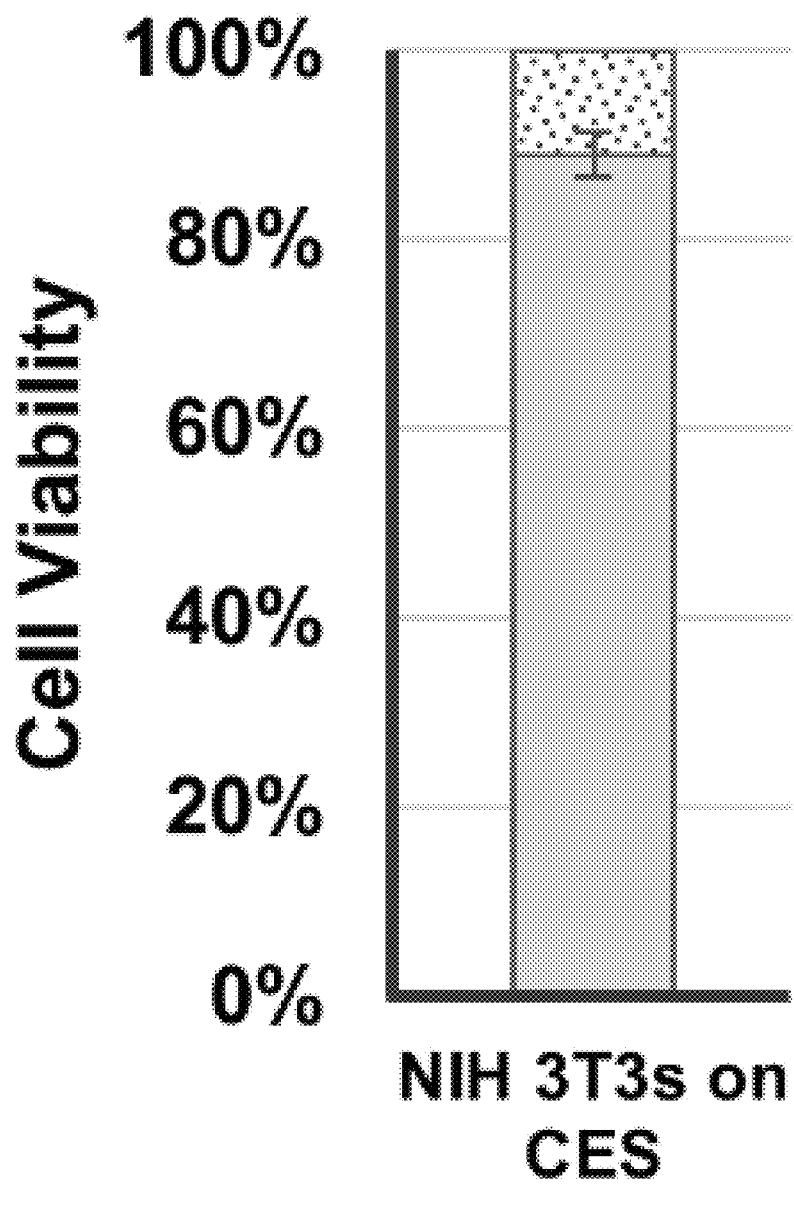
Figure 16C:
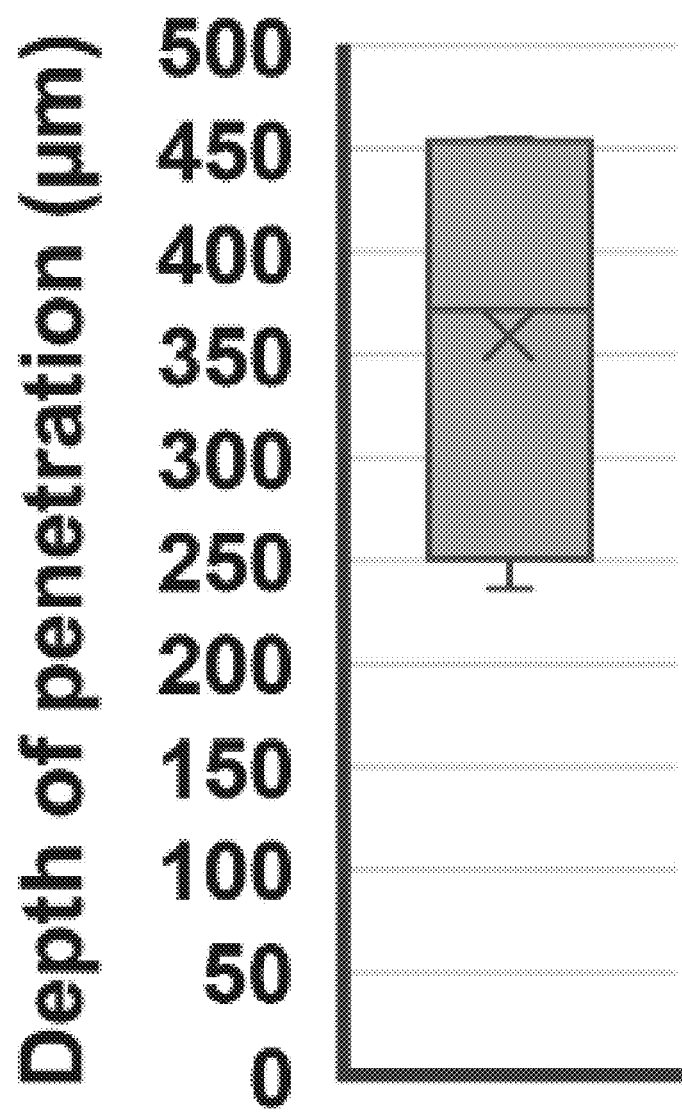

To investigate the ability of elastin-alginate honeycomb CES to support viable 3D stromal growth, NIH 3T3 fibroblasts, a well-established model mesenchymal cell line, were grown on honeycomb CES for 24 hours followed by Live/Dead staining to determine the viability of attached cells. The majority of the cells (89%±2%) attached to honeycomb CES were viable after 24 hours (FIGS. 16A and 16B). The cells on the honeycomb CES formed 3D clusters (FIG. 16A) with penetration depths ranging between ~250 to 450 μm, with an average of 359±96.48 μm (FIG. 16C). Furthermore, CellTiter Glo-3D viability assay was performed to evaluate cell growth on CES-H. The time course of cell growth showed the trend of slightly (but not significantly) increasing cell number of NIH 3T3 fibroblasts attached on the scaffold from day 1 to 4 and then leveling off, confirming cell survival on the honeycomb scaffolds for 7 days (FIG. 16D).

Figure 16D:
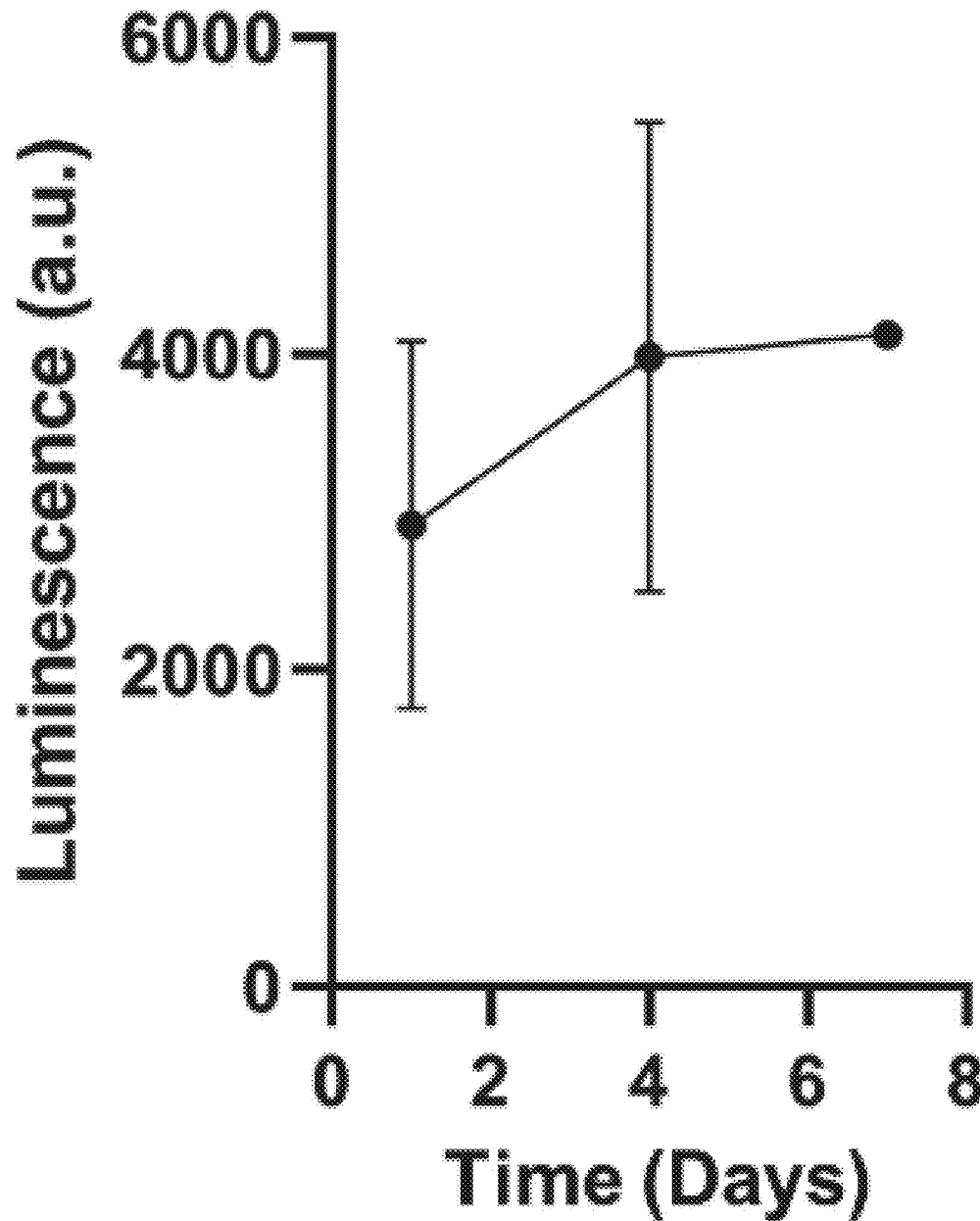

More specifically, FIGS. 16A-16D depict elastin-alginate cryoelectrospun scaffolds with honeycomb topography (CES-H) promoting viable 3D cell penetration and growth. FIG. 16A depicts confocal images of Live/Dead stained NIH 3T3 fibroblasts on CES-H showing that majority of attached cells are viable and penetrate deep into the scaffold to form 3D clusters. FIG. 16B depicts quantification of cell viability on CES-H after 24 hours using ImageJ. FIG. 16C depicts quantification of cell penetration revealing that NIH 3T3 cells infiltrate into CES-H with depths ranging between 250 to 450 μm and have an average infiltration depth of 359±96.48 μm. FIG. 16D depicts time course of NIH 3T3 fibroblast growth on CES-H using Cell Titer-Glo® 3D Cell Viability Assay.

Figure 17A:
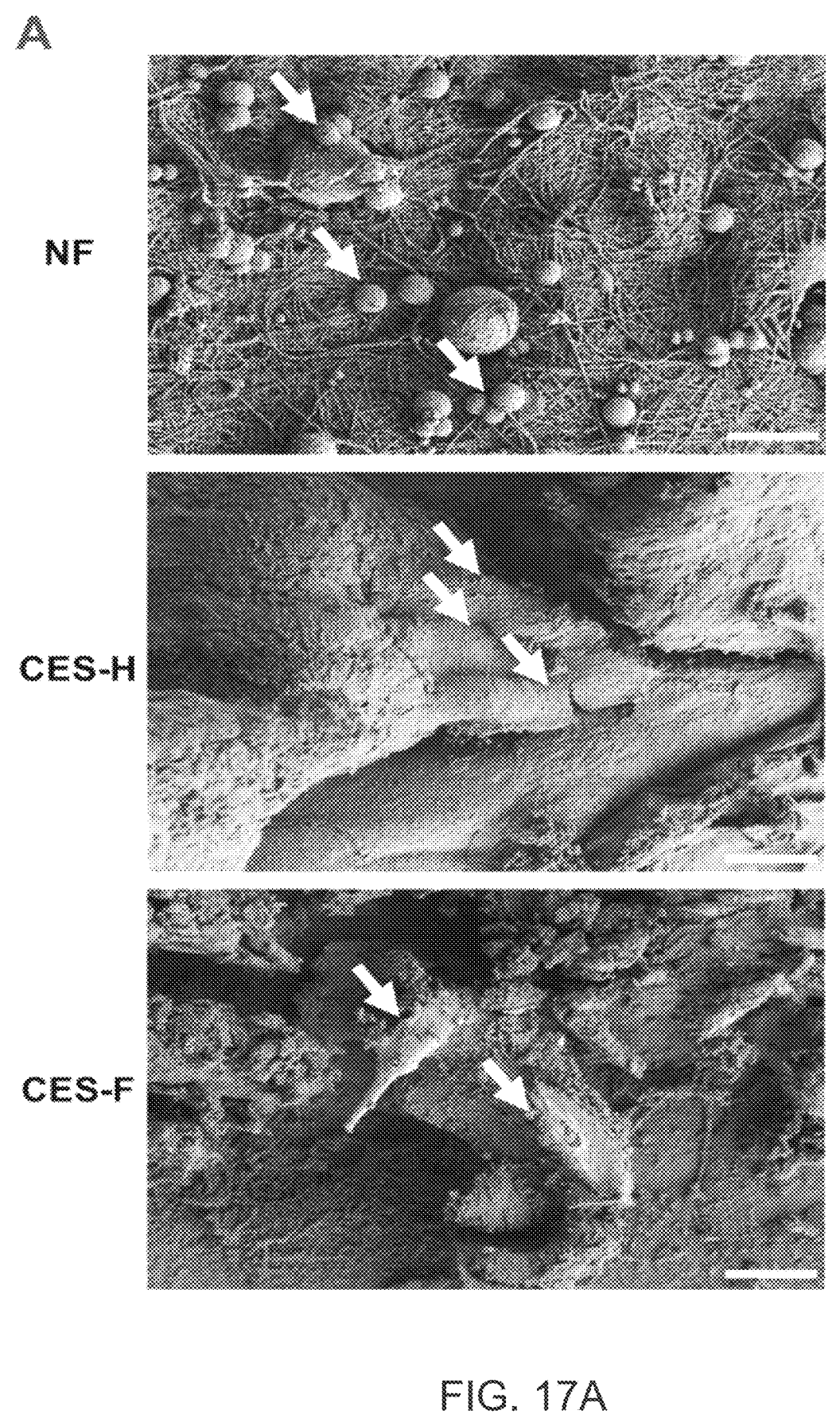
Figure 17B:
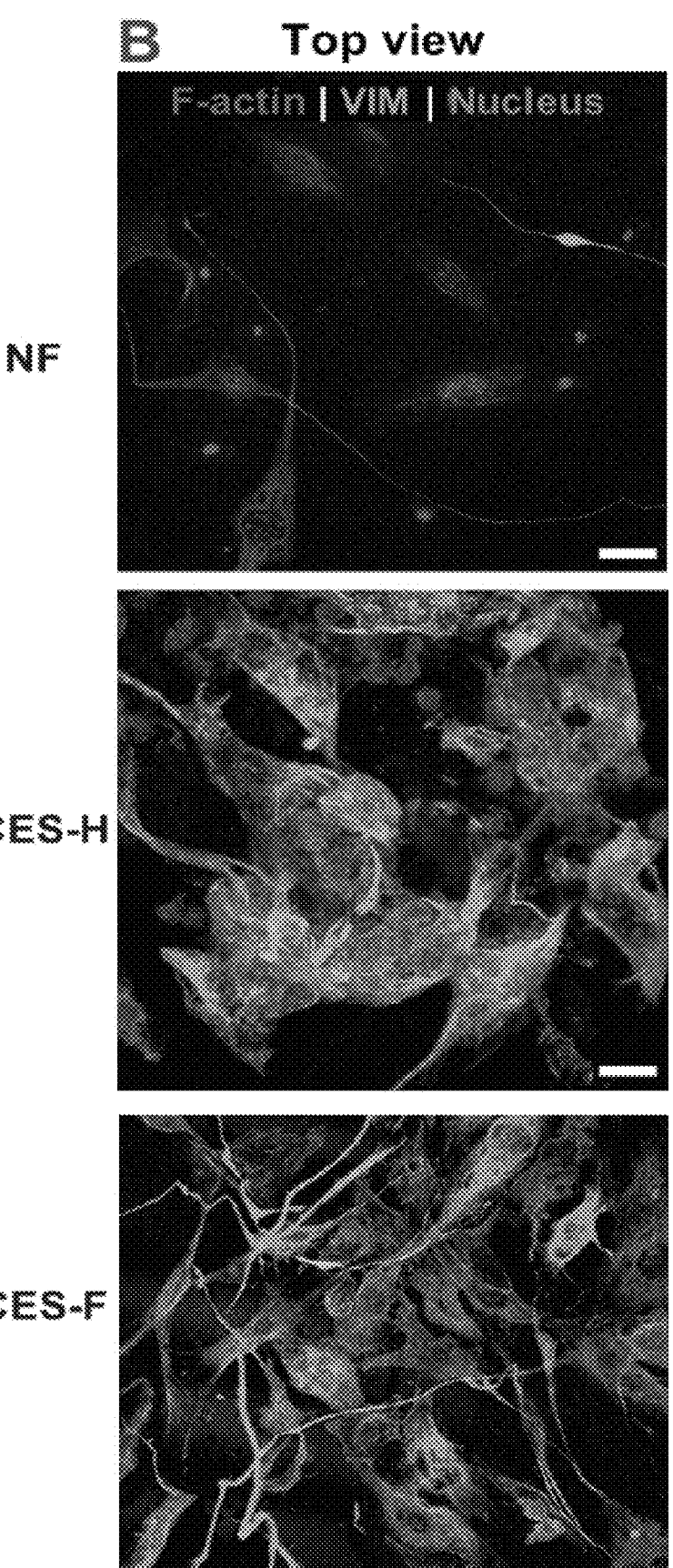

Honeycomb CES Promote Typical Adherent Fibroblast Morphology of NIH 3T3 Fibroblasts To evaluate the ability of elastin-alginate cryoelectrospun scaffolds to support typical adherent morphology, NIH 3T3 fibroblasts were cultured on traditionally electrospun elastin-alginate nanofiber (NF) mats, honeycomb CES (CES-H), and fibrous CES (CES-F) (See e.g., FIGS. 17A-17D). To analyze adherent cell morphology, NIH 3T3 cells were cultured on the scaffolds for 1 day followed by SEM imaging. NIH 3T3 fibroblasts remained rounded on NF mats (FIG. 17A, top panel); however, they demonstrated a spread-out, fibroblast morphology on both honeycomb CES (FIG. 17A, middle panel) and fibrous CES (FIG. 17A, bottom panel). The maintenance of characteristic adherent morphology of NIH 3T3 fibroblasts grown on honeycomb CES (FIG. 17B, middle panel) and fibrous CES (FIG. 17B, bottom panel) was confirmed by the distribution of cytoskeletal F-actin (in red) and vimentin (in green). However, very few cells attached and grew on NF mats (FIG. 18, FIG. 19 top panel), or exhibited elongated F-actin stress fibers (red) (FIG. 17B top panel). NIH 3T3 fibroblasts formed 3D clusters with notable infiltration in honeycomb CES (FIG. 17C, middle panel), but only a cell sheet on fibrous CES (FIG. 17C bottom panel), demonstrating that the honeycomb topography of the cryoelectrospun scaffolds is essential for infiltrated cell growth and 3D cell distribution.

Figure 18B:
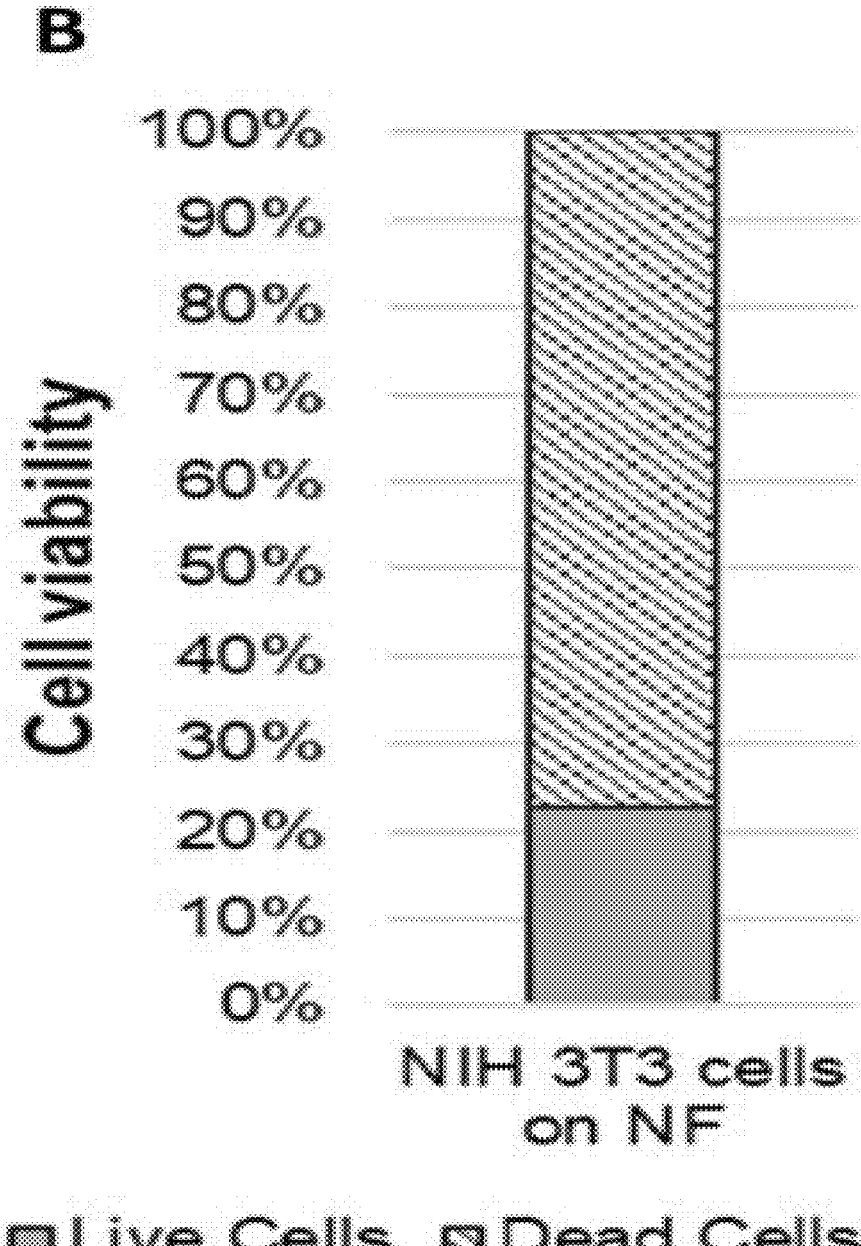

More specifically, FIGS. 18A and 18B depict conventionally electrospun nanofiber (NF) mats for cell growth. FIG. 18A depicts SEM images showing that nanofibers formed a unified hydrogel layer post-hydration with medium. FIG. 18B depicts quantification of LIVE/DEAD assay showing that viability of NIH 3T3 fibroblasts were severely impeded on nanofibers.

Figure 19:
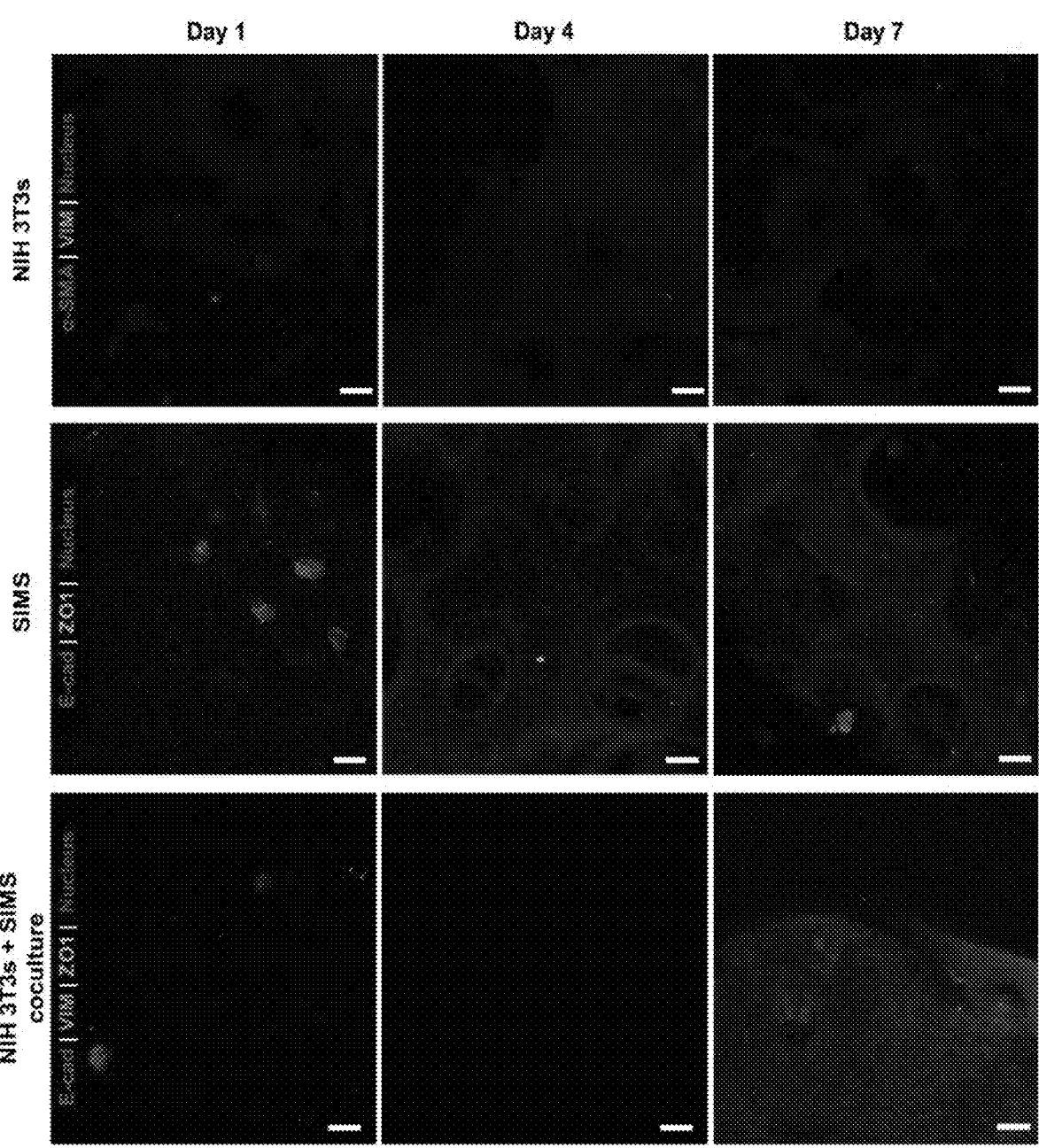
FIG. 19 depicts cell attachment on conventionally electrospun nanofiber (NF) mats.

With respect to FIG. 19, FIG. 19 depicts cell attachment on conventionally electrospun nanofiber (NF) mats. Confocal images of immunochemistry of monocultured and co-cultured NIH 3T3 fibroblasts and SIMS cells demonstrating poor cell attachment and growth on elastin-alginate nanofibers (for up to 7 days). For NIH 3T3s, Red: α-SMA, Green: Vimentin. For SIMS, Red: E-cadherin, Cyan: ZO-1. For SIMS and NIH 3T3 coculture, Red: E-cadherin, Cyan: ZO-1, Green: Vimentin. Blue: DAPI-stained cell nuclei. Scale bar=25 μm.

To determine if honeycomb CES inhibit myofibroblast transition, NIH 3T3 fibroblasts were cultured on honeycomb CES for 1, 4, and 7 days and assayed for expression of the myofibroblast marker α-smooth muscle actin (α-SMA) (See e.g., Nagaraju C K, Robinson E L, Abdesselem M, et al. Myofibroblast Phenotype and Reversibility of Fibrosis in Patients With End-Stage Heart Failure. *J Am Coll Cardiol*. Published online 2019. doi:10.1016/j.jacc.2019.02.049; Bharath Rao K, Malathi N, Narashiman S, Rajan S T. Evaluation of myofibroblasts by expression of alpha smooth muscle actin: A marker in fibrosis, dysplasia and carcinoma. *J Clin Diagnostic Res*. Published online 2014. doi:10.7860/JCDR/2014/7820.4231; Ina K, Kitamura H, Tatsukawa S, Fujikura Y. Significance of α-SMA in myofibroblasts emerging in renal tubulointerstitial fibrosis. *Histol Histopathol*. Published online 2011; and Pan D, Zhe X, Jakkaraju S, Taylor G A, Schuger L. P311 induces a TGF-β1-independent, nonfibrogenic myofibroblast phenotype. *J Clin Invest*. Published online 2002. doi:10.1172/JCI0215614). Maintenance of vimentin (in green) and reduction in α-SMA (in red) was observed on honeycomb CES over the course of 7 days (FIG. 17D), confirming that the honeycomb CES prevent myofibroblast transition.

Figure 17C:
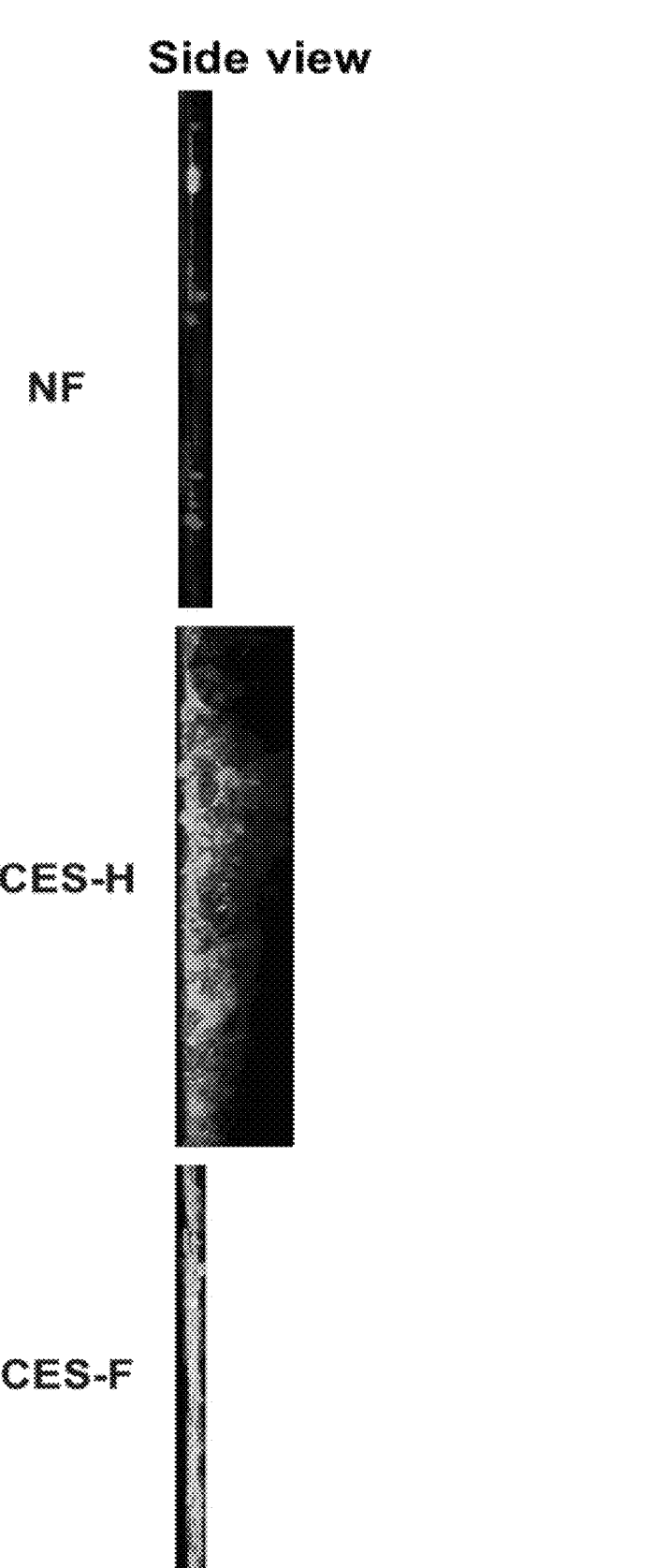
Figure 17D:
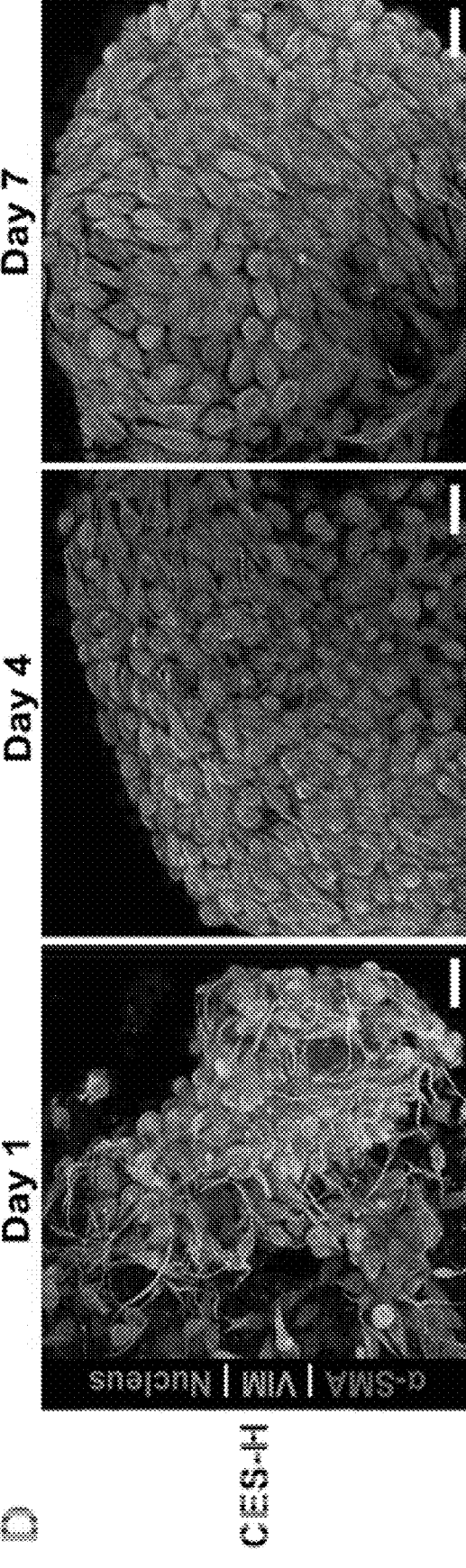

More specifically, FIGS. 17A-17D depict effects of scaffold properties on morphology, 3D organization, and marker expression of NIH 3T3 fibroblasts. FIG. 17A depicts SEM images showing the effect of scaffold topography on NIH 3T3 cell morphology. NIH 3T3 fibroblasts maintaining spread-out morphology on cryoelectrospun scaffolds with fibrous (CES-F) and honeycomb topography (CES-H) but remaining isolated and rounded on traditionally electrospun nanofibers (NF) on day 1. Arrows denoting individual cells. Scale bar=25 μm. FIGS. 17B and 17C depict confocal images of top view (FIG. 17B) and side view (FIG. 17C) of F-actin cytoskeleton organization and vimentin expression showing the effect of scaffold topography on attachment and infiltration of NIH 3T3 fibroblasts as well as mesenchymal marker expression on day 4. FIG. 17D depicts confocal images showing maintenance of expression of mesenchymal marker vimentin (in green) and loss of myofibroblast marker α-SMA (in red) over 7 days when NIH 3T3 fibroblasts growing on CES-H. Scale bar=25 μm.

Figure 20B:
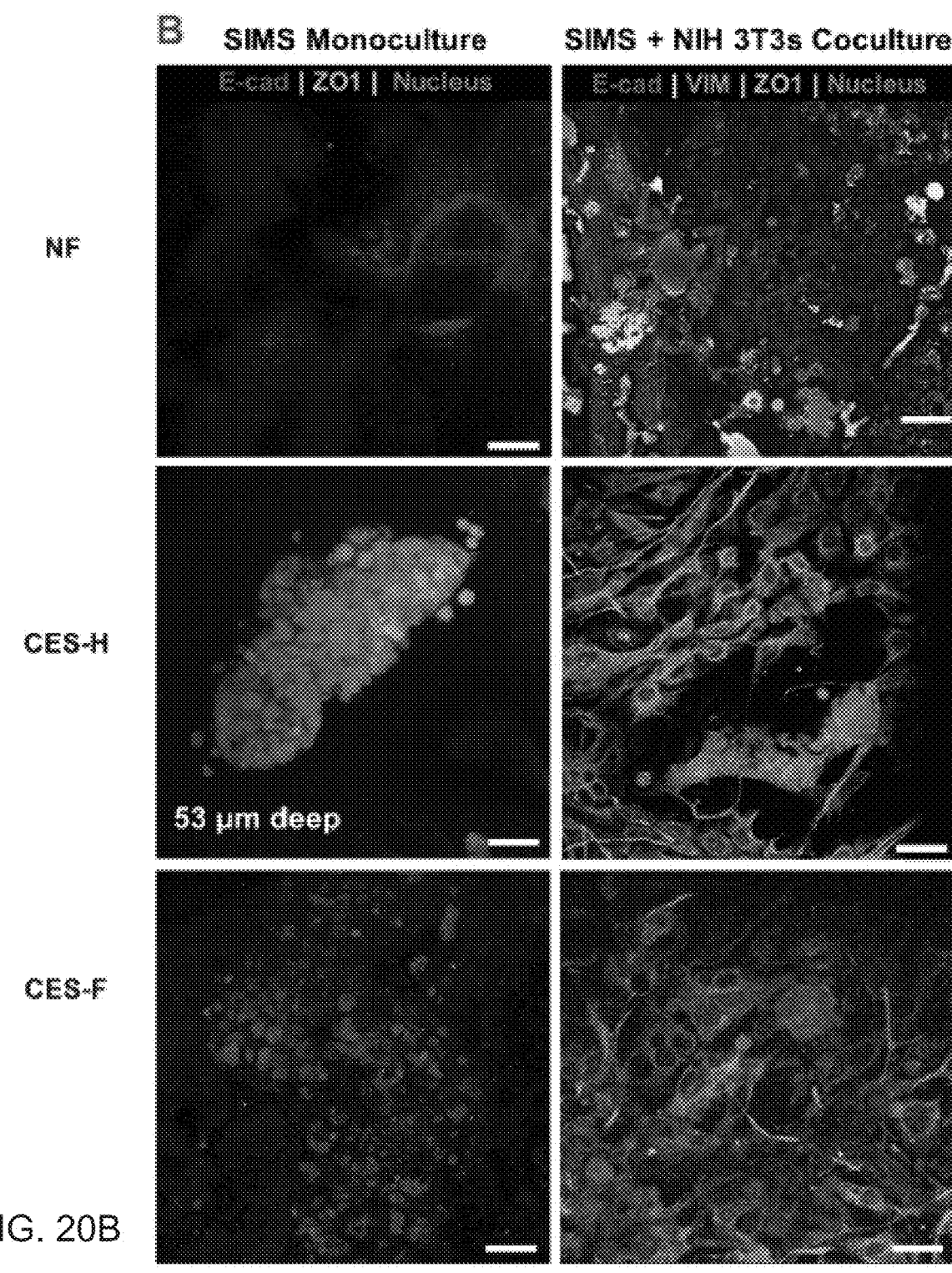
Figure 20C:
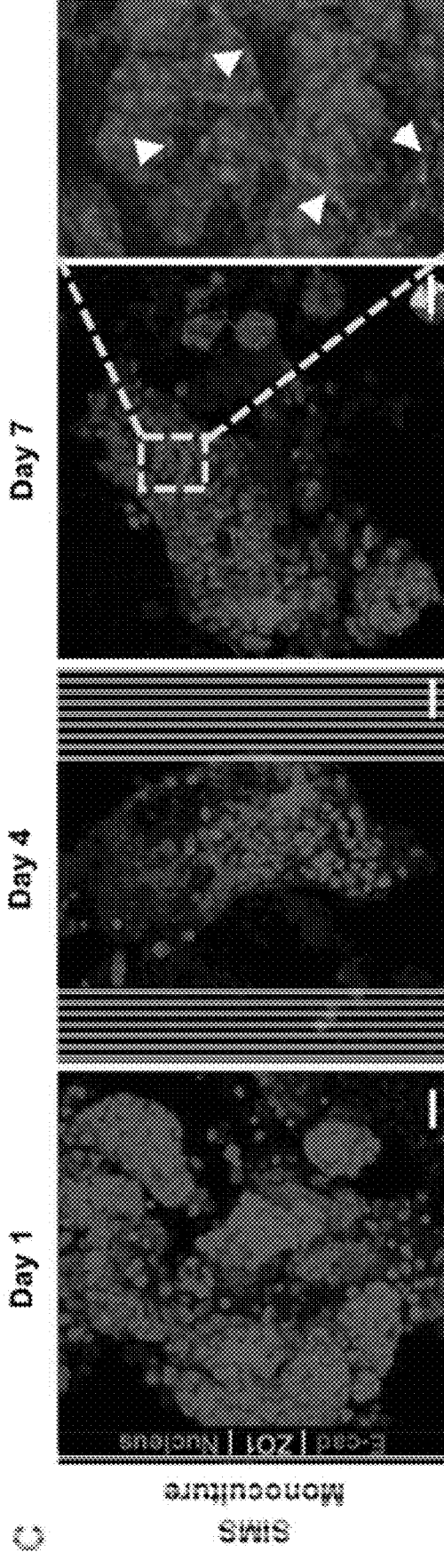

NIH 3T3 Fibroblasts Grown on Honeycomb CES Scaffolds Support Maintenance of Salivary Epithelial Morphology To evaluate the ability of CES to support epithelial cell morphology, SIMS cells were cultured, an established salivary gland ductal epithelial cell line[44], on honeycomb CES, fibrous CES, and traditionally electrospun NF mats (FIGS. 20A-20D). To analyze epithelial cell morphology, SIMS cells were cultured on scaffolds for 1 day followed by SEM imaging. The epithelial cells remained rounded on NF mats (FIG. 20A, top panel) and clustered together on both honeycomb CES (FIG. 20A, middle panel) and fibrous CES (FIG. 20A, bottom panel). To evaluate the ability of honeycomb CES to support 3D epithelial cell growth and morphology, and the possible need for stromal support, SIMS epithelial cells were cultured alone (SIMS monoculture) or cocultured with NIH 3T3 fibroblasts on NF mats, honeycomb CES, and fibrous CES for 7 days. For stromal-epithelial cocultures, NIH 3T3 cells were seeded and allowed to expand for 2 days to act as stromal support for the SIMS cells that were subsequently seeded. To both visualize the cells in monocultures and distinguish between cell types in cocultures, SIMS cells were immunostained for E-cadherin and ZO-1, tight junction epithelial markers, along with DAPI stain to reveal the nuclei of the total cell population, while NIH 3T3 cells were identified by immunostaining for vimentin, a mesenchymal cell marker. Conventional electrospun NF mats did not support adequate cell attachment for either SIMS monocultures or SIMS and NIH 3T3 coculture (FIG. 20B top panel, FIG. 19 middle and bottom panel). However, similar to NIH 3T3 fibroblasts grown on honeycomb CES, monocultures of SIMS cells formed deep 3D clusters on honeycomb CES (FIG. 20B, middle left panel) and formed thin cell sheets on fibrous CES (FIG. 20B, bottom left panel). Further, the cocultured cells on honeycomb CES organized into distinct clusters, whereas the cells were randomly attached on fibrous CES (FIG. 20B, middle and bottom right panel). While monocultured SIMS salivary epithelial cells attached and grew as clusters in honeycomb CES and exhibited membrane-localized expression of E-cadherin by day 4, they did not show membrane-localized ZO-1 (FIG. 20C). However, in cocultures with NIH 3T3 cells grown on honeycomb CES as a stromal support, the SIMS epithelium formed more robust 3D clusters with improved membrane localization of both E-cadherin and ZO-1 (FIG. 20D) by day 4 through day 7, highlighting the ability of stromal cells grown on honeycomb CES to better support the epithelial cell phenotype than monoculture.

Figure 20D:
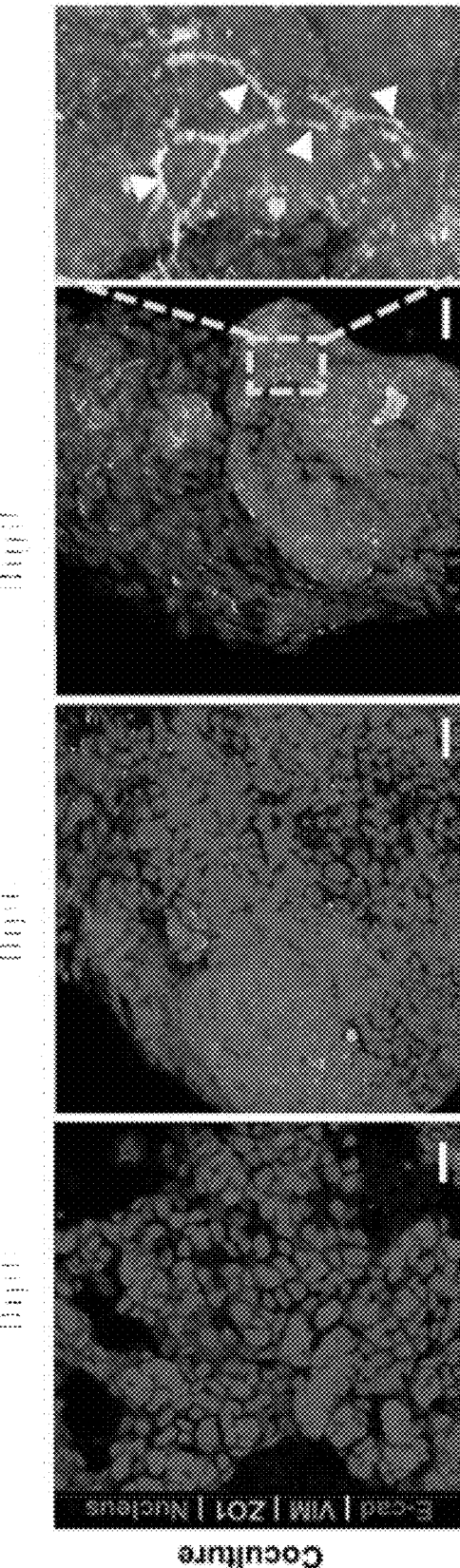

More specifically FIGS. 20A-20D depict effects of scaffold properties on morphology and 3D organization of SIMS epithelial cells. FIG. 20A depicts SEM images showing the effect of scaffold topography on SIMS epithelial cell morphology. SIMS cells forming cell clusters on cryoelectrospun scaffolds with fibrous (CES-F) and honeycomb topography (CES-H) but remaining isolated and rounded on traditionally electrospun nanofibers (NF) on day 1. Arrows denoting cells. FIG. 20B depicts confocal images of SIMS monoculture (left panel) or SIMS epithelial cells cocultured with NIH 3T3 fibroblasts on scaffolds being immunostained with epithelial markers (E-cadherin in red and ZO-1 in cyan) and mesenchymal marker (vimentin in green) along with DAPI-stained nuclei (in purple) on day 4. SIMS monoculture forming deep 3D clusters in CES-H and thin cell sheets on CES-F. SIMS and NIH 3T3 coculture showing distinct organization of cells into separate clusters on CES-H reminiscent of tissues in vivo but remaining random on CES-F. Very few cells attaching and growing on NF. FIG. 20C depicts confocal images of SIMS monoculture on CES-H demonstrating 3D growth of cells with membrane-localized expression of E-cadherin but not ZO-1. FIG. 20D depicts coculture of SIMS with NIH 3T3 cells allowing membrane-localized expression of both epithelial markers, ZO-1 and E-cadherin. Monocultures of SIMS salivary epithelial cells being immunostained for E-cadherin (red) and ZO-1 (cyan). Cocultures of SIMS and NIH 3T3 being immunostained for vimentin (green), E-cadherin (red), and ZO-1 (cyan) along with DAPI stain of nuclei (purple). Scale bar=25 μm.

Honeycomb CES Scaffolds Promote Retention of CD140a and CD140b Expression in Primary Embryonic Day 16 (E16) Salivary Gland Mesenchyme Cells Honeycomb CES was tested to support the use of stromal mesenchymal phenotype of primary E16 mesenchyme isolated from mouse salivary glands. Primary E16 mesenchyme cells were grown on the honeycomb CES for up to 7 days and assayed for retention of the stromal cell markers CD140a and CD140b, which are known to be expressed by stromal cells during the organogenesis of the salivary gland (See e.g., Yamamoto S, Fukumoto E, Yoshizaki K, et al. Platelet-derived Growth Factor Receptor Regulates Salivary Gland Morphogenesis via Fibroblast Growth Factor Expression *. *J Biol Chem.* 2008; 283(34):23139-23149. doi: 10.1074/JBC.M710308200) along with vimentin (FIG. 21), by immunostaining. Indeed, primary E16 salivary mesenchyme cells cultured on the honeycomb CES maintained some vimentin expression while they exhibited robust CD140a and CD140b protein expression levels for up to 7 days, demonstrating that the honeycomb CES can promote phenotype retention of endogenous salivary mesenchyme cells in culture.

Figure 21:
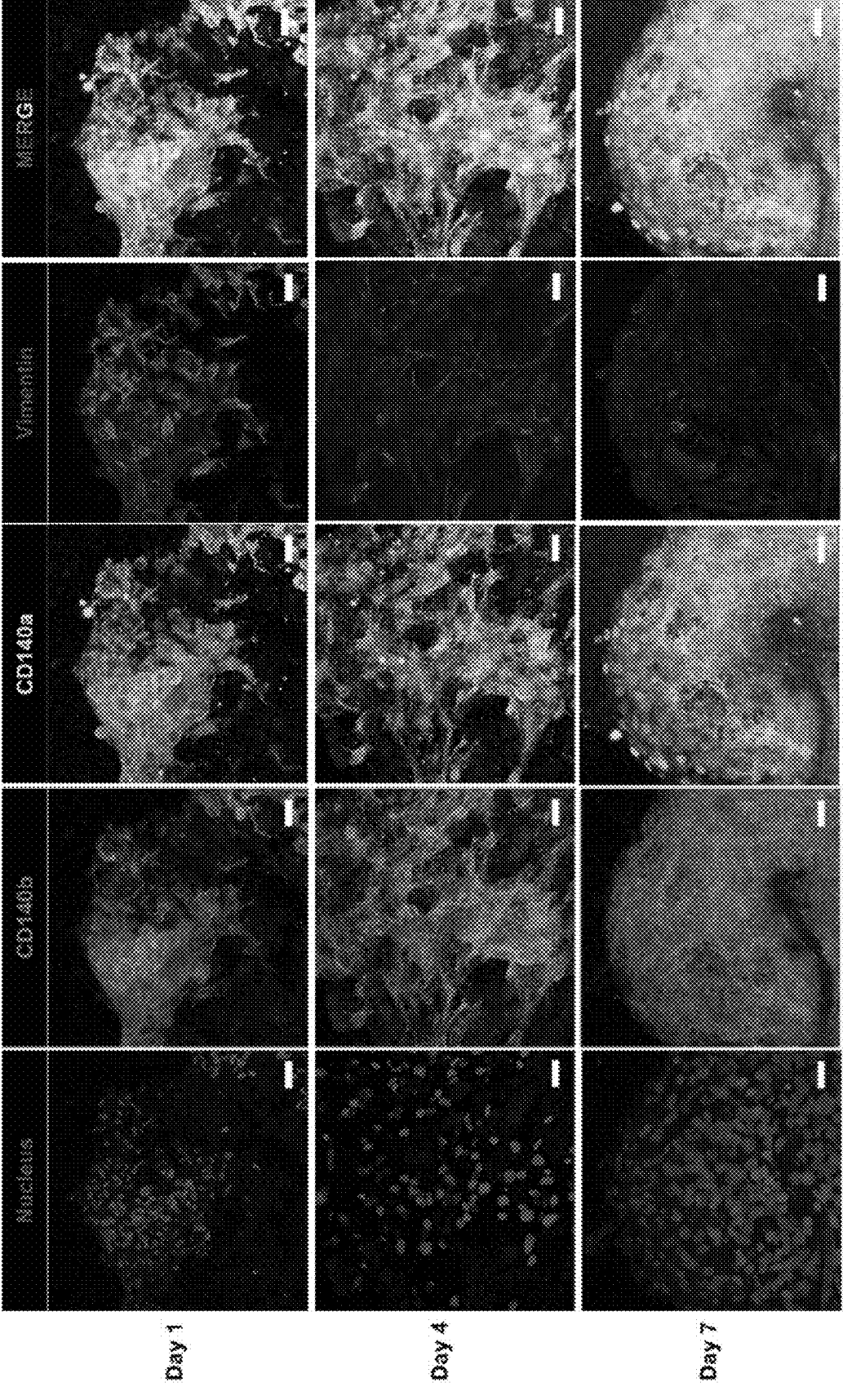
FIG. 21 depicts the effect of honeycomb CES scaffold on maintenance of MSC-like, primary mesenchymal cells.
Figure 22A:
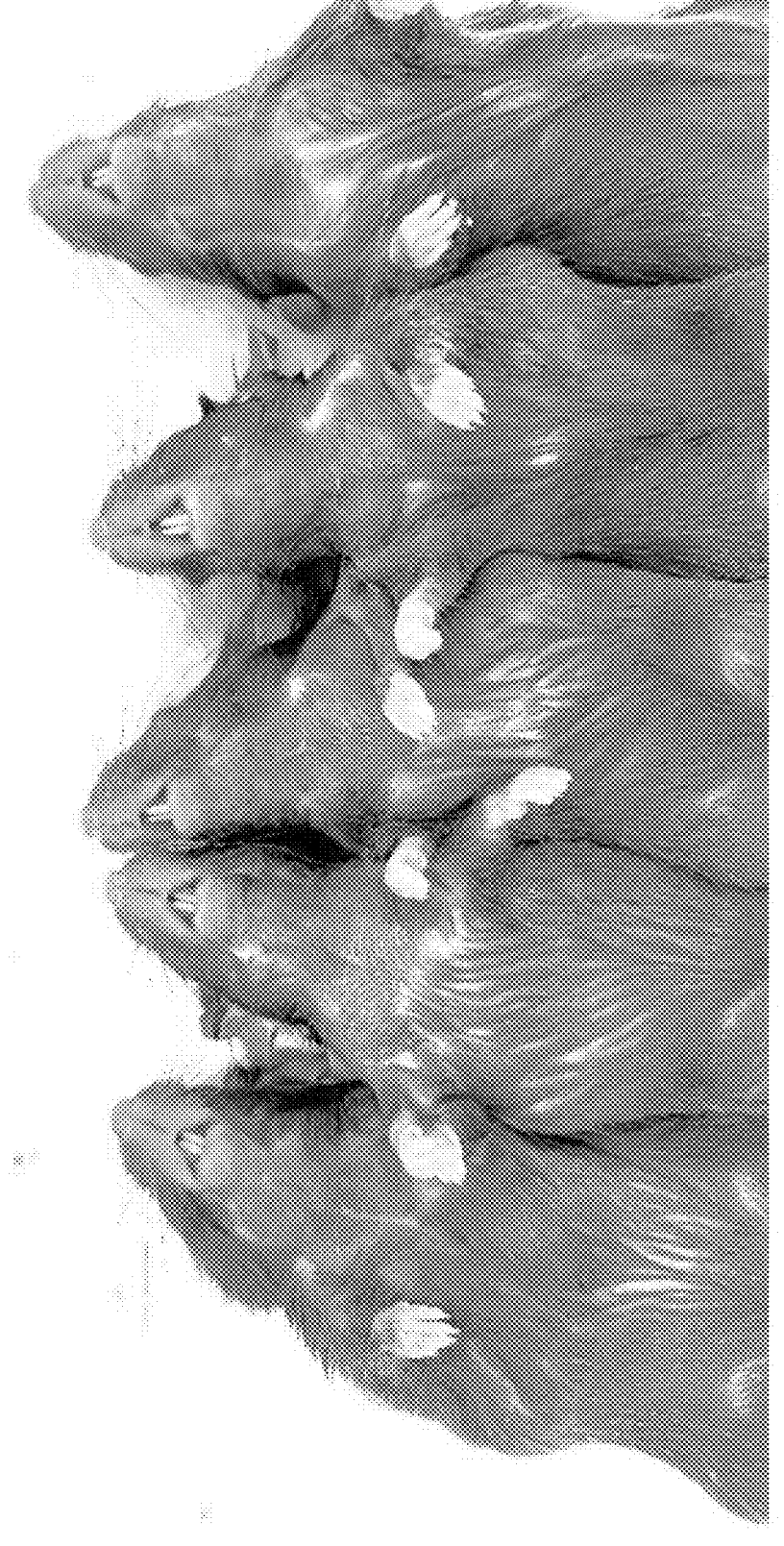
FIGS. 22A-22D depict data relating to use of a scaffold embodiment of the present disclosure and inflammation.
Figure 22B:
Figure 22C:
Figure 22D:
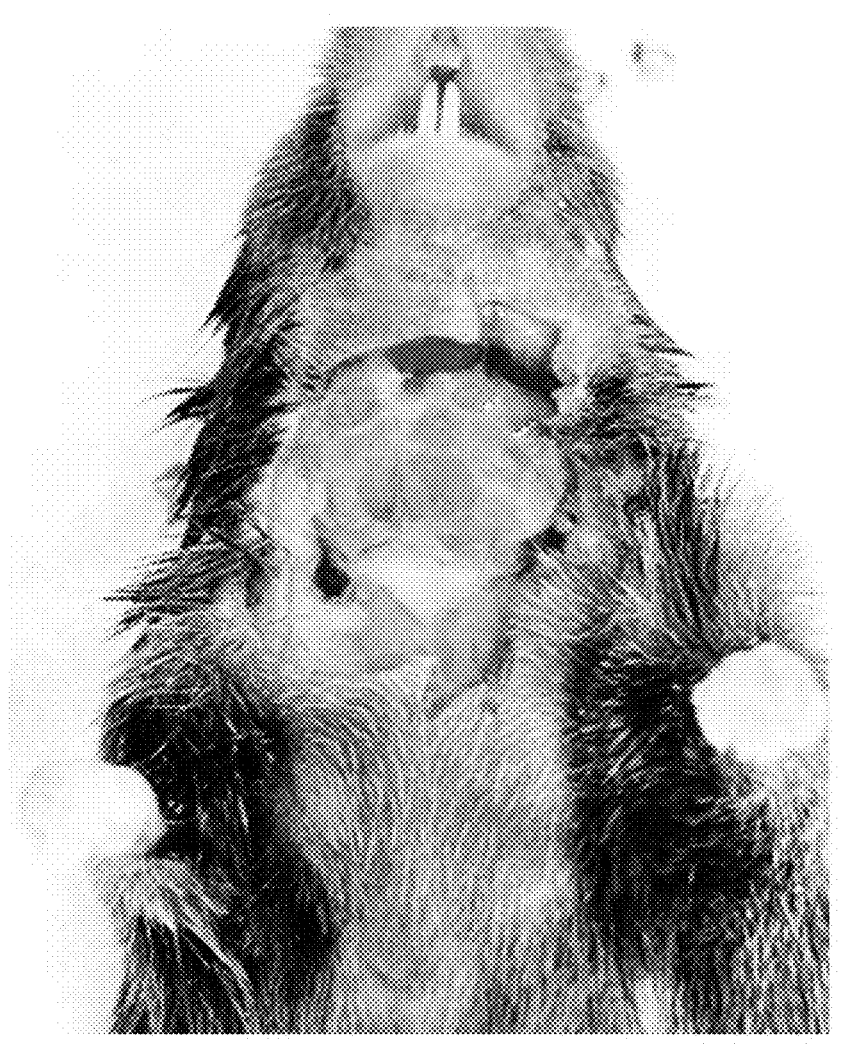

More specifically, FIG. 21 depicts the effect of honeycomb CES scaffold on maintenance of MSC-like, primary mesenchymal cells. Confocal images of primary embryonic day 16 (E16) salivary gland mesenchyme cells demonstrating robust expression of native salivary stromal markers (CD140a in green and CD140b in yellow), maintenance of mesenchymal marker (vimentin in red) for up to 7 days with reduction of expression of vimentin from day 1 to day 7. Scale bar=25 μm.

Several pathologies arise in the human body due to an imbalance in the biochemical and mechanical cues delivered by the ECM to cells in organs (See e.g., Cox T R, Erler J T. Remodeling and homeostasis of the extracellular matrix: Implications for fibrotic diseases and cancer. *DMM Dis Model Mech.* 2011; 4(2):165-178. doi:10.1242/dmm.004077; Dityatev A. Remodeling of extracellular matrix and epileptogenesis. *Epilepsia.* 2010; 51(SUPPL. 3):61-65. doi:10.1111/j.1528-1167.2010.02612.x; Sonbol H. Extracellular matrix remodeling in human disease. *J Microsc Ultrastruct.* Published online 2018. doi:10.4103/jmau.jmau_4_18; Ma Y, Iyer R P, de Castro Brás L E, et al. Cross Talk Between Inflammation and Extracellular Matrix Following Myocardial Infarction. In: *Inflammation in Heart Failure;* 2015. doi:10.1016/b978-0-12-800039-7.00004-9; Zhang Y, Reif G, Wallace D P. Extracellular matrix, integrins, and focal adhesion signaling in polycystic kidney disease. *Cell Signal.* 2020; 72:109646. doi:10.1016/j.cellsig.2020.109646; and Ito J T, Lourenço J D, Righetti R F, Tibério IFLC, Prado C M, Lopes FDTQS. Extracellular engineer tissues that mimic not only the biochemical cues but also the physical and mechanical cues of healthy ECM (See e.g., Trappmann B, Gautrot J E, Connelly J T, et al. Extracellular-matrix tethering regulates stem-cell fate. *Nat Mater.* 2012; 11 (7):642-649. doi:10.1038/nmat3339; Akhmanova M, Osidak E, Domogatsky S, Rodin S, Domogatskaya A. Physical, Spatial, and Molecular Aspects of Extracellular Matrix of in Vivo Niches and Artificial Scaffolds Relevant to Stem Cells Research. *Stem Cells Int.* 2015; 2015. doi:10.1155/2015/167025; Engler A J, Sen S, Sweeney H L, Discher D E. Matrix Elasticity Directs Stem Cell Lineage Specification. *Cell.* Published online 2006. doi:10.1016/j.cell.2006.06.044; Reilly G C, Engler A J. Intrinsic extracellular matrix properties regulate stem cell differentiation. *J Biomech.* Published online 2010. doi: 10.1016/j.jbiomech.2009.09.009; and Cameron A R, Frith J E, Cooper-White J J. The influence of substrate creep on mesenchymal stem cell behaviour and phenotype. *Biomaterials.* Published online 2011. doi:10.1016/j.biomaterials.2011.04.003. In this work, a novel fabrication strategy was developed to produce 3D scaffolds (FIG. 10C) that closely mimic the honeycomb topography, porosity, and pore size of endogenous salivary gland ECM (FIG. 15A-C) and potentially other soft tissues, e.g., lung, liver (See Aryan Z, Sabetkish N, Orangian S, et al. WholeMatrix Component Remodeling in Respiratory Diseases: What Has Been Found in Clinical and Experimental Studies? *Cells.* 2019; 8(4):342. doi:10.3390/cells8040342). Hence, in addition to cell engineering strategies for regenerative medicine and in vitro culture purposes, scaffold engineering strategies are also critical. There is a pronounced need to -organ tissue engineering: Decellularization and recellularization of three-dimensional matrix liver scaffolds. *J Biomed Mater Res Part A.* 2014; 103(4):1498-1508. doi:10.1002/jbm.a.3529; Zhang J, Wang Z, Lin K, et al. In vivo regeneration of renal vessels post whole decellularized kidneys transplantation. *Oncotarget.* 2015; 6(38). doi:10.18632/oncotarget.6321; and Gupta S K, Dinda A K, Potdar P D, Mishra N C. Modification of decellularized goat-lung scaffold with chitosan/nanohydroxyapatite composite for bone tissue engineering applications. *Biomed Res Int.* 2013; 2013. doi:10.1155/2013/651945).

The use of water as the solvent is key to generating honeycomb topography using cryoelectrospinning. The aqueous solvent, in combination with the atmospheric water deposition, increased ice nucleation and improved 3D growth and porosity of the scaffold (FIG. 10A, 10C). The increased water content and water solubility of solutes might have allowed for phase separation of the materials and the unique honeycomb topography (FIG. 10D), which has not been previously reported with cryoelectrospinning.

Figure 15A:
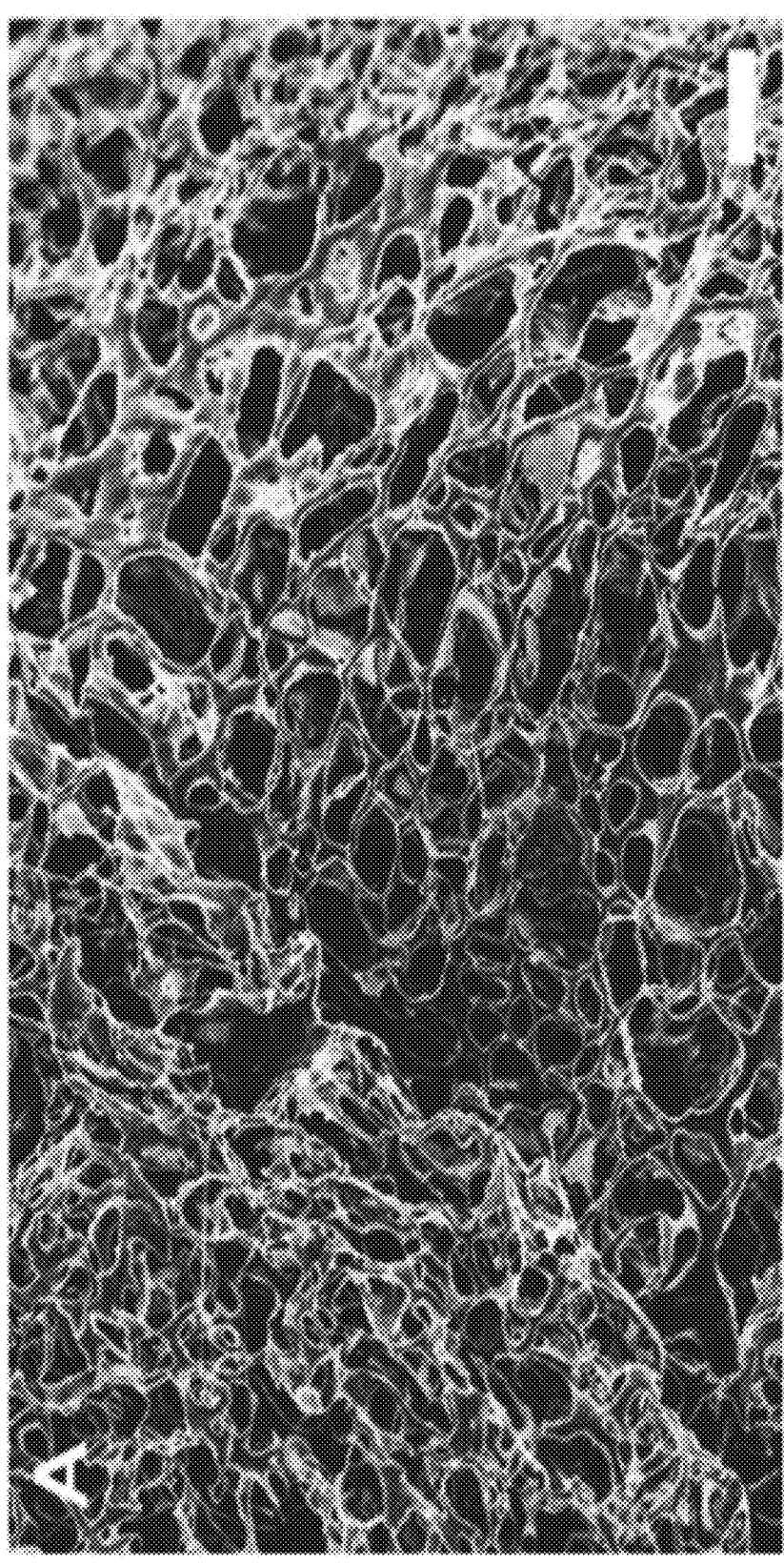
FIGS. 15A-15E depict elastin-alginate cryoelectrospun scaffolds with honeycomb topography (CES-H) mimicking decellularized adult salivary gland ECM in topographic and viscoelastic properties.
Figure 15B:
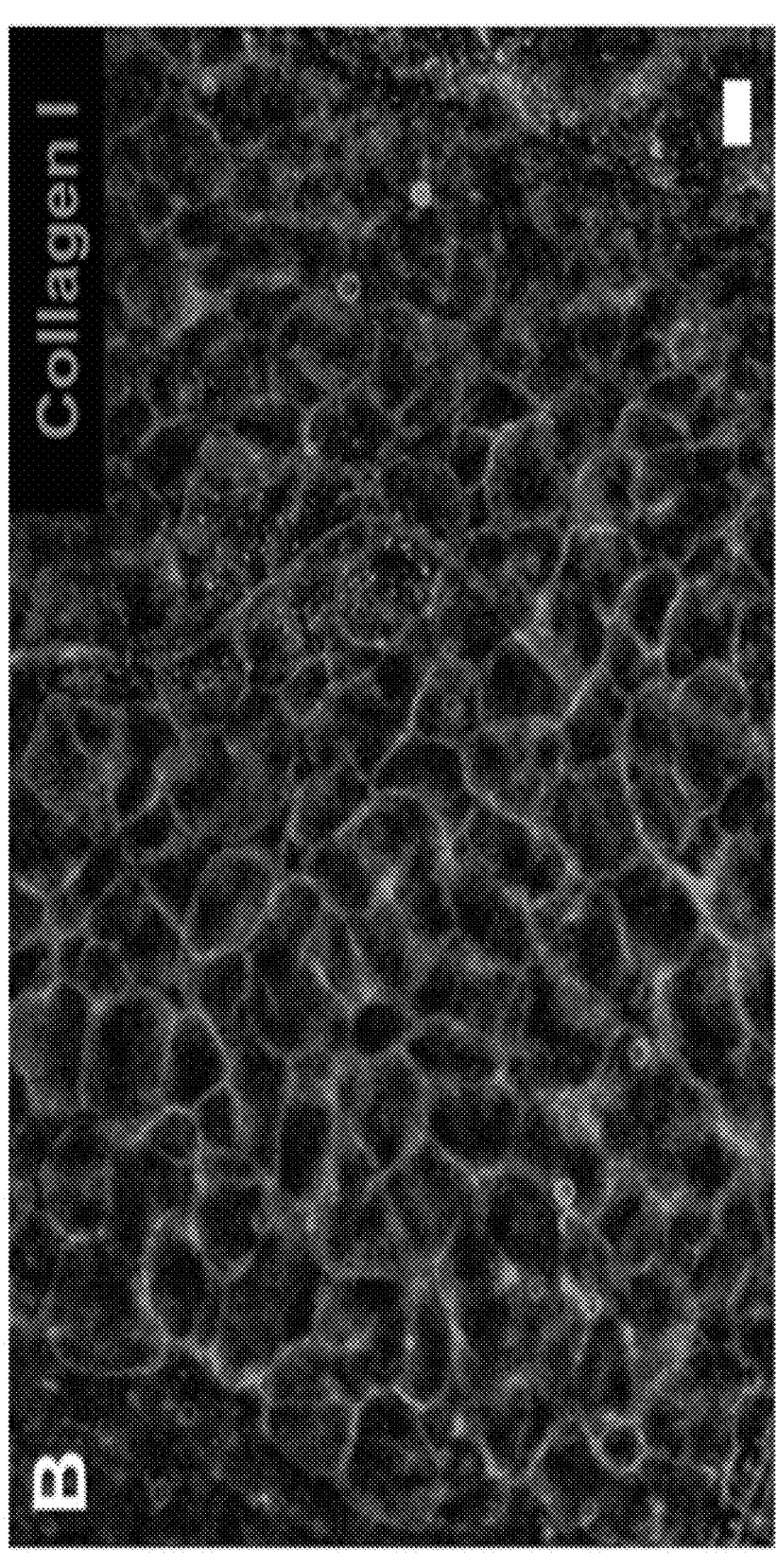
Figure 15C:
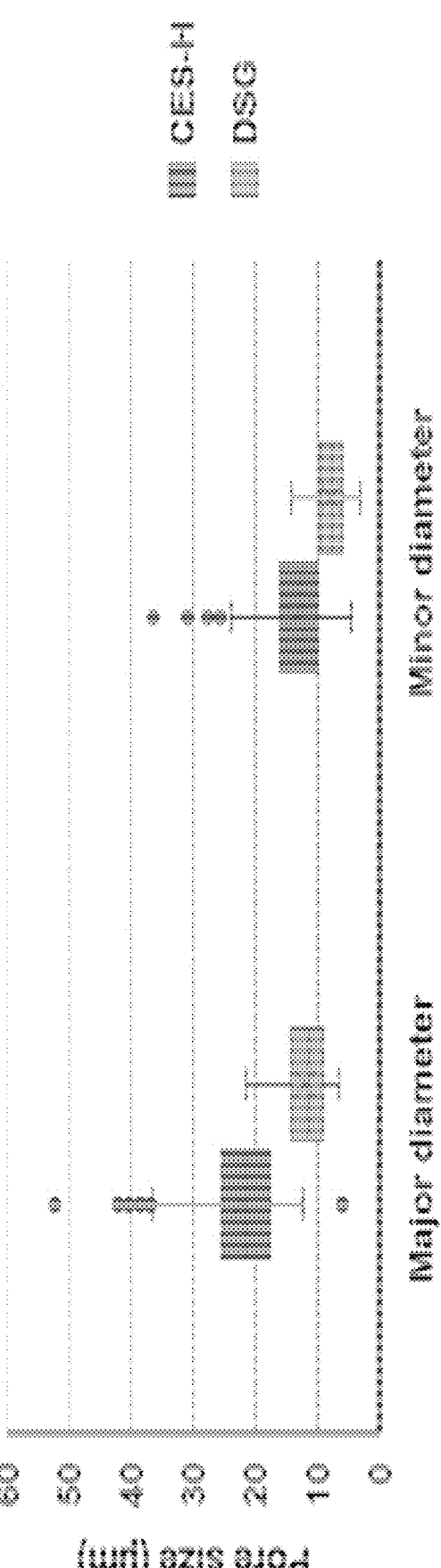
Figure 15D:
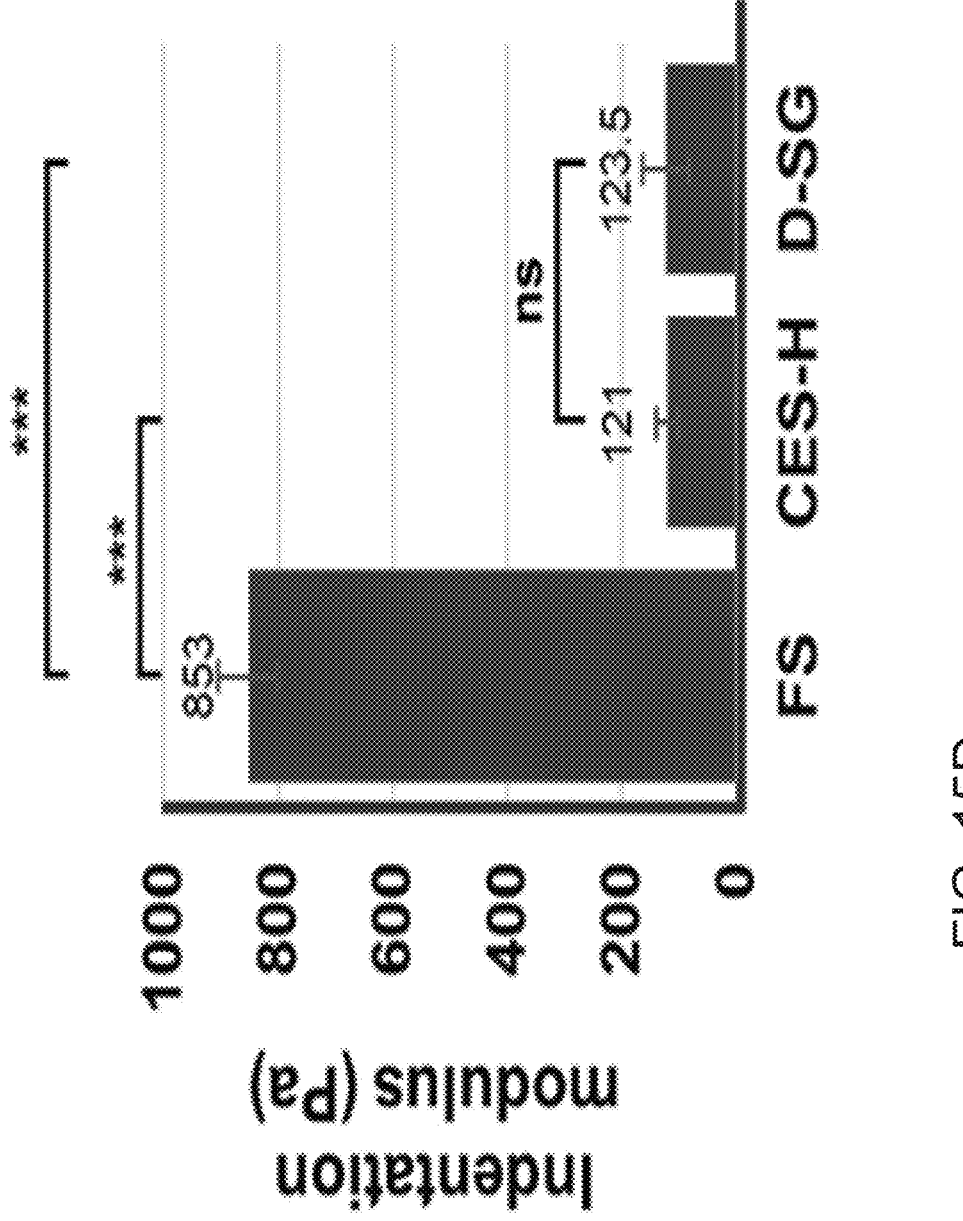
Figure 15E:
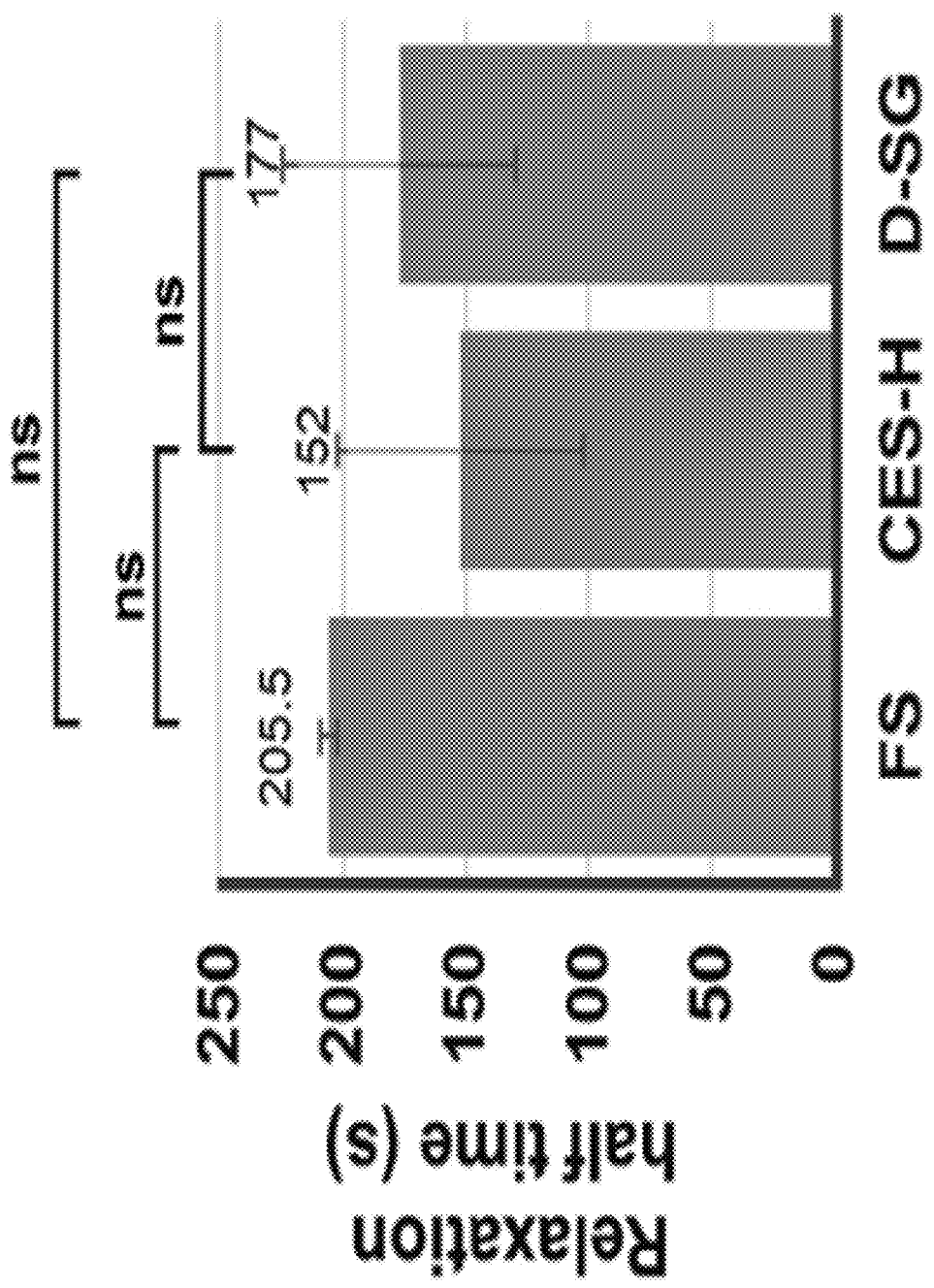

More specifically, FIGS. 15A-15E depict elastin-alginate cryoelectrospun scaffolds with honeycomb topography (CES-H) mimicking decellularized adult salivary gland ECM in topographic and viscoelastic properties. FIG. 15A depicts SEM image of CES-H and FIG. 15B depicts fluorescence image of decellularized adult salivary gland matrix (D-SG) showing topographical similarities. Scale bar=20 μm. FIG. 15C depicts pore size analysis using ImageJ. Comparison of FIG. 15D compression modulus and FIG. 15E relaxation half time of 1% elastin-1.5% alginate freeze-dried sponges (FS), 1% elastin-1.5% alginate-3% PEG CES-H and D-SG showing that CES-H exhibited viscoelastic properties similar to D-SG. ***, P<0.0001; ns, not significant.

The fabrication strategy we developed incorporates ECM proteins and hydrogel materials in one step, in contrast to other fabrication strategies, where fibrous components are fabricated and subsequently embedded into hydrogel materials. (See e.g., Formica F A, Öztürk E, Hess S C, et al. A Bioinspired Ultraporous Nanofiber-Hydrogel Mimic of the Cartilage Extracellular Matrix. *Adv Healthc Mater.* 2016; 5(24):3129-3138; Castilho M, Hochleitner G, Wilson W, et al. Mechanical behavior of a soft hydrogel reinforced with three-dimensional printed microfibre scaffolds. *Sci Rep.* Published online 2018. doi:10.1038/s41598-018-19502-y; and Li X, Cho B, Martin R, et al. Nanofiber-hydrogel composite-mediated angiogenesis for soft tissue reconstruction. *Sci Transl Med.* Published online 2019. doi:10.1126/scitranslmed.aau6210) before crosslinking. The technique reported here should allow for electrospinning of any water soluble, ECM protein-hydrogel material combination with a long-chain polymer, such as PEG-400 kD, to ensure the electrical conductivity, viscosity, and chain entanglement required for electrospinning. Our chosen biomaterials of 1% elastin-1.5% alginate mimicked the elastic modulus and relaxation properties of native salivary ECM (FIG. 4D, E) and can be supplemented with additional ECM components to engineer custom microenvironments. Embryonic microenvironments are pliable and have a low elastic modulus of 50-300 Pa (See e.g., Zhu M, Tao H, Samani M, et al. Three-dimensional tissue stiffness mapping in the mouse embryo supports durotaxis during early limb bud morphogenesis. *bioRxiv.* Published online 2018. doi: 10.1101/412072), to facilitate morphogenesis, cell expansion, and migration. Hence, the low elastic modulus of the elastin-alginate honeycomb CES at ~120 Pa makes them promising candidates for biomimetic matrices to regenerate or model a range of soft tissues.

The complex effects of process parameters on the cryoelectrospinning process generate a need for reproducible and homogenous scaffold growth. We improved the scaffold consistency, homogeneity, and yield by establishing thresholds for process parameters and evaluating alternative collector plate geometries. We successfully confirmed our hypothesis that electric field homogenization would improve scaffold homogeneity and yield through COMSOL simulation and fabrication optimization (FIG. 3). The homogeneous electric field and the geometry of the metallic probe array regulated individual scaffold growth, scaffold distribution and size, and increased the scaffold yield of each cryoelectrospinning run to >100 scaffolds. While probe-array collector plates have been used in traditional electrospinning to improve the scaffold porosity (See e.g., Blakeney B A, Tambralli A, Anderson J M, et al. Cell infiltration and growth in a low density, uncompressed three-dimensional electrospun nanofibrous scaffold. *Biomaterials.* 2011; 32(6):1583-1590. doi:10.1016/j.biomaterials.2010.10.056; Qiao Y, Liu X, Fu G, et al. An ordered electrospun polycaprolactone-collagen-silk fibroin scaffold for hepatocyte culture. *J Mater Sci.* 2018; 53(3):1623-1633. doi:10.1007/s10853-017-1670-9; and Phipps M C, Clem W C, Grunda J M, Clines G A, Bellis S L. Increasing the pore sizes of bone-mimetic electrospun scaffolds comprised of polycaprolactone, collagen I and hydroxyapatite to enhance cell infiltration. *Biomaterials.* 2012; 33(2):524-534. doi: 10.1016/j.biomaterials.2011.09.080), they have not been previously used for cryoelectrospinning for distributed and homogenous growth. Further, delineation of the effects of solvent, air temperature, relative humidity and collector plate temperature on the cryoelectrospun scaffold topography (FIG. 2E) allowed us to determine the boundary conditions for these parameters to reproducibly produce scaffolds with honeycomb topography.

To demonstrate cell growth, viability, and phenotype maintenance on honeycomb CES, we cultured stromal mesenchyme NIH 3T3 fibroblasts and salivary ductal epithelial SIMS cells on honeycomb CES, fibrous CES, and conventional electrospun NF mats. We demonstrated viable 3D cell growth on the honeycomb CES (FIG. 16A, B) and determined that honeycomb CES and fibrous CES topography allowed both stromal fibroblasts and salivary epithelial cells to maintain their characteristic morphology, while NF mats did not (FIGS. 17A, 20A, 19), emphasizing the role of scaffold architecture on 3D cell growth. The high porosity of honeycomb CES and fibrous CES may have maintained scaffold topography despite the alginate swelling, which could have, in turn, permitted cell attachment, growth, and cell-cell interaction in contrast to NF mats (FIGS. 18A, B). Further, we observed that the honeycomb CES backbone possessed surface roughness (FIG. 11) and hypothesize that the inherent surface roughness of the honeycomb CES backbone improved cell attachment on honeycomb CES, despite the lack of cell adhesion motifs in alginate. Therefore, even though honeycomb CES, fibrous CES, and NF mats were fabricated using the same material composition (1% elastin, 1.5% alginate, and 3% PEG-400 kD), cryoelectrospun scaffolds such as honeycomb CES and fibrous CES offered a topographical advantage for cell attachment and maintenance of cell morphology over traditional electrospinning.

One of the key factors influencing cell phenotype in vivo is cell communication through cell-cell contacts in 3D. It was demonstrated that honeycomb CES, but not NF mats or fibrous CES, permitted 3D cell cluster growth and the organization of cells of different types into separate clusters, reminiscent of cellular organization and interaction in vivo (FIG. 20B). Though fibrous CES favored cell attachment and maintenance of cell morphology, cells were randomly attached and grew as mono- or bilayers (FIG. 20B bottom panel). Furthermore, in the coculture experiment condition, the fibroblasts and epithelium organized themselves into distinct clusters on honeycomb CES; however, no distinct organization was observed on fibrous CES. Honeycomb CES supported cell growth in all orientations, deep into the scaffold; however, fibrous CES favored the growth of cells only in the horizontal orientation and as cell sheets. Hence, the topography of honeycomb CES facilitates cell-cell interactions similar to tissues in vivo by promoting cell growth in random orientations and grouping of cells of different types into separate clusters.

It was also demonstrated that honeycomb CES not only maintained the an adherent morphology of NIH 3T3 fibroblasts but also limited the expression of α-SMA (FIG. 17D), a protein reported to be expressed by myofibroblasts, which are derived from fibroblasts and other cells that undergo a maladaptive differentiation in a stiff or fibrotic microenvironments (See e.g., Baum J, Duffy H S. Fibroblasts and myofibroblasts: What are we talking about? *J Cardiovasc Pharmacol.* Published online 2011. doi:10.1097/FJC.0b013e3182116e39). Further, we demonstrated maintenance of native salivary mesenchyme markers (CD140a and CD140b) in primary embryonic mesenchyme (FIG. 21). While the maintenance of vimentin in primary E16 mesenchyme demonstrates retention of mesenchymal phenotype, the reduction of vimentin expression from day 1 to day 7 indicates possible repression of myofibroblast differentiation since vimentin is known to be upregulated in fibrotic environments (See e.g., Surolia R, Li F J, Wang Z, et al. Vimentin intermediate filament assembly regulates fibroblast invasion in fibrogenic lung injury. *JCI Insight.* 2019; 4(7). doi:10.1172/JCI.INSIGHT.123253).

The similar viscoelastic properties between honeycomb CES and healthy, native ECM might be the primary contributing factor for the reduced fibrotic phenotype of the stromal cells grown on the honeycomb CES scaffolds. We also observed that honeycomb CES promoted 3D growth of epithelial clusters; in particular, the presence of mesenchyme in the honeycomb CES matrix permitted retention of epithelial phenotype (FIG. 20D). This behavior might be due to the fact that honeycomb CES better mimics the bulk properties of ECM rather than that of basement membranes that underlie the epithelium in vivo. Hence, even though honeycomb CES supported the viable growth of epithelial clusters, the presence of stromal cells on honeycomb CES might have enabled an in vivo-like stromal-epithelial interaction, which facilitated the retention of epithelial phenotype. These results demonstrate the feasibility of using honeycomb CES to support healthy stromal growth and function for multi-cellular salivary tissue engineering and lay the foundation for further exploratory work with other soft tissues/organs.

Overall, a cryoelectrospinning process has been developed to bioengineer a 3D porous matrix with minimal backbone and interconnected pores. The bulk honeycomb topography, in combination with the biomaterials chosen, yielded a scaffold with physical and mechanical properties similar to native salivary gland ECM. Stromal cells, including NIH 3T3 fibroblasts and MSC-like, primary embryonic mesenchyme, attached to the scaffolds and maintained their mesenchymal phenotype and NIH 3T3 fibroblasts on honeycomb CES supported salivary gland epithelial cell growth and organization.

Example II

Method and Results

To test if implantation of cryoelectrospun scaffolds induces inflammatory response in vivo in mice, mice were first operated on to resect a portion of the salivary gland and one set of mice were sutured up and another set were implanted with scaffolds prior to suturing the incision site. Mice were observed for 14 days for behavioral changes usually observed with discomfort and inflammation, and redness and swelling at incision site. Both sets of mice with and without scaffolds implanted remained alert and active with no signs of distress. No inflammation was observed externally or internally 14 days after the surgery. Referring now to FIGS. 22A-D, FIGS. 22A-D depict data indicating implanted cryoelectrospun scaffolds are biocompatible and do not trigger an inflammatory response: External (FIG. 22A) and internal (FIG. 22B) images of the incision site in mice not implanted with scaffolds. External (FIG. 22C) and Internal (FIG. 22D) images of incision site in mice implanted with scaffolds. Both external and internal incision sites show lack of redness and inflammation 14 days post resection surgery in mice with and without scaffold implantation. Mice in both experimental conditions were alert and active post-surgery.

Example III

Introduction to Example III: Mesenchymal stem/stromal cell (MSC) therapy has shown promise in treating many cancers, fibrosis, degenerative disorders, and recently in COVID-19. MSC therapy has gained significant traction in the past few decades for remediating degeneration of the brain, heart, liver, kidney, salivary gland, etc. through regenerative, immunomodulatory, and anti-fibrotic mechanisms. Fibrosis and cancer are both a huge disease burden, contributing to 45% and 21% deaths, respectively in the US. Moreover, many degenerative diseases (e.g., arthritis, osteoporosis, neurodegenerative diseases) can currently only be managed but not cured. MSC therapy offers the advantage of being a non-palliative treatment for many of these diseases and could possibly be a lifetime cure.

Fibrosis is an organ-impairing disease caused by a chronic inflammatory insult, characterized by aberrant secretion of ECM. Fibrosis is associated with high mortality due to its ability to impair almost any organ system including the liver, kidney, lung, salivary gland, heart, cornea and skin. Fibrosis in the salivary gland impairs the ability of the stroma to support epithelial secretory function, thereby leading to salivary hypofunction, which can be caused by the autoimmune disorder Sjögren's syndrome, diabetes mellitus, or radiation therapy in head and neck cancer patients. Current treatments for salivary hypofunction include topical mucosal lubricants, saliva substitutes, sugar-free lozenges, saliva stimulators pilocarpine and cevimeline, acupuncture, or transcutaneous electrostimulation, all of which are palliative and often produce side effects more severe than the symptoms of the condition. MSC therapy has shown improved salivary gland function in patients with radiation therapy-induced salivary hypofunction, by remediation of fibrosis, increased serous tissue composition, and improvement of saliva output. While MSC therapy has demonstrated tremendous potential in improving organ function, current MSC delivery strategies suffer from poor homing/target-specific engraftment rates and transient therapeutic effects.

Current therapeutic strategies for MSC delivery are predominantly systemic, intramuscular, or transepidermal delivery or direct injection into tissues/organs. Systemic delivery of MSCs, either through intravenous or intraarterial routes has been the most sought out MSC delivery strategy due to the ease of implementation. However, the clinical translation of this therapeutic strategy has faced some severe limitations, including lack of control over the biodistribution of MSCs delivered, poor retention of MSCs for over 7 days, poor engraftment of MSCs delivered, formation of emboli in organs with microcapillaries, and poor targeting of organs/homing. Further, the biodistribution of MSCs in organs has been shown to be dependent on the age of the organism with very poor retention in vivo in aged animals, the main target population for MSC therapy to remediate degenerative diseases. Topical delivery of MSCs through subcutaneous routes has demonstrated improved outcomes in burn and chronic cutaneous wounds, and intramuscular routes have shown improved retention of MSCs for up to 5 months in mice; however, these delivery routes may not be appropriate to target internal organs. Thus, the full potency of MSC therapy is yet to be explored, and a better delivery strategy is required to improve retention of MSCs post-implantation for therapeutic efficacy.

Scaffold-based cell delivery is a promising strategy to improve targeted delivery, engraftment rate, and duration of retention of MSCs. Scaffold-based approaches can improve the efficacy of MSC delivery, enhance the long-term persistence of MSCs at the target site and hence, boost the potency of the treatment. Further, mechanical cues derived from scaffolds have been shown to modulate the secretory and regenerative potential of MSCs. Ideal scaffolds for MSC delivery should preserve the pro-regenerative and anti-inflammatory properties of MSCs and prevent their transdifferentiation. MSCs or stromal cells typically reside in a soft ECM in vivo and therefore, scaffolds that emulate native soft tissue ECM could potentially maintain the MSC phenotype. We have shown that elastin-alginate cryoelectrospun scaffolds recapitulate the honeycomb topography and mechanical properties of salivary gland ECM and support the growth of immortalized stromal cells. Further, matrices that mimic physiological ECM could themselves prove therapeutic and in combination with MSCs, have the potential to maximize therapeutic efficiency as observed in functional motor recovery in spinal cord injury patients.

We have examined the potential of using elastin-alginate cryoelectrospun scaffolds with honeycomb topography for stromal cell delivery targeting fibrosis remediation. Using primary embryonic day 16 (E16) mesenchyme as MSC-like cells, we compared the ability of cryoelectrospun scaffolds to support stromal cell maintenance with that of traditionally electrospun elastin-alginate nanofiber mats and bulk hydrogels. Decellularized salivary gland matrices, which recapitulate the in vivo microenvironment, and Matrigel, which is the conventional vehicle for salivary gland organoid culture, were used as positive controls for comparison. We examined the expression of healthy stromal markers and myofibroblast markers, to determine the scaffold best suited for MSC delivery. We established in vitro analyses to evaluate the ability of FGF2 to improve stromal phenotype and the ability of the scaffold, primary E16 mesenchyme and FGF2 to remediate the fibrotic phenotype of TGFβ1-induced myofibroblasts.

Materials and Methods

Animals

Mice used to source salivary glands were either CD-1 strain from Charles River Laboratories (Wilmington, MA) or C57B6 strain from Jackson Laboratories (Bar Harbor, ME). The care and handling of mice and tissue collection were carried out in accordance with the National Institutes of Health Guide for the Care and Use of Laboratory Animals and conformed to the requirements of and was approved by the Institutional Animal Care Use Committee (IACUC) of the University at Albany.

Cell Culture

Isolation and Cell Culture of Mouse Primary E16 Salivary Mesenchyme:

Primary mesenchyme was isolated from embryonic day 16 (E16) submandibular salivary glands dissected from timed-pregnant CD-1 female *Mus musculus* (Charles River Laboratories), as described previously. The isolated primary E16 mesenchyme cells were cultured in DMEM/F12 medium (Cat. #11039047, ThermoFisher Scientific, Carlsbad, CA) supplemented with 10% Fetal Bovine Serum (FBS) (Cat. #10082147, ThermoFisher Scientific) and 1% penicillin and streptomycin (PenStrep, 10,000 U/mL, ThermoFisher Scientific) and incubated in a 37° C., 5% CO2 humidified incubator for 3-4 days until 90-95% confluent. The primary E16 mesenchyme cells were cultured for 1 passage before use. The medium was typically replaced every day.

Myofibroblast induction and culture: Myofibroblasts were differentiated from the primary E16 mesenchyme cells by subculturing them for 4 or 5 passages and then treating them with 5 ng/mL of TGFβ1 (Cat. #240-B, R&D Systems, Minneapolis, MN) for 1 or 2 passages until exhibiting myofibroblast morphology, determined by an increase in cell surface area and the number of podia.

Scaffold Preparation

Elastin-alginate nanofiber mats (NF) were fabricated using 1% elastin (Elastin Products Company, Owensville, MI), 1.5% alginate and 3% PEG-400 kD (Sigma-Aldrich, St. Louis, MO) solution in deionized water as described previously and in supplementary materials.

Elastin-alginate bulk hydrogels (BH) were fabricated by preparing 2% elastin and 3% alginate solutions in sterile deionized water and by mixing them in equal parts with the cell suspension for a final material composition of 1% elastin and 1.5% alginate that matches elastin-alginate nanofibers or cryoelectrospun scaffolds followed by crosslinking with 100 mM CaCl2 (Sigma-Aldrich) for 30 min to cross-link the hydrogel and form hydrogel-cell constructs, which were thereafter switched to cell culture medium with 25 mM CaCl2.

Elastin-alginate cryoelectrospun scaffolds with honeycomb topography (CES) were fabricated by cryoelectrospinning 1% elastin, 1.5% alginate and 3% PEG-400 kD solution in deionized water as described previously and in supplementary materials.

Decellularized salivary gland matrices (DSG) were obtained by decellularization of whole organs were resected from adult female CD-1 or C57Bl/6 mice as described in our previous work. The decellularized salivary gland was stabilized using forceps on the stage (sterilized by 70% ethanol) of a dissecting microscope and sliced into sections using a vibratome blade into equally sized pieces. These decellularized salivary gland matrices were stored at 4° C. in cell culture medium.

Matrigel scaffolds were prepared by mixing 5 µL each of Matrigel (Cat. #356234, Corning Inc., Corning, NY) and cell suspension (10,000 cells/µL). 10 µL of the Matrigel-cell suspension solution was pipetted onto a 0.1 µm Nuclepore polycarbonate filter (Cat. #0930051, Cytiva, Marlborough, MA). The filter was floated on cell culture medium in 50 mm glass-bottom dishes (Cat. #P50G-1.5-14F, MatTek Corporation, Ashland, MA) and incubated at 37° C. in a humidified tissue culture incubator with 5% $CO_2$.

Nanofibers, cryoelectrospun scaffolds, and decellularized salivary gland matrices were soaked in 70% ethanol for 30 min, washed with 0.9% NaCl for 10 min, and then hydrated in cell culture medium and 4% penicillin-streptomycin-amphotericin B (R&D Systems) overnight prior to cell seeding for culture.

Cell Culture on Scaffolds

Stromal Cell Culture on Scaffolds:

Primary E16 mesenchyme were seeded on scaffolds as detailed in supplementary materials. After 24 hours, the cell-scaffold constructs, except Matrigel were transferred into wells of a 24-well plate that were coated with lipidure (Amsbio, Cambridge, MA) and grown in 300 µL media for improved oxygen-mass transfer and cell viability while incubating without rotary shaking. For experiments requiring treatment with FGF2 (Cat. #Z200015, Applied Biological Materials, Vancouver, CA) and TGβ1, the growth factors were added to the medium at a final concentration of 100 ng/ml FGF2 and 5 ng/ml TGβ1, respectively, 1 day after cell seeding, to allow these cells to first acclimate to the new environment. Cell culture media were replenished every day by removing 150 µL of spent media from each well and replenishing it with 200 µL of fresh media to avoid nutrient depletion and to retain certain amount of the conditioned media. Cells were cultured on scaffolds for up to 7 days after growth factor addition.

Co-Culture of Primary E16 Mesenchyme Cells and Myofibroblasts on Scaffolds

To mimic stromal cell delivery to a fibrotic microenvironment, 50,000 primary E16 mesenchymal cells were first seeded on the scaffold as described in supplementary materials and grown for 4 days as described above, mimicking preparation for scaffold-based cell delivery. Subsequently, 50,000 myofibroblasts were seeded as described above to mimic their interaction post-implantation. Cells were cultured on scaffolds in the absence or presence of growth factors (100 ng/ml FGF2 and/or 5 ng/ml TGFβ1) for up to 7 days after growth factor addition. Media were changed as described above.

LIVE/DEAD Assay

Cell-scaffold constructs were incubated with 0.2 M calcein-AM and 0.4 M ethidium homodimer (Sigma-Aldrich) for 25 min at 37° C. and imaged using a Leica SP5 confocal laser scanning microscope (Leica Microsystems, Mannheim, Germany) to reveal live cells in green and dead cells in red fluorescence. Quantitative analysis of live and dead cells was performed using ImageJ as described previously.

Immunocytochemistry and Confocal Imaging

Cell culture samples were fixed in 4% paraformaldehyde (Thermo Fisher Scientific) in 5% (w/v) sucrose (Sigma-Aldrich), 0.6×PBS (Thermo Fisher Scientific) for 15 minutes, permeabilized with 0.1% Triton X-100 (Sigma-Aldrich) in 1×PBS for 15 min, blocked with 20% (Jackson ImmunoResearch Laboratories, West Grove, PA)/3% bovine serum albumin (Thermo Fisher Scientific) in wash buffer (0.9% NaCl-50 mM CaCl2 in deionized water) for 2 hours at room temperature, incubated with primary antibodies at 4° C. overnight, followed by incubation with DAPI and secondary antibodies at room temperature for 2 hours. Primary E16 mesenchyme were immunostained for PDGFRα/CD140a, PDGFRB/CD140b, vimentin, calponin, and α-SMA while myofibroblast alone or coculture of myofibroblast and primary mesenchyme cells were stained for PDGFRα, calponin, and α-SMA. Antibody details and concentrations used are detailed in Table 51. All cells were co-stained with DAPI (Sigma-Aldrich) to reveal the nuclei within the total cell population. Samples were then mounted using a glycerol-based mounting medium for imaging. Confocal imaging was performed using a Leica SP5 confocal laser scanning microscope (Leica Microsystems, Mannheim, Germany).

TABLE S1

| Primary Antibody | Host Species | Company | Catalog No | Lot No. | Dilution |
|---|---|---|---|---|---|
| Anti-CD140a | Rat | ThermoFisher Scientific | 14-1401-81 | 2015727 | 1:100 |
| Anti-CD140b | Rabbit | Abcam | ab32570 | GR3241180-2 | 1:200 |
| AF-488 conjugated Anti-Vimentin | Rabbit | Cell Signaling Technology | 9854S | 12 | 1:200 |

TABLE S1-continued

| Anti-Calponin 1 | Rabbit | Abcam | ab46794 | | 1:600 |
|---|---|---|---|---|---|
| Anti-α-SMA | Mouse | Sigma Aldrich | A5228 | | 1:1000 |

| Secondary Antibody | Species | Company | Catalog No. | Lot No. | Dilution |
|---|---|---|---|---|---|
| Alexa Fluor ® 488 AffiniPure F(ab')₂ Fragment IgG | Host: Donkey Target: Anti-Rabbit | Jackson ImmunoResearch | 711-226-152 | 132511 | 1:250 |
| Cy ™ 3 AffiniPure F(ab')₂ Fragment IgG (H + L) | Host: Donkey Target: Anti-Rat | Jackson ImmunoResearch | 712-166-153 | 139421 | 1:250 |
| Alexa Fluor ® 647 AffiniPure F(ab')₂ Fragment IgM, μ chain specific | Host: Donkey Target: Anti-Mouse-μ chain specific | Jackson ImmunoResearch | 715-606-020 | 135520 | 1:250 | qPCR Analysis

Primary E16 mesenchyme cells were grown on cryoelectrospun scaffolds, decellularized salivary gland matrices, and Matrigel with and without TGFβ1 and/or FGF2 for 1 or 7 days. Three or four samples of each scaffold type and experimental condition were pooled together to extract enough RNA using RNeasy Micro kit (Qiagen, Germantown, MD) for PCR analysis. Lysis buffer was added to samples, followed by vigorous pipetting and vortexing to break apart the scaffold and lyse all cells. RNA was then isolated as per the protocol specified by Qiagen. RNA was measured by the Qubit™ fluorometer (Invitrogen, Waltham, MA) and cDNA synthesized using Maxima H minus First Strand cDNA synthesis kit (Thermo Fisher Scientific). The concentration of the synthesized cDNA was measured on the Qubit™ fluorometer as well. Primers (Table S2) for housekeeping gene (UBC), mesenchymal markers (PDGFRα, PDGFRβ, and vimentin), and myofibroblast marker (α-SMA) from Integrated DNA Technologies (Coralville, IA), cDNA, and SYBR Green PCR master mix (Thermo Fisher Scientific) were added to the respective wells of a 0.1 mL 96 well PCR plate and assayed on the StepOne Plus Real-Time PCR system (Applied Biosystems, Waltham, MA).

TABLE S2

Primers used for PCR analysis

| Primer | Direction | Gene Sequence |
|---|---|---|
| UBC | Forward | ACAGACGTACCTTCCTCACCA |
| | Reverse | CCCCATCACACCCAAGAACAA |
| Vimentin | Forward | CGCCCTCATTCCCTTGTTGC |
| | Reverse | GGTAGGAGGACGAGGACACAG |
| aSMA | Forward | AATGTCCCCGCCATGTATGT |
| | Reverse | TTTCGTGGATGCCCGCTG |
| CNN1 | Forward | CGGCGTCACCTCTATGATCC |
| | Reverse | GCTCCTAAACAACTGGCCCC |
| PDGFRα | Forward | CACAATAACGGGAGGCTGGT |
| | Reverse | CACCTCCACCACGAACTCTC |
| PDGFRβ | Forward | TTCGAGGCTTATCCGATGCC |
| | Reverse | AGTCGTAAGGCAACTGCACA |

Figure 26:
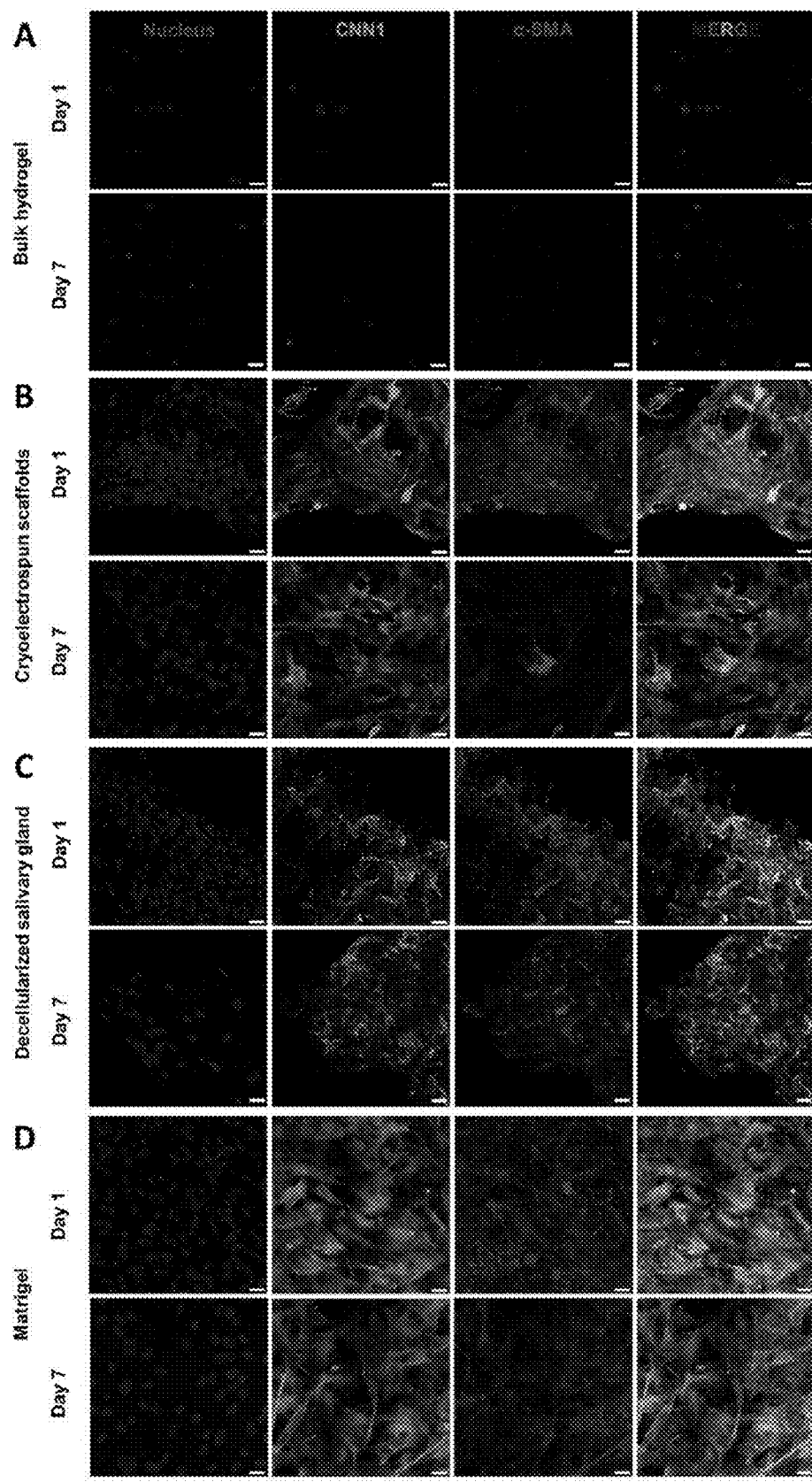
FIGS. 26A-26D depicts data related markers in bulk hydrogels (BH), CES, decellularized salivary gland (DSG) and Matrigel.

Intensity Quantification of 3D Images Using IMARIS 3D images (z-stacks) in '.lif' format obtained from confocal imaging on the Leica SP5 confocal microscope were converted to '.ims' files on the IMARIS software. The number of nuclei in the 3D image was quantified by opening the file in surpass view, creating a new surface, setting the smoothing surface grain size to ~0.6 μm, selecting background subtraction, and manually setting the threshold value to select all nuclei. Artifacts that were not cell nuclei were excluded by using the filter option and filtering based on quality, area, or sphericity. The individual nuclei were viewed in a grid pattern in the vantage view using the 'gallery' option to count the number of nuclei. Merged nuclei were either segmented in the surpass view by enabling 'split touching objects' and setting the seeding diameter to >8 μm, or manually counting merged nuclei based on the number of merged nuclei. To quantify the sum of the intensity of each voxel for each channel in the region of interest (ROI), a new surface was created again in surpass view. The channel which had the most robust protein expression was used to identify the ROI for intensity sum calculation. The smoothing surface grain size was set to ~1.5 μm and the threshold value manually adjusted to select the ROI. Artifacts that were not to be included in the ROI were excluded by using the filter option and filtering based on quality and area. The intensity sum values for each channel in the ROI were exported to an excel file in the vantage view. The protein expression levels in each image were quantified by normalizing the intensity sum for each channel to the number of nuclei in the 3D image (FIG. 26). Fold changes of protein expression levels were determined by normalizing expression levels on day 7 to day 1.

Statistical Analysis

Data are presented as mean±standard deviation. All in vitro cell culture experiments were performed in triplicate unless otherwise indicated. One-way ANOVA followed by Tukey's post hoc test was performed using GraphPad Prism 9.3.0. $p < 0.05$ was considered significant.

Results

Figure 23:
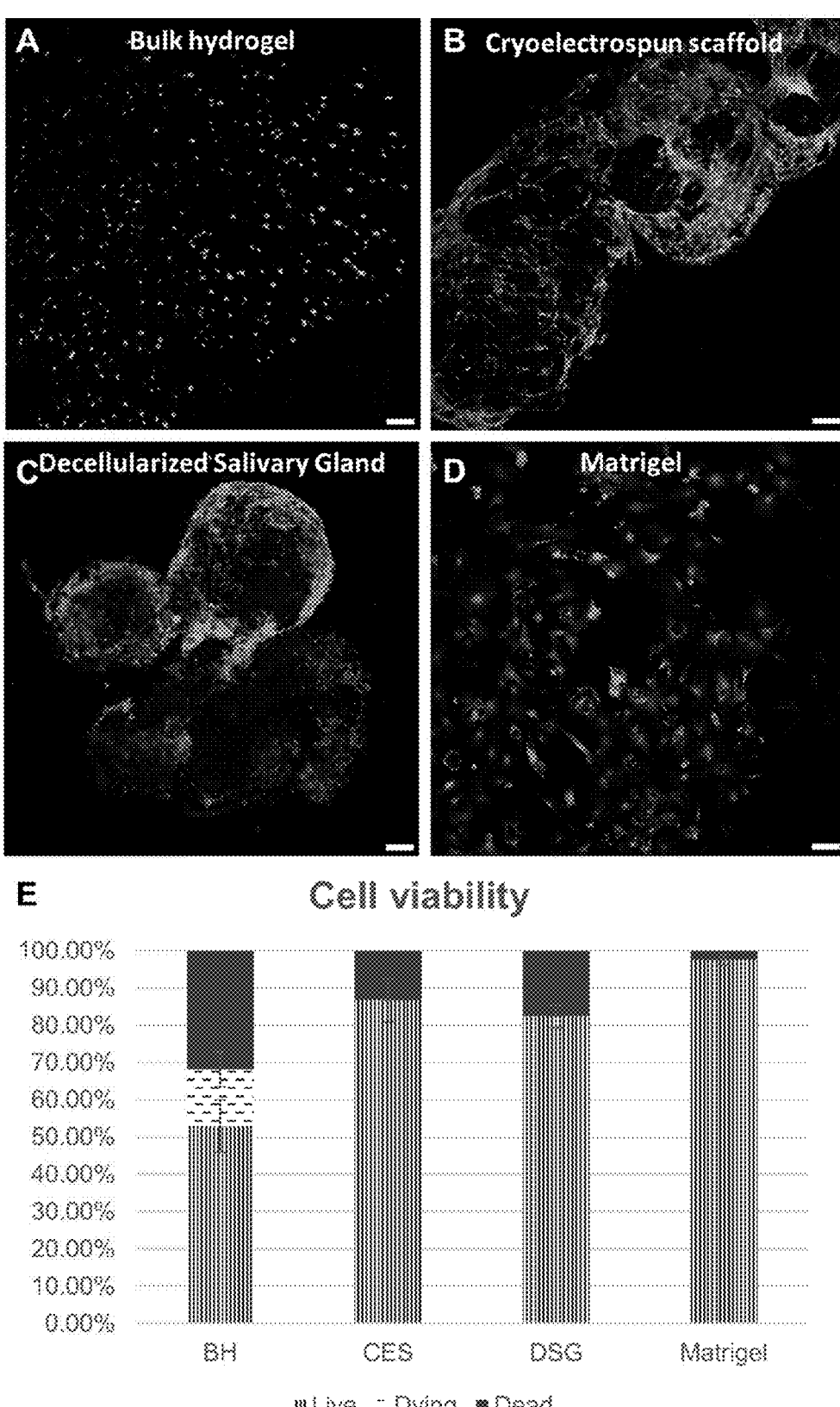
FIGS. 23A-23E depict data relating to cell viability in bulk hydrogel, cryoelectrospun scaffolds, decellularized salivary gland matrices, and Matrigel cultured for 7 days in 24 well plate format.

Cryoelectrospun Scaffolds Allow Viable 3D Stromal Growth Comparable to Decellularized Salivary Gland Matrices To test the feasibility of using elastin-alginate cryoelectrospun scaffolds as a stromal cell delivery vehicle that permits viable long-term stromal cell growth and maintenance for delivery in vivo, we first examined its ability to retain stromal cell viability. We chose to use MSC-like, primary E16 mesenchyme cells since they retain stemness, and are available in large quantities after one passage to satisfy the sheer number of cells required for our elaborate experiments. We grew primary E16 mesenchyme cells for 7 days on elastin-alginate nanofibers (NF), bulk hydrogel (BH), and cryoelectrospun scaffolds (CES) and compared cell viability with decellularized salivary gland matrices (DSG) for physiological relevance and with Matrigel, a standardized in vitro cell culture matrix for stem cells and organoids. We have validated the ability of elastin-alginate CES to mimic the native physical and mechanical properties of ECM and enable healthy stromal growth. Hence, we fabricated NF and BH scaffolds made of the same composition (1% elastin and 1.5% alginate) as CES and compared their ability to retain viable primary E16 mesenchyme for up to 7 days. To ensure high cell attachment efficiency, primary E16 mesenchyme in CES and DSG were grown with mild rotary shaking of 30 rpm for the first 24 hours in ultra-low adhesion polymer-coated, round-bottom wells in a 96-well plate, which improved cell attachment efficiency and reduced the variability in cell attachment compared to static culture (FIG. 23). After the first 24 hours of cell seeding on the scaffolds (BH, CES and DSG), cell-scaffold-constructs were transferred to a 24-well plate with 300 μL media in each well for improved oxygen diffusion and cell viability. We did not choose a 48-well plate for 3D cell culture since it only permitted cell viability of about 50% (FIG. 24), much lower than in Matrigel where cells formed cell-sheets. We observed that the primary E16 mesenchyme cells barely attached to NF, which is consistent with our previous work using other cell types, and negligible numbers of cells remained on the scaffold on day 7 (FIG. 25). As shown in FIG. 23, only 53±7% of the cells encapsulated in the BH were viable, while 15±4.7% were dying (stained for both calcein-AM in green and ethidium homodimer in red) and 32±4.8% were dead, showing no improvement in 24-well plates. Cell viabilities on the CES and DSG improved considerably in 24-well plates and were comparable at 87±5.7% and 82±3%, respectively. Cells on Matrigel showed the highest viability at 98±1.4% possibly due to better nutrient transfer to cell sheets than the 3D cell growth observed in BH, CES and DSG.

Figure 24:
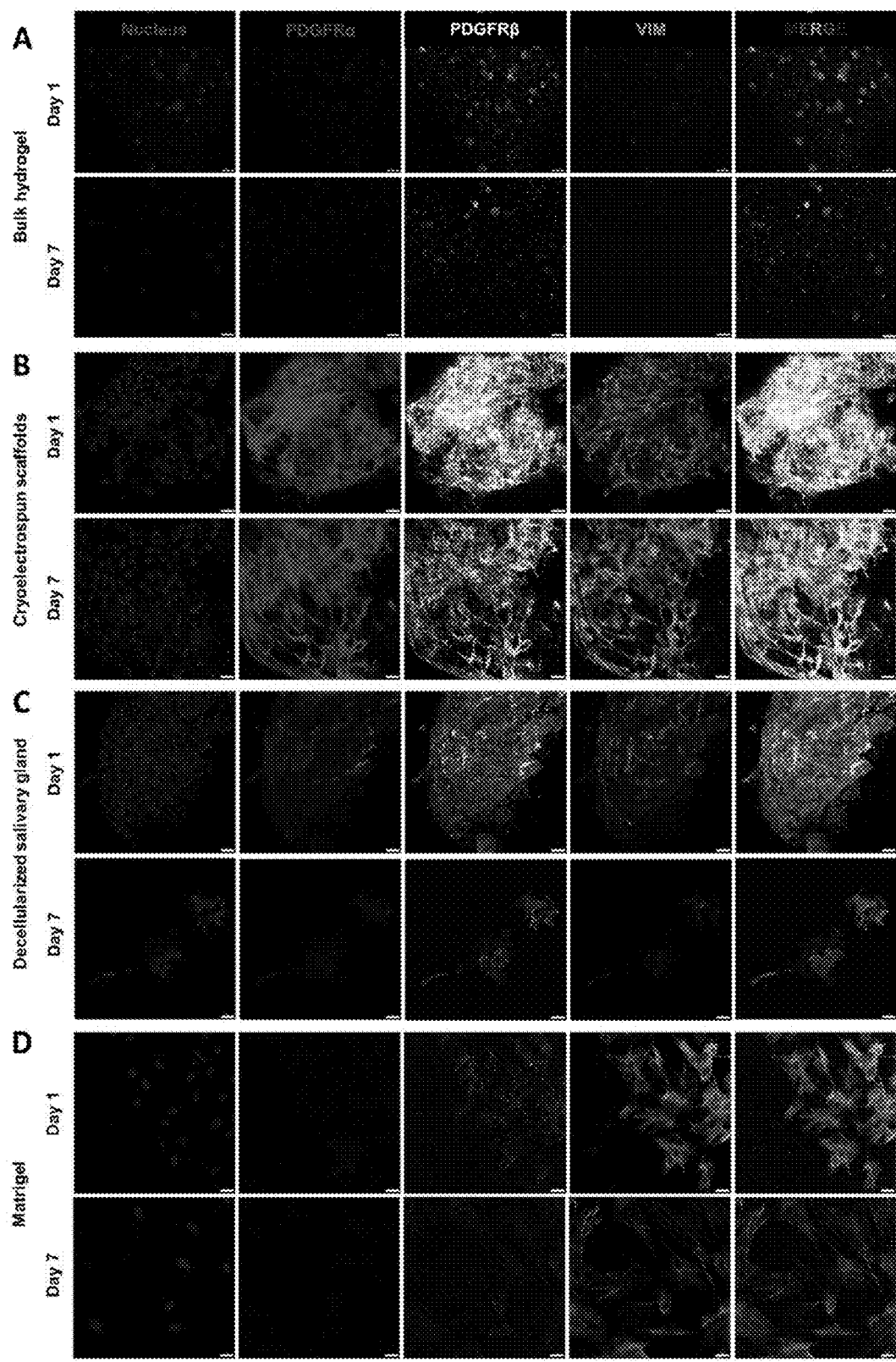
FIGS. 24A-24D depict data analysis validating the ability of CES to promote a healthy stromal phenotype.
Figures 25A, 25B, 25C, 25D:
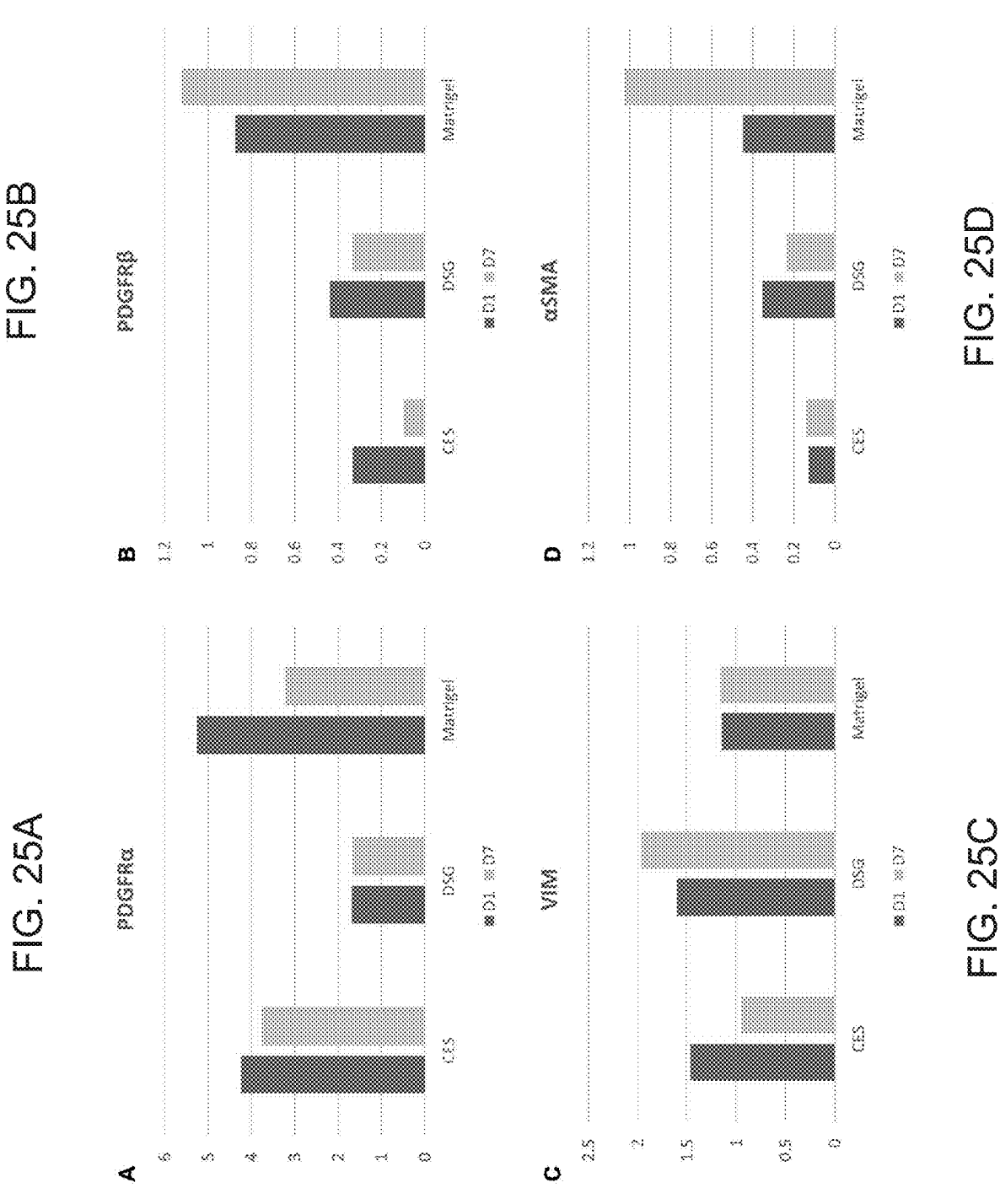
FIGS. 25A-25D depicts data related to analysis of gene expression.

Cryoelectrospun Scaffolds Promote Preferential Healthy Stromal Phenotype in Primary E16 Mesenchyme Cells To test the feasibility of using elastin-alginate CES for MSC delivery, we compared their ability to maintain healthy stromal phenotype with BH, DSG and the accepted standard for organoid culture, Matrigel. We grew primary E16 mesenchyme cells for up to 7 days on the scaffolds and evaluated stromal health through expression of CD140a (PDGFRα), CD140b (PDGFRβ), and vimentin by immunostaining and confocal imaging. PDGFRα and PDGFRβ are membrane receptors of the PDGFR family that are expressed in stromal cells in the salivary gland during the organogenesis phase. We have demonstrated that PDGFRα+ stromal cell subpopulations regulate secretory epithelial phenotype. Vimentin is a standard mesenchymal marker that is up regulated in fibrotic conditions. We observed that the stromal cells remained rounded on BH but had characteristic spread-out fibroblast morphology on CES, DSG, and Matrigel (FIG. 24). Further, the expression of PDGFRα and PDGFRβ was the highest in primary E16 mesenchymal cells grown in CES for 7 days (FIG. 24B), compared to DSG (FIG. 24C), BH (FIG. 2A), and Matrigel (FIG. 24D), highlighting the potential of CES to maintain stromal cells in prime health to support secretory epithelial function in vivo. The expression of vimentin in all scaffold types except BH confirms the maintenance of fibroblast phenotype (FIG. 24A-24D).

Analysis of gene expression confirmed that PDGFRα expression was higher in CES (FIG. 25A), whereas PDGFRβ (FIG. 25B) and vimentin (FIG. 25C) expression were relatively lower in CES compared to DSG, contradicting the observed protein expression levels (FIG. 24B, 24C). BH were excluded from gene expression analysis due to poor cell viability (FIG. 23A, 23E) and rounded cell morphology (FIG. 24A). Further, gene expression levels of PDGFRα and PDGFRβ were much higher in primary E16 mesenchymal cells grown in Matrigel than in CES and DSG, contradictory to the protein expression levels, indicating translational regulation. Vimentin gene expression levels were slightly lower in Matrigel, agreeing with the trend observed with protein expression. The analysis of gene expression confirms the maintenance of the above-mentioned stromal markers in primary E16 mesenchyme grown on CES comparable to or even to a greater degree than in DSG, validating the ability of CES to promote a healthy stromal phenotype.

Cryoelectrospun Scaffolds Repress Myofibroblast Marker Expression in Primary E16 Mesenchyme Cells To probe the ability of cryoelectrospun scaffolds to repress any fibrotic activity in healthy stroma, or prevent their differentiation to myofibroblasts, we grew primary E16 mesenchyme cells for up to 7 days in BH, CES, DSG, and Matrigel and examined expression of myofibroblast markers, α-SMA and calponin-1 (CNN1) by immunostaining and confocal imaging. α-SMA and CNN1 are cytoskeletal proteins that are up-regulated in fibrotic conditions and indicate myofibroblast activity. Lower levels of the myofibroblast markers were observed after 7 days culture in BH (FIG. 26A bottom panel), CES (FIG. 26B bottom panel) and DSG (FIG. 26C bottom panel) compared to Matrigel (FIG. 26D bottom panel). However, because cells were less viable with rounded cell morphology in bulk hydrogels they were excluded from protein and gene expression analysis. Gene expression analysis of α-SMA (FIG. 25D) in CES, DSG, and Matrigel revealed that α-SMA expression was even lower in CES compared to DSG and Matrigel, agreeing with the trend observed with protein expression and confirming cryoelectrospun scaffold's potential to maintain healthy stroma without differentiation to myofibroblasts.

FGF2 Imparts Anti-Fibrotic Properties and Represses Fibrotic Conversion of Primary E16 Mesenchyme Cells to Myofibroblasts in TGFβ1-Induced Fibrotic Microenvironment We have identified that FGF2 regulates PDGFRα+ mesenchymal cells to improve secretory epithelial phenotype. To evaluate whether FGF2 improves the healthy stromal phenotype on cryoelectrospun scaffolds and if it can repress any fibrotic activity in the stroma, we first compared the gene expression of PDGFRα, PDGFRβ, vimentin, and α-SMA in cells grown on CES, DSG, and Matrigel with and without FGF2 supplementation for 7 days. We observed that FGF2 improves PDGFRα expression (FIG. 27A) in all three culture types and that the expression levels in CES and DSG were comparable. PDGFRβ expression (FIG. 27B) remained mostly unaffected in CES and DSG and reduced in Matrigel with FGF2 supplementation. Vimentin (FIG. 27C) and α-SMA (FIG. 27D) decreased in all three types of culture with the addition of FGF2, with α-SMA showing the more substantial decrease.

Figure 27:
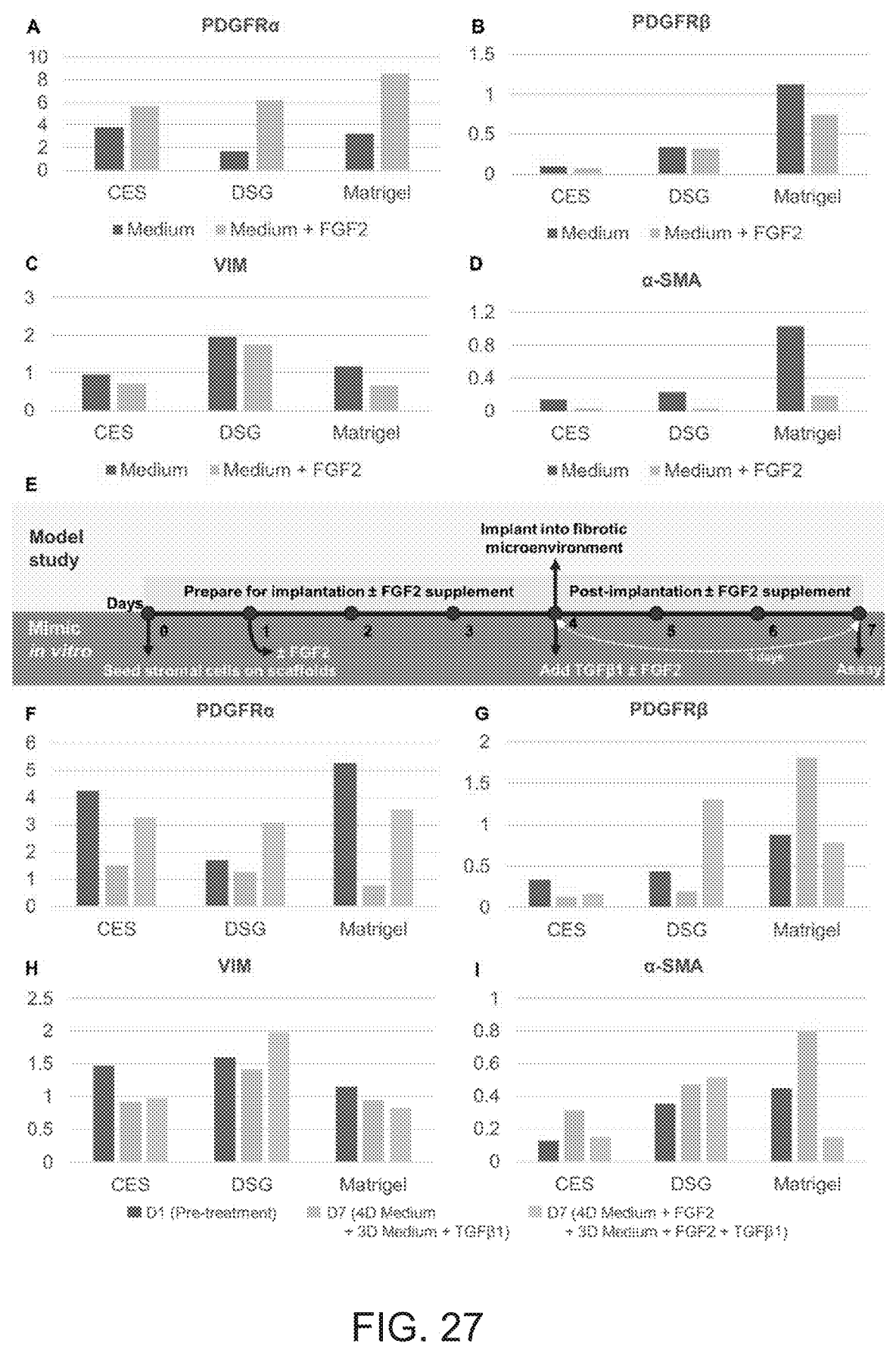

To determine if FGF2 supplementation would promote healthy stromal phenotype and repress the induction of fibrotic activity in healthy stroma when introduced to a fibrotic environment, we created an in vitro culture model to mimic the in-vivo cell delivery and implantation process. We grew primary E16 mesenchyme cells on CES, DSG, and Matrigel for 4 days with and without FGF2 supplementation, and then added TGFβ1 to mimic implantation into a fibrotic environment (FIG. 27E). We chose day 4 as the timepoint to mimic implantation since in our previous studies we have observed mild expansion and improved cell spreading on the scaffold after 4 days in culture. The samples were continued in culture with or without FGF2 supplement post TGFβ1 addition for 3 days, and gene expression of stromal markers (PDGFRα, PDGFRβ, and vimentin) and myofibroblast marker (α-SMA) was analyzed. PDGFRα expression was reduced after the addition of TGFβ1 but the continued presence of FGF2 rescued its expression in cells on CES, DSG, and Matrigel (FIG. 27F). PDGFRβ expression was reduced after the addition of TGFβ1 in CES and DSG but increased in Matrigel (FIG. 27F). Supplementation with FGF2 did not seem to affect PDGFRβ expression in CES but improved its expression in DSG and reduced its expression in Matrigel. Vimentin expression was reduced with TGFβ1 addition and was rescued by FGF2 supplementation in DSG but not in CES or Matrigel (FIG. 27G). α-SMA expression increased with TGFβ1 addition and was repressed with FGF2 addition in CES and Matrigel but not DSG (FIG. 27H).

Cryoelectrospun Scaffolds Repress Fibrotic Activity in Myofibroblasts

Figure 28:
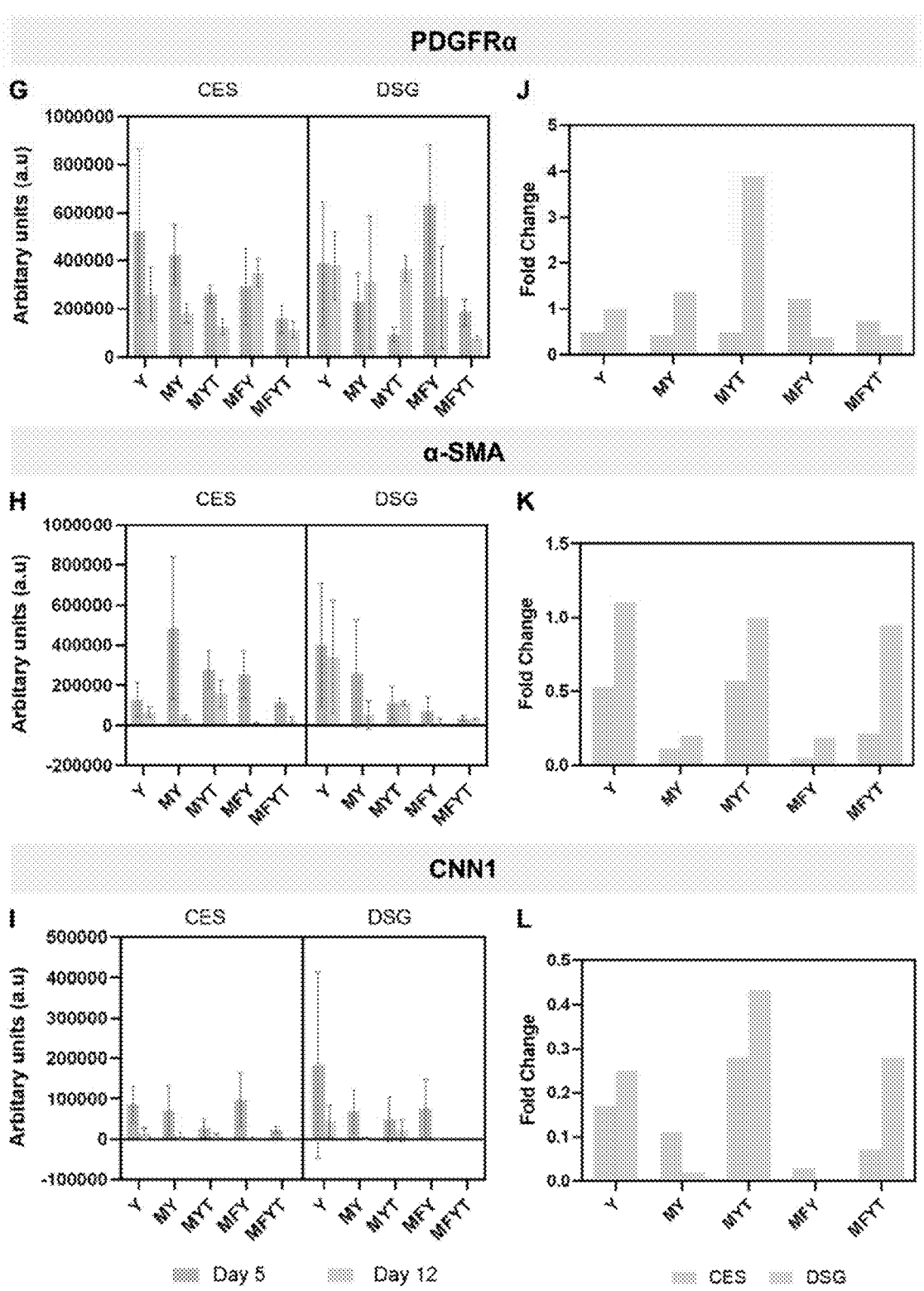
FIGS. 28A-28L depicts data related to effects of cryoelectrospun scaffolds and primary E16 mesenchyme on fibrotic activity of myofibroblasts in the presence of regenerative and fibrotic stimulants.

To further examine the potential of the CES in repressing fibrotic activity in myofibroblasts through mechanical cues, myofibroblasts alone were cultured on CES for 7 days (Group Y, FIG. 28B) and compared with growth on DSG. We observed that CES could repress the fibrotic activity of myofibroblasts as observed through the reduction in α-SMA expression by ~47% and CNN1 expression by ~83% after 7 days in culture, whereas DSG elevated α-SMA expression by ~10% and repressed CNN1 expression by ~75% (FIG. 28B, H, I, K, L). PDGFRα expression levels in myofibroblasts reduced in CES by ~51% but were maintained in DSG (FIG. 28B, G, J). PDGFRα has been shown to have not only pro-regenerative but also pro-fibrotic functions and the maintenance of α-SMA and PDGFRα expression in DSG indicates maintenance of fibrotic phenotype of myofibroblasts whereas the reduction in both α-SMA and PDGFRα expression in CES indicates repression of fibrotic phenotype. Further, the absolute expression levels of α-SMA and CNN1 on CES were lower than that on DSG, reinforcing the anti-fibrotic effects of CES.

Primary E16 Mesenchyme on Cryoelectrospun Scaffolds Repress Fibrotic Activity in Myofibroblasts To determine if primary E16 mesenchyme on CES can repress fibrotic activity in myofibroblasts, we primed primary E16 mesenchyme on CES and DSG for 4 days prior to seeding myofibroblasts (Group MY, FIG. 28C) to mimic their interaction in an in vivo implantation study. We observed that primary E16 mesenchyme could repress fibrotic activity in myofibroblasts evidenced by the reduction of α-SMA expression by ~89% on CES and ~80% on DSG, and CNN1 expression by ~89% on CES and ~98% on DSG after 7 days in culture (FIG. 28C, H, I, K, L). PDGFRα expression decreased by 57% in cells grown on CES and increased by 37% in DSG (FIG. 28C, G, J) and since α-SMA and calponin levels decreased in both conditions, PDGFRα could be functioning in a pro-regenerative role in DSG but not CES. The absolute expression levels of PDGFRα, α-SMA and CNN1 for scaffold only and primary E16 mesenchyme on scaffolds (CES/DSG) were not significantly different indicating comparable performance.

To determine if primary E16 mesenchyme on CES can continue to repress fibrotic activity in myofibroblasts in a TGFβ1-induced fibrotic microenvironment, we primed samples similar to group MY TGFβ1 (Group MYT, FIG. 28D). We observed a reduction in α-SMA and CNN1 expression by ~43% and 72% respectively in CES samples after 7 days in culture, whereas α-SMA expression was maintained and CNN1 expression reduced by ~57% in DSG samples (FIG. 6D, H, I, K, L). PDGFRα expression levels in myofibroblasts reduced in CES by ~52% but increased by ~289% in DSG samples (FIG. 28D, G, J). The maintenance of α-SMA and tremendous increase in PDGFRα expression in DSG indicates the inability of primary E16 mesenchyme on DSG to repress fibrotic activity on DSG in the presence of TGFβ1, whereas the reduction in both α-SMA and PDGFRα expression in CES indicates the ability of primary E16 mesenchyme on CES to repress fibrotic activity despite TGFβ1 stimulation.

FGF2 Augments the Anti-Fibrotic Effects of Primary Mesenchyme on Cryoelectrospun Scaffolds on Myofibroblasts To determine if primary E16 mesenchyme on CES stimulated by FGF2 demonstrates improved repression of fibrotic activity in myofibroblasts, we primed primary E16 mesenchyme on CES with FGF2 supplemented media for 4 days prior to the addition of myofibroblasts (Group MFY, FIG. 28E). FGF2 stimulation was continued 1 day after myofibroblast seeding to allow the cells to attach and acclimate to the environment and then continued for 7 days in this experimental condition. FGF2 stimulation of primary mesenchyme and myofibroblasts on both CES and DSG indicated >95% repression in α-SMA and CNN1 expression levels (FIG. 28E, H, I, K, L). Whereas PDGFRα levels increased by ~20% in CES and decreased by ~60% in DSG, demonstrating an improved suppression of fibrotic activity in both CES and DSG and indicating a pro-regenerative function of PDGFRα in CES (FIG. 28E, G, J).

To determine if FGF2 primed primary E16 mesenchyme on CES could continue to repress the fibrotic activity of myofibroblasts in a TGFβ1-induced fibrotic microenvironment, samples were prepared similar to group MFY but with the inclusion of TGFβ1 in addition to FGF2 one day after myofibroblast seeding (Group MFYT, FIG. 6F). We observed a reduction in α-SMA and CNN1 expression by ~78% and >90% respectively in CES samples after 7 days in culture, whereas α-SMA expression was maintained and CNN1 expression reduced by ~72% in DSG samples (FIG. 28F, H, I, K, L). PDGFRα expression levels in myofibroblasts reduced by ~28% in CES and by ~58% in DSG (FIG. 28F, G, J). The maintenance of α-SMA in DSG indicates the inability of primary E16 mesenchyme on DSG to repress fibrotic activity on DSG in the presence of TGFβ1 despite FGF2 stimulation, whereas the reduction in both α-SMA and PDGFRα expression in CES indicates the ability of FGF2-stimulated primary E16 mesenchyme on CES to repress fibrotic activity despite TGFβ1 stimulation. However, absolute expression levels of PDGFRα, α-SMA and CNN1 on CES/DSG were not significantly different, indicating comparable performance.

Discussion

ECM plays a critical role in modulating cell health and is a key player in driving disease and organ dysfunction. Excessive accumulation of ECM or fibrosis impairs organ function by converting healthy tissue-resident stromal cells to myofibroblasts and limiting their ability to support parenchymal cell function. Exogenous MSC delivery has been shown to remediate fibrosis and improve organ function through pro-regenerative, anti-inflammatory and anti-fibrotic biochemical cues. Mechanical cues from soft scaffolds with stiffness lower than the fibrotic environment have also demonstrated repression of fibrosis. Cell therapy strategies can therefore benefit greatly from combination with ECM-mimicking scaffold therapy strategies by improving not only localization and engraftment of MSCs at the target site but also modulating the behavior of both the delivered cells and the tissue-resident cells to repress fibrosis.

Stromal cells are sensitive to matrix stiffness, the number of cell adhesion sites, and the ECM proteins with which they interact. Scaffolds for MSC therapy targeting fibrosis remediation should maintain the stromal cells in their MSC state and prevent their differentiation into myofibroblasts. Stromal cells typically reside in a soft ECM. We predicted that scaffolds that mimic the topography, pore size, and viscoelasticity of native healthy soft tissues/organ ECM might best preserve stromal health. We have identified elastin-alginate cryoelectrospun scaffolds to mimic the topography, pore size, and viscoelastic properties of decellularized salivary gland ECM. Hence, we tested our hypothesis by growing MSC-like, primary E16 mesenchyme cells in elastin-alginate cryoelectrospun scaffolds, traditionally electrospun nanofibers, and bulk hydrogels with the same material composition but different topographical cues, probing their ability to support viable stromal cell maintenance for cell delivery in comparison to decellularized salivary gland matrices and Matrigel, a standard for in vitro organoid culture, including salivary gland organoids.

Cell delivery vehicles should ideally maintain the majority of the cells in a viable state and permit 3D cell-cell and cell-substrate interaction for retention of optimal cell function. We identified that the MSC-like, primary E16 mesenchyme cells formed 3D clusters with characteristic spread-out fibroblast morphology in cryoelectrospun scaffolds and decellularized salivary gland matrices (FIG. 23B, FIG. 23C) with >80% cell viability, formed cell sheets in Matrigel (FIG. 23D) with >95% cell viability, and were rounded in bulk hydrogels with <55% cell viability. High cell viability in Matrigel culture is expected due to improved oxygen and nutrient diffusion to cell-sheets and stimulation from enriched growth factors in Matrigel. However, Matrigel, which is the basement membrane extract derived from the Engelbreth-Holm-Swarm mouse tumor, is heterogenous, ill-defined, and not suitable for cell delivery to treat diseases. Cryoelectrospun scaffolds, which support viable cell growth comparable to decellularized salivary glands, provide an alternative to Matrigel for cell culture and delivery.

Analysis of stromal health through the expression of healthy stromal markers, PDGFRα, PDGFRβ, and vimentin (FIG. 24) and myofibroblast markers, α-SMA and CNN1 (FIG. 26) revealed that cryoelectrospun scaffolds promoted the robust expression of PDGFRα and PDGFRβ, maintenance of vimentin in primary E16 mesenchyme, and repression of α-SMA and CNN1 expression in comparison to decellularized salivary gland matrices and Matrigel at the protein/translational level. Further, the relatively greater α-SMA and CNN1 expression in decellularized salivary gland matrices and Matrigel could be due to the interaction of cells with stiff ECM components like collagen, which are not included in the fabrication of the elastin-alginate CES. Hence, even though the bulk viscoelastic properties of CES and DSG are similar, the material composition of CES and DSG induce slightly varied cell responses. Analysis of the mRNA expression of PDGFRα, PDGFRβ, vimentin, and α-SMA revealed that expression levels in CES were comparable to that of DSG and were much less than in Matrigel, contradicting the protein level expression. This indicates translational regulation of these markers. Mechanical stimulation has been shown to regulate translational processes in skeletal muscle cells and cardiomyocytes and increase the rate of protein synthesis in skeletal muscle cells. The differences observed in PDGFRα, PDGFRβ, vimentin, and α-SMA expression at the transcriptional and translational levels in CES, DSG and Matrigel could possibly be attributed to the differences in mechanical stimulation by these scaffolds. Overall, cryoelectrospun scaffolds demonstrated the retention of optimal stromal phenotype for cell delivery applications.

Boosting the regenerative and antifibrotic potential of stromal cells can be very beneficial for in vivo cell delivery. We observed that FGF2 stimulation improved PDGFRα expression (FIG. 27A) and repressed vimentin (FIG. 27C) and α-SMA (FIG. 27D) expression. Vimentin, though a mesenchymal marker, is a protein that can be overexpressed in fibrotic environments. The repression of vimentin and α-SMA in primary E16 mesenchyme cells on CES with FGF2 stimulation indicates the anti-fibrotic effect of FGF2. Further, the ability of FGF2 to promote PDGFRα (FIG. 27F) and PDGFRβ (FIG. 27G) and repress αSMA (FIG. 27I) even in the presence of TGFβ1, a fibrosis-inducing growth factor, speaks to the potential of FGF2 to maintain the regenerative and anti-fibrotic properties of primary E16 mesenchyme on cryoelectrospun scaffolds.

An in vitro analysis of the ability of cryoelectrospun scaffolds, primary E16 mesenchyme, and FGF2 to repress the fibrotic activity of myofibroblasts in the presence or absence of TGFβ1 revealed that each of cryoelectrospun scaffolds, primary mesenchyme, and FGF2 had an anti-fibrotic effect on myofibroblasts, demonstrated through repression of α-SMA and CNN1, even in the presence of TGFβ1 (FIG. 28A et seq.). The low initial expression levels and the time-dependent reduction in levels of α-SMA and CNN1 in CES but not DSG for myofibroblast only (Group M) specifically attests to the antifibrotic effects of CES but not DSG. DSG consists of ECM of the homeostatic salivary gland and micro-mechanical cues from collagen and other basement membrane proteins in DSG might be the cause for retention of fibrotic activity and lack of anti-fibrotic effects. The additional biochemical cues from the ECM in DSG might also be the reason for better fibrotic activity repression by primary E16 mesenchyme (Group MY) in DSG in comparison to CES, indicating that DSG better supports the anti-fibrotic stromal function of primary E16 mesenchyme with and without FGF2 stimulation (Groups MY, MFY) in comparison to CES. Further, less drastic fold changes observed in DSG in comparison to CES for experimental conditions with TGFβ1-induced fibrotic microenvironment (Group MYT, MFYT) could be due to the interplay of biochemical cues from the ECM in DSG and the growth factor supplements. Overall, although the interplay of ECM and growth factor cues give DSG an edge over CES for relatively lower initial fibrotic activity in myofibroblast and primary E16 mesenchyme cocultures, the anti-fibrotic effects of CES compensate for the effect with a time-dependent repression in fibrotic activity. These results highlight the potential of CES, MSC-like primary E16 mesenchyme and FGF2 to synergistically modulate an in vivo fibrotic environment for remediation of fibrosis.

Herein, we substantiated the ability of cryoelectrospun scaffolds to function as an optimal stromal cell delivery vehicle for anti-fibrotic therapy. We validated the ability of cryoelectrospun scaffolds to support viable long-term stromal cell maintenance, healthy stromal marker expression, and repression of myofibroblast marker expression, comparably or even better than decellularized salivary gland matrices. We demonstrated that FGF2 could potentiate stromal maintenance on cryoelectrospun scaffolds and that these scaffolds could compound the anti-fibrotic effects of FGF2 and primary E16 mesenchyme on myofibroblasts.

This study performed fundamental, in vitro analyses demonstrating the potential of cryoelectrospun scaffolds for stromal cell delivery to remediate salivary gland fibrosis, with the possibility of addressing fibrosis in other soft tissue organs as well.

Example IV

Example IV is directed to the effect of stromal cells seeded into the cryoelectrospun scaffolds of the present invention and rescue of fibrosis resulting from the effects of partial resection of the submandibular salivary gland of 12-week-old C57BL/6 mice.

Figure 29A:
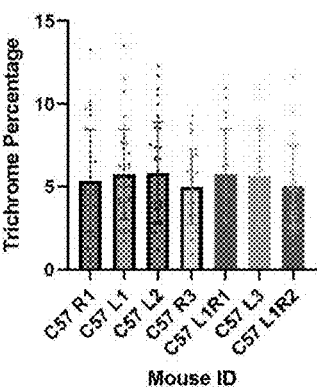
FIGS. 29A-29C depicts data related to fibrosis levels in resected glands, resected glands plus implant, and resected glands plus implant plus cells.
Figure 29B:
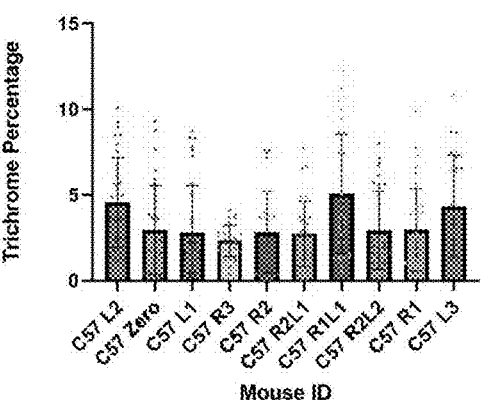
Figure 29C:
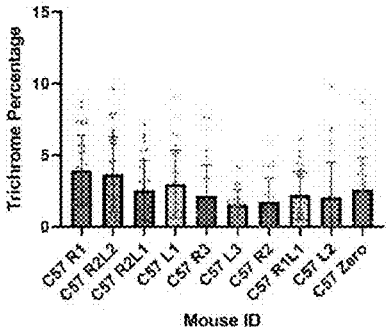
Figure 30:
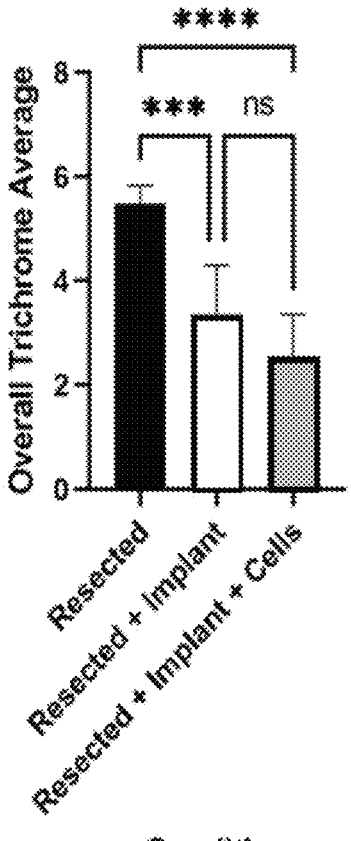
FIG. 30 depicts data related overall ECM staining/trichrome average.

Specifically, primary embryonic day 16 (E16) mesenchymal/stromal cells were seeded onto cryoelectrospun scaffolds and grown for 3 days. 50,000 primary E16 mesenchyme cells in DMEM/F12 medium containing 10% FBS, 1% PenStrep were seeded onto the scaffolds in 25 μL of medium. The cell culture medium was supplemented with 25 mM CaCl2, to maintain the alginate in its crosslinked form and prevent rapid disintegration of the scaffold. Cryoelectrospun scaffolds were incubated on a rotary shaker at 30 rpm for 2 hours, to enhance cell attachment to the 3D scaffolds. After two hours, each scaffolding-containing well was supplemented with 175 μL of fresh medium, and the well plate was incubated with rotary shaking for another 22 hours to increase the cell attachment efficiency. Cell culture on scaffolds was continued for two additional days. Separately, 12-week-old C57BL/6 mice were subjected to partial resection of the submandibular salivary gland to remove 40% of the distal tip of the gland. Scaffold alone or scaffold+ cells were implanted into 10 mice, and the mice were sacrificed 14 days after implantation and the submandibular gland harvested and frozen over liquid nitrogen. The frozen glands were then cut into 10 μm sections, and 36 sections from each mouse were stained with trichrome stain to quantify the amount of collagen in each gland, since collagen is an extracellular matrix (ECM) protein that is overexpressed during fibrosis; quantifying collagen (blue stain) would be a measure of the level of fibrosis. Images were captured on a Nanozoomer slide scanner and the sections were quantified using FIJI to quantify the area occupied by blue stain (FIGS. 29A, 29B, 29C). As shown in FIG. 30, the trichrome staining, indicating collagen in the ECM, is substantially reduced in the resected glands with scaffold implants including in the glands containing implants previously seeded with cells, demonstrating the ability of the scaffolds and/or stromal cells to reduce the fibrotic phenotype.

Trichrome analysis in resected glands is presented in FIG. 29A; trichrome analysis in resected glands plus implant is presented in FIG. 29B; and trichrome analysis in resected glands plus implant plus cells is FIG. 29C. The overall trichrome average is provided in FIG. 30.

Example V

Example V provides various alternate methods of the technology of the present invention and are intended to supplement the other methods provided in the specification, as additional non-limiting exemplars of the present technology. The data are inclusive of FIGS. 31, 32, 33, and 34, and the information presented in Tables S1 and S2, supra.

Materials and Methods

Scaffold preparation: Elastin-alginate nanofibers (NF). Traditionally electrospun nanofiber mats were fabricated from a solution of 1% elastin, 1.5% alginate and 3%

PEG-400 kD in deionized water. Briefly, the viscous solution was loaded into a 3 mL syringe and pumped out of a 25 G needle at a constant flow rate of 10 μL/min. The needle voltage was maintained at 17 kV, and the needle tip-to-collector spacing at 15 cm for electrospinning for 1 hour onto a flat collector plate lined with 5 mm glass coverslips. The nanofiber mats were crosslinked by EDC-NHS chemistry (0.49 mg EDC (Sigma Aldrich) and 0.59 mg NHS (Thermo Fisher Scientific) per 100 μL of 95% ethanol per scaffold) by rocking the scaffolds at 45 rpm for 30 min, followed by a series of graded ethanol washes with 95, 70, 50, and 0% ethanol in the presence of 1.5% CaCl2 for 5 min each to wash away residual EDC and NHS, and simultaneously ionically crosslink the alginate chains.

Elastin-alginate bulk hydrogels (BH): Bulk hydrogel were fabricated by preparing 2% elastin and 3% alginate solutions in sterile deionized water and by mixing it in equal parts with the cell suspension for a final material composition of 1% elastin and 1.5% alginate that matches elastin-alginate nanofibers or cryoelectrospun scaffolds. 10 μL of the hydrogel-cell suspension solution was incubated in 100 μL of cell culture medium with 100 mM CaCl2 (Sigma-Aldrich) for 30 min to crosslink the hydrogel and form hydrogel-cell constructs and thereafter switched to cell culture medium with 25 mM CaCl2.

Elastin-alginate cryoelectrospun scaffolds with honeycomb topography (CES): Cryoelectrospun scaffolds were fabricated using 1% elastin, 1.5% alginate and 3% PEG-400 kD solution in deionized water. Briefly, the viscous solution was loaded into a 3 mL syringe and pumped out of a 25 G needle at a constant flow rate of 10 μL/min. The needle voltage was maintained at 17 kV, and the needle tip-to-collector spacing at 15 cm, relative humidity at >40%, and air temperature <2° C. for cryoelectrospinning for 1 hour onto a 5 mm metallic probe array collector plate maintained at ~−20° C. The cryoelectrospun scaffolds were then lyophilized for 3 hours and crosslinked by EDC-NHS chemistry (1.48 mg EDC and 1.78 mg NHS per 100 μL of 95% ethanol per scaffold) by rocking the scaffolds at 45 rpm for 2 hrs, followed by a series of graded ethanol washes with 95, 70, 50, and 0% ethanol in the presence of 1.5% CaCl2 for 15 min each to wash away residual EDC and NHS, and simultaneously ionically crosslink the alginate chains. The crosslinked scaffolds were frozen at −80° C. overnight and lyophilized again for 4 hours. The lyophilized scaffolds were UV sterilized.

Cell Seeding on Scaffolds

Well plate preparation for cell seeding: To improve cell attachment efficiency and prevent cells from attaching to the well bottom after cell seeding, well-plates were coated with the ultra-low adhesion polymer lipidure. Flat bottom 96 wells were used for nanofiber scaffolds and round bottom 96 wells were used for bulk hydrogel, cryoelectrospun scaffolds and decellularized salivary gland matrices. Each well was coated thrice by adding 75 μL of 0.64% lipidure in 96% ethanol to each well, aspirating after 1 minute and air-drying for 15 minutes. After the third coating, the well plate was UV sterilized for 1 hour and air-dried overnight before placing scaffolds for cell culture.

Figure 32:
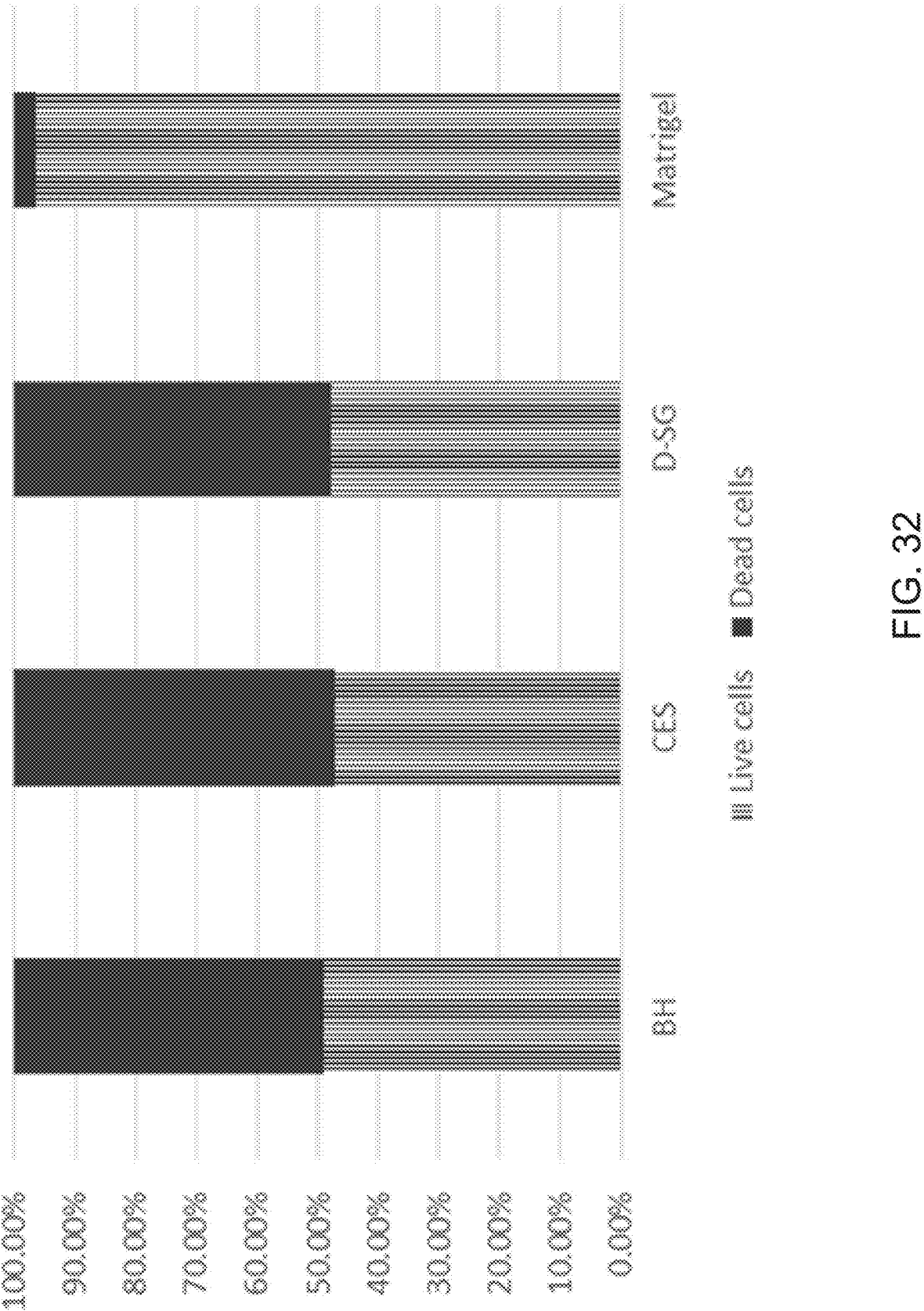
FIG. 32 depicts data related to viability of primary E16 mesenchymal cells grown for up to 7 days in 48 well plate format.
Figure 33:
FIG. 33 depicts data related to Live/Dead stained cells reveal low attachment to nanofibers.
Figure 34:
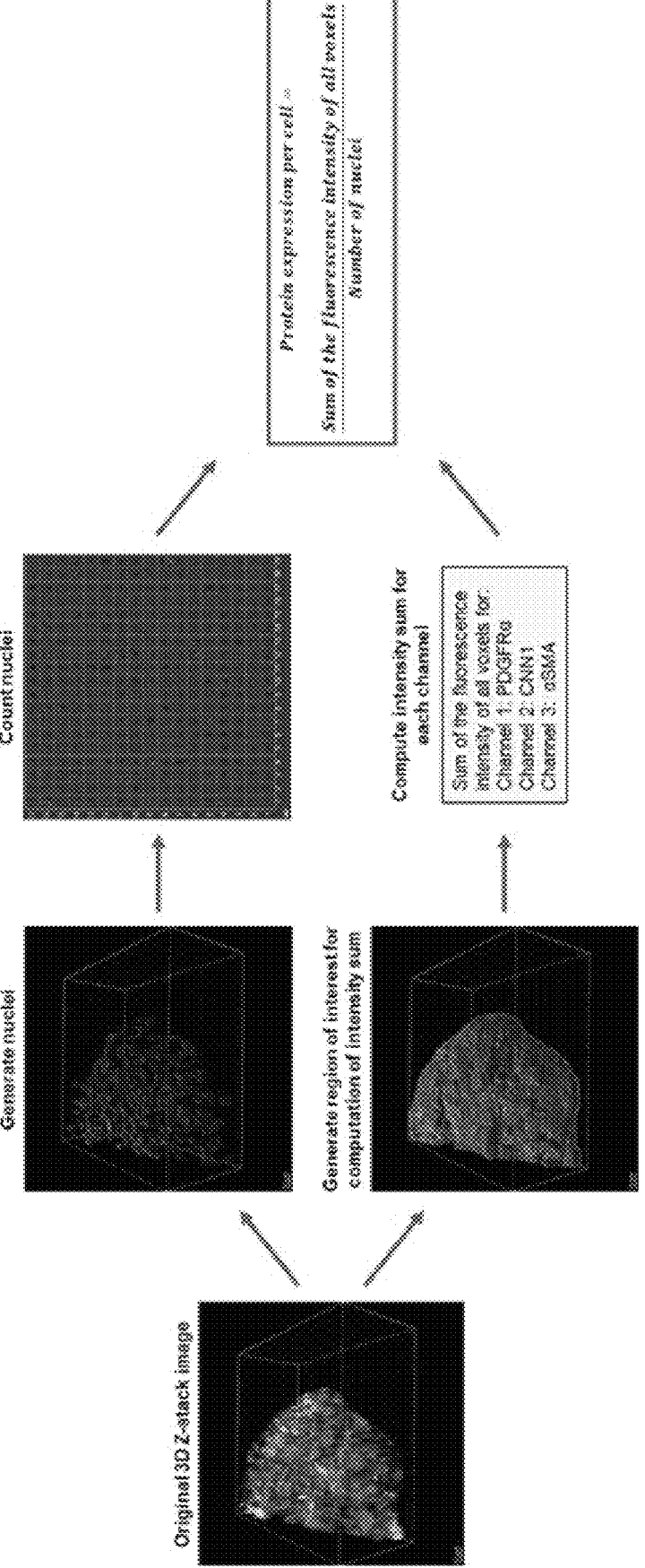
FIG. 34 depicts data presented in a schematic diagram detailing the protocol for quantification of protein expression/cell.

Cell seeding onto scaffolds: Primary E16 mesenchyme cells in DMEM/F12 medium containing 10% FBS, 1% PenStrep were seeded at concentrations as detailed in Table SM1 for immunocytochemistry experiments. The cell culture medium was supplemented with 25 mM CaCl2, a concentration at which cell culture was not negatively impacted for the nanofiber, bulk hydrogel and cryoelectrospun scaffolds to maintain the alginate in its crosslinked form and prevent rapid disintegration of the scaffold. Cryo-electrospun scaffolds and decellularized salivary gland matrices were incubated on a rotary shaker at 30 rpm for 2 hours, to enhance cell attachment to the 3D scaffolds. After two hours, each well was supplemented with 175 μL of fresh medium, and the well plate was incubated with rotary shaking for another 22 hours to increase the cell attachment efficiency.

gland matrices (DSG) and Matrigel after 7 days of cell growth using ImageJ revealed that cells on CES but not BH have viability levels comparable to DSG, see FIG. 32.

Co-immunostaining cell-scaffold constructs with PDGFRβ and vimentin rabbit antibodies: Samples to be co-stained for PDGFRα, PDGFRβ, vimentin were first stained with PDGFRα, PDGFRβ antibodies primary antibodies and their respective secondary antibodies as per the

TABLE SM1

Cell seeding and culture strategy for improved cell attachment and viability

| Scaffold | Cells seeded | Cell attachment (first 24 hours) | |
| --- | --- | --- | --- |
| | | Culture dish | Culture strategy |
| Nanofibers | 5,000 cells/200 μL media | Flat-bottom lipidure coated 96 well plate | Static culture |
| Bulk Hydrogel | 10,000 cells/20 μL hydrogel-cell suspension in 200 μL media | Round-bottom lipidure coated 96 well plate | Static culture |
| Cryoelectrospun scaffolds | 50,000 cells/25 μL media | Round-bottom lipidure coated 96 well plate | Rotary culture |
| Decellularized salivary gland matrix | 50,000 cells/25 μL media | Round-bottom lipidure coated 96 well plate | Rotary culture |
| Matrigel | 50,000 cells/10 μL matrigel-cell suspension in 180 μL media | 0.1 μm Nuclepore filter in Mattek dish | Static culture |

Cells on nanofiber mats, bulk hydrogels and Matrigel were grown in static culture because the cells attach to a 2D surface for nanofibers and the cells are in a crosslinked suspension for bulk hydrogels and Matrigel, not requiring enhanced cell attachment. All scaffolds were incubated in a humidified incubator at 37° C. and 5% $CO_2$. For PCR analysis the number of cells seeded was increased to 75,000 cells/scaffold for cryoelectrospun scaffolds, decellularized salivary gland matrices and Matrigel for increased mRNA yield.

Cell attachment efficiency analysis: Cells were seeded at a set concentration and allowed to attach for 24 hours. After 24 hours, unattached cells were aspirated by gently pipetting. The scaffold was rinsed gently in cell culture media to collect any remaining unattached cells. The scaffold was moved to a new well and any cells attached to the bottom of the well were trypsinized, neutralized and added to the suspension of cells not attached to the scaffold. The cell suspension was centrifuged at 450 g for 5 minutes, resuspended in cell culture media and the number of cells were counted. Cell attachment efficiency was determined by subtracting the number of cells not attached to the scaffold from the number of cells seeded by using the formula Cell attachment efficiency =

$$\frac{\text{No. of cells seeded} - \text{No. of cells not attached}}{\text{No. of cells seeded}} * 100.$$

Figure 31:
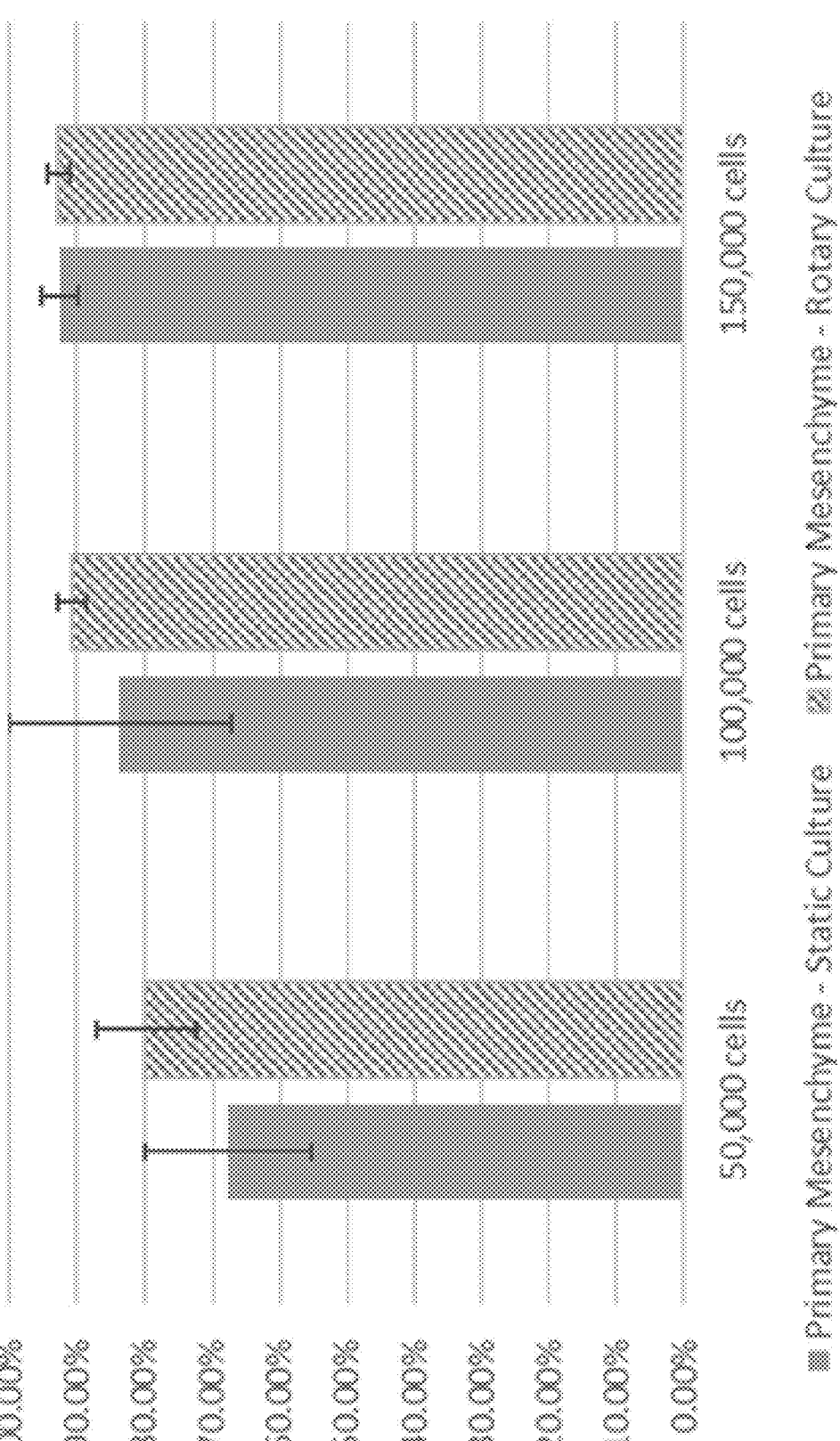
FIG. 31 depicts data related to cell attachment with rotary culture of cells for the first 24 hours at 30 rpm.

Rotary culture of cells for the first 24 hours at 30 rpm improves cell attachment and reduces variability in cell attachment, see FIG. 31.

Viability of primary E16 mesenchymal cells grown for up to 7 days in 48 well plate format was examined. The quantification of cell viability on bulk hydrogels (BH), cryoelectrospun scaffolds (CES), decellularized salivary protocol detailed in the immunocytochemistry, as discussed herein above. Afterwards, the samples were blocked with 20% rabbit serum-3% bovine serum albumin in wash buffer (0.9% NaCl-50 mM CaCl2 in deionized water) for 2 hours at room temperature, and then incubated with AF488-vimentin direct conjugate antibody with gentle rocking at 45 rpm at room temperature for 2 hours. All cells were co-stained with DAPI (Sigma-Aldrich) to reveal the nuclei within the total cell population. Samples were then mounted using a glycerol-based mounting medium 181 for imaging. Confocal imaging was performed using a Leica SP5 confocal laser scanning microscope (Leica Microsystems, Mannheim, Germany).

Quantification of LIVE/DEAD Assay: Colocalized live and dead cells observed in hydrogel samples were counted by using object-based colocalization in Imaris. The 3D image ('lif' image) obtained on the confocal microscope was opened in the Imaris software and converted to '.ims' file. The image was opened in surpass view and two 'Spots' objects were created for counting live cells in the green channel and dead cells in the red channel. The spot size was set to 15 μm to identify the cells in each channel and the 'shortest distance to spots' feature was used to identify colocalized live and dead cells that were less than 2 μm apart. The number of colocalized and non-colocalized cells were exported from the 'Statistics' tab. The percentage of live, dying and dead cells was computed for all scaffolds for a minimum of 3 replicates. Live/Dead stained cells reveal low attachment to nanofibers. Negligible number of cells remain on nanofibers on Day 7, see FIG. 33. A schematic diagram detailing the protocol for quantification of protein expression/cell is presented in FIG. 34.

The entire disclosure of all applications, patents, and publications cited herein are herein incorporated by reference in their entirety. While the foregoing is directed to embodiments of the present disclosure, other and further embodiments of the disclosure may be devised without departing from the basic scope thereof.

What is claimed is:

1. A scaffold, comprising: a cryoelectrospun alginate and elastin material that mimics decellularized extracellular matrix (ECM), wherein the alginate and elastin are cross-linked.

2. The scaffold of claim 1, wherein the scaffold is characterized as lyophilized scaffold, and wherein the lyophilized scaffold comprises 99.9 percent weight to 0.1 percent weight alginate, and 0.1 percent weight to 99.9 percent weight elastin, wherein the percent weight is the percent weight of the total lyophilized scaffold.

3. The scaffold of claim 2, wherein the scaffold is rehydratable following lyophilization.

4. The scaffold of claim 1, wherein the scaffold further comprises one or more biodegradable or biocompatible polymers.

5. The scaffold of claim 1, wherein the scaffold further comprises electrospun collagen.

6. The scaffold of claim 1, wherein the scaffold further comprises natural polymer, collagen, gelatin, silk fibroin, hyaluronic acid, chitosan, agarose, synthetic polymer, poly (alpha esters), poly(lactate acid), poly(glycolic acid), polyorthoesters, polyanhydrides and their copolymers, or combinations thereof.

7. The scaffold of claim 1, wherein the scaffold further comprises one or more ECM proteins such as collagen, laminin, and combinations thereof.

8. The scaffold of claim 1, wherein the scaffold is characterized as a cryoelectrospun scaffold that mimics the decellularized ECM of one or more soft tissue, salivary tissue, mammary tissue, heart tissue, pancreatic tissue, or the like.

9. The scaffold of claim 1, wherein the scaffold is characterized as a scaffold that mimics a decellularized ECM of one or more soft tissue organs such as salivary tissue, lung tissue, liver tissue, and the like.

10. The scaffold of claim 1, wherein, when hydrated, one or more fibers and/or pores of the scaffold have a similar organization and reticulated topography as native ECM of a preselected organ or preselected tissue.

11. The scaffold of claim 1, wherein the scaffold is capable of supporting growth and/or differentiation of one or more cells to become fibrotic cells, mimicking fibrotic tissues, or to serve as fibrosis model.

12. The scaffold of claim 1, wherein the scaffold contains a plurality of stromal cells.

13. The scaffold of claim 12, wherein the plurality of stromal cells are primary E16 mesenchyme cells.

14. The scaffold of claim 12, wherein the scaffold contains one or more fibroblast growth factor 2 (FGF2) proteins.

15. The scaffold of claim 14, wherein the scaffold provides an anti-fibrotic activity in vitro.

16. The scaffold of claim 13, wherein the scaffold promotes stromal and non-fibrotic phenotype of stromal cells in vitro.

17. The scaffold of claim 12, wherein the scaffold promotes an anti-fibrotic activity of stromal cells in vitro.

18. The scaffold of claim 13, wherein the scaffold reduces a fibrotic phenotype of myofibroblasts in vitro.

19. The scaffold of claim 18, wherein the scaffold reduces the fibrotic phenotype in vitro in the presence of a fibrotic stimulant Transforming Growth Factor Beta 1 (TGFb1).

20. The scaffold of claim 13, wherein the scaffold is viscoelastic and provides an anti-fibrotic activity in vitro.

21. The scaffold of claim 13, wherein the scaffold is viscoelastic and provides an anti-fibrotic activity in vivo.

22. The scaffold of claim 1, wherein the scaffold is viscoelastic and provides an anti-fibrotic activity in vitro.

23. The scaffold of claim 1, wherein the scaffold is viscoelastic and provides an anti-fibrotic activity in vivo.

24. The scaffold of claim 1, wherein the scaffold reduces a fibrotic phenotype of myofibroblasts in vitro.

25. The scaffold of claim 1, wherein the scaffold reduces a fibrotic phenotype in vitro in the presence of fibrotic stimulant TGFb1.

* * * * *